(12) United States Patent
Jones et al.

(10) Patent No.: US 8,748,446 B2
(45) Date of Patent: Jun. 10, 2014

(54) HALOGENATED COMPOUNDS FOR PHOTODYNAMIC THERAPY

(75) Inventors: Gary W. Jones, Newcastle, WA (US); Anatoliy L. Tatarets, Kharkiv (UA); Leonid D. Patsenker, Kharkiv (UA)

(73) Assignee: Nanoquantum Sciences, Inc., Bellevue, WA (US)

( * ) Notice: Subject to any disclaimer, the term of this patent is extended or adjusted under 35 U.S.C. 154(b) by 0 days.

(21) Appl. No.: 13/411,539

(22) Filed: Mar. 3, 2012

(65) Prior Publication Data

US 2013/0231604 A1    Sep. 5, 2013

(51) Int. Cl.
| | |
|---|---|
| *A61K 31/438* | (2006.01) |
| *A61K 31/404* | (2006.01) |
| *A61K 31/403* | (2006.01) |
| *A61N 5/10* | (2006.01) |
| *C07D 401/02* | (2006.01) |
| *C07D 209/58* | (2006.01) |
| *C07D 209/04* | (2006.01) |

(52) U.S. Cl.
CPC ............ *A61K 31/438* (2013.01); *A61K 31/404* (2013.01); *A61K 31/403* (2013.01); *A61N 5/10* (2013.01); *C07D 401/02* (2013.01); *C07D 209/58* (2013.01); *C07D 209/04* (2013.01)
USPC ............ 514/278; 514/411; 514/145; 546/17; 548/427; 548/452; 548/510; 604/20

(58) Field of Classification Search
CPC . A61K 31/438; A61K 31/404; A61K 41/403; A61N 5/10; C07D 401/02; C07D 209/58; C07D 209/04
USPC ............. 514/278, 411, 415; 546/17; 548/427; 548/451, 510; 604/20
See application file for complete search history.

(56) References Cited

U.S. PATENT DOCUMENTS

| | | | |
|---|---|---|---|
| 5,830,526 | A | 11/1998 | Wilson et al. |
| 6,770,787 | B2 | 8/2004 | Danaboyina et al. |
| 6,797,449 | B2 | 9/2004 | Nakamura et al. |
| 2007/0167350 | A1 | 7/2007 | Ramaiah et al. |
| 2010/0323389 | A1 | 12/2010 | Xu et al. |
| 2011/0251386 | A1* | 10/2011 | Masuda et al. ............... 548/200 |

FOREIGN PATENT DOCUMENTS

| | | |
|---|---|---|
| RU | 2088228 C1 | 8/1997 |
| WO | 0044742 A1 | 8/2000 |
| WO | 2007098182 A2 | 8/2007 |

OTHER PUBLICATIONS

Teague, Simon J. Synthesis of benzimidazole based JNK inhibitors. Tetrahedron Letters. 46 (2005) 4613-4616.*

"Polymethine", "Wiktionary, the free dictionary" (accessed on Jul. 18, 2012 via http://en.wiktionary.org/wiki/polymethine).

Hamblin, M., et al. (Ed.), "Advances in Photodynamic Therapy: Basic, Translational, and Clinical", 2008, pp. 1, 426, and 516.

Kalb, L, et al., "Ueber substituierte Indol-2-carbonsaeure-3-propion-saeuren und einige jodierte Benzolderivate", "Chem Ber.", 1926, pp. 1860-1870, vol. 59.

Kalb, L, et al., "Ueber substituierte Indol-2-carbonsaeure-3-propion-saeuren und einige jodierte Benzolderivate", "Chem Ber.", 1926, pp. 1860-1870, vol. 59 (Partial English translation of original German p. 1862).

Lackowicz, J., "Fluorophores", "Principles of Fluorescence Spectroscopy 3rd Edition", 1986, pp. 63-95, Publisher: Plenum Press: New York, London.

Lackowicz, J., "Introduction to Fluorescence", "Principles of Fluorescence Spectroscopy 3rd Edition", 1986, pp. 1-26, Publisher: Plenum Press: New York, London.

Molecular Probes, Inc., "Introduction to Fluorescence Techniques", Oct. 22, 2005, pp. 1-5.

Tietze, L., et al., "Reaktionen und Synthesen im organisch-chemischen Praktikum und Forschungslaboratorium", 1991, pp. 159-160, Publisher: Georg Thieme Verlag, Stuttgart, New York (German and Corresponding English Translation of Portions of pp. 159-160).

Volkova, K, et al., "Spectroscopic study of squaraines as protein-sensitive fluorescent dyes", "Dyes and Pigments", 2005, pp. 1-8 (Article in Press).

Agostinis, P., et al., "Photodynamic Therapy of Cancer: An Update", "CA Cancer J Clin", May 26, 2011, pp. 250-281, vol. 61.

Altinoglu, E., et al., "Near-Infrared Emitting Fluorophore-Doped Calcium Phosphate Nanoparticles for In Vivo Imaging of Human Breast Cancer", "ACS Nano", Sep. 19, 2008, pp. 2075-2084, vol. 2, No. 10.

(Continued)

*Primary Examiner* — Samantha Shterengarts
(74) *Attorney, Agent, or Firm* — Hultquist, PLLC; Steven J. Hultquist; David Bradin

(57) ABSTRACT

Halo-organic heterocyclic compounds are described, which have the formulas

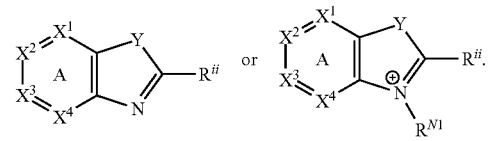

Ring A is an aromatic ring bound to at least two halogen atoms, at least one of which is iodine or bromine. Also described are polymethine dyes based on these heterocyclic compounds, and dendrimeric compounds and conjugates of such polymethine dyes. The polymethine dyes are characterized by enhanced properties, e.g., brightness, photostability, sensitivity and/or selective affinity that make them useful to target cancer cells, pathogenic microorganisms, and/or other biological materials, in applications such as photodynamic therapy, photodynamic antimicrobial chemotherapy (PACT), cancer treatment, selective removal or attachment of biological materials, antimicrobial coating materials, and other diagnostic, theranostic, spectrum shifting, deposition/growth, and analytic applications.

25 Claims, 6 Drawing Sheets

(56) References Cited

OTHER PUBLICATIONS

Astruc, D., et al., "Dendrimers Designed for Functions: From Physical, Photophysical, and Supramolecular Properties to Applications in Sensing, Catalysis, Molecular Electronics, Photonics, and Nanomedicine", "Chem. Rev.", Mar. 31, 2010, pp. 1857-1959, vol. 110.

Berube, M., et al., "Synthesis of Simplified Hybrid Inhibitors of Type 1 17Beta-Hydroxysteroid Dehydrogenase via Cross-Metathesis and Sonogashira Coupling Reactions", "Organic Letters", Aug. 7, 2004, pp. 3127-3130, vol. 6, No. 18.

Bocci, V., et al., "Restoration of Normoxia by Ozone Therapy May Control Neoplastic Growth: A Review and a Working Hypothesis", "The Journal of Alternative and Complementary Medicine", 2005, pp. 257-265, vol. 11, No. 2.

Cardillo, J., et al., "Experimental selective choriocapillaris photothrombosis using a modified indocyanine green formulation", "Br J Ophthalmol", 2008, pp. 276-280, vol. 92.

Fedyunyayeva, I., et al, "The synthesis, structure and spectral properties of new long-wavelength benzodipyrroleninium-based bis-styryl dyes", "Dyes and Pigments", Dec. 15, 2010, pp. 201-210, vol. 90.

Hamblin, M., et al., "Photodynamic therapy: a new antimicrobial approach to infectious disease?", "Photochem. Photobiol. Sci.", Feb. 12, 2004, pp. 436-450, vol. 3.

Istomin, Y., et al., "The Effect of Hypoxia on Photocytotoxicity of Tics Tricarbocyanine Dye In Vitro", "Exp Oncol", Mar. 2006, pp. 80-82, vol. 28, No. 1.

Kachkovski, A., et al, "Electronic Properties of Polymethine Compounds. 2. Electron Donor Ability and Relative Stability", "Dyes and Pigments", 1993, pp. 83-97, vol. 22.

Kaestner, L., "Evaluation of Human Erythrocytes as Model Cells in Photodynamic Therapy", "Gen. Physiol. Biophys.", 2003, pp. 455-465, vol. 22.

Kim, E., et al., "Discovery of New Fluorescent Dyes: Targeted Synthesis or Combinatorial Approach?", "Springer Series on Fluorescence: Methods and Applications: Advanced Fluorescence Reporters in Chemistry and Biology I", 2010, pp. 149-186, vol. 8.

MacDonald, I., et al., "Basic principles of photodynamic therapy", "Journal of Porphyrins and Phthalocyanines", 2001, pp. 105-129, vol. 5.

Mishra, A., et al., "Cyanines during the 1990s: A Review", "Chem. Rev.", 2000, pp. 1973-2011, vol. 100.

Mitsunaga, M., et al., "Cancer cellselective in vivo near infrared photoimmunotherapy targeting specific membrane molecules", "Nature Medicine", Nov. 6, 2011, pp. 1685-1692, vol. 17, No. 12.

Mojzisova, H., et al., "Photosensitizing properties of chlorins in solution and in membrane-mimicking systems", "Photochemical & Photobiological Sciences", Mar. 30, 2009, pp. 778-787, vol. 8.

O'Connor, A., et al., "Porphyrin and Nonporphyrin Photosensitizers in Oncology: Preclinical and Clinical Advances in Photodynamic Therapy", "Photochemistry and Photobiology", 2009, pp. 1053-1074, vol. 85.

Patsenker, L., et al., "Fluorescent Probes and Labels for Biomedical Applications", "Ann. N.Y. Acad. Sci.", 2008, pp. 179-187, vol. 1130.

Patsenker, L, et al., "Long-Wavelength Probes and Labels Based on Cyanines and Squaraines", "Springer Series on Fluorescence: Methods and Applications: Advanced Fluorescence Reporters in Chemistry and Biology I", 2010, pp. 65-104, vol. 8.

Ramaiah, D., et al., "Squaraine Dyes for Photodynamic Therapy: Study of Their Cytotoxicity and Genotoxicity in Bacteria and Mammalian Cells", "Photochemistry and Photobiology", 2002, pp. 672-677, vol. 76, No. 6.

Santos, P., et al., "Singlet oxygen generation ability of squarylium cyanine dyes", "Journal of Photochemistry and Photobiology A: Chemistry", 2003, pp. 159-161, vol. 160.

Santos, P., et al., "Synthesis and Photochemical Evaluation of Iodinated Squarylium Cyanine Dyes", "Helvetica Chimica Acta", 2005, pp. 1135-1143, vol. 88.

Shirinian, V., et al., "Merocyanines: Synthesis and Application", "Topics in Heterocyclic Chemistry: Heterocyclic Polymethine Dyes: Synthesis, Properties and Applications", 2008, vol. 14, No. 75-105.

Spiller, W., et al., "Singlet Oxygen Quantum Yields of Different Photosensitizers in Polar Solvents and Micellar Solutions", "Journal of Porphyrins and Phthalocyanines", 1998, pp. 145-158, vol. 2.

Szacilowski, K., et al., "Bioinorganic Photochemistry: Frontiers and Mechanisms", "Chem. Rev.", 2005, pp. 2647-2694, vol. 105.

Tatarets, A., et al., "Synthesis of novel squaraine dyes and their intermediates", "Dyes and Pigments", Jul. 19, 2004, pp. 125-134, vol. 64.

Tatarets, A., et al., "Synthesis of water-soluble, ring-substituted squaraine dyes and their evaluation as fluorescent probes and labels", "Analytica Chimica Acta", Apr. 25, 2006, pp. 214-223, vol. 570.

Terpetschnig, E., et al, "Luminescent Probes for NIR Sensing Applications", "Near-Infrared Dyes for High Technology Applications vol. 52 of NATO Science Partnership Sub-Series 3", 1998, pp. 161-182.

Wainwright, M., "Photodynamic antimicrobial chemotherapy (PACT)", "Journal of Antimicrobial Chemotherapy", 1998, pp. 13-28, vol. 42.

Yu, J., et al., "Self-Assembly Synthesis, Tumor Cell Targeting, and Photothermal Capabilities of Antibody-Coated Indocyanine Green Nanocapsules", "J. Am. Chem. Soc.", Jan. 21, 2010, pp. 1929-1938, vol. 132.

\* cited by examiner

HALOGENATED COMPOUNDS FOR PHOTODYNAMIC THERAPY

FIELD

The present disclosure relates in one aspect to halo organic compounds, and more specifically to fluorinated, chlorinated, brominated, and iodinated nitrogen-containing heterocyclic compounds with two or more halogen atoms, having utility as precursors for synthesis of highly efficient reporting and sensitizing dyes, among other uses. The disclosure also relates to organic dyes, in particular polymethine dyes based on these heterocyclic compounds, dendrimeric compounds containing these polymethine dyes, and conjugates of these halogenated dyes, e.g., with other organic compounds, inorganic compounds, particles (including nanoparticles), and/or biological molecules and compounds, as well as methods to synthesize these halogenated compounds and conjugates thereof, having properties such as brightness, photostability, sensitivity and/or selective affinity that make them useful to target cancer cells, pathogenic microorganisms, and/or other biological materials. The compounds, conjugates, and materials of the present disclosure have applications as fluorescent reporters and/or sensitizers for photodynamic therapy, photodynamic antimicrobial chemotherapy (PACT), cancer treatment, selective removal or attachment of biological materials, and antimicrobial coating materials, as well as use in diagnostics, theranostics, spectrum shifting applications, deposition and growth of materials (e.g., polymerization and solids formation), and analysis and diagnosis related to biological materials, in vitro or in vivo. The disclosure further relates to corresponding methods of use of the disclosed compounds, conjugates, and materials in such applications.

DESCRIPTION OF THE RELATED ART

Organic dyes and compositions based on these dyes are known to be used as photoluminescent (fluorescent and phosphorescent) reporters, photo-sonic reporters, and/or as sensitizers for photodynamic therapy, photodynamic antimicrobial chemotherapy (PACT), cancer treatment, selective removal or attachment of biological materials, and/or antimicrobial coating materials. The principle related to functioning of these reporters and sensitizers is known. An example of the use of photosensitizers on targeting carriers is given in Mitsunaga M., Cancer cell—selective in vivo near infrared photoimmunotherapy targeting specific membrane molecules. Nature Medicine, 2011, 17, 1685-1691.

The reporting principle is based on detecting light emitted by a luminescent (luminophore) or fluorescent (fluorophore) dye, and using properties of that light to understand properties of the luminophore/fluorophore and its environment. Luminescence methods may be based on chemiluminescence and/or photoluminescence, among others, and may be used in spectroscopy, microscopy, imaging, immunoassays, and hybridization assays, among others. Photoluminescence is a particular type of luminescence that involves the absorption and subsequent re-emission of light. In photoluminescence, a luminophore is excited from a low-energy ground state into a higher-energy excited state by the absorption of a photon of light. The energy associated with this transition is subsequently lost through one or more of several mechanisms, including production of a photon through fluorescence or phosphorescence.

Photoluminescence may be characterized by a number of parameters, including the extinction coefficient ($\epsilon$), excitation and emission spectrum characterized by the absorption and emission maxima among other parameters, Stokes' shift ($\Delta\lambda_{St}$), luminescence lifetime ($\tau$), polarization (FP), and quantum yield ($\Phi_F$).

Luminescence methods may be influenced by extinction coefficient, excitation and emission spectra, Stokes' shift, and quantum yield, among others, and may involve characterizing fluorescence intensity (FI), fluorescence polarization (FP), fluorescence resonance energy transfer (FRET), fluorescence lifetime (FLT), total internal reflection fluorescence (TIRF), fluorescence correlation spectroscopy (FCS), fluorescence single molecule spectroscopy (SMS), fluorescence recovery after photobleaching (FRAP), and their phosphorescence analogs, among others.

Luminescence methods have several significant potential strengths. First, luminescence methods may be very sensitive, because currently available detectors, such as photomultiplier tubes (PMTs) and charge-coupled devices (CCDs), can detect very low levels of light. Second, luminescence methods may be very selective, because the luminescence signal may come almost exclusively from the luminophore.

Despite these potential strengths, luminescence methods may suffer from a number of shortcomings, at least some of which relate to the luminescent dye. For example:

1) The luminophore may have insufficient brightness, with an extinction coefficient and/or quantum yield that is too low to permit detection of an adequate amount of light when in low concentrations or when activation and detection is desired through significant distances of tissue or bone.
2) The luminophore also may have an excitation spectrum that does not permit it to be excited by wavelength-limited light sources, such as common lasers, light emitting diodes (LEDs), and arc lamps.
3) The luminophore also may be unstable, so that it is readily bleached and rendered non-luminescent.
4) The luminophore also may have an excitation and/or emission spectrum that overlaps with the well-known autoluminescence of biological and other samples. Such autoluminescence is particularly significant at wavelengths below about 600 nm.
5) The luminophore also may be expensive, especially if it is difficult to manufacture.
6) The luminophore may be highly quenched when labeled to proteins or other biomolecules or carriers at higher dye-to-biomolecule ratios.

A simultaneous solution for all the above disadvantages has been elusive for the near-IR spectral range.

Known luminescent photo-reporters for the long-wavelength region are based on cyanines (ICG, Cypate, Cy5, Cy7, Alexa 647), squaraines (Square-750), fused oxazines (ATTO 655), carbopyronins (ATTO 635), and some metal-ligand complexes (Os(bpy)$_2$dcbpy). The advantages and disadvantages of these dyes classes are well known in the art.

Sensitizing properties are based on light-induced generation of reactive oxygen species (ROS) that kill cells or microorganisms and/or remove or enhance accumulation of biological material. Reactive oxygen species (ROS) generated by photosensitizers typically consist of singlet oxygen and/or superoxide anion radicals, but the generation of other oxygen-based reactive species (e.g., hydroxyl radical-anion and peroxide species) and non-oxygen-based reactive species also can be directly or indirectly effected. A photosensitizer molecule can therefore create a large amount of cell-killing reactive species that have short lifetimes, permitting high cytotoxic activity only within tens of nanometers of the photosensitizer molecule.

A significant weakness of most conventional photodynamic therapies (PDT) is that for most applications they require highly accurate light source placement relative to the targeted biological material. Accuracy of light intensity distributions can be difficult given the variable light transmission in various tissues, organs, and bone that may be in the vicinity of the target, as well as variable shapes of and transmission characteristics within the targeted biological material itself. Photosensitizers that are more sensitive to light in the near-IR spectrum can provide greater depth of activation through tissue or bone.

In the case of cancer or pathogens, it is desirable to minimize damage to nearby untargeted tissue, while concurrently minimizing the probability of survival of any targeted cancer cells or pathogens. Even minimal non-selectivity of photosensitizers can result in damage to tissue exposed to the activating spectrum light. Therefore, materials and related methodology are desired that can permit activation of the photosensitizer on targeted biological material with minimal risk to nearby tissue, to achieve desired treatment effectiveness, patient safety and comfort, ease of treatment, speed of patient recovery, and overall cost of treatment. In some cases the photosensitizer itself can provide target selectivity as in the case of lipid-affinity photosensitizers that also exhibit low probability transport through mammalian cell membranes.

Additionally, analytical and diagnostic mechanisms for determining the effectiveness of the targeting of the photosensitizers prior to activation and the effectiveness of the treatment post-activation are valuable tools to attending physicians to improve long-term prognosis of patients receiving photodynamic therapy.

Various issues are important for the applicability of organic dyes as sensitizers for non-invasive or non-precision light placement applications, as discussed below.

High efficiency reactive oxygen species (ROS) generation is usually required for effective treatment at reasonable photosensitizer concentrations and light doses.

A photosensitizer's ability to generate singlet oxygen and other ROS such as superoxide anion and hydroxyl radicals and peroxide, can induce apoptosis or necrosis in cells and disrupt local vascular structure. Other photosensitizers induce catalyzed compounds and ROS induced compounds also can provide controlled toxicity in situations such as low oxygen environments, even though mostly singlet oxygen generation may be sufficient in many situations. Oxygen supplementation may be helpful in some situations.

The photosensitizer or dye should ideally possess adequate peak absorption in the long-wavelength region of near-infrared (NIR) between 700 and 850 nm, where biological tissues and bone exhibit most pronounced light transparency. For some photodynamic therapy applications in which (a) the targeted biological material can be placed very near the incident light, (b) the target material translucence and distance are easily predictable or determinable, or (c) limited light penetration is desired, activating light spectra under 700 nm can be efficiently used. Preferably, the photosensitizer should also exhibit minimal absorption over most of the visible spectral range (e.g., from 400 nm to 600 nm) to reduce the risk of patient skin and eye damage.

Extinction coefficients at the desirable excitation wavelength, and the ROS efficiency of the photosensitizer or dye, together limit the practical activation depth for a selected wavelength range of light. The dyes or photosensitizers should exhibit a favorable excitation spectrum that permits the excitation with desirable and available light sources. Low extinction coefficients relate to lower probability of photon absorption and therefore require higher photosensitizer or reporter concentrations and/or higher light doses than may be desirable.

The photosensitizer or dye should be thermally and chemically stable enough for practical storage and use. The photosensitizer or dye should also be sufficiently photostable, chemically stable, and stable in biological environments (e.g., in presence of enzymes) to provide adequate ROS generation for effectiveness at the targeted biological material, and/or to accurately report its presence over a practical desired timeframe. Poor stability can lead to inadequate effectiveness on the targeted biological material, unless the ROS efficiency and/or concentration of photosensitizer is high.

A photosensitizer should also not be so photochemically stable that it is non-photolabile. Since some non-selectivity by carriers and/or photosensitizers is likely, some photosensitizer is likely to be present in non-targeted tissue. When the light source is located at some distance from the targeted tissue, with non-targeted tissue closer to the light source, it is likely that non-targeted tissue can be exposed to many times higher light intensities and overall light doses than the targeted tissue. Therefore, limiting the total ROS that can be generated per photosensitizer molecule at a desired level, regardless of the total activating light dose, is important. High photostability and proper photo-oxidation sensitivity are important. Total ROS dose at the targeted biological material can be varied by changing the photo-oxidation sensitivity of the photosensitizer, the concentration of photosensitizer on the carrier, the selectivity of the carriers, and/or the total dose of the carriers containing the photosensitizer, to achieve the desired activity on the targeted biological material with minimal effect on other tissue exposed to the activating light.

Many near-infrared photosensitizers exhibit high dark toxicities (toxicity even when no activation light is provided). Concentrations of the photosensitizer can build and do damage at locations at which the body removes excess drugs, such as the liver, kidneys, and spleen. Other organs or tissue may also concentrate the dye or the carriers of the dye. Photosensitizers almost always accumulate in organs such as the liver, even when the photosensitizer is used with highly selective carriers that do not target these organs, and therefore very low toxicity without activating light is of high importance.

Clearing rates of dyes and dyes conjugated with other materials and carriers in biological organisms must be within practical ranges. Ideally, even photosensitizers that become disassociated from drug carriers should clear rapidly from the body. Latency of the photosensitizer (whether or not on carriers) in the body should be just long enough to reasonably ensure an acceptable probability of attachment to the biological targets. Even when cleared by the liver or other organs, latency should be minimal in these organs. Additionally, for treatments involving cancer or pathogens in or near organs such as the liver that concentrate photosensitizer even when not targeted, the latency on the targeted material needs to be high enough to permit clearing of the healthy portion of the organ unless accurate activating light distribution control is utilized.

The dye or photosensitizer may be expensive to synthesize, especially if it is difficult to manufacture, purify and bind to a carrier. High purity dyes or photosensitizers are desired to provide known and controlled effectiveness, and high selective affinity to a target biological material, while exhibiting low affinity to and/or effect on non-targeted biological material(s). Some materials may be easier to synthesize or purify than others.

Low sensitivity of a photosensitizer under 600 nm can be important for patient safety and comfort for many photodynamic therapy treatments. Eye damage and skin sensitivity risks due to visible light can be lower during and after treatment if a photosensitizer is highly sensitive to near-IR but has low sensitivity in most of visible range. Low sensitivity of light in the visible spectral range can be an intrinsic quality of the photosensitizer or aided by the addition of one or more quenchers in a photosensitizer conjugate (with or without a carrier).

Even minor non-selective placement in normal tissue near a targeted tumor or infection can induce unacceptable damage to cells between the light source and the targeted biological materials. This consideration is especially important when the light source is closer to the non-targeted tissue than to the targeted biological material, or when the targeted region of the body exhibits highly variable optical densities and/or irregular shapes. For many situations, it is possible to select a photosensitizer and targeting carrier system that will permit minimal damage in non-selected regions while being highly effective at the target material. It is important that the maximum total dose of ROS per photosensitizer molecule be limited. The optimal stability range for photosensitizers is dependent on the parameters of ROS generation efficiency, absorption probability of the photosensitizers, interference and absorption in the tissue or materials being radiated, the concentration of photosensitizers on the targeting carriers, the dosage and affinity of the targeting carriers to the targeted biological materials, and the relative affinity of the carriers to targeted biological materials in relation to non-targeted materials in the region being radiated, among other parameters.

A number of organic dyes and dye conjugates have been proposed as the photodynamic therapy agents. One of the most widespread used classes of compounds is represented by porphins and porphyrins. In general, FDA-approved photodynamic dyes absorb in the red spectral region (630 to ~690 nm), have moderate ROS generation efficiencies, and have low-to-moderate extinction coefficients in the longer wavelength red spectral range on the typical order of 1,100-110,000 $M^{-1}cm^{-1}$. Another disadvantage of many of these dyes such as Chlorin $e_6$ and many of its derivatives such as Talaporfin® sodium (Light Sciences Oncology™) is that they also exhibit intensive absorption in visible range at about 350-450 nm (extinction coefficients up to 300,000 $M^{-1}cm^{-1}$), which makes them sensitive to usually undesirable excitation in this spectral range. High visual range light sensitivity can lead to damage to patient's skin and eyes unless great care is taken during treatment, and after treatment until the drug has cleared the exposed tissue. Sensitivity of these dyes to center-of-the-visible-light-spectrum is about seven-fold higher compared to even visible red light. Natural porphyrin dye Chlorin $e_6$ and Talaporfin® have high SOG activity but are excitable at 630-680 nm, and therefore are not useful for treatment of deep tumors.

Natural dyes are usually a complicated mixture of compounds, which is difficult to separate and isolate in the individual form for further synthetic modification and binding to a carrier. A general problem with any natural sensitizers resides in the fact that they are difficult to standardize.

Artificial porphins and porphyrins are also very difficult to synthesize and purify and therefore they are expensive and hardly available.

Cyanine dyes can be synthesized in forms that are amenable to further modification. These dyes ensure absorption in a wide spectral range with high extinction coefficients (typically 100,000-250,000 $M^{-1}cm^{-1}$). Heptamethine cyanines such as Indocyanine Green (ICG) absorb light at ~780 nm with high extinction coefficients (~200,000 $M^{-1}cm^{-1}$). Longer-wavelength absorption makes heptamethine cyanines useful for treatment of large or deep tumors where photoactivation through several centimeters of tissue is required. The singlet oxygen generation (SOG) effectiveness of cyanine dyes is poor when compared to porphins and porphyrins, but they have more pronounced ROS generation effectiveness, making them useful for treatment of cells at tumor hypoxia. The overall ROS generation efficiency of ICG is very low when compared to the chlorins, bacteriochlorins, bacteriopurinimides, naphthalocyanines, texapyrins, and phthalocyanines. For example, over 100× higher ICG concentrations are required to obtain the same photocytotoxic effectiveness in vitro as that of Chlorine e6. ICG cyanine dye does exhibit desirable characteristics, the most notable of which are that it is FDA-approved for intra-human use, exhibits very low dark toxicity, has a high extinction coefficient (high light absorption) in the ~800 nm near infrared spectral range, and possesses modifiable hydrophilicity characteristics, thereby facilitating ease of processing, and ease of synthesis as reactive versions that can be bound to carriers such as monoclonal antibodies. While low ROS generation efficiency has been overcome by concentrating many cyanine molecules onto nanoparticle carriers, there is a desire to achieve higher overall ROS generation using significantly fewer molecules to permit high biological activity on a broader range of selective carriers. Reducing the number of photosensitizer molecules per carrier can correlate with improved selective carrier affinity and target selectivity.

Because of the ionic structure of their chromophore system, cationic cyanine dyes are difficult to penetrate through cell walls and tissues, which is a serious limitation of these dyes.

Cyanines such as ICG also exhibit low photostability and as a result they photobleach quickly under light exposure before generating enough ROS to be effective against cancers and pathogens unless they are highly concentrated at or in the targeted cancer cells or pathogens. Photobleaching is considered a negative issue for ICG primarily due to its poor ROS generation efficiency. If the ROS generation efficiency of ICG were over 20 times higher, photo-oxidation related photobleaching could be a positive attribute in several important therapeutic applications, especially if concentrated at the targeted cells. ROS dose generated by the photosensitizer can be self-limiting if controlled by photo-oxidation, photostability, photosensitizer concentration, and oxygen concentration. Self-limiting of ROS dose would better enable non-invasive treatments and the ROS generation type and efficiency. Higher light exposure doses can then be used to generate an amount of ROS proportional to the localized photosensitizer concentration and not light dose because photobleaching of the photosensitizer limits the total ROS generation. The photosensitizer in the treated tissues would deactivate more slowly in low oxygen tissue such as hypoxic tumors, and can be deactivated after exposure. These are both positive benefits that can better enable killing of tumors with minimal damage to healthy tissue even though high intensity light may pass through non-targeted tissue containing trace amounts of photosensitizer. An overly high stability and efficient photosensitizer could generate excessive amounts of ROS per photosensitizer molecule near the light source even if that tissue were not targeted for destruction. The use of targeted carriers for photosensitizers such as monoclonal antibodies still exhibits some non-selectivity, especially when sequences of antibodies are used to effect high killing ratios of targeted cancers and other pathogens.

It is desirable to develop new photosensitizers that enable the above matrix of synergistic benefits, and that overcome reporter deficiencies of existing agents.

For example, in addition to its low ROS generation efficiency, ICG is a low quantum yield reporter (~0.5-1.3% in water), making it even a marginal reporter unless the concentration is made high by correspondingly high loading on carriers and high incident activation light intensity is employed.

Accordingly, sensitizers and reporters with many characteristics similar to ICG, but with much higher ROS generation, higher reporter quantum yield and improved photostability are highly desirable. Attempts have been made to overcome ICG's ROS efficiency limitations by loading many ICG molecules into nanoparticles, with some success. Available nanoparticles to date, however, exhibit limited selectivity. Loading limitations on carriers such as monoclonal antibodies while still retaining the antibody make ICG a marginal photosensitizer and/or a marginal reporter, at best. A much higher efficiency ROS generator and/or higher efficiency reporter is desired.

Oxosquaraines (SqO), which are a subclass of cyanines, contain a cyclic squaraine moiety in the polymethine chain, providing better photostability. Compared to cyanines, the oxosquaraine chromophore has a zwitter-ionic structure, which facilitates penetration of these dyes in cells and tissues. However, the sensitizing effectiveness of these dyes is low.

Thus, although photosensitizer dyes have been developed for photodynamic therapy applications, and dyes have been attached to various selective carriers, e.g., monoclonal antibodies, polymers, and peptides, to improve selective affinity to targeted biological materials for cancer and pathogen treatments, the existing reporters and sensitizers used in photodynamic therapy and related applications are characterizable by associated deficiencies that have limited their use and effectiveness.

In consequence, the art continues to seek improvements in dyes for use as reporters and sensitizers in photodynamic therapy and related applications.

SUMMARY

The present disclosure relates to: iodinated, brominated, and other halogenated nitrogen containing heterocyclic compounds; organic dyes, in particular polymethine dyes including cyanines and squaraines based on these heterocyclic compounds; dendrimeric compounds comprising these halogenated polymethine dyes; conjugates of these polymethine and dendrimeric dyes with other organic and inorganic compounds, nanoparticles, biological molecules, and/or biological compounds that ensure improved brightness and photostability and/or sensitivity and selective affinity to target cancer cells, pathogenic microorganisms, and/or other biological materials; reporting and sensitizing compositions based on these polymethine compounds, dendrimers and conjugates of these compounds, and methods to make and use these compounds and compositions.

In one aspect, the disclosure relates to classes of fluorinated, chlorinated, brominated, and/or iodinated compounds, wherein at least two halogen atoms are directly bound to a nitrogen-containing heterocyclic terminal moiety of the compound, and wherein at least one of such halogen atoms is iodine or bromine.

In another aspect, the disclosure relates to heterocyclic compound of the formula

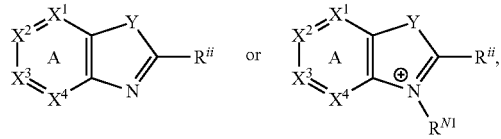

wherein:
ring A is an aromatic or heterocyclic ring wherein each of $X^1$, $X^2$, $X^3$, and $X^4$ is independently selected from the group consisting of N, $^+NR^{N3}$, and C—$R^X$, with the proviso that ring A has at least two halo substituents thereon, and at least one of said halo substituents is iodine or bromine;

$R^X$ is H, F, Cl, Br, I, L-$S_c$, L-$R^R$, L-$R^\pm$; aliphatic, alicyclic, or aromatic group; amino or substituted amino; sulfo, trifluoromethyl, hydroxy, alkoxy, carboxy, phosphate, phosphonate, or sulfate; or adjacent $R^X$ substituents, taken in combination, form a fused aromatic or heterocyclic ring that is itself optionally further substituted by H, F, Cl, Br, I, L-$S_c$, L-$R^R$, L-$R^\pm$; aliphatic, alicyclic, or aromatic group; amino or substituted amino; sulfo, trifluoromethyl, hydroxy, alkoxy, carboxy, phosphate, phosphonate, or sulfate;

$R^N$ is selected from H, L-$S_c$, L-$R^R$, L-$R^\pm$, aliphatic groups, alicyclic groups, alkylaryl groups, and aromatic groups, wherein each aliphatic residue may incorporate up to ten heteroatoms selected from N, O, and S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

Y is O, S, Se, Te, $C(R^{C1})(R^{C2})$, or N—$R^{N2}$;

each $R^{C1}$ and $R^{C2}$ is independently $R^C$, or adjacent substituents ($R^{C1}$, $R^{C2}$) form a cyclic or heterocyclic system that further may be substituted or fused;

$R^C$ is H, L-$S_c$, L-$R^R$, L-$R^\pm$, aliphatic, alicyclic, aromatic, heteroatom-substituted aliphatic, polyether, alkyl-aryl, aryl-alkyl, F, Cl, Br, I, $NH_2$, —COOH, —CN, azido, —OH, —$NO_2$, —$SO_3H$, —$SO_2NHR'''$, —$SO_2NHN(R''')_2$, —$SO_2R^C$, —$C_6H_4$—$SO_3H$, —$C_6H_4$—$PO_3H$, —$CH_2$—$C_6H_4$—$SO_3H$, —$CH_2$—$C_6H_4$—$PO_3H$, pyridylium, pyrylium, —$PO(OH)_2$, —O—$PO(OH)_2$, —$PO(OH)(OR''')$, —O—$P(OH)(OR''')$, —$PO(OR''')_2$, —$(CH_2CH_2O)_nPO(OR''')_2$, —$(OCH_2CH_2)_nPO(OR''')_2$, wherein n=1-30, —$CONH_2$, —$CON(R''')_2$, —$CONHN(R''')_2$, —COO—NHS or —COO—$R'''$, wherein $R'''$ is selected from a group consisting of H, L-$S_c$, L-$R^R$, L-$R^\pm$, aliphatic substituents, and aromatic substituents, and each aliphatic residue may incorporate up to ten heteroatoms selected from N, O, S, and can be substituted by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

L is a single covalent bond or is a covalent linkage that is linear or branched, cyclic or heterocyclic, saturated or unsaturated, having 1-20 non-hydrogen atoms selected from the group consisting of C, N, P, O and S, arranged so that the linkage contains any combination of ether, thioether, amine, ester, amide bonds; single, double, triple or aromatic carbon-carbon bonds; or carbon-sulfur bonds, carbon-nitrogen bonds, phosphorus-sulfur, nitrogen-nitrogen, nitrogen-oxygen or nitrogen-platinum bonds, or aromatic or heteroaromatic bonds;

$R^R$ is a reactive group;
$S_c$ is a conjugated substance;
$R^\pm$ is an ionic or hydrophilic group;
$R^{N1}$, $R^{N2}$ and $R^{N3}$ may be independently selected from the substituents $R^N$;
$R^{ii}$ is $CH_2R^1$, $SR^S$, $SO_3H$;
$R^1$ is selected from H, F, Cl, Br, I, L-$S_c$, L-$R^R$, L-$R^\pm$, aliphatic group, alicyclic group, heteroatom-substituted aliphatic group, aromatic group, polyether, cyano, carboxy, carboxamide, carboxylic ester, formyl, amine group, nitro, sulfonic acid, phosphonic acid, phosphonic ester, sulfone, and sulfamide, or ($R^1$ and $R^{C1}$) or ($R^1$ and $R^{C2}$) may form a cyclic or heterocyclic system, which further may be substituted or fused; and
$R^S$ is H or alkyl.

In a further aspect, the disclosure relates to a heterocyclic compound selected from the group consisting of compounds of the formulae:
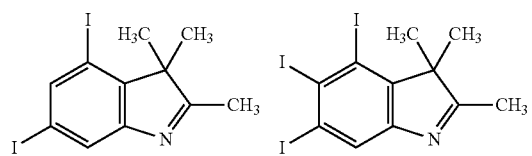
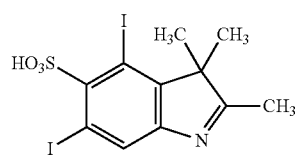
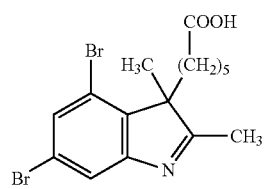
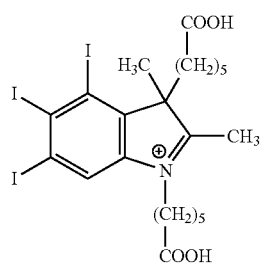
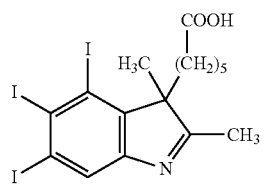
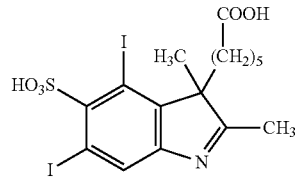
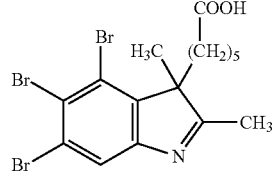
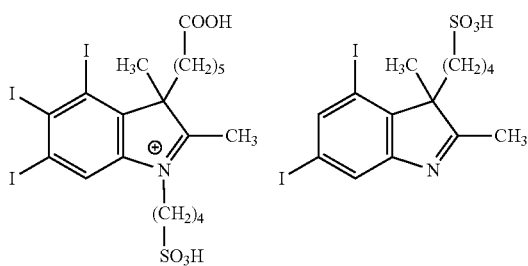
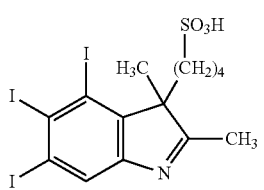
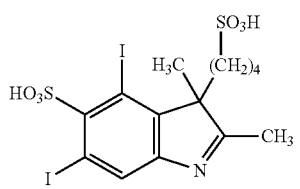
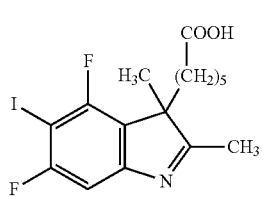
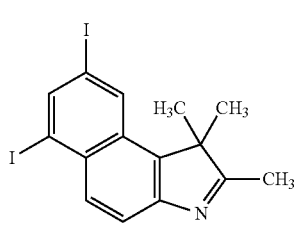
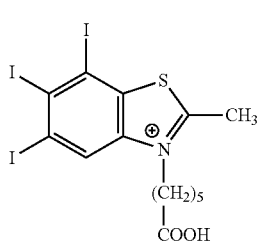
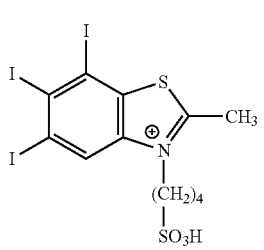

-continued

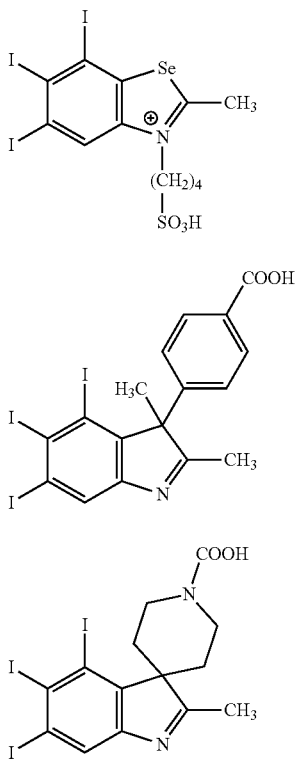

Another aspect of the disclosure relates to a method of synthesizing a polymethine dye, comprising:

providing a heterocyclic compound as described above; and reacting the heterocyclic compound in a polymethine dye synthesis process, wherein the heterocyclic compound is a precursor, starting material, or intermediate in the polymethine dye synthesis process.

A further aspect of the disclosure relates to a compound useful as a reporter or sensitizer, comprising a reaction product of a heterocyclic compound as described above, from a reaction wherein the heterocyclic compound is a precursor, starting material, or intermediate.

A further aspect of the disclosure relates to a dye comprising at least one of moieties Het and Het$^+$, wherein Het and Het$^+$ have the formulae:

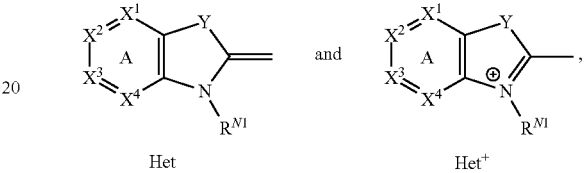

wherein $X^1$, $X^2$, $X^3$, $X^4$, Y, and $R^{N1}$ are as defined above, and ring A is an aromatic or heterocyclic ring having at least two halo substituents thereon, wherein at least one of the halo substituents is iodine or bromine.

A still further aspect of the disclosure relates to a dendrimeric compound comprising the dye described above.

In another aspect, the disclosure relates to a dendrimeric compound selected from the group consisting of compounds of the following formulae 1-20:

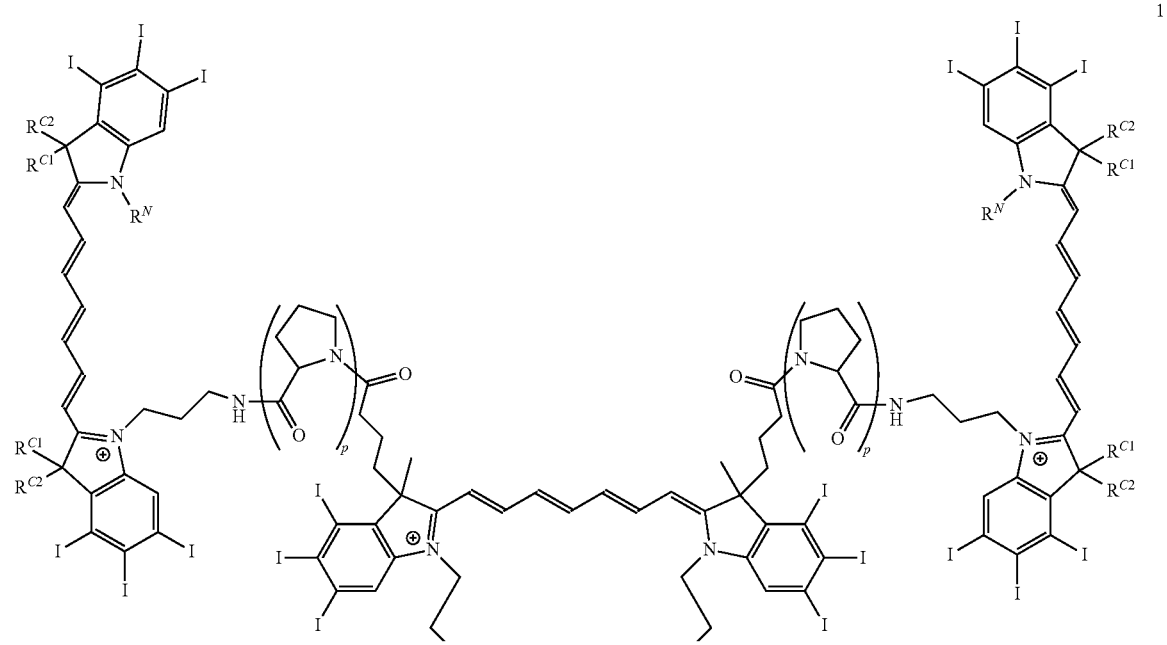

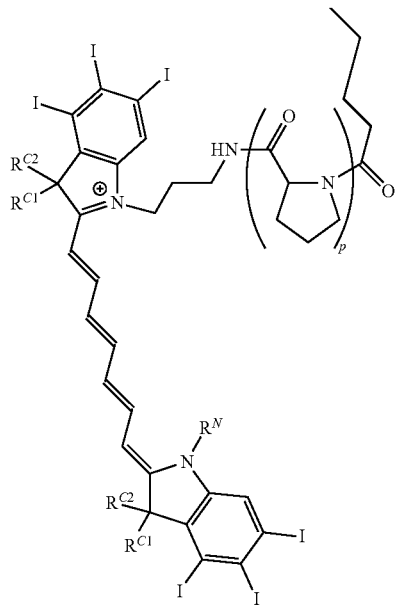
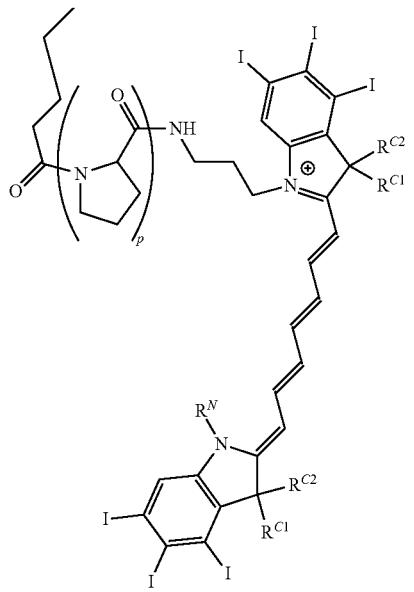
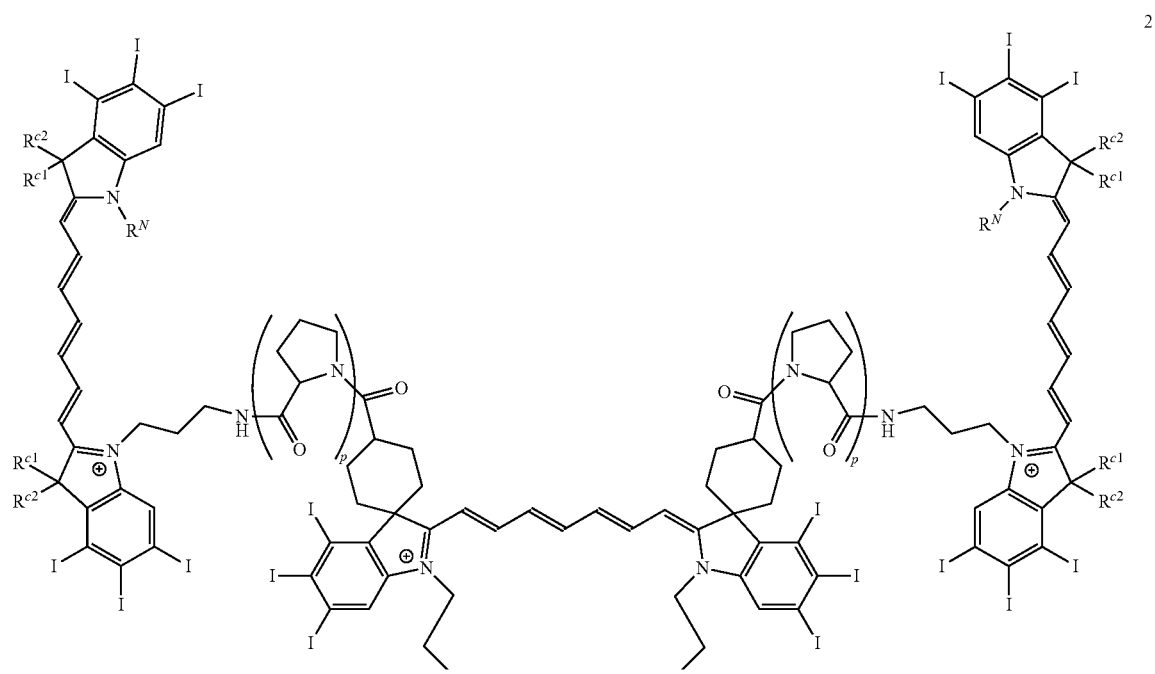

-continued
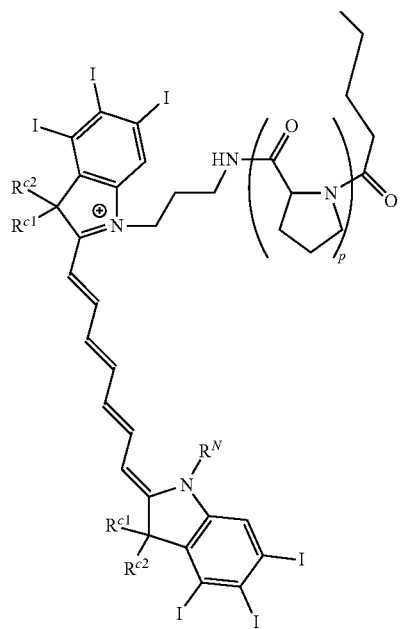
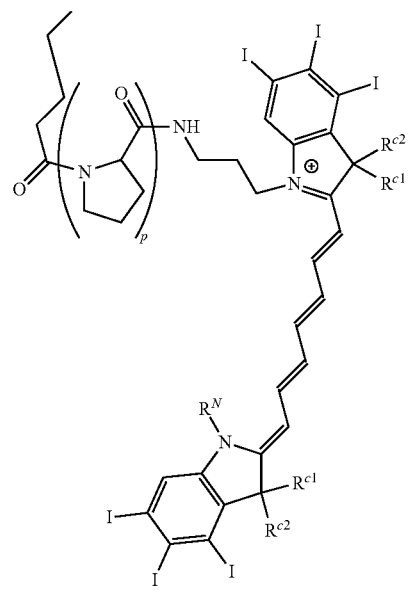
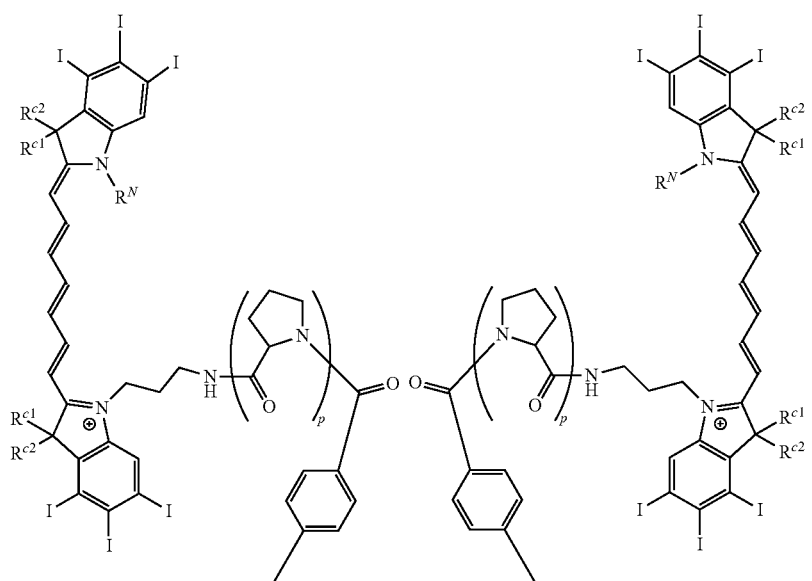

-continued
17
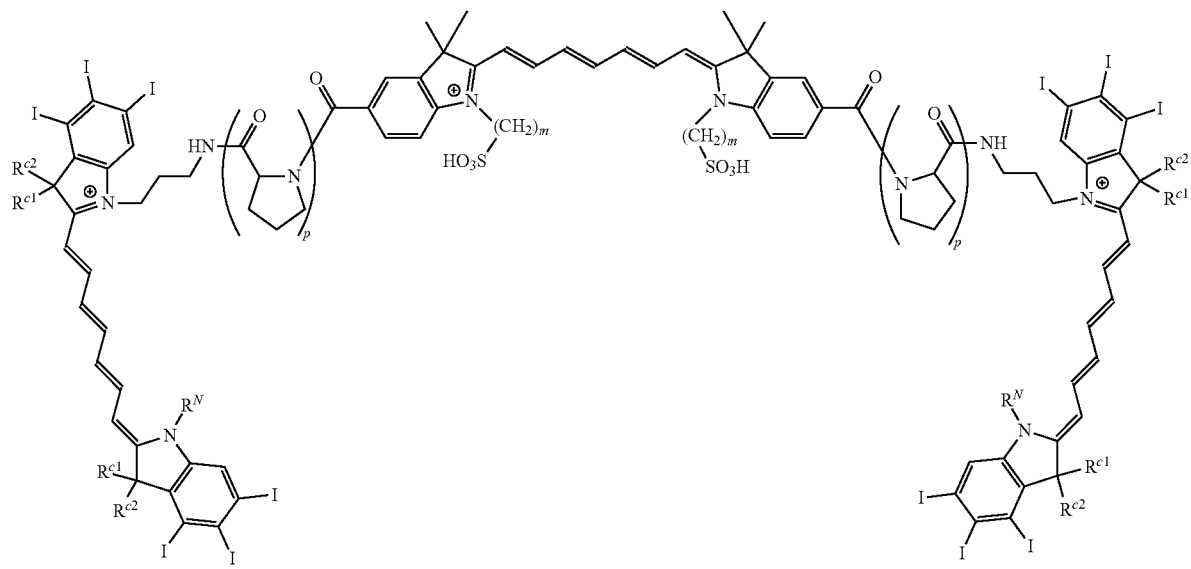
18
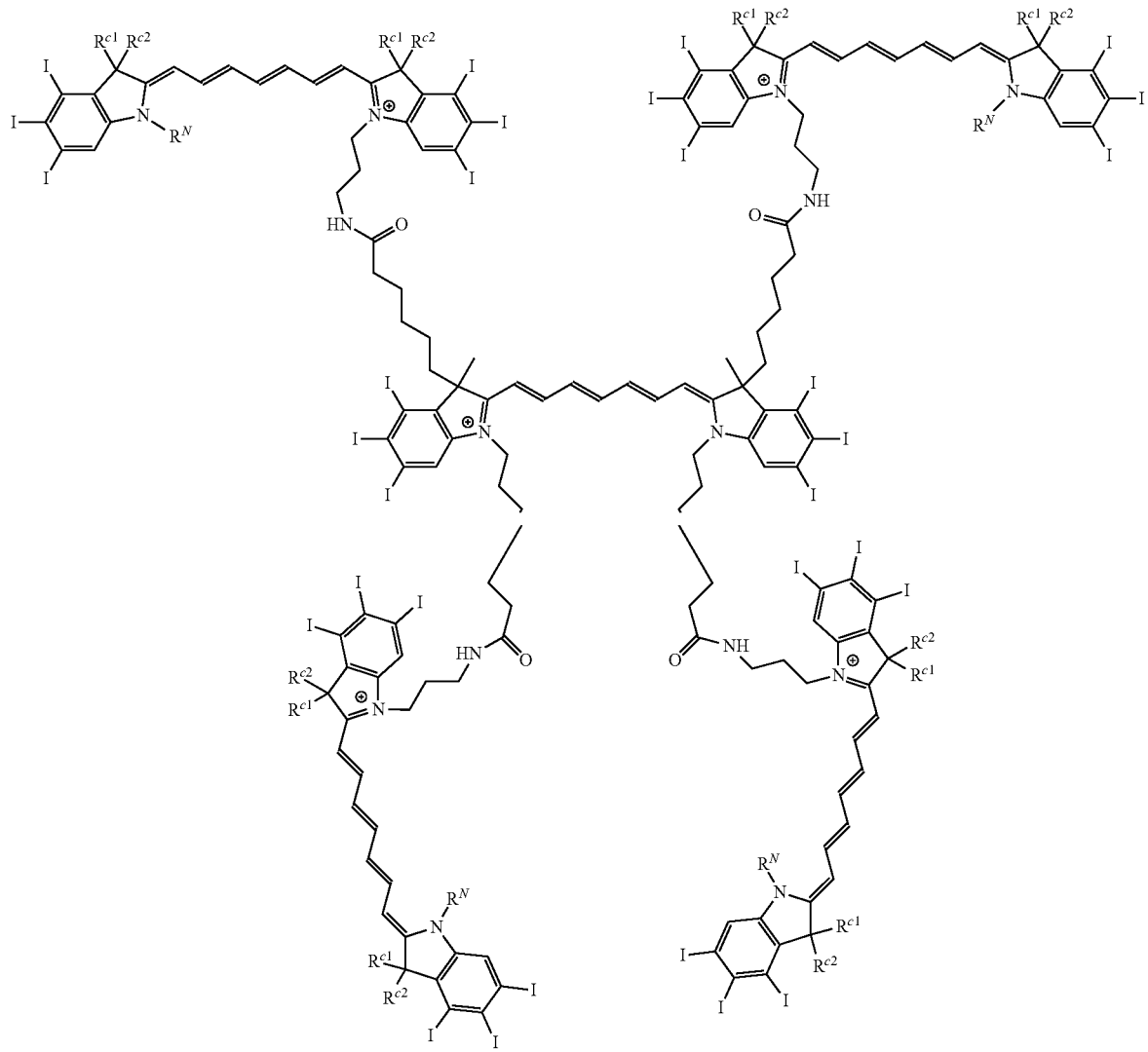

-continued
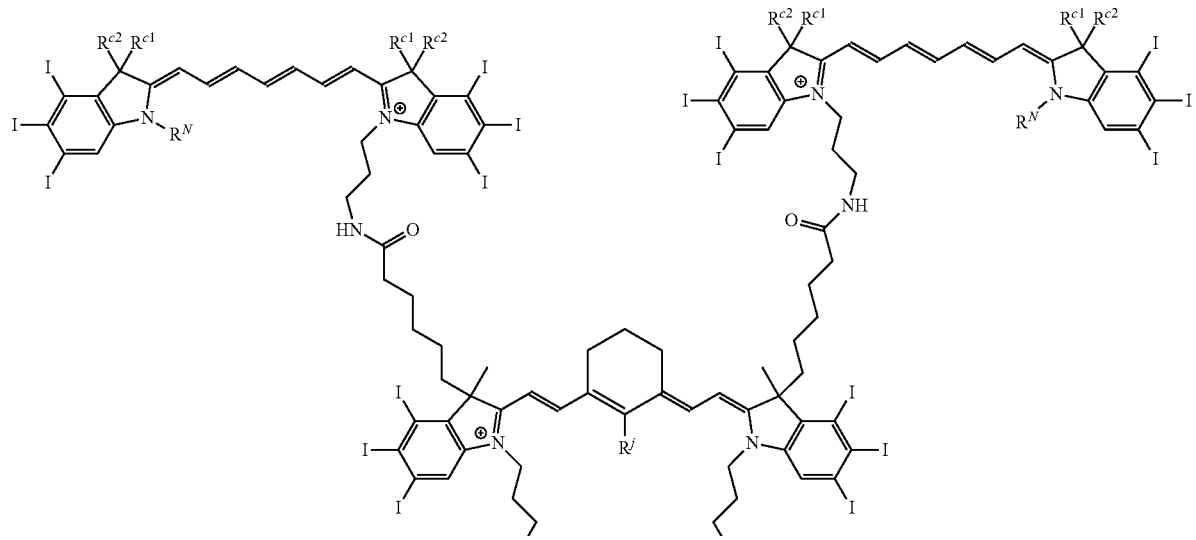
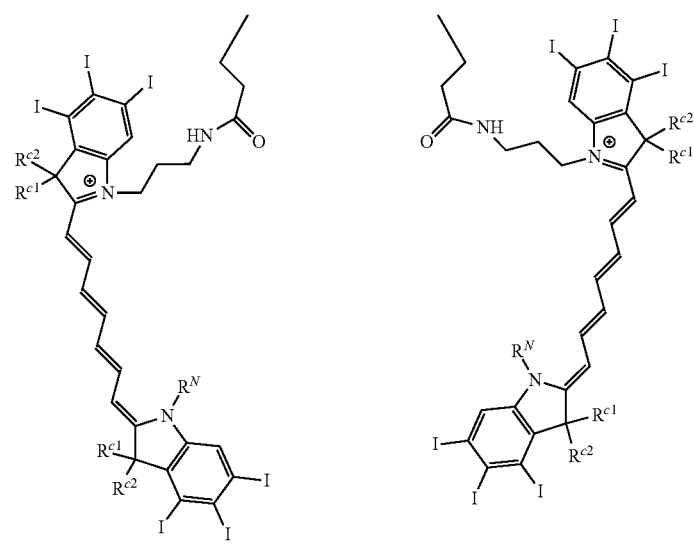
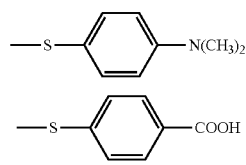

-continued
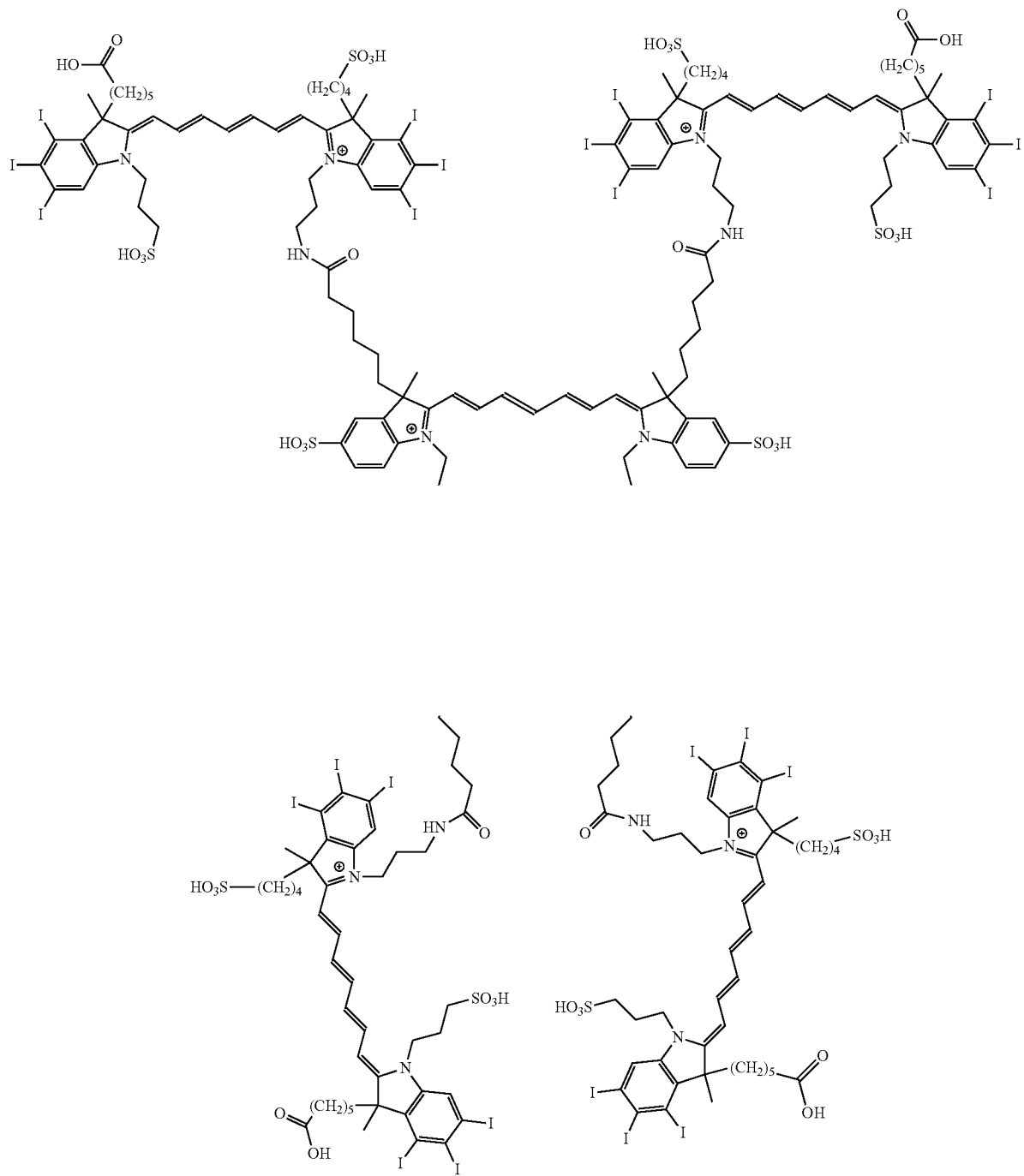

-continued
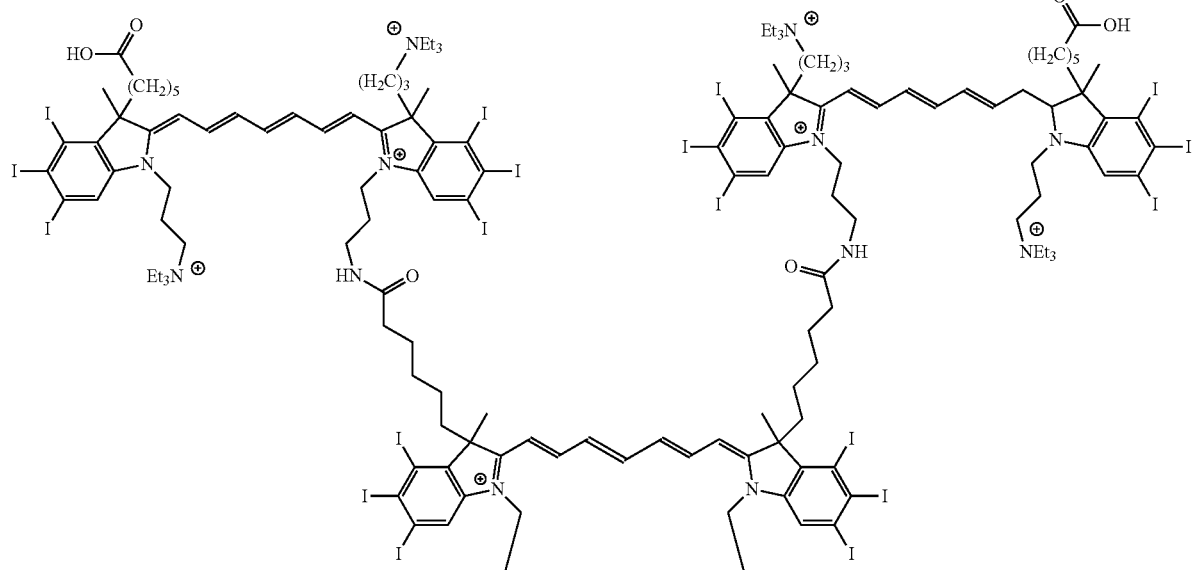
7
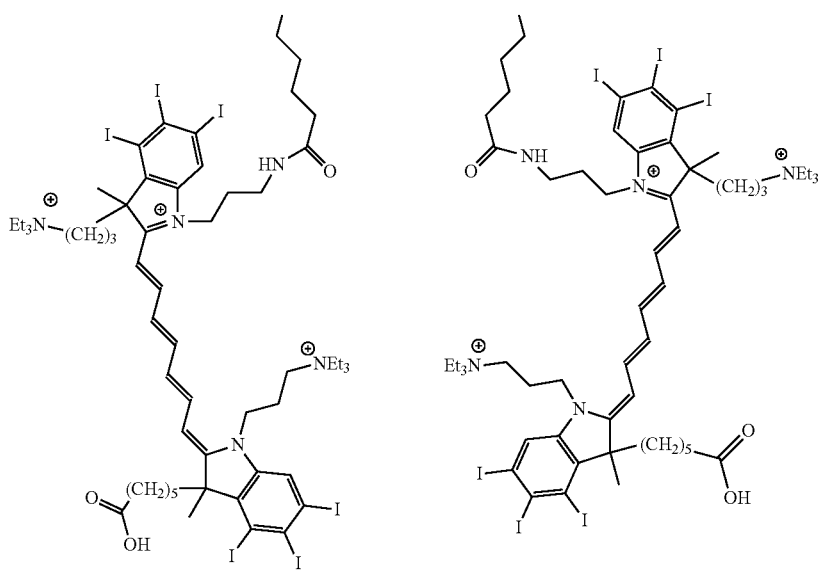

8
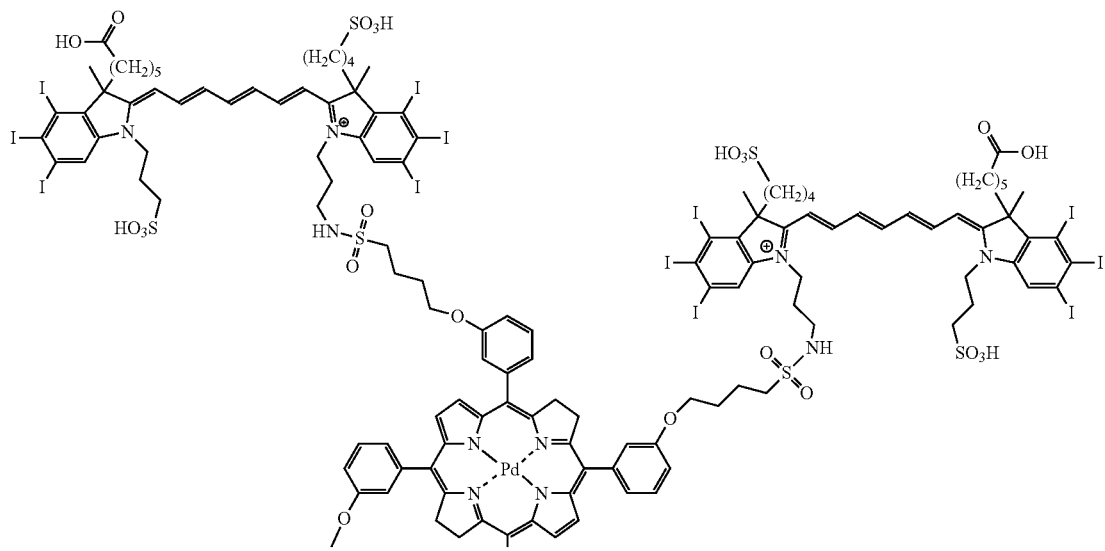
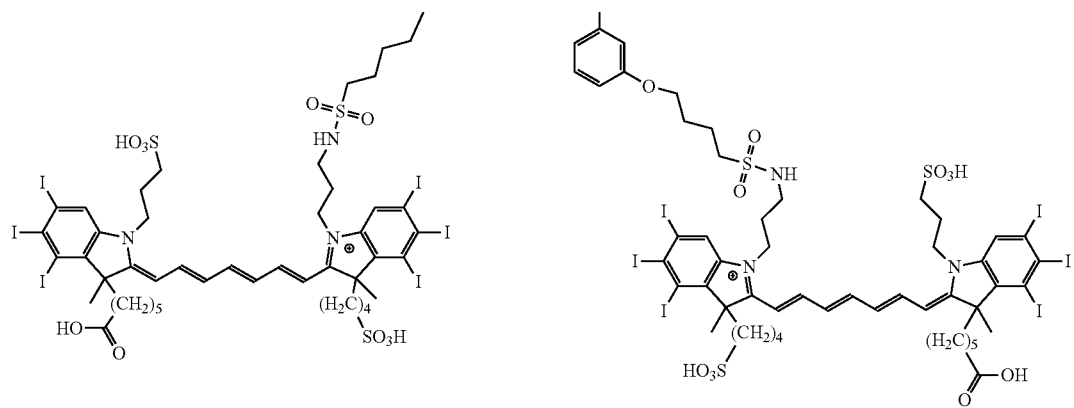
9
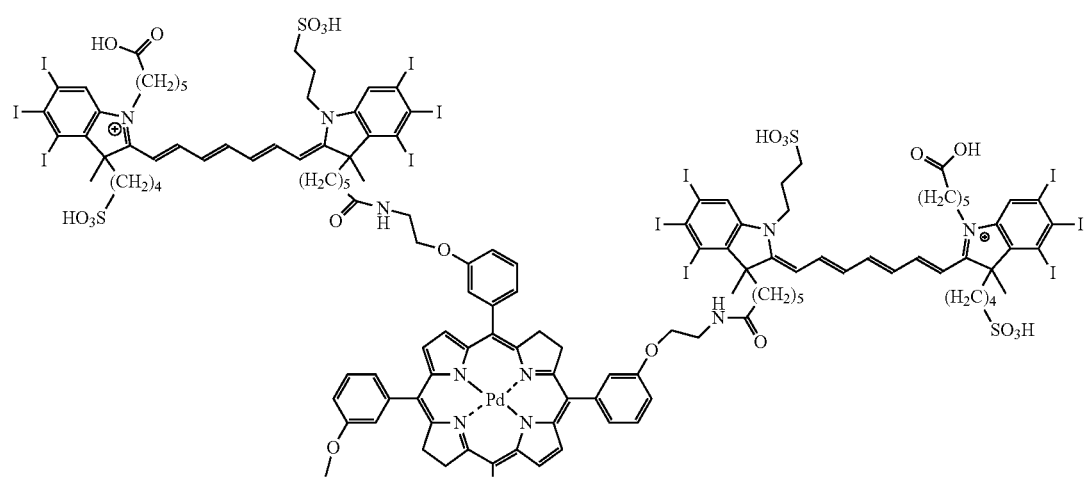

-continued
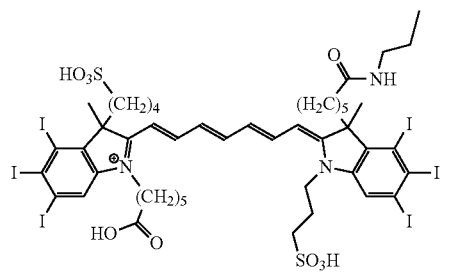
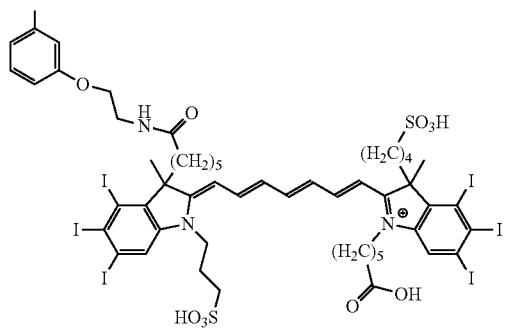
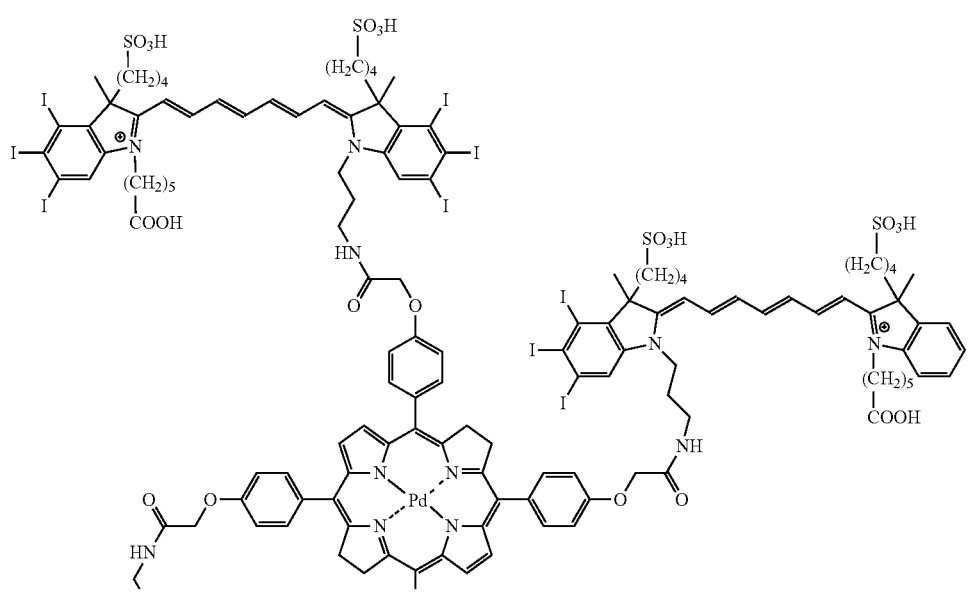
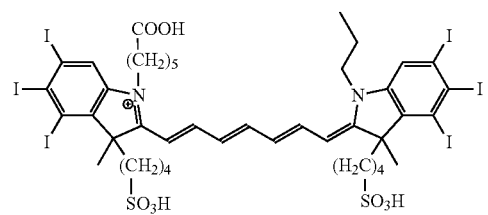
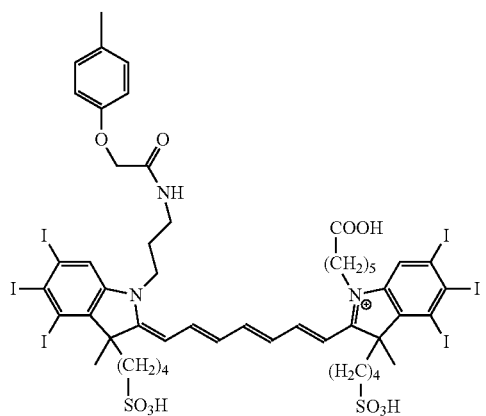

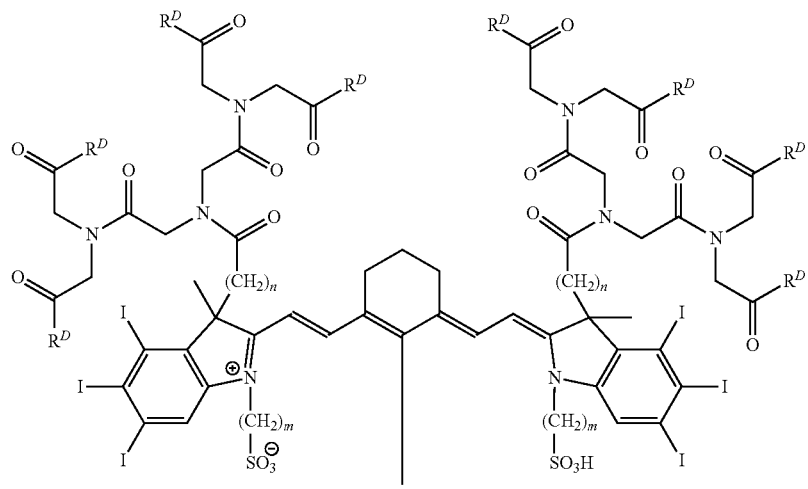
11
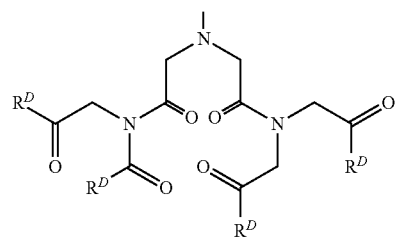
where $R^D$ contains a dye;
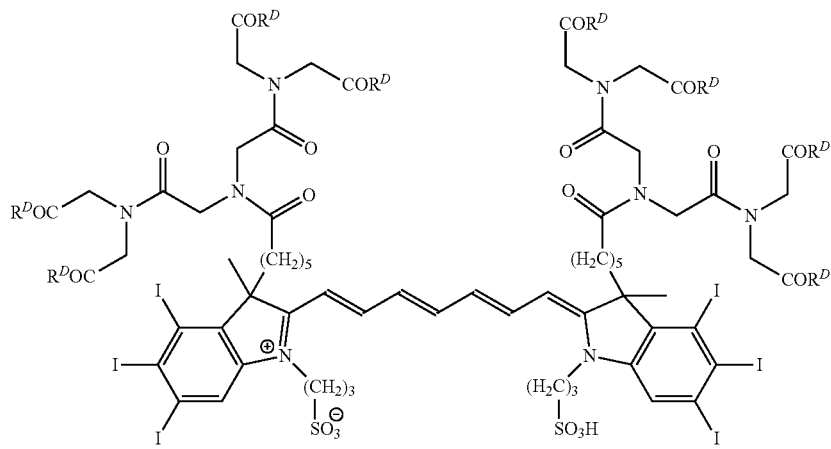
12
where $R^D$ contains a dye;

-continued
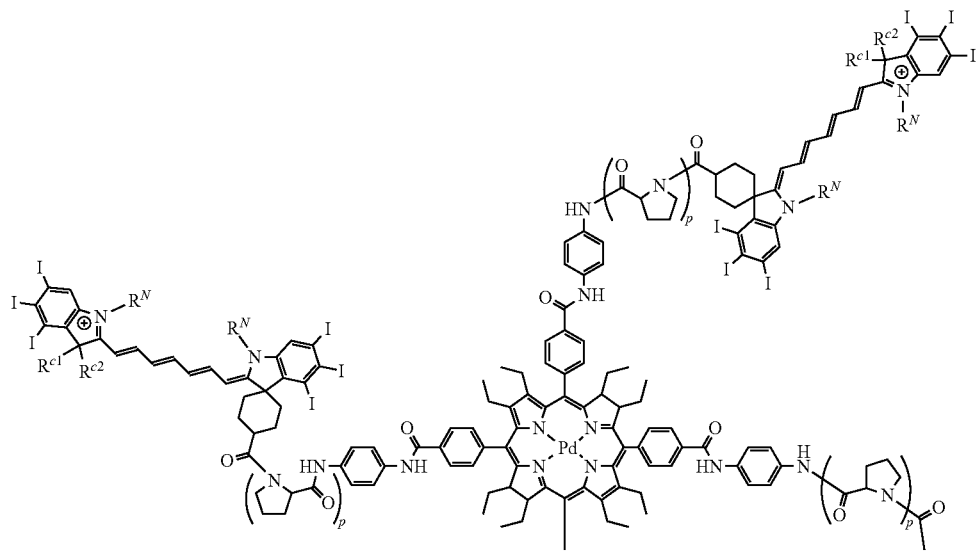
13
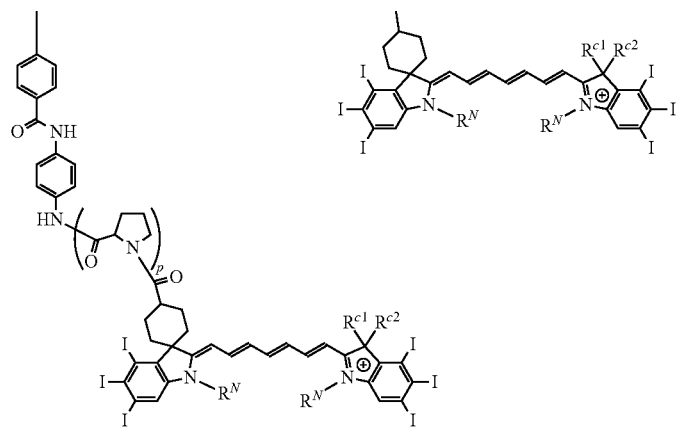
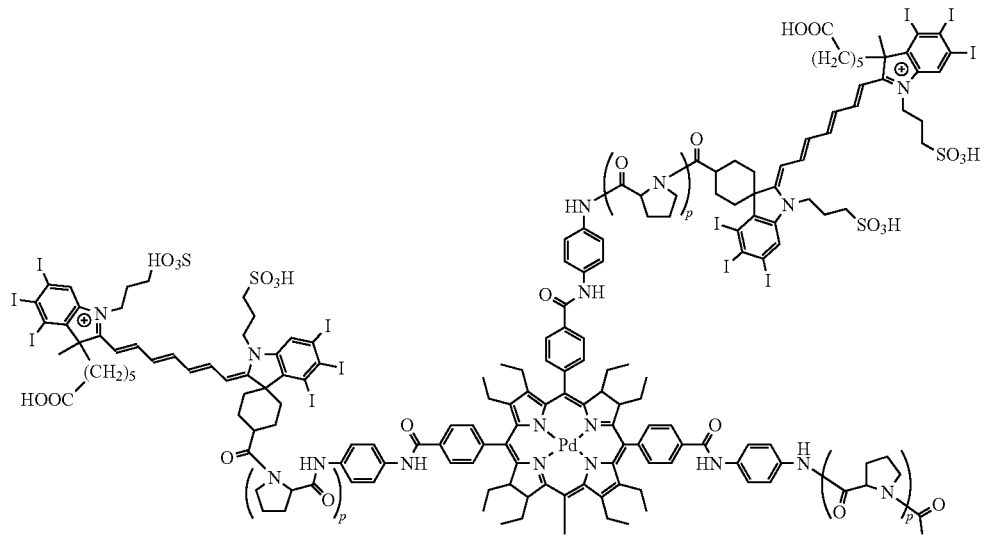
14

33
-continued
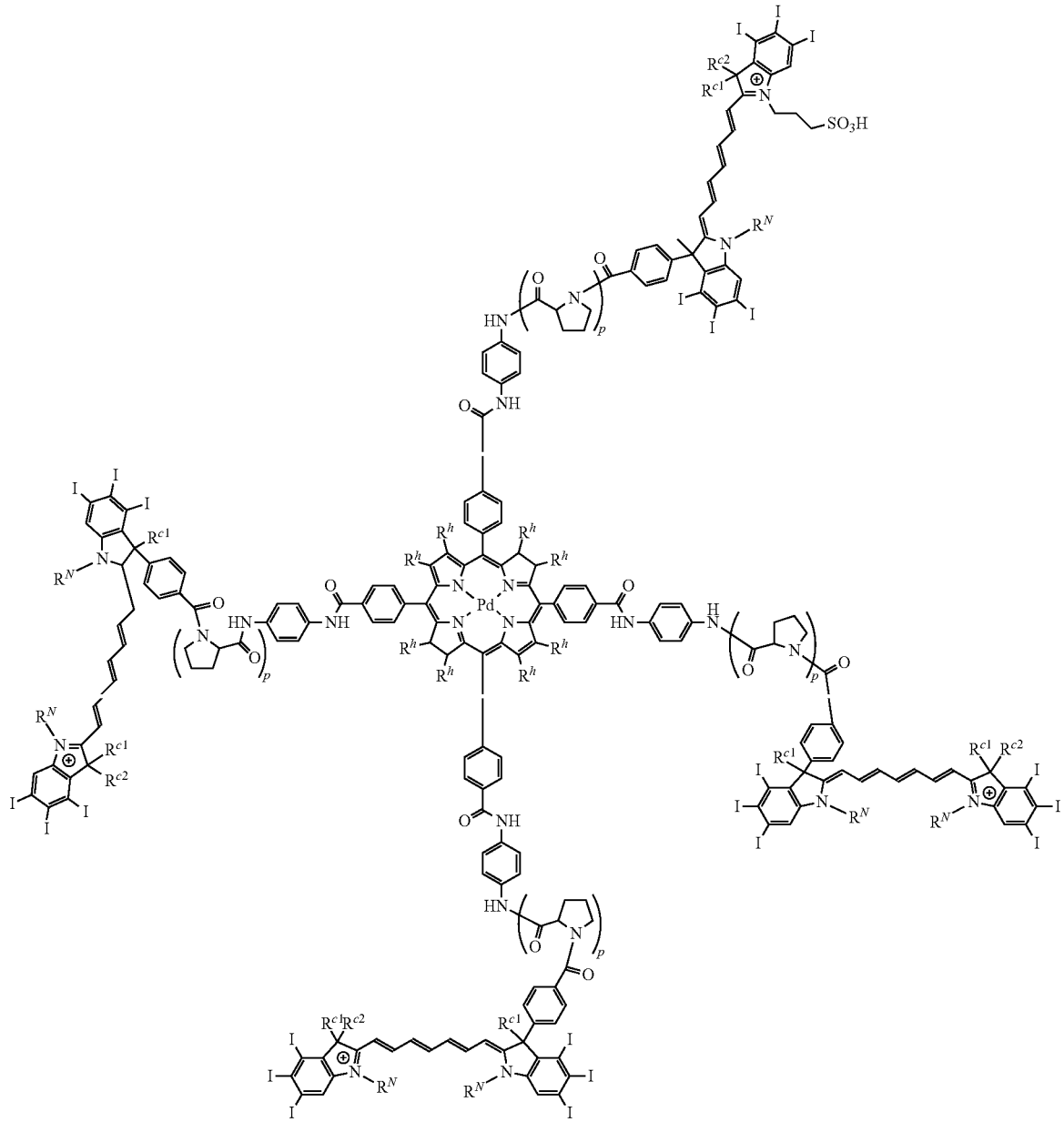
34
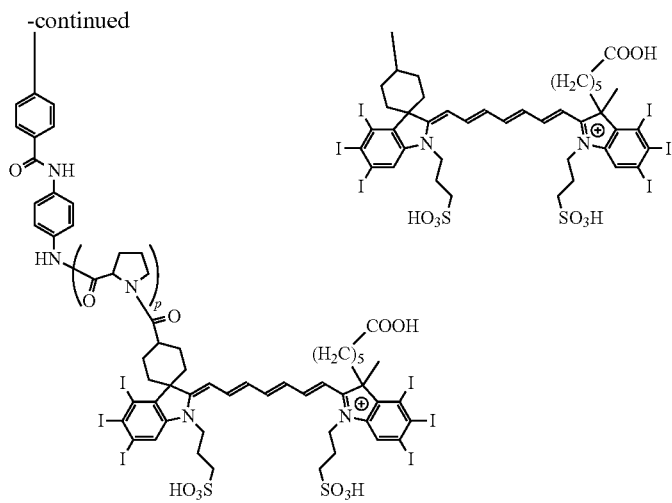

-continued
16
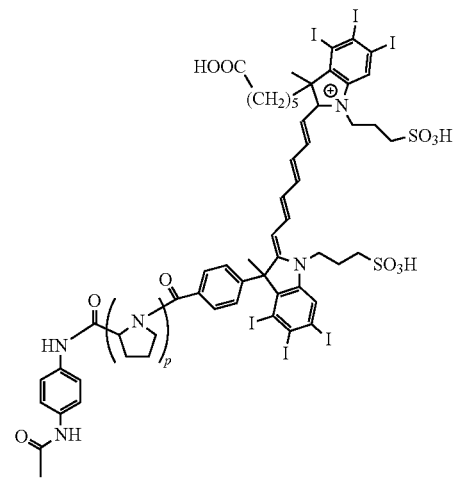
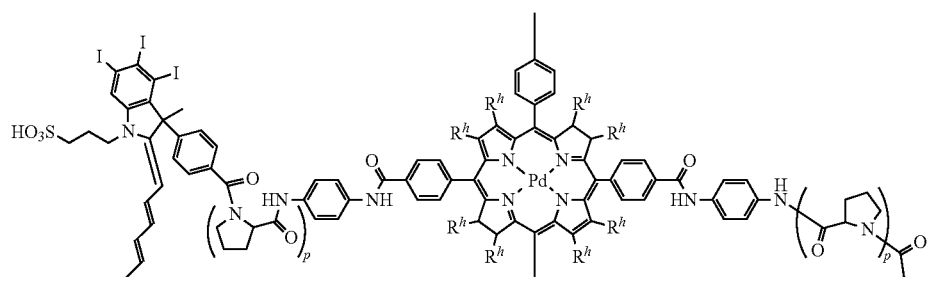
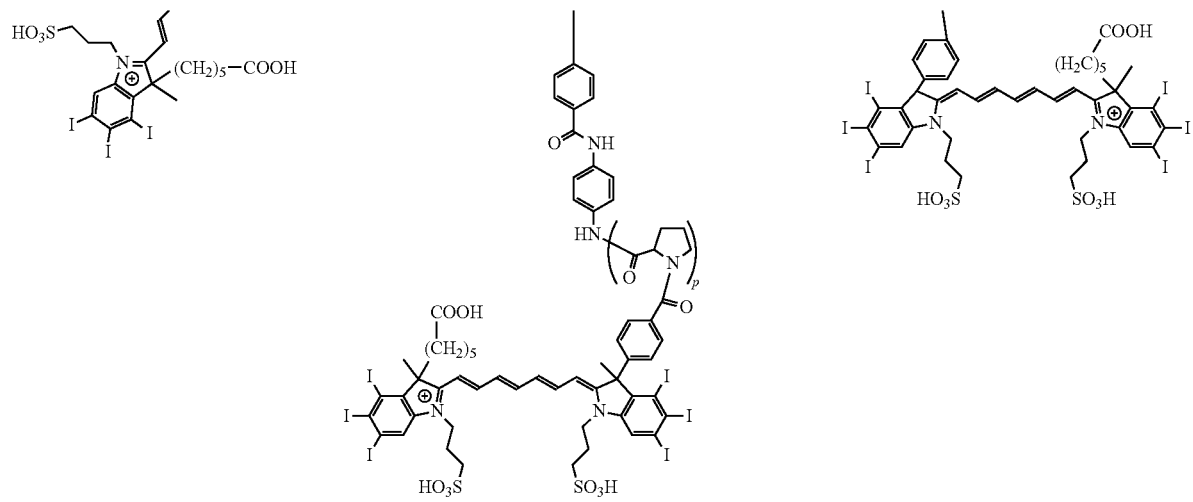

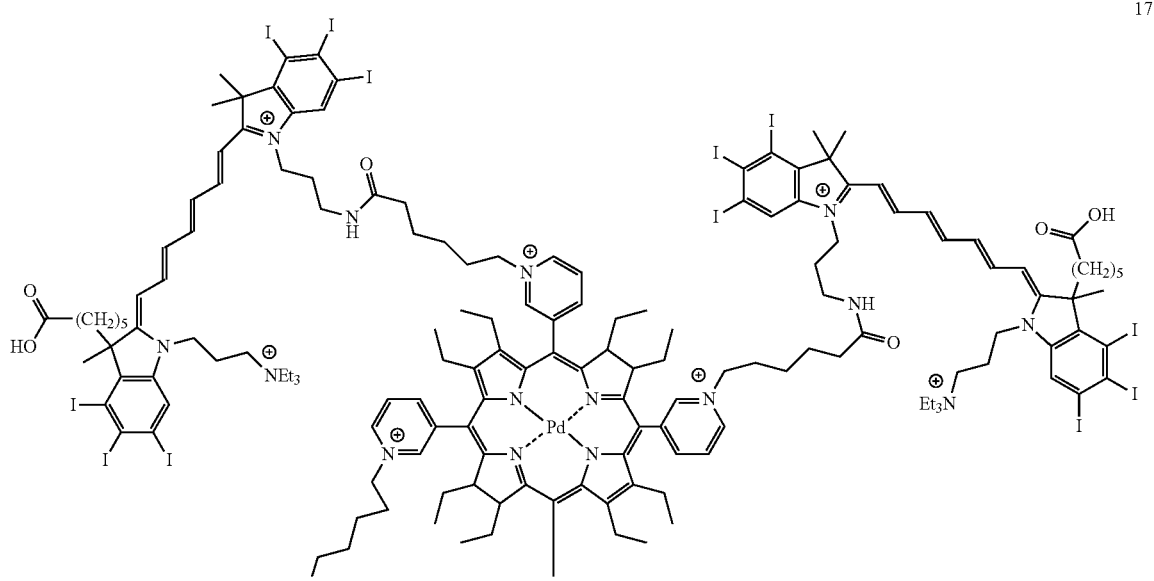
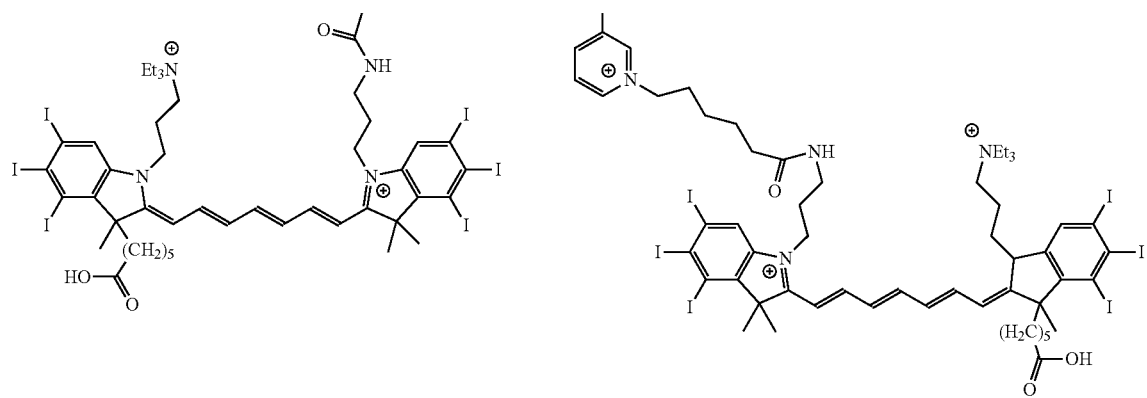
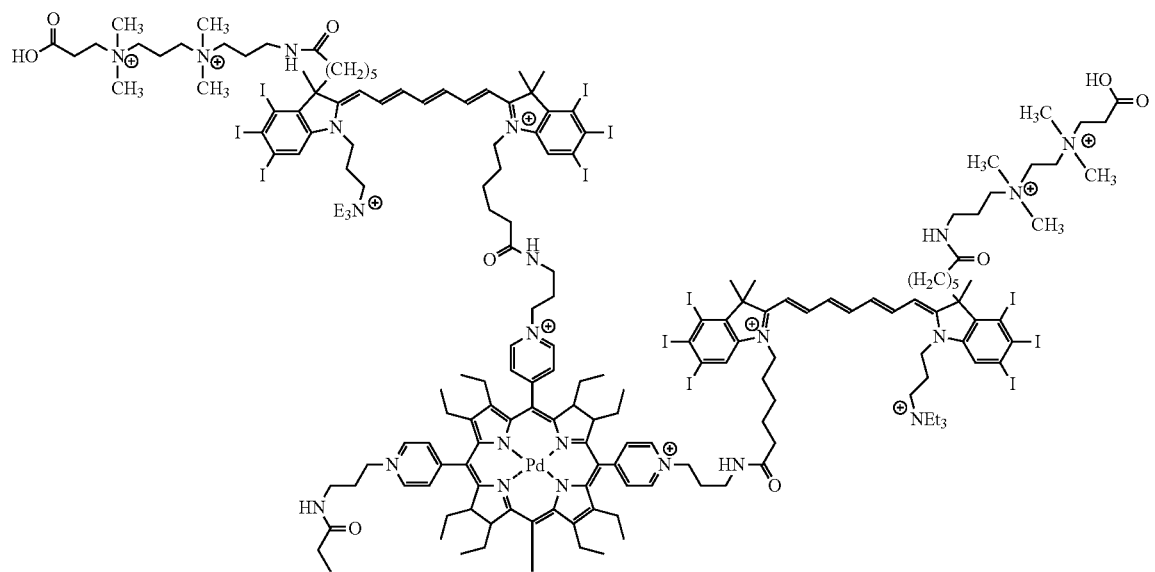

-continued
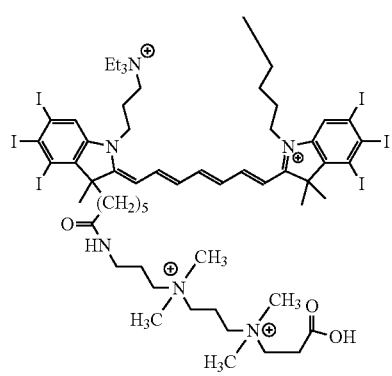
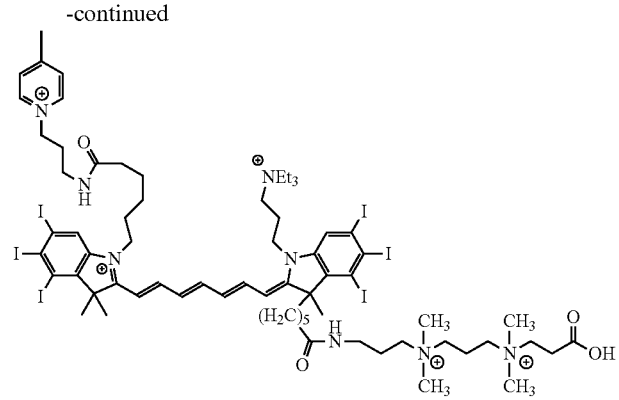
19
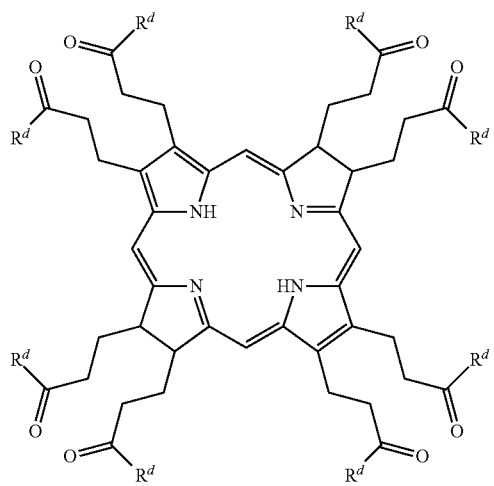
where: $R^d$ is:
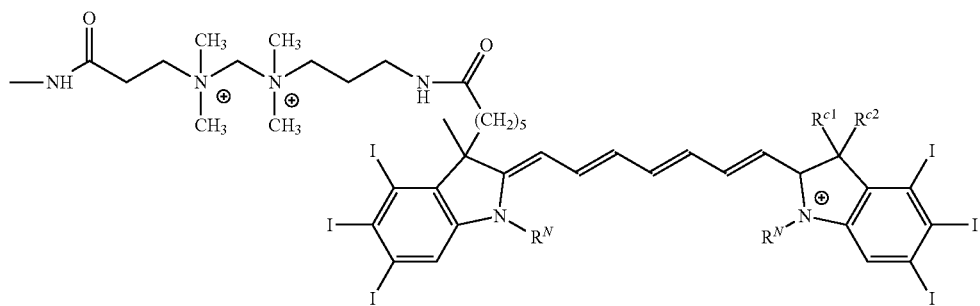
20
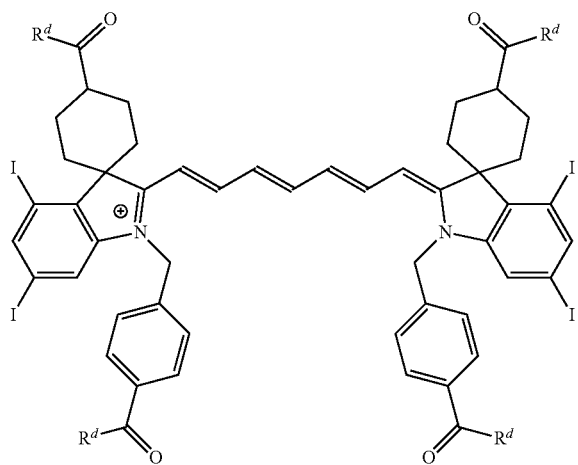

where $R^d$ is:

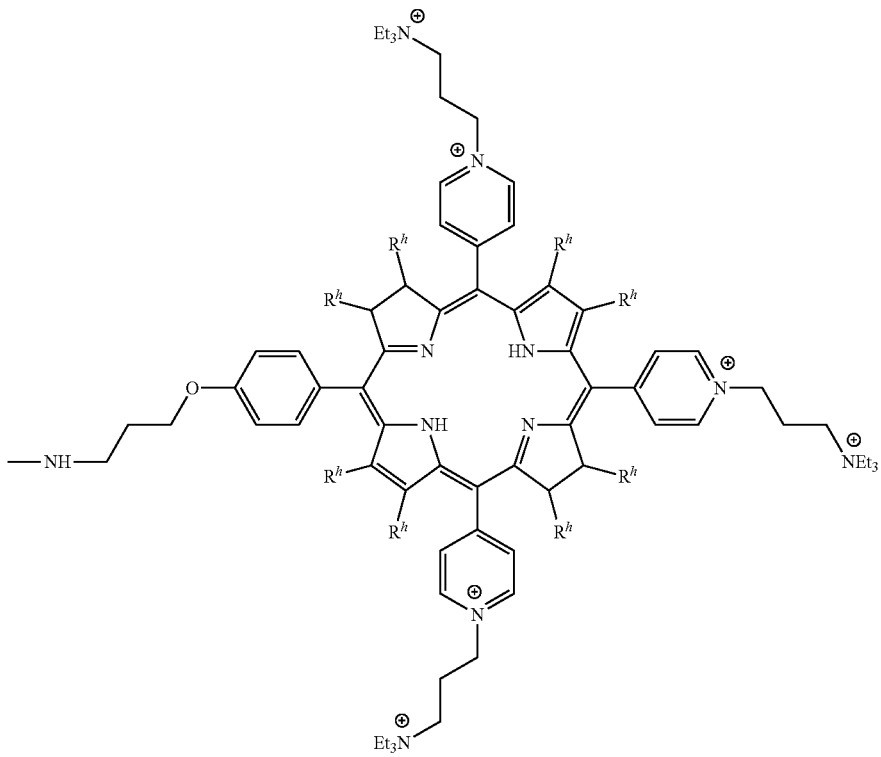

where:

each $R^{c1}$ and $R^{c2}$ is independently selected from alkyl, $—(CH_2)_n—COOH$, $—(CH_2)_n—SO_3H$,

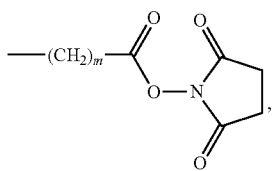

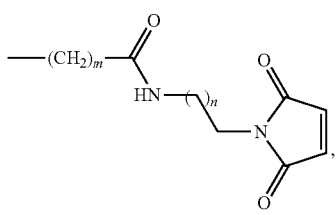

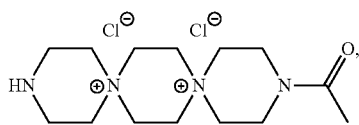

$—(CH_2)_n—PO(OEt)_2$, $—(CH_2)_n—PO(OH)(OEt)$, or $—(CH_2)_n—PO(OH)_2$, or contains a dye;

each $R^N$ is independently selected from alkyl, $—(CH_2)_k—COOH$, $—(CH_2)_k—SO_3H$,

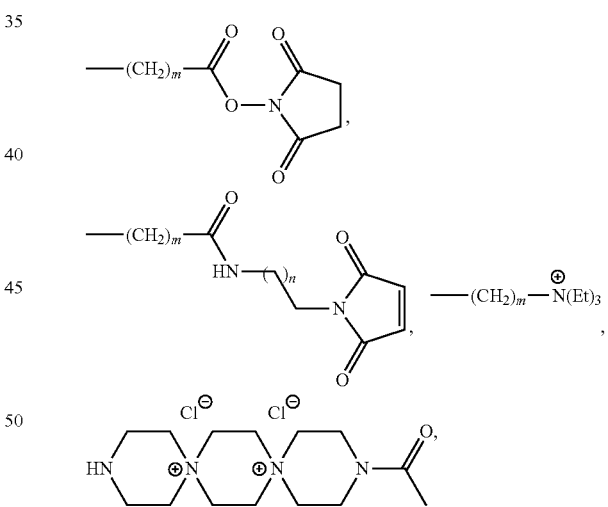

$—(CH_2)_k—PO(OEt)_2$, $—(CH_2)_k—PO(OH)(OEt)$, or $—(CH_2)_k—PO(OH)_2$, or contains a dye;

each $R^h$ is independently selected from hydrogen, alkyl, aryl, or adjacent substituents $R^h$ form a cycle; and k=1-20; m=1-20; n=1-20; p=1-20.

In a further aspect, the disclosure relates to a composition comprising a dye of the disclosure, or a conjugate thereof.

The disclosure relates in another aspect to a method of generating reactive oxygen species (ROS) at a biological locus, comprising introducing a composition of the disclosure to such locus, and transmitting radiation to the composition at the locus that is effective to cause the composition to generate ROS at the locus.

The disclosure relates to a further aspect to a method of treating a subject to whom photosensitizer has been administered resulting in presence of photosensitizer in a bodily region of the subject that is non-targeted for phototherapy, comprising transmitting to the non-targeted bodily region deactivatingly effective light that is frequency modulated in a range of from 100 kHz to 100 THz, to deactivate photosensitizer present in such region.

Other aspects, features and embodiments of the disclosure will be more fully apparent from the ensuing description and appended claims.

DETAILED DESCRIPTION

Figure 1:
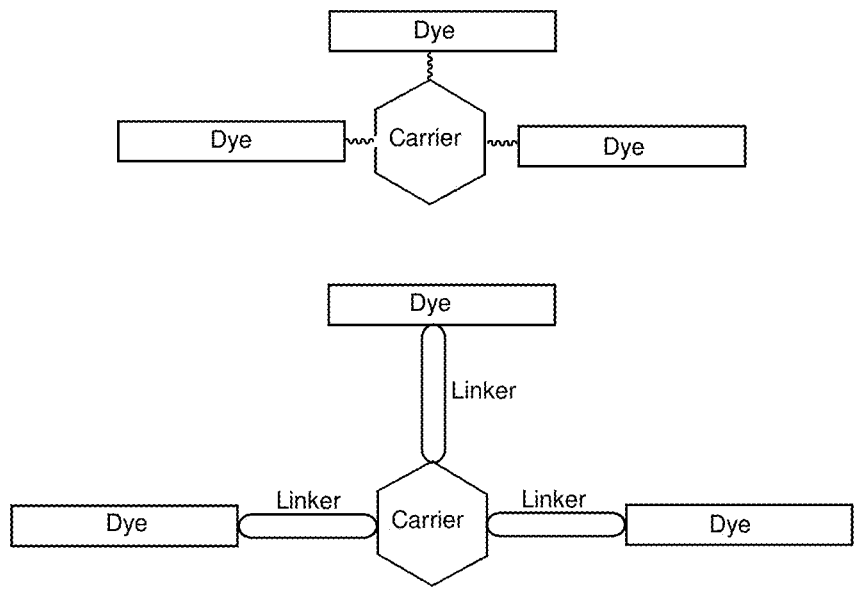
FIG. 1 is a schematic representation of dye molecules bound to a carrier.

As used herein, the following abbreviations shall have the following definitions.

| Abbreviation | Definition |
| --- | --- |
| A | Absorbance (Optical density) |
| Alk | Alkyl group |
| arom | Aromatic |
| BSA | Bovine serum albumin |
| Bu | Butyl |
| d | Doublet signal |
| cm | Centimeter ($10^{-2}$ meter) |
| DCC | Dicyclohexylcarbodiimide |
| DMF | Dimethylformamide |
| DMSO | Dimethyl sulfoxide |
| D/P | Dye-to-protein ratio |
| Et | Ethyl |

-continued

| Abbreviation | Definition |
| --- | --- |
| FDA | US Food and Drug Administration |
| g | Grams |
| h | Hours |
| HITC | 1,1',3,3,3',3'-hexamethylindotricarbocyanine (CAS 19764-96-6) |
| $^1$H-NMR | Proton nuclear magnetic resonance (hydrogen-1 nuclear magnetic resonance) |
| Hz | Hertz |
| ICG | Indocyanine green (CAS 58984-23-9) |
| IgG | Immunoglobulin G |
| IR | Infrared |
| NIR | Near-infrared |
| L | Liters |
| LED | Light emitting diode |
| m | Milli ($10^{-3}$) |
| m | Multiplet signal in $^1$H-NMR |
| max | Maximum |
| M | Molar |
| mg | Milligram ($10^{-3}$ gram) |
| Me | Methyl |
| MHz | Megahertz ($10^6$ Hertz) |
| mol | Mole |
| nm | Nanometer ($10^{-9}$ meter) |
| NHS | N-hydroxysuccinimide |
| NIR | Near infrared |
| PACT | Photodynamic antimicrobial chemotherapy |
| PB | Phosphate buffer |
| PDT | Photodynamic therapy |
| ppm | Parts per million |
| Py | Pyridine |
| q | Quartet signal in $^1$H-NMR |
| ROS | Reactive oxygen species (in this disclosure we include oxygen and non-oxygen containing reactive species induced by photosensitizers) |
| s | Singlet signal in $^1$H-NMR |
| SOG | Singlet oxygen generation or singlet oxygen generator or sensitizer |
| t | Triplet signal in $^1$H-NMR |
| TMS | Tetramethylsilane |
| TSTU | N,N,N',N'-tetramethyl(succinimido)uronium tetra-fluoroborate |
| W | Watt |
| λ | Wavelength |
| $\lambda_{max}$ (abs) | Wavelength of absorption maximum |
| $\lambda_{max}$ (em) | Wavelength for emission (fluorescence) maximum |
| ε | Extinction coefficient |
| µ | Micro ($10^{-6}$) |
| $\Phi_F$ | Fluorescence (luminescence) quantum yield |
| $\Phi_\Delta$ | Quantum yield of singlet oxygen generation |

As used herein, the following terms shall have the following meanings, unless the context shall otherwise expressly require.

Effects

"Photodynamic" means generating ROS or localized toxicity from the absorption of light.

"Sonodynamic" means generating ultrasound from the absorption of modulated light, or generation of light or photoreactivity using ultrasound.

Parameters

"Extinction coefficient" (ε) is a wavelength-dependent measure of the absorbing power of a luminophore.

"Excitation spectrum" is the dependence of emission intensity on the excitation wavelength ($\lambda_{Ex}$), measured at a single constant emission wavelength.

"Emission spectrum" is the wavelength distribution of the emission, measured at excitation with a single constant excitation wavelength.

"Stokes' shift" ($\Delta\lambda_{St}$) is the difference in wavelengths between the maximum of the emission spectrum and the maximum of the absorption spectrum.

"Luminescence lifetime" (τ) is the average time that a luminophore spends in the excited state prior to returning to the ground state.

"Fluorescence quantum yield" ($\Phi_F$) is the ratio of the number of photons emitted to the number of photons absorbed by a luminophore.

"Brightness" is an extinction coefficient multiplied by a fluorescence quantum yield.

"Singlet oxygen generation quantum yield" ($\Phi_\Delta$) is the ratio of the number of generated singlet oxygen molecules to the number of photons absorbed by a sensitizing dye.

"Clearing rate" is an efficiency of compound removal from the body or some portion of the body.

Compounds by Application

"Dye" is a compound absorbing light in the ultraviolet (UV), visible, near-infrared (NIR, near-IR), or infrared (IR) spectral range.

"Chromophore" is a part of a molecule responsible for the light absorption.

"Fluorophore" is a molecule or a part of a molecule responsible for the fluorescence (luminescence) of the dye molecule.

"Reporter" is a molecule or a part of a molecule that provides a signal, which is of sufficient character to be detected.

"Fluorescent (luminescent) reporter" is a molecule or a part of a molecule that provides a fluorescence (luminescence) signal that is of sufficient character to be detected.

"Quencher of fluorescence (luminescence)" is a molecule or a part of a molecule, the fluorescence (luminescence) of which is not strong enough to be measured and/or that reduces fluorescence (luminescence) quantum yield of a fluorophore. Quenchers can absorb light in certain spectral regions to reduce photosensitizer efficiency when excited in that spectral region. Quenchers can be used as reporters in photo-acoustic measurements.

"Sensitizer" is a molecule or a part of a molecule that provides generation of reactive species or initiation of chemical reaction.

"Photosensitizer" is a molecule or a part of a molecule that provides generation of reactive species or initiation of chemical reaction under photo-excitation.

"Environment sensitive molecule or compound" means a molecule or compound, the spectral and/or photosensitizing characteristics of which are dependent on its microenvironment. The environment sensitive molecules include, but not limited to, pH-sensitive, polarity sensitive and potential sensitive molecules, and ion indicators.

Compounds by Structure

"Terminus" means a terminal heterocyclic end group particular in polymethine dyes.

"Nitrogen containing heterocyclic compounds" (heterocycles) are any cyclic compounds containing at least one ring that contains at least one nitrogen atom in the ring. Preferably these are five- and six-membered rings. These compounds can be formed by fusion of a nitrogen containing cycle with another cycle or multiple cycles.

"Indolenines" are any compounds or fragments containing indolenine (3H-indole) moiety. Examples of indolenines and related nitrogen containing heterocyclic fragments are benzo[cd]indole, 3H-pyrrolo[2,3-b]pyridine, benzoxazole, benzothiazole, benzoselenazole, benzotellurazole, and their derivatives as shown below:

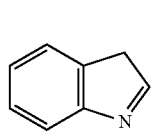
Indolenine
(3H-Indole)

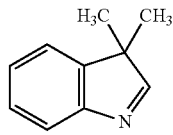
3,3-Dimethylindolenine
(3,3-Dimethyl-3H-indole)

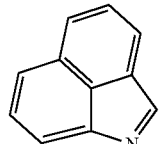
Benzo[cd]indole

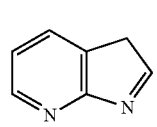
3H-pyrrolo[2,3-b]pyridine

6,6-dimethyl-6H-
thieno[3,2-b]pyrrole

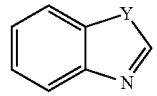
1,3-Benzoxazole (Y = O)
1,3-Benzothiazole (Y = S)
1,3-Benzoselenazole (Y = Se)
1,3-Benzotellurazole (Y = Te)

Although some indole derivatives such as benzo[cd]indole are not 3H-indoles, in this disclosure they are also referred to as indolenines.

"Halogenated (iodinated, brominated, chlorinated, and fluorinated) derivatives" (compounds or moieties) are heterocycles that contain iodine, bromine, chlorine, and/or fluorine atom(s) in the aromatic or heterocyclic ring, such as the following illustrative examples:

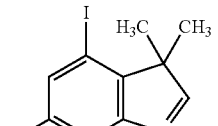
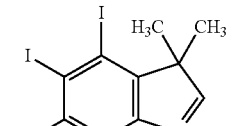
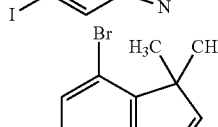
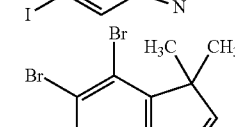
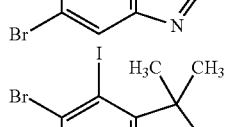
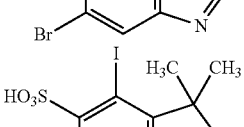
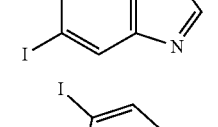
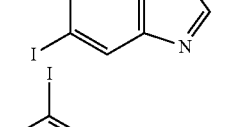
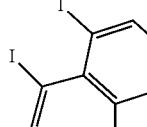

"Polymethines" are compounds containing one or more methine groups (CH) bound together by alternating single and double bonds (A. D. Kachkovski, M. L. Dekhtyar, Dyes and Pigments, 22 (1993) 83-97; http://en.wiktionary.org/wiki/polymethine). Monomethine dyes are also considered polymethine dyes in this disclosure. Polymethines can be neutral, zwitter-ionic, positively or negatively charged, and can include a single or multiple charge (−2, −1, +1, +2, etc.). One or more substituent(s) (R) can be introduced in any position of the polymethine chain. The possibility of introducing these substituents in any structures disclosed herein is implicit. These substituents can form one or more cyclic systems or branch polymethine chains.

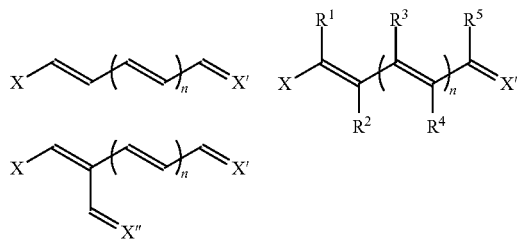

"Cyanines" are polymethine dyes consisting of two terminal nitrogen centers, one of which is positively charged and is linked by a conjugated chain of an odd number of carbon atoms to the other nitrogen; as a result the positive charge is delocalized (A. P. Demchenko (ed.), Advanced Fluorescence Reporters in Chemistry and Biology I: Fundamentals and Molecular Design, Springer Ser. Fluoresc. (2010) 8: 149-186, DOI 10.1007/978-3-642-04702-2_5, # Springer-Verlag Berlin Heidelberg 2010; A. Mishra et al. Cyanines during the 1990s: A Review. Chem. Rev., 2000, 100, 1973-2011). One or both nitrogen atoms can be included in a cyclic system.

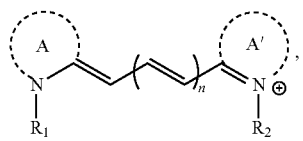

wherein A and A' are independently alicyclic or heterocyclic groups but in this disclosure at least one on these groups is a heterocycle.

"Stryryls" belong to a subclass of polymethine dyes bearing a positive charge delocalized within the polymethine chain; however, contrary to cyanines which contain an odd number of methine groups, styryl dyes have an even number of these groups in the polymethine chain (I. A. Fedyunyayeva et al, Dyes and Pigments, 90 (2011), 201-210).

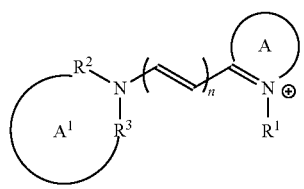

wherein A is alicyclic or heterocyclic groups; $R^2$ and $R^3$ may form a cycle $A^1$. In this disclosure group A and/or $A^1$ is a heterocycle.

"Merocyanines" are unsymmetrical polymethine dyes with neutral chromophore comprised of two terminal fragments—nitrogen donor and oxygen or sulfur acceptor connected by an ethylene or polyvinylene (polymethine) chain (A. P. Demchenko (ed.), Advanced Fluorescence Reporters in Chemistry and Biology I: Fundamentals and Molecular Design, Springer Ser. Fluoresc. (2010) 8: 149-186, DOI 10.1007/978-3-642-04702-2_5, # Springer-Verlag Berlin Heidelberg 2010; Top Heterocycl Chem (2008) 14: 75-105, DOI 10.1007/7081_2007_110).

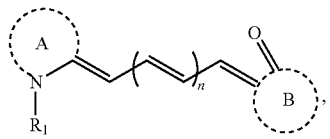

wherein A and B are independently alicyclic or heterocyclic groups, but in this disclosure group A is a heterocycle.

"Squaraines" (squaraine or squarylium dyes) are a subclass of polymethines containing a derivatized 3-oxo-1-cyclobutene-1-olate substructure (a squaric acid residue) inside polymethine chain and represented by the structure:

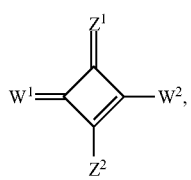

wherein substituents $Z^1$, $Z^2$, $W^1$, and $W^2$ are as disclosed below.

"Croconates" or croconium dyes are a subclass of polymethines containing a croconium or derivatized croconium substructure (a croconic acid residue) inside polymethine chain and represented by structure:

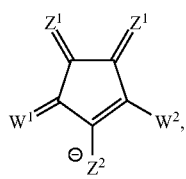

wherein substituents $Z^1$, $Z^2$, $W^1$, and $W^2$ are as disclosed below.

"Dendrimers" are repetitively branched molecules (D. Astruc et at. (2010). Chem. Rev. 110 (4): 1857-1959). In this disclosure dendrimers may consist of uniform or non-uniform (different) molecules. Dendrimers may be symmetric or non-symmetric. In this disclosure dendrimers also include dendron molecules.

Groups and Substituents

"Hydrophilic group" means any group, which increases solubility of a compound in aqueous media. These groups include, but are not limited to, sulfo, sulfonic, phosphate, phosphonate, phosphonic, carboxylate, boronic, ammonium, cyclic ammonium, hydroxy, alkoxy, ester, polyethylene glycol, polyester, glycoside, and saccharide groups.

"Reactive group" means any group allowing covalent or noncovalent binding to other molecule or carrier. These groups include, but are not limited to, activated carboxylic esters, acyl azides, acyl halides, acyl halides, acyl nitriles, aldehydes, ketones, alkyl halides, alkyl sulfonates, anhydrides, aryl halides, aziridines, boronates, carboxylic acids, carbodiimides, diazoalkanes, epoxides, haloacetamides, halotriazines, imido esters, isocyanates, isothiocyanates, N-hydroxysuccinimide, maleimides, phosphoramidites, silyl halides, sulfonate esters, sulfonyl halides, biotin, avidin, and streptavidin. In particular, the following reactive functional groups, among others, are especially useful for the preparation of labeled molecules or substances, and are therefore suitable reactive functional groups for the purposes of the reporter compounds:

a) N-hydroxysuccinimide esters, isothiocyanates, and sulfonylchlorides, which form stable covalent bonds with amines, including amines in proteins and amine-modified nucleic acids;
b) Iodoacetamides and maleimides, which form covalent bonds with thiol-functions, as in proteins;
c) Carboxyl functions and various derivatives, including N-hydroxybenzotriazole esters, thioesters, p-nitrophenyl esters, alkyl, alkenyl, alkynyl, and aromatic esters, and acyl imidazoles;
d) Alkylhalides, including iodoacetamides and chloroacetamides;
e) Hydroxyl groups, which can be converted into esters, ethers, and aldehydes and iodoacetamides;
f) Aldehydes and ketones and various derivatives, including hydrazones, oximes, and semicarbozones;
g) Isocyanates, which may react with amines;
h) Activated C=C double-bond-containing groups, which may react in a Diels-Alder reaction to form stable ring systems under mild conditions;
i) Thiol groups, which may form disulfide bonds and react with alkylhalides (such as iodoacetamide);
j) Alkenes, which can undergo a Michael addition with thiols, e.g., maleimide reactions with thiols;
k) Phosphoramidites, which can be used for direct labeling of nucleosides, nucleotides, and oligonucleotides, including primers on solid or semi-solid supports;
l) Primary amines that may be coupled to variety of groups including carboxyl, aldehydes, ketones, and acid chlorides, among others;
m) Boronic acid derivatives that may react with sugars;
n) Pyrylium moieties react with primary amines;
o) Haloplatinates form stable platinum complexes with amines, thiols and heterocycles;
p) Aryl halides react with thiols and amines;
q) Azide, alkyne or other groups, which can be used for click chemistry reactions;
r) Biotin, avidin, and streptavidin providing strong non-covalent binding.

Aliphatic groups include groups of organic compounds characterized by straight- or branched-chain arrangement of the constituent carbon atoms. Aliphatic hydrocarbons comprise three subgroups: (1) paraffins (alkanes), which are saturated and comparatively unreactive; (2) olefins (alkenes or alkadienes), which are unsaturated and quite reactive; and (3) acetylenes (alkynes), which contain a triple bond and are highly reactive. In complex structures, the chains may be branched or cross-linked and may contain one or more heteroatoms (such as polyethers and polyamines, among others).

Alicyclic groups include hydrocarbon substituents that incorporate closed rings. Alicyclic substituents may include rings in boat conformations, chair conformations, or conformations resembling bird cages. Most alicyclic groups are derived from petroleum or coal tar, and many can be synthesized by various methods. Alicyclic groups may optionally include heteroalicyclic groups that include one or more heteroatoms, typically nitrogen, oxygen, or sulfur. These compounds have properties resembling those of aliphatics and should not be confused with aromatic compounds having the hexagonal benzene ring. Alicyclics may comprise three subgroups: (1) cycloparaffins (saturated), (2) cycloolefins (unsaturated with two or more double bonds), and (3) cycloacetylenes (cyclynes) with a triple bond. The best-known cycloparaffins (sometimes called naphthenes) are cyclopropane, cyclohexane, and cyclopentane; typical of the cycloolefins are cyclopentadiene and cyclooctatetraene. Most alicyclics are derived from petroleum or coal tar, and many can be synthesized by various methods.

Aromatic groups may include groups of unsaturated cyclic hydrocarbons containing one or more rings. A typical aromatic group is benzene, which has a 6-carbon ring formally containing three double bonds in a delocalized ring system. Aromatic groups may be highly reactive and chemically versatile. Most aromatics are derived from petroleum and coal tar. Heterocyclic rings include closed-ring structures, usually of either 5 or 6 members, in which one or more of the atoms in the ring is an element other than carbon, e.g., sulfur, nitrogen, etc. Examples include pyridine, pyrrole, furan, thiophene, and purine. Some 5-membered heterocyclic compounds exhibit aromaticity, such as furans and thiophenes, among others, and are analogous to aromatic compounds in reactivity and properties.

Any substituent of the compounds of the invention, including any aliphatic, alicyclic, or aromatic group, may be further substituted one or more times by any of a variety of substituents, including without limitation, F, Cl, Br, I, carboxylic acid, sulfonic acid, CN, nitro, hydroxy, phosphate, phosphonate, sulfate, cyano, azido, amine, alkyl, alkoxy, trialkylammonium or aryl. Aliphatic residues can incorporate up to six heteroatoms selected from N, O, and S. Alkyl substituents include hydrocarbon chains having 1-22 carbons, more typically having 1-6 carbons, sometimes called "lower alkyl".

Squaraine moiety is a 3-oxo-1-cyclobutene-1-olate substructure, where one or both oxygen atoms may be substituted with a heteroatom or a group of atoms (substituents $Z^1$ and $Z^2$):

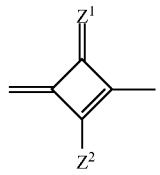

If a dye described in this disclosure has a total positive or negative electronic charge, an appropriate counterion is implied but may not be shown. Counterion can be organic or inorganic. Organic counterion can be covalently attached to the dye.

To simplify drawings of chemical structures, a methyl group may be shown in this disclosure as a single bond. Thus, the structures on the left column below represent the same compound as on the right column:

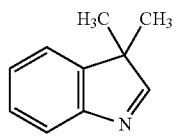 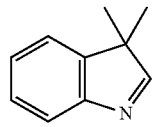

3,3-Dimethylindolenine (3,3-Dimethyl-3H-indole)

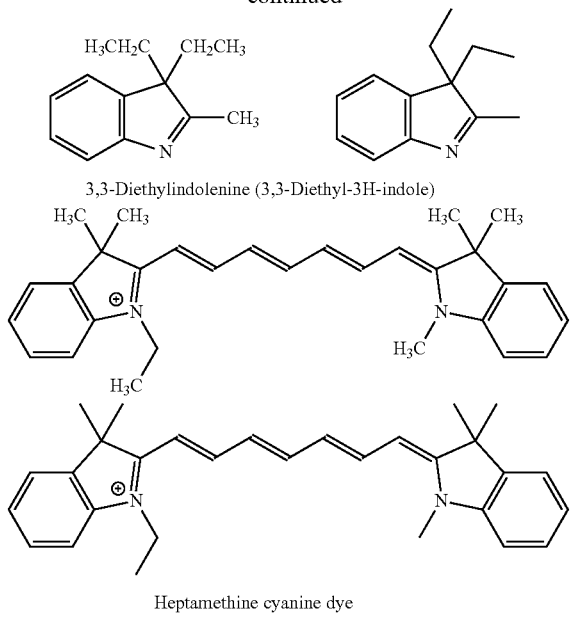

3,3-Diethylindolenine (3,3-Diethyl-3H-indole)

Heptamethine cyanine dye

The present disclosure relates to: iodinated, brominated, and other halogenated nitrogen containing heterocyclic compounds; organic dyes, in particular polymethine dyes including cyanines and squaraines based on these heterocyclic compounds; dendrimeric compounds comprising these halogenated polymethine dyes; conjugates of these polymethine and dendrimeric dyes with other organic and inorganic compounds, nanoparticles, biological molecules, and/or biological compounds that ensure improved brightness and photostability and/or sensitivity and selective affinity to target cancer cells, pathogenic microorganisms, and/or other biological materials; reporting and sensitizing compositions based on these polymethine compounds, dendrimers and conjugates of these compounds, and methods to make and use these compounds and compositions.

More specifically, the disclosure relates to classes of fluorinated, chlorinated, brominated, and/or iodinated compounds, wherein at least two halogen atoms are directly bound to a nitrogen-containing heterocyclic terminal moiety of the compound, and wherein at least one of such halogen atoms is iodine or bromine. The disclosure also relates to derivatives and conjugates of these halogenated compounds, as well as to applications of such compounds and conjugates. In some embodiments, the dye compound includes a second halogenated terminal moiety.

The compounds and compositions of the present disclosure reflect the discovery that introduction of heavy atoms such as iodine and bromine in polymethine dyes surprisingly and unexpectedly increase sensitizing efficiency, photostability, and fluorescence quantum yields of the dye, in contradiction to conventional wisdom in the art, according to which sensitizing efficiency is increased at the cost of decreased fluorescence quantum yields. The dyes of the present disclosure thereby provide a unique, unexpected, and highly useful matrix of properties affording new functional advantages for reporting, diagnostics, and/or photodynamic therapies, among other applications.

The multiply halogenated polymethine dyes of the disclosure can be used to form dendrimers, thereby enabling increased reactive oxygen species (ROS) generation per molecule, all other factors being equal, in relation to a single isolated polymethine dye.

It will be recognized that quantum yield achievable by multiply halogenated polymethine dyes species of the present disclosure will vary among different compounds and classes of such compositions, and that the particular multiply halogenated polymethine dye desirably employed to achieve a predetermined quantum yield in a specific application can be readily determined within the skill in the art based on the disclosure herein.

The disclosure also contemplates the provision and use of multiply halogenated polymethine dyes species wherein at least two halogen atoms are directly bound to a nitrogen-containing heterocyclic terminal moiety of the compound, and wherein the halogen atoms include two or more fluorine or chlorine atoms, optionally wherein two or more fluorine or chlorine atoms are directly bound to nitrogen-containing heterocyclic terminal moieties at two terminal regions of the molecule. In still other embodiments, such fluorinated or chlorine analogs may be conjugated with multiply iodinated or brominated molecules of the disclosure to form protected dendrimers.

The disclosure thus broadly contemplates fluorinated, chlorinated, brominated, and iodinated nitrogen containing heterocyclic compounds, and in particular indolenines, benzoxazoles, benzothiazoles, benzoselenazoles, and benzotellurazoles having the formula:

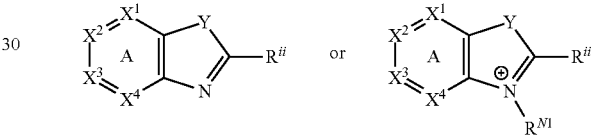

wherein:
$X^1$, $X^2$, $X^3$, and $X^4$ are independently selected from the group consisting of N, $^+NR^{N3}$, and C—$R^X$ with the proviso that at least two of the substituents $X^1$, $X^2$, $X^3$ or $X^4$ contain halogen atoms directly attached to aromatic or heterocyclic ring "A" wherein at least one of these halogen atoms is iodine or bromine. Fluorine and/or chlorine in these compounds can be introduced in the ring "A" to obtain additional identifiable reporters with high fluorescence quantum yield and photostability;
Y is O, S, Se, Te, $C(R^{C1})(R^{C2})$, N—$R^{N2}$; and
other substituents are as disclosed herein.

The disclosure further contemplates methods to synthesize the heterocycles and polymethine dyes of the disclosure, including methods for synthesizing the polymethine dyes wherein at least one of the heterocycle compounds of the disclosure is utilized as a starting or intermediate material or precursor.

In another aspect, the disclosure relates to polymethine dyes and compositions of matter comprising the polymethine dyes containing at least one of the heterocyclic moieties Het and Het$^+$:

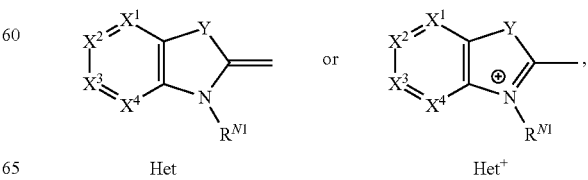

Het  Het$^+$ wherein at least one of the heterocyclic moieties contains at least two substituents attached to the aromatic or heteroaromatic ring, selected from iodine, bromine, chlorine and fluorine atoms, wherein at least one of these halogen atoms is iodine or bromine.

Polymethine compounds and compositions of the disclosure are used for reporting and sensitizing applications, among others, and include compounds and compositions that absorb light in the greater-visible light range, e.g., in the red and NIR spectral range, to effect generation of ROS, as well as compounds and compositions that are effective to generate ROS under ultrasonic exposure. The compounds and compositions can be fluorescent or non-fluorescent, reactive or non-reactive, and/or hydrophilic or hydrophobic.

The most significant and unpredicted features of the halogenated heterocyclic dyes of the present disclosure are increased brightness (identified as the extinction coefficient multiplied by the fluorescence quantum yield) and photostability simultaneously with increased sensitizing efficiency as compared to the dyes without these halogen atoms.

One class of preferred dyes of the present disclosure includes iodinated and brominated indolenine-based pentamethine and heptamethine cyanines that absorb and emit in the red and near-infrared spectral region, where biological tissues demonstrate minimal auto-absorbance and auto-fluorescence.

Heterocyclic compounds of the present disclosure include the following indolenines:

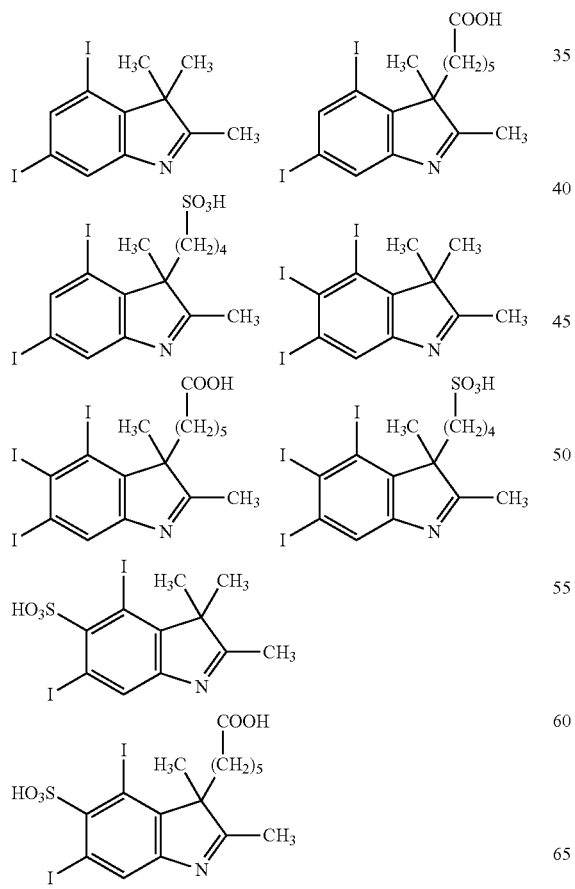

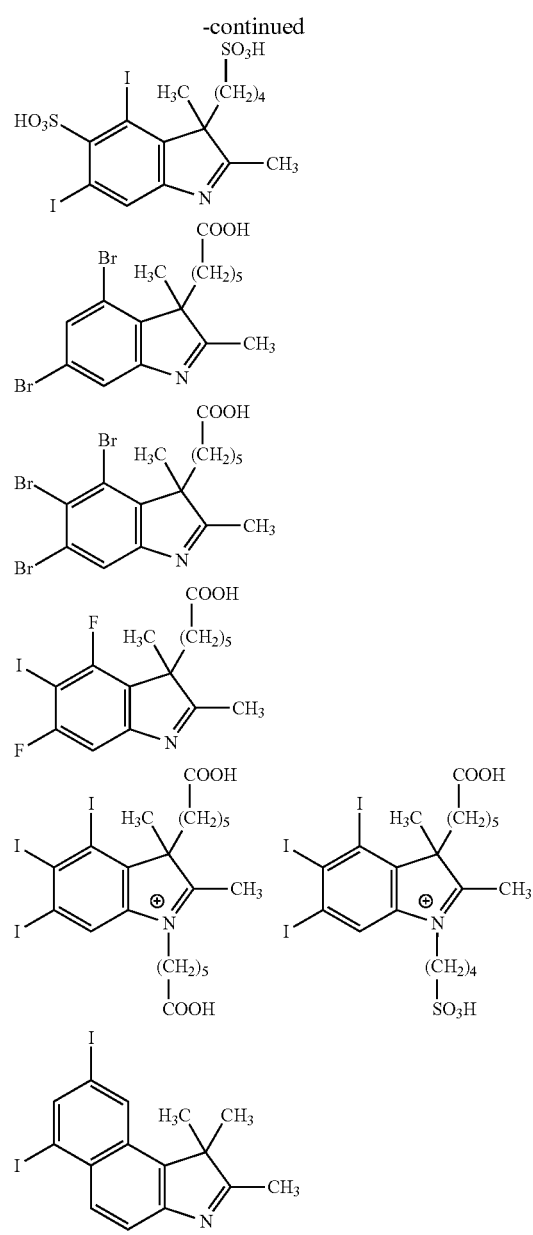

and the following polymethines:

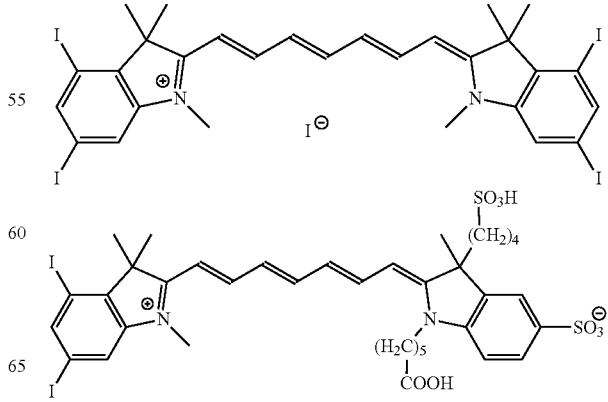

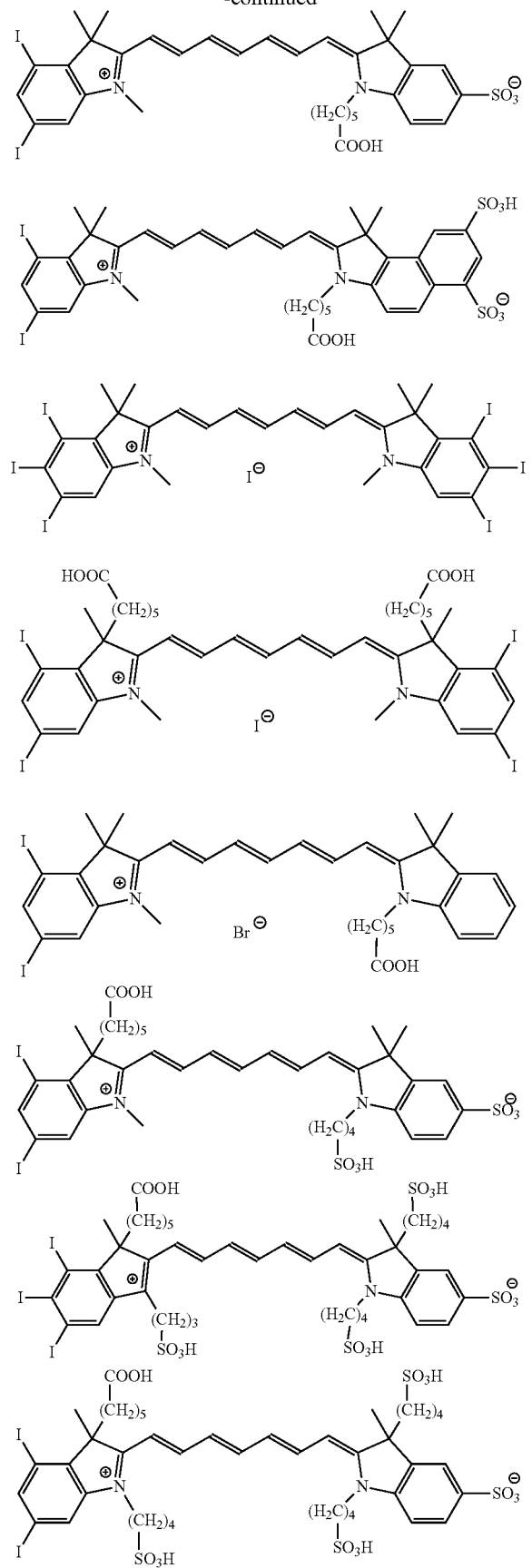

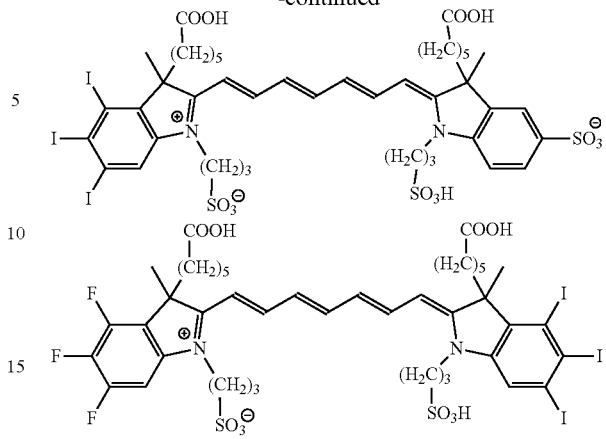

Molecular structures of the present disclosure comprise two or more halogen atoms, including at least one of either iodine and/or bromine, in the dye molecule that are effective to increase not only sensitizing efficiency but also fluorescence quantum yields. At least one of the termini of the molecular structure contains two or more halogen atoms, at least one of which is iodine or bromine. More than one terminus may contain such halogen atoms, and such molecular structures can be conjugated to form larger molecular structures characterized by high fluorescence brightness and photosensitizer ROS generation efficiency.

Although cyanines and other polymethines have been previously utilized as fluorescent dyes, the conventional wisdom in the art has been that introduction of heavy atoms such as iodine and bromine in dye molecules will decrease fluorescence quantum yield, as well as generally the photostability of the dye. In consequence of such conventional wisdom, relating to the heavy atom effect of iodine and/or bromine halogen atoms as being correlative to expected low performance, the art has avoided use of multiple heavy halogen atoms in photosensitive dyes. The present disclosure therefore reflects a radical departure from prior practice in the provision of polymethine dyes with one or multiple heavy halogen atoms on one or more heterocyclic terminal groups, as a new class of fluorophores that in contradiction to accepted heavy-atom effect expectations exhibits high reactive oxygen species (ROS) generation efficiency photosensitizing characteristics with high fluorescence quantum yield.

The disclosure contemplates conjugates of the halogenated heterocycle compounds herein disclosed as including two or more iodine and/or bromine atoms on heterocyclic terminal group(s), as well as ionic pairs collocated on carriers, and dendrimeric dyes comprising these halogenated dyes.

Molecular structures of the present disclosure can be used as precursors to synthesize iodinated, brominated, and other halogenated dyes, in particular polymethines. The high ROS generation efficiency and high fluorescence quantum yield of the halogenated polymethine dyes of the disclosure, and their superior brightness and photostability, enable such improved reporting and sensitizing properties to be exploited in a wide variety of applications, including research, analysis, diagnostics, photodynamic therapies, theranostics, and photoinitiated deposition or growth of materials.

Further improvement of the halogenated dyes of the disclosure can be achieved by conjugation of these dye molecules to a dendrimeric structure. The resulting dendrimer can be formed by the same dye molecules described herein, or combinations of different dye molecules with the dye molecules described herein. Any appropriate linker can be used to conjugate the dye molecules to a dendrimeric structure. The dendrimers can be hydrophilic, hydrophobic, reactive, or non-reactive. Dye molecules in a dendrimer may play a role of a reporter, sensitizer, or both. Dendrimeric structures comprised of dyes of the present disclosure have been found to improve light sensitivity, brightness, SOG and ROS efficiency.

Thus, the disclosure contemplates iodinated, brominated, and other halogenated compounds having utility as photosensitive dyes, their conjugates, and methods of synthesizing and using these compounds and conjugates as reporters, sensitizing agents for photodynamic and sonodynamic therapy, photodynamic antimicrobial chemotherapy (PACT), cancer treatment, and antimicrobial coating materials. The utility of such halogenated compounds and their conjugates in such applications may be particularly advantageous as a result of enhancement of one or more of the following characteristics: (i) fluorescence quantum yield, (ii) sensitizing (photodynamic) efficiency, which can be estimated via the SOG or ROS generation effectiveness or performance to destroy certain cells, (iii) the sensitivity to excitation light, which can be estimated via the extinction coefficient at the excitation wavelength, (iv) spectral range causing depth of treatment, (v) dark toxicity, and (vi) photostability, as compared with compounds and conjugates other than those of the present disclosure.

Compositions of the present disclosure include dyes useful as reporters for diagnosis or analysis in vitro or in vivo. The disclosure contemplates determining the presence and/or concentration of dyes described herein by various techniques, e.g., photoluminescent excitation or detection, or light absorption induced ultrasonic generation. Photodynamically active compounds of the present disclosure also can be remotely detected, thereby providing an intrinsic mechanism for reporting. High and low photodynamic activity molecules may be conjugated or otherwise linked to optimize chemical activity reporting functions.

Compounds of the present disclosure include polymethine dyes such as cyanines, styryls, merocyanines, squaraines, and croconates, among others, as well as nitrogen-containing heterocyclic compounds (heterocycles) that can be used to synthesize such polymethines. All of these compounds (dyes and heterocycles) contain at least two halogen atoms in the heterocyclic compound or heterocyclic terminus, but at least one of these halogens is iodine or bromine.

Nitrogen-containing heterocyclic compounds useful as precursors to synthesize polymethines include halogenated indolenines, benzo[cd]indole, 3H-pyrrolo[2,3-b]pyridine, benzoxazole, benzothiazole, benzoselenazole, benzotellurazole, and their derivatives. As previously indicated, the halogenated dyes themselves or in combination with other dyes can be bound together via linkers to form dendrimeric structures.

Specific embodiments of indolenines and other nitrogen-containing heterocyclic compounds are set out below.

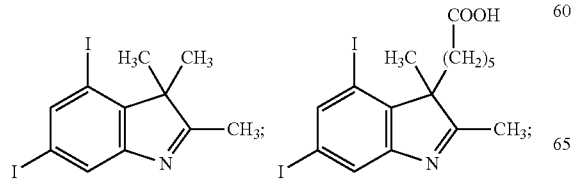

-continued

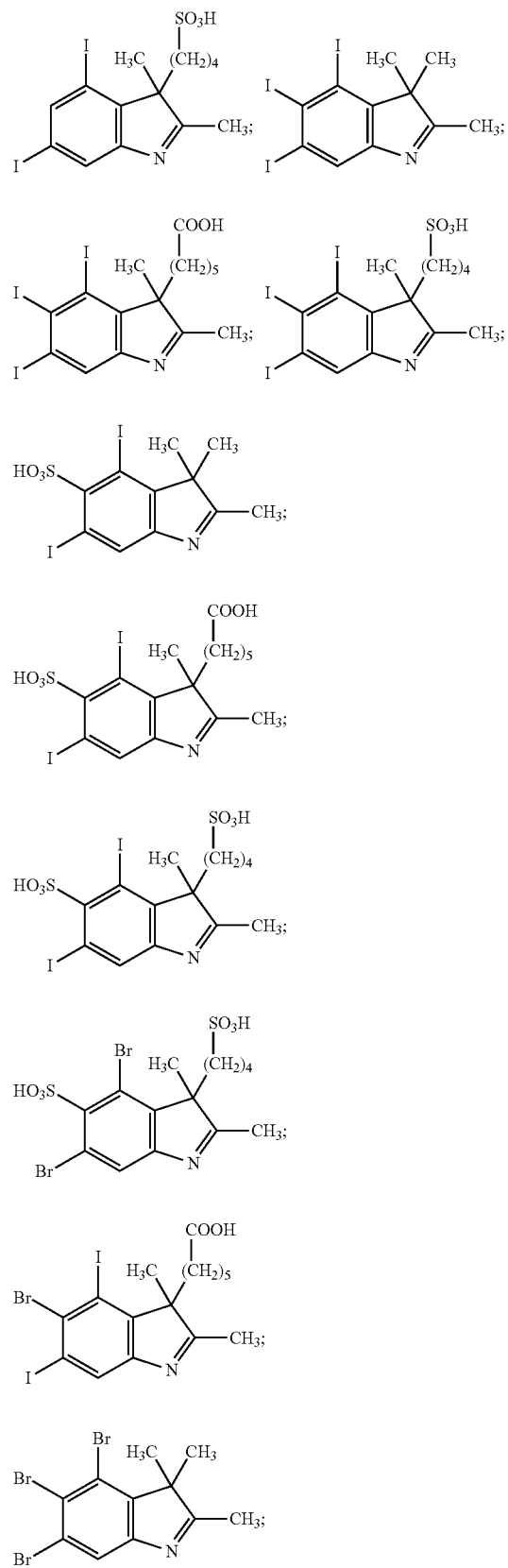

-continued
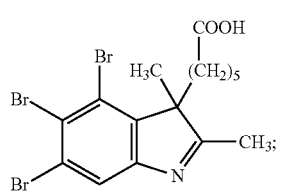
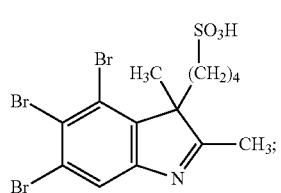
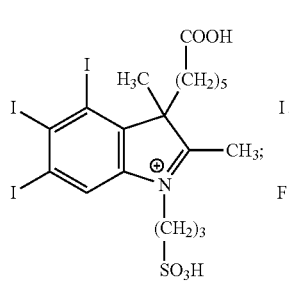
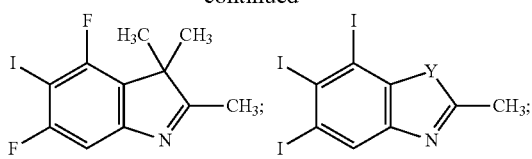
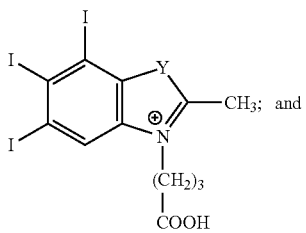
Y = O, S, Se
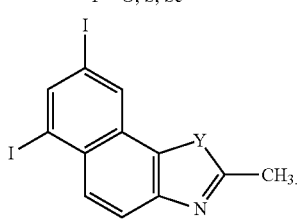
Y = O, S, Se
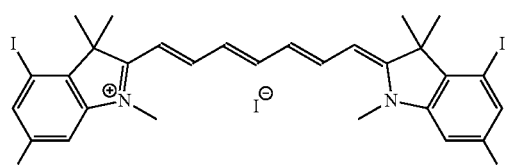
Y = O, S, Se, C(CH$_3$)$_2$
Specific embodiments of polymethines are set out below.
1
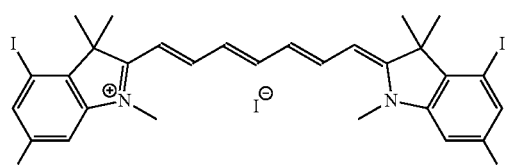
2
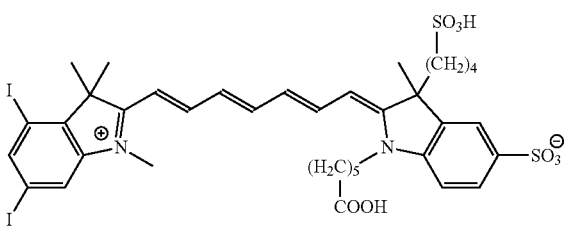
3
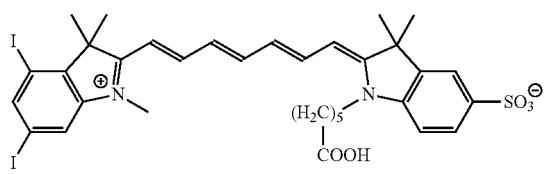
4
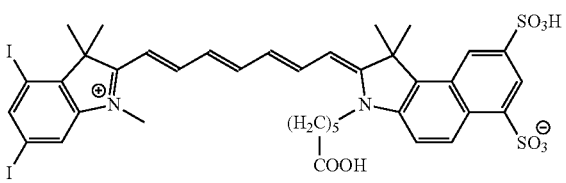
5
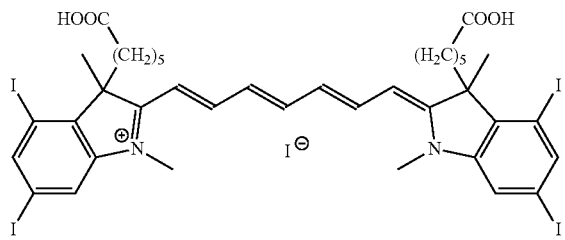
6
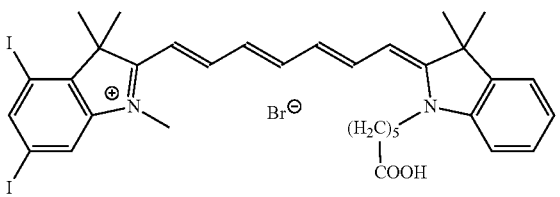

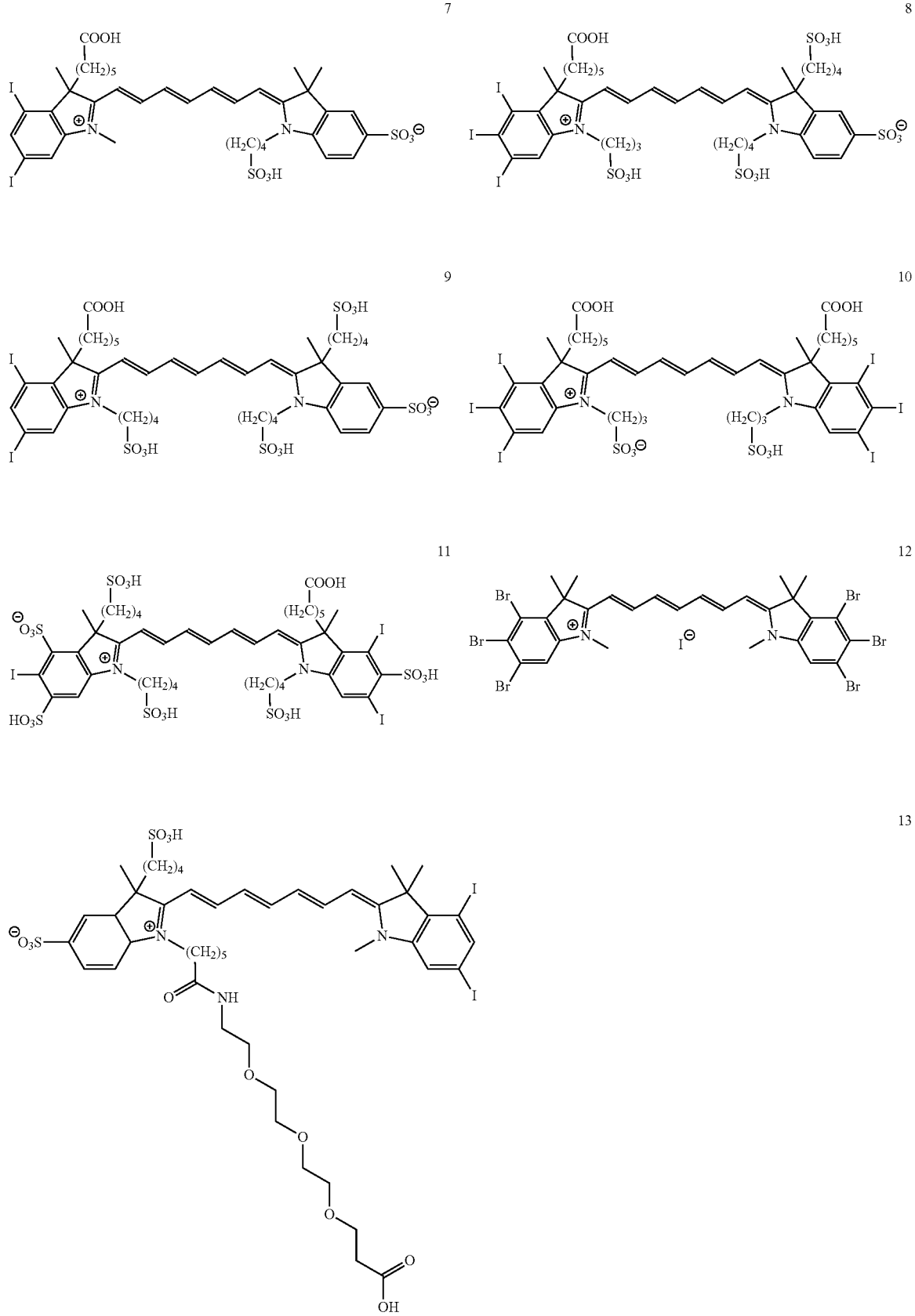

-continued
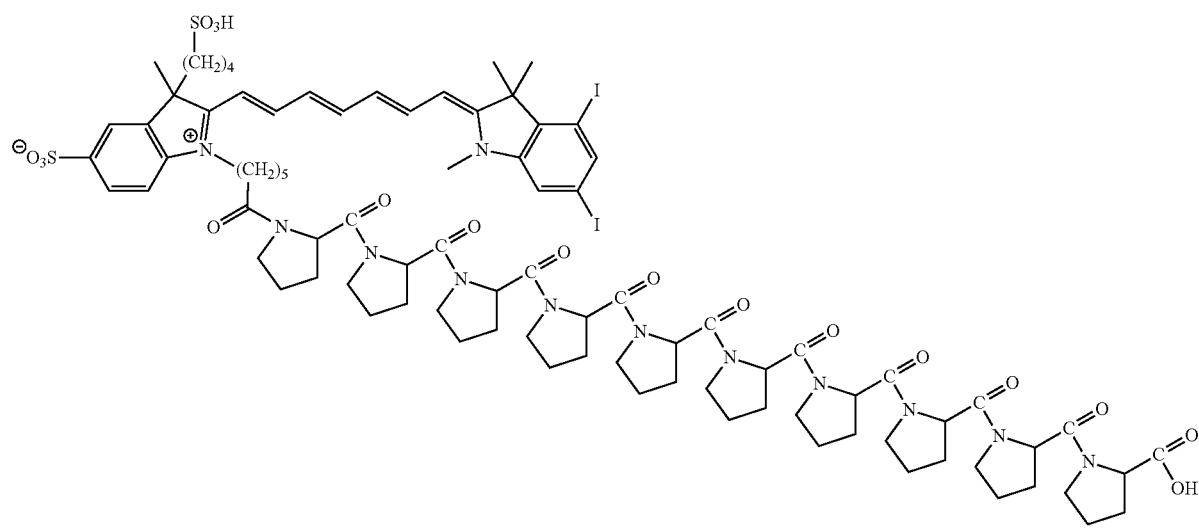
14
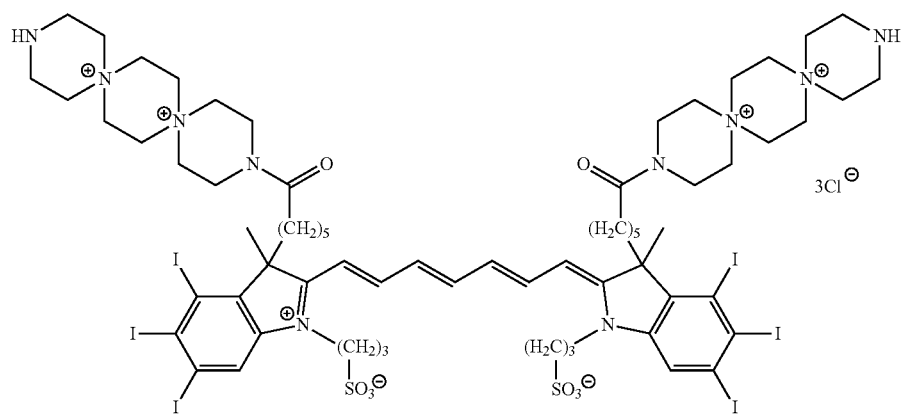
15
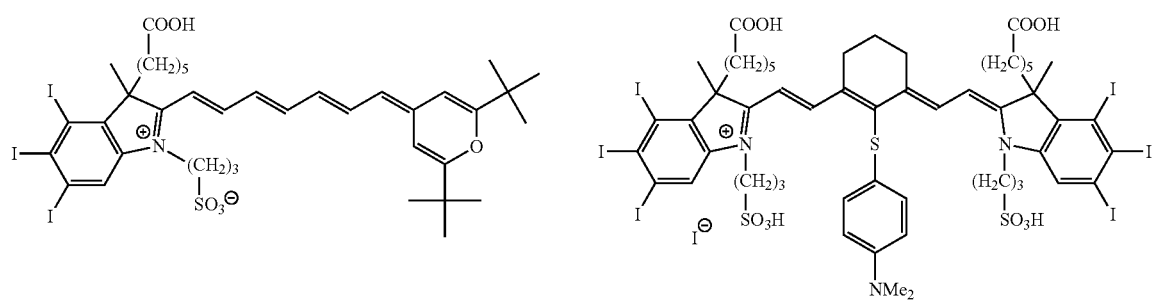
16   17
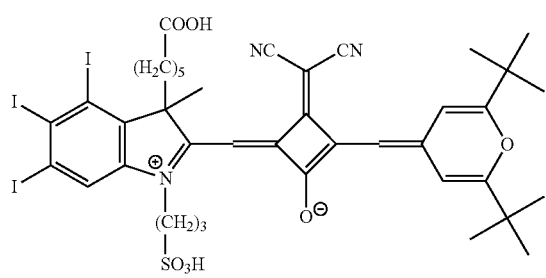
18

Specific embodiments of dendrimers are set out below.
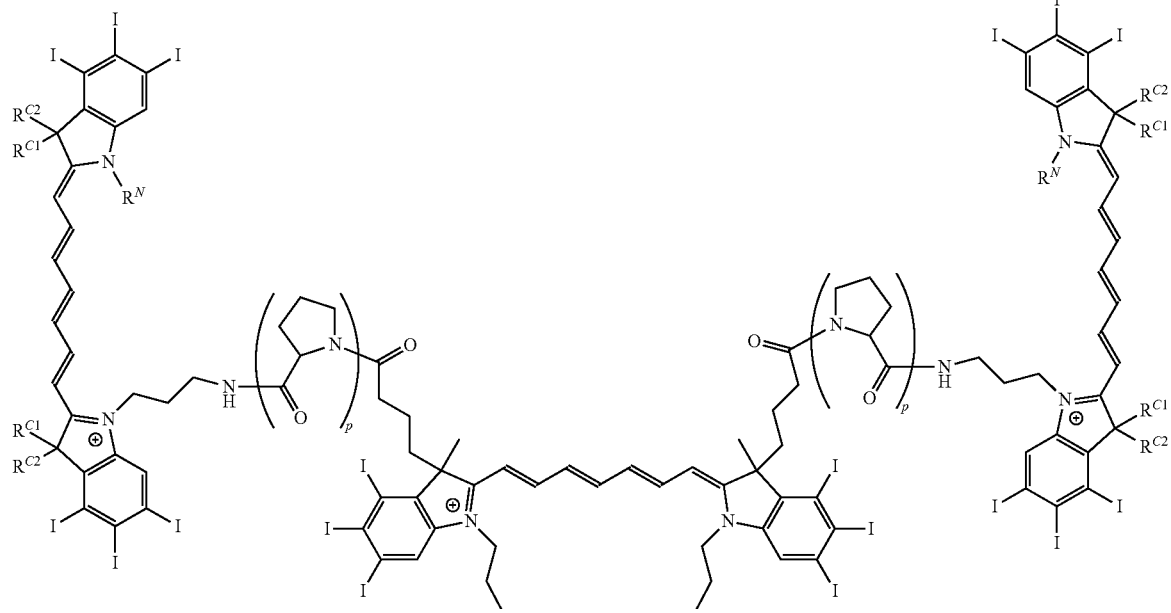
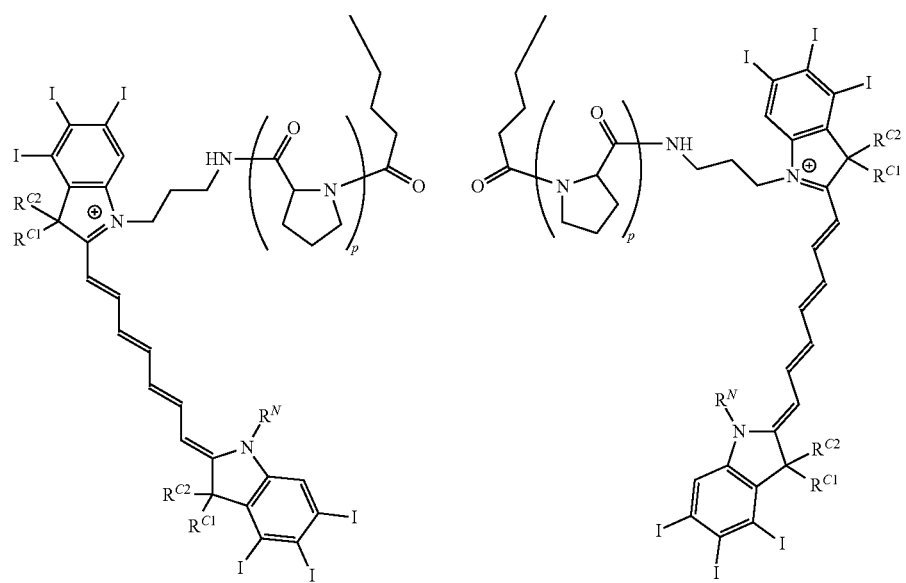

-continued
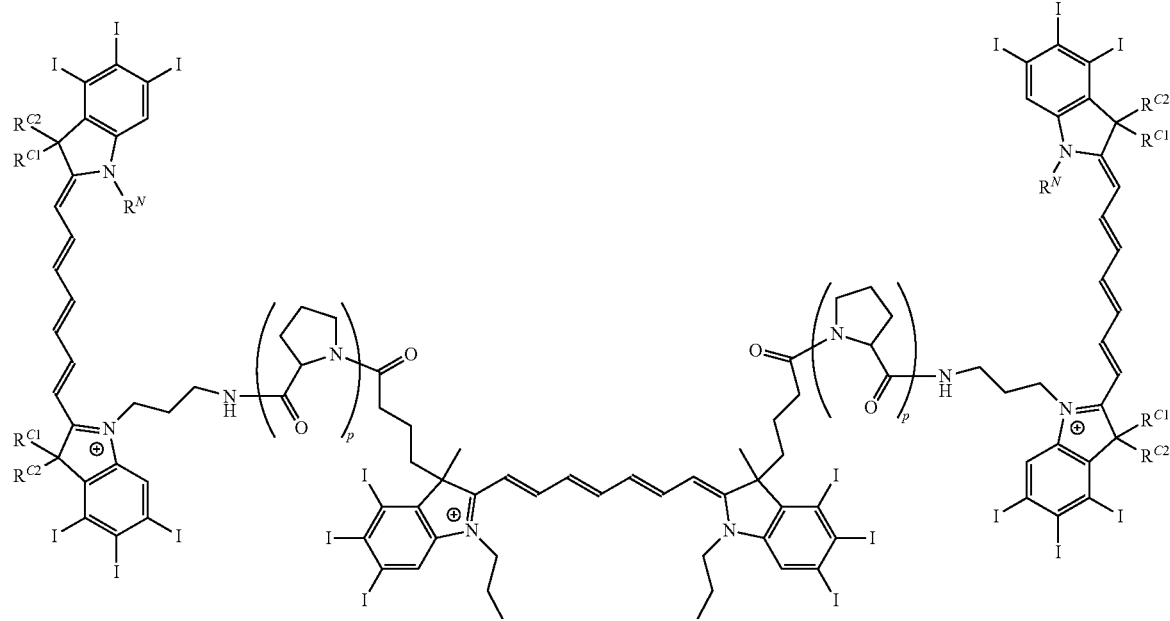
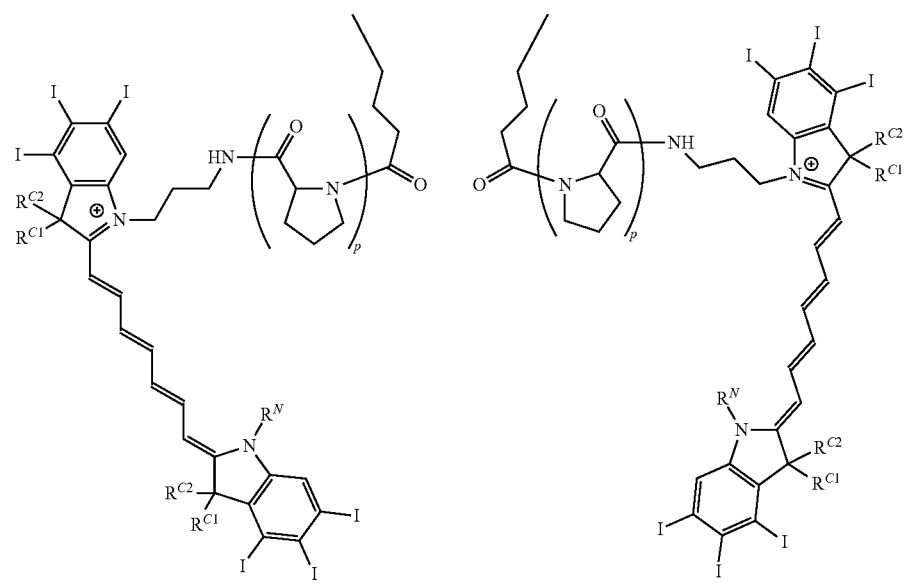

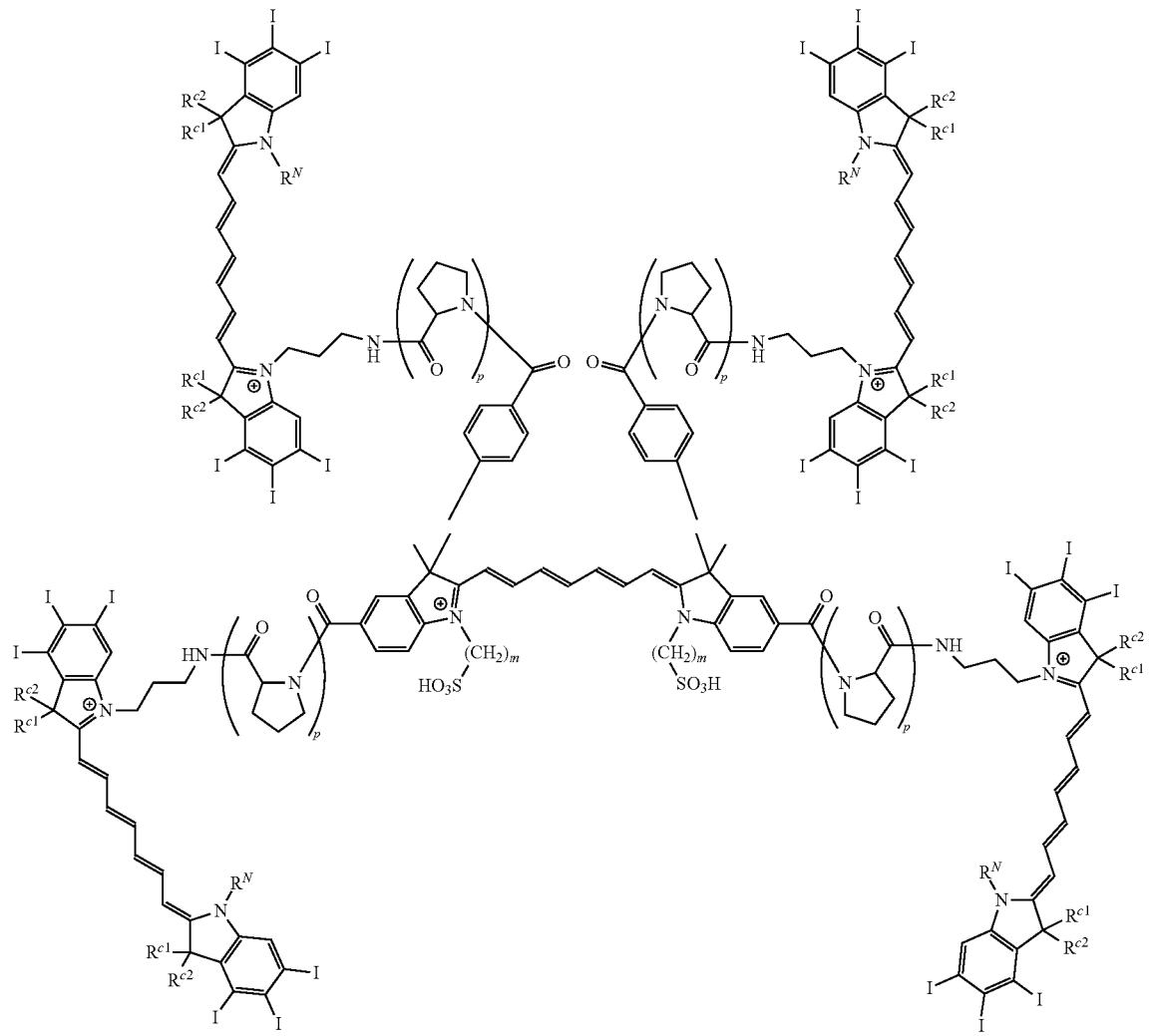
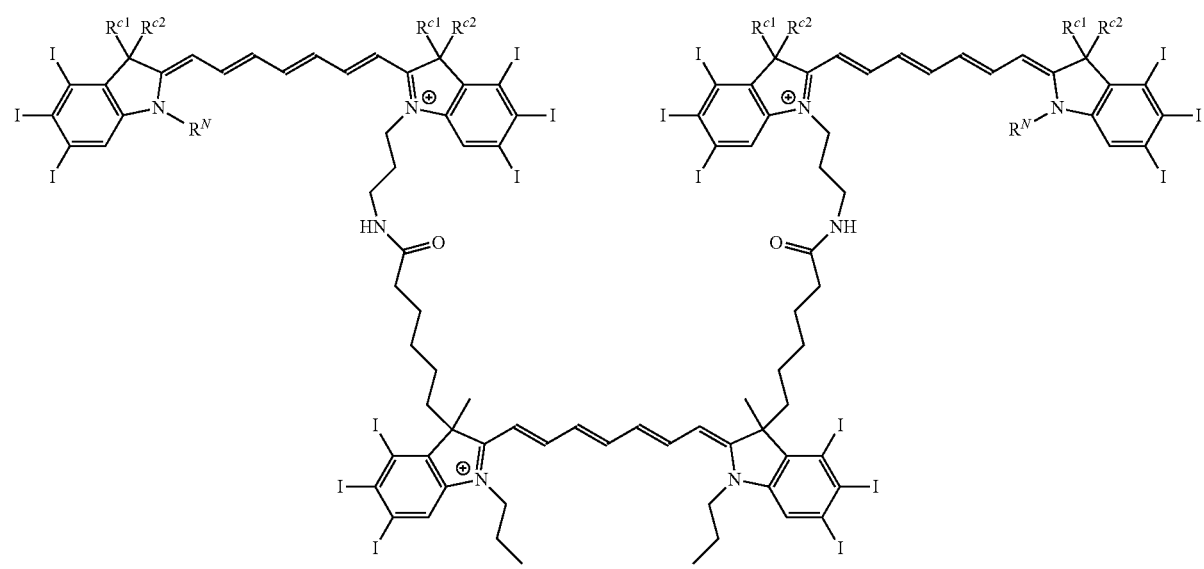

-continued
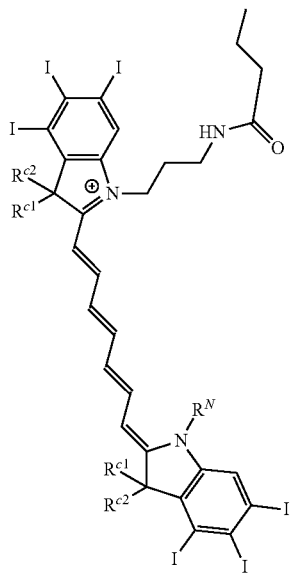 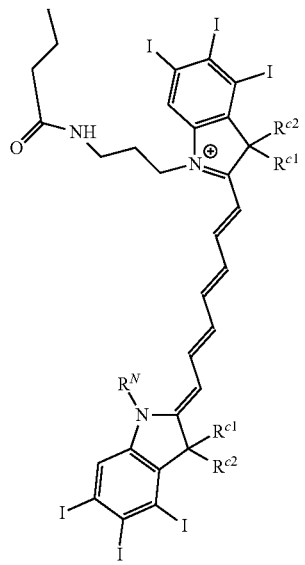
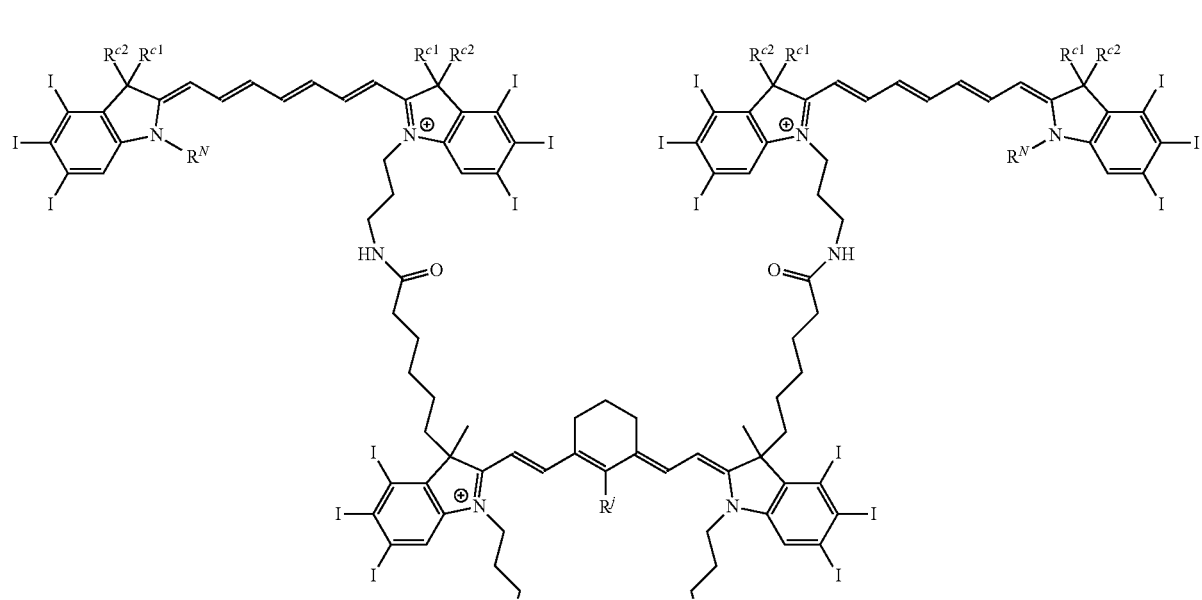

-continued
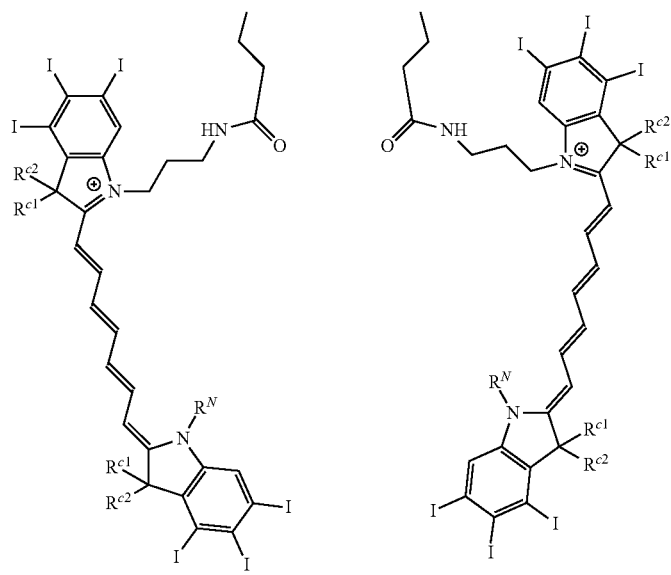
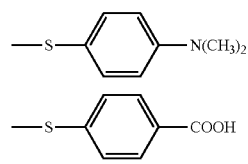
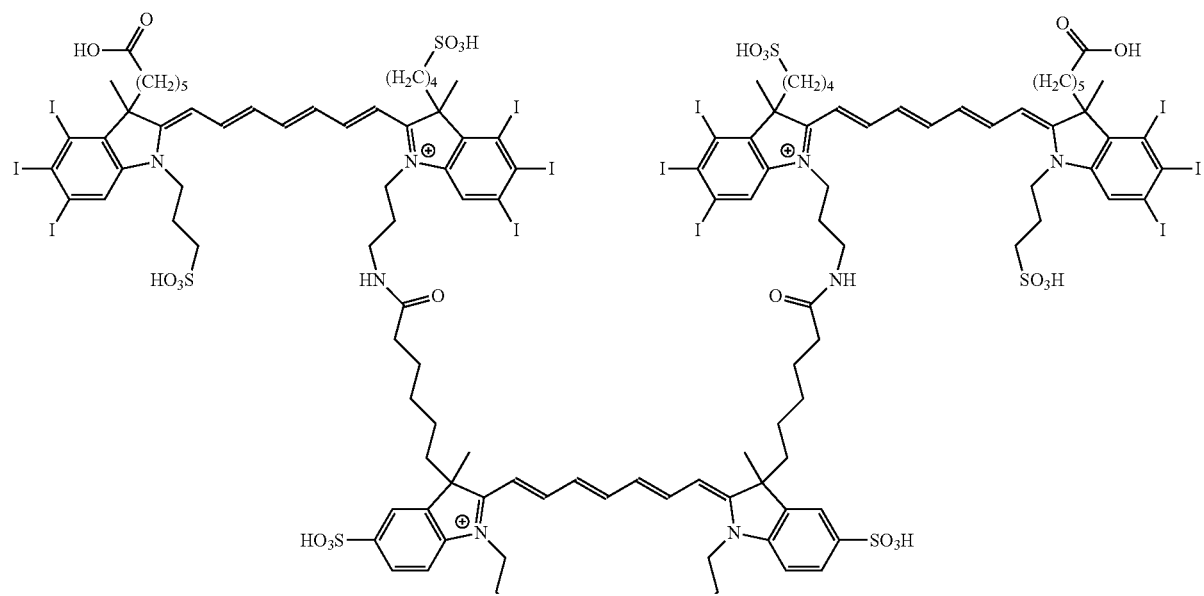

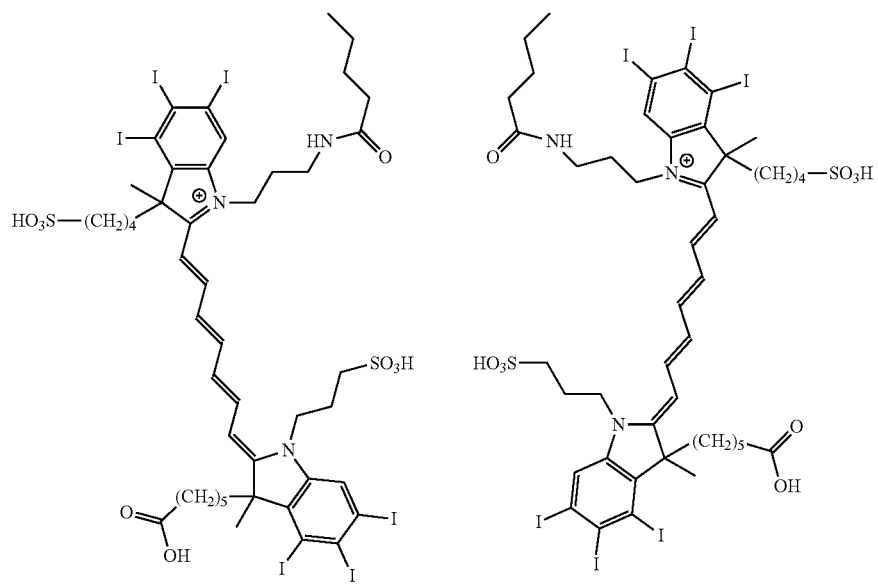
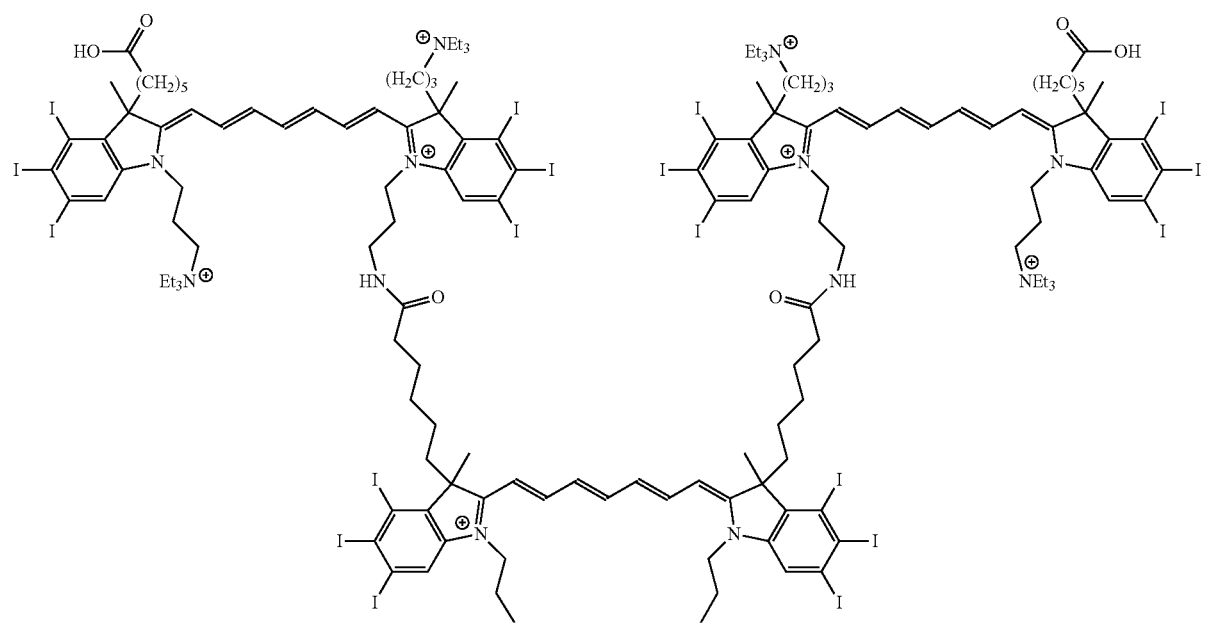

-continued
77
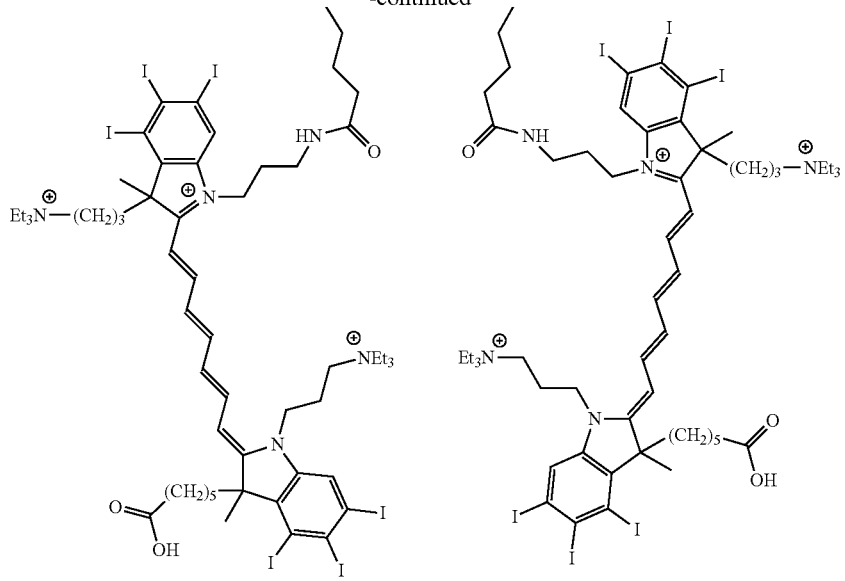
78
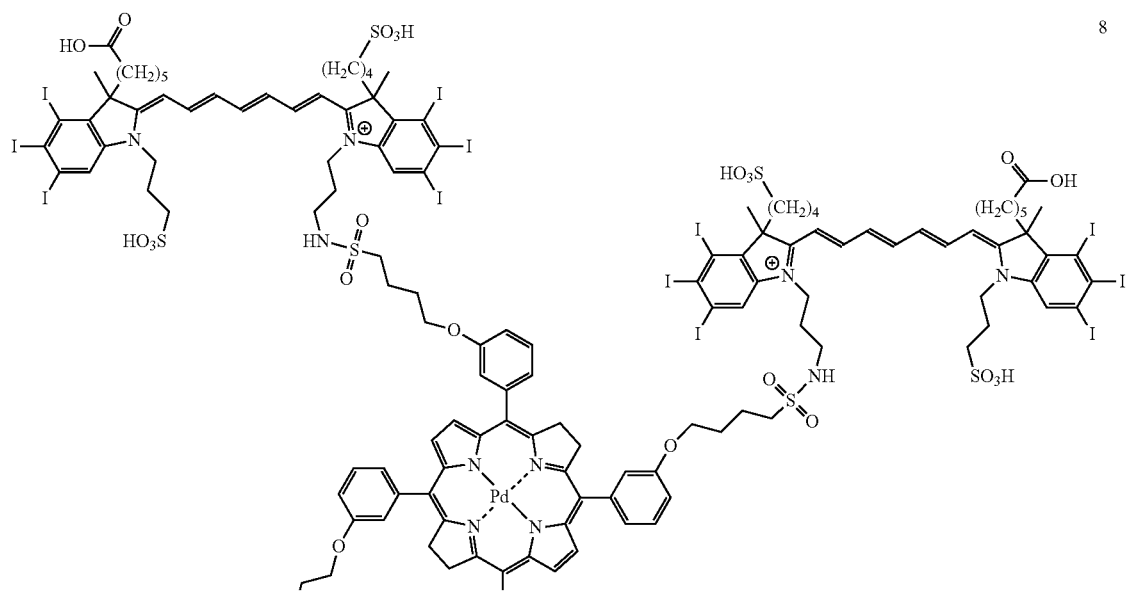
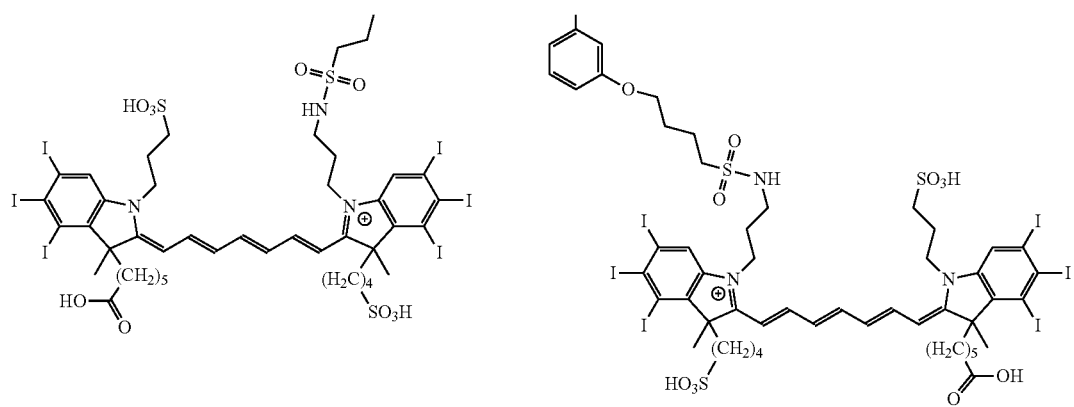

9
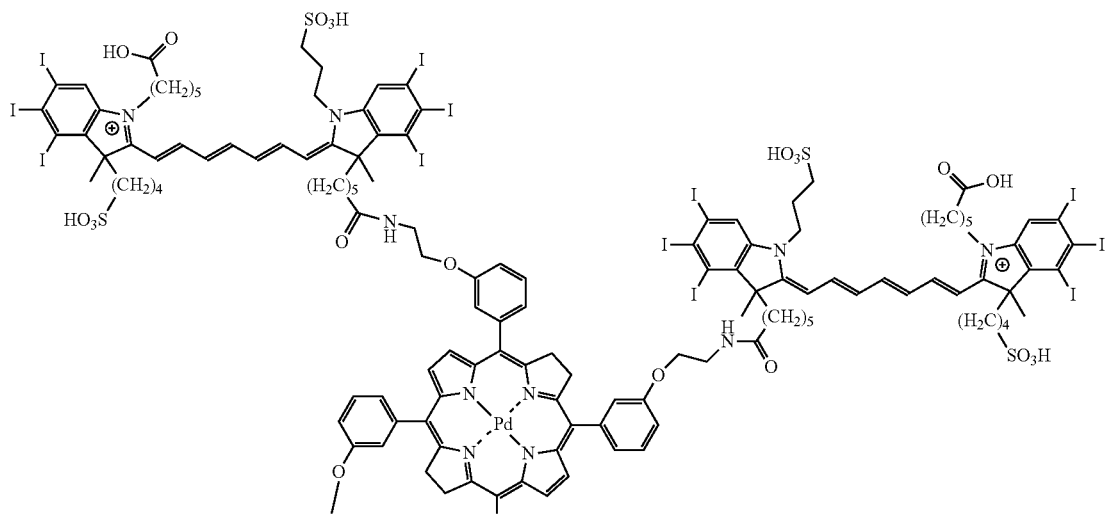
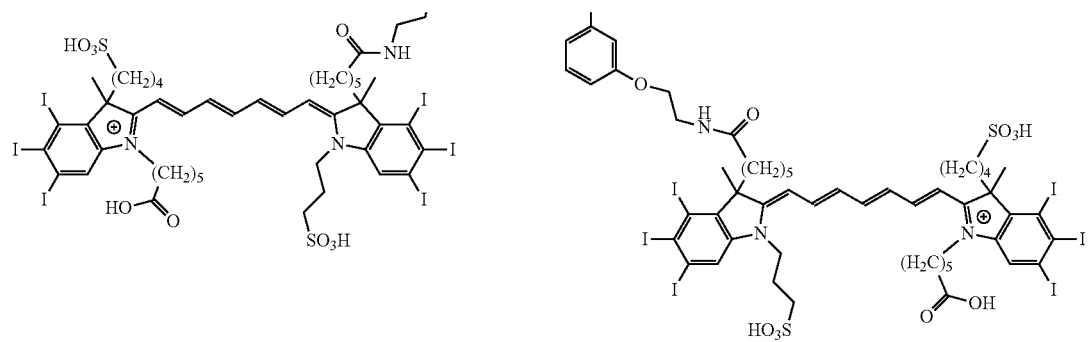
10
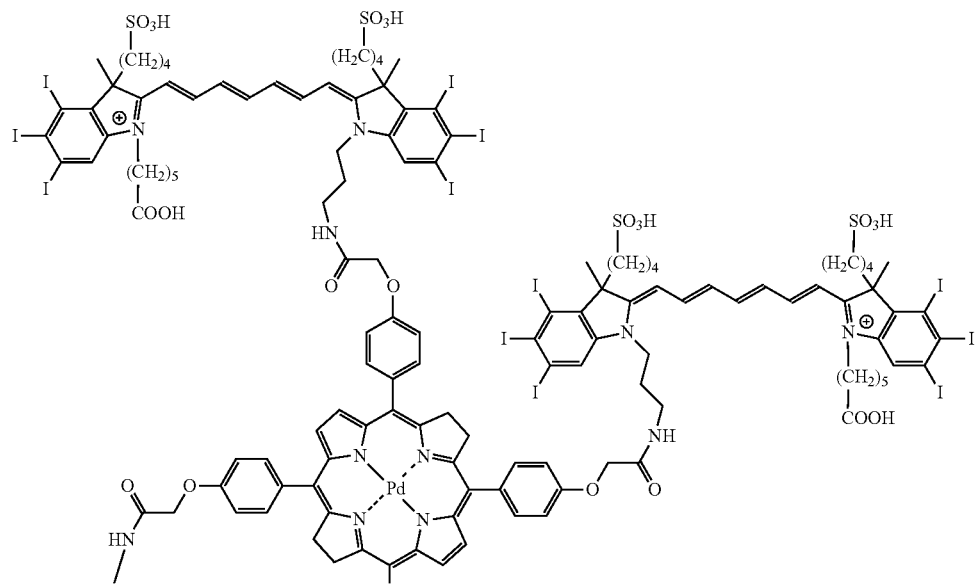

-continued
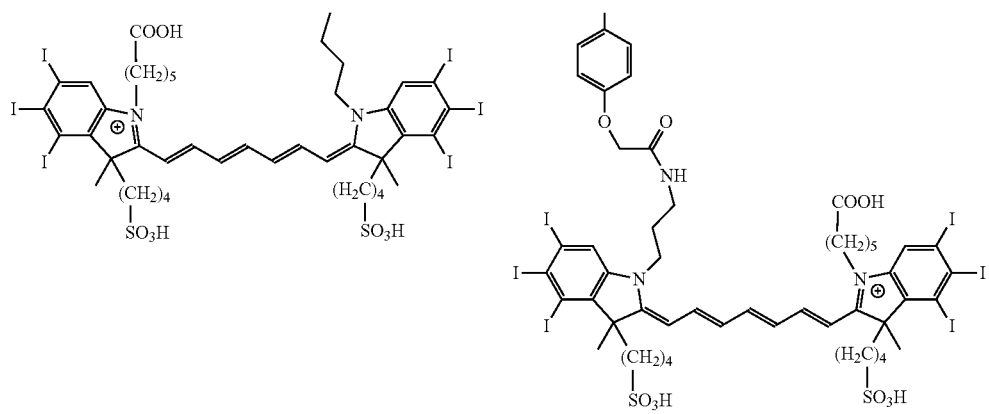
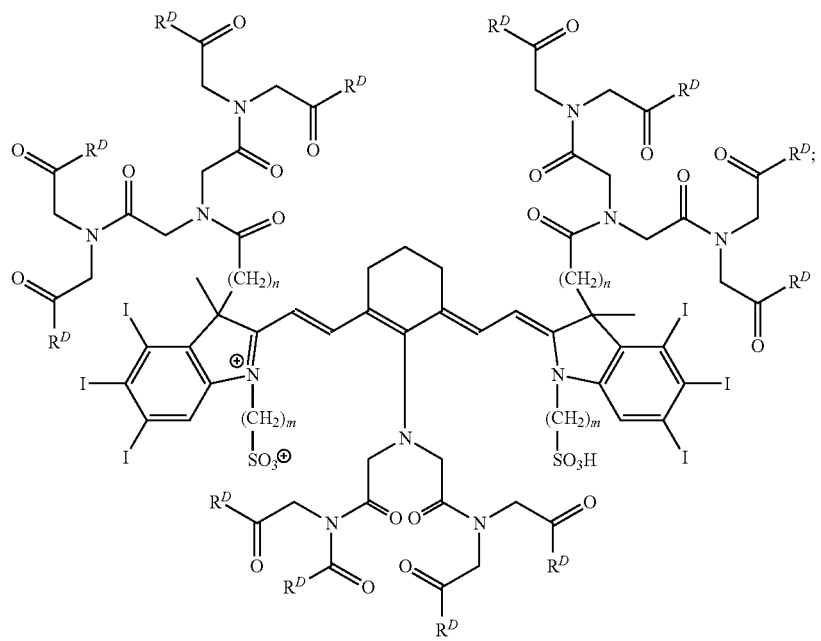
where $R^D$ contains a dye
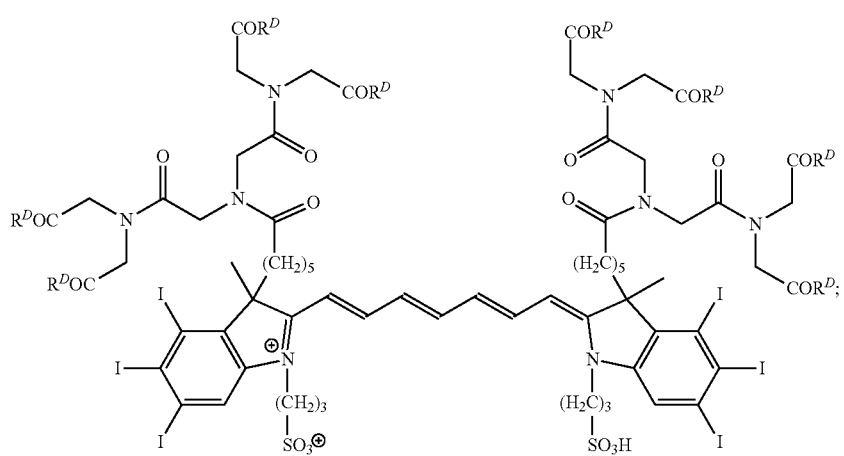
where $R^D$ contains a dye -continued
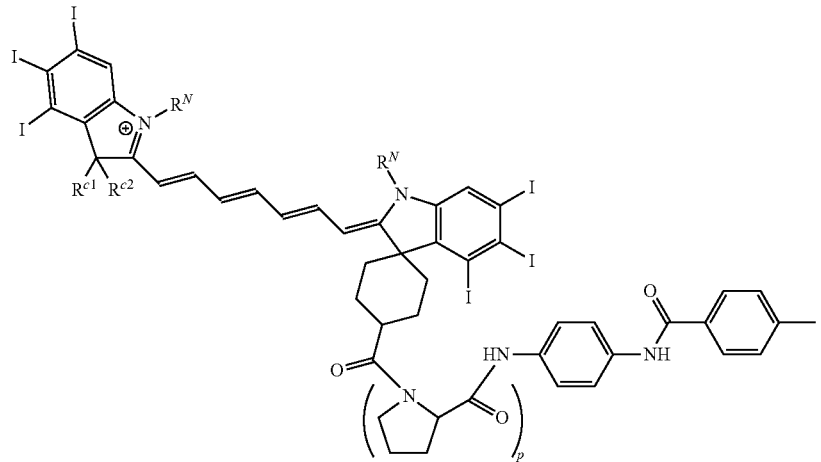
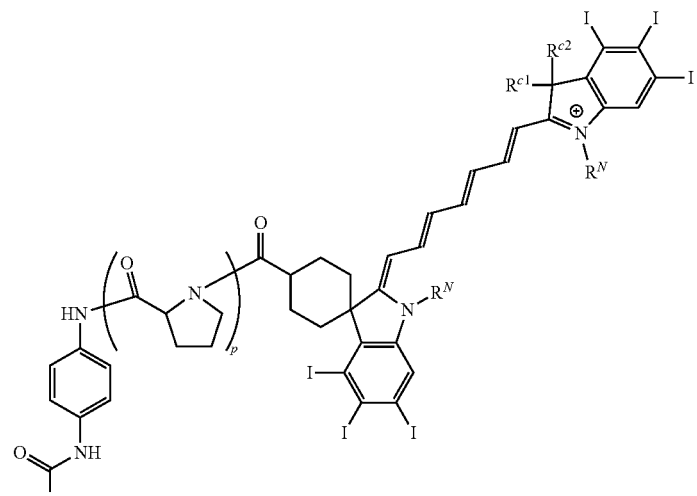
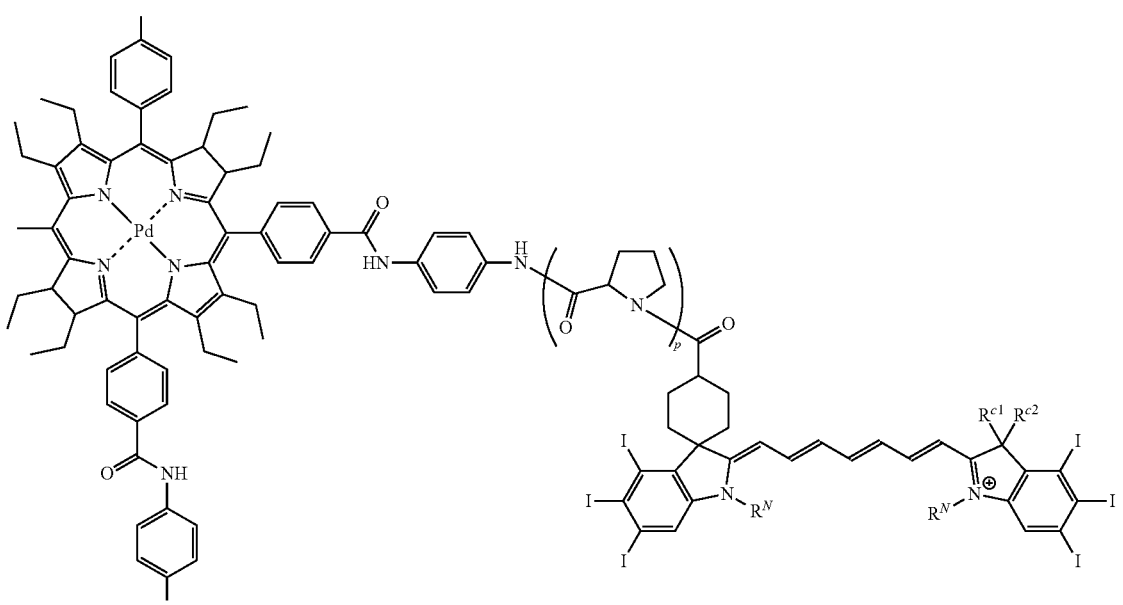

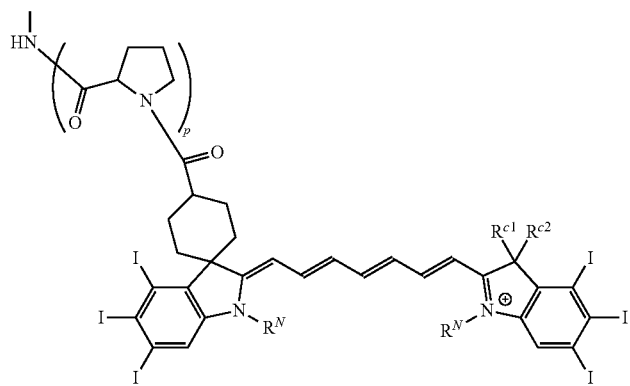
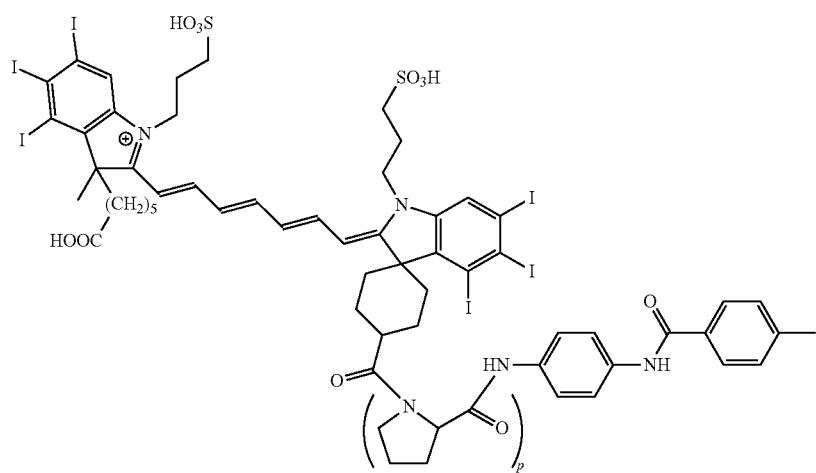
14
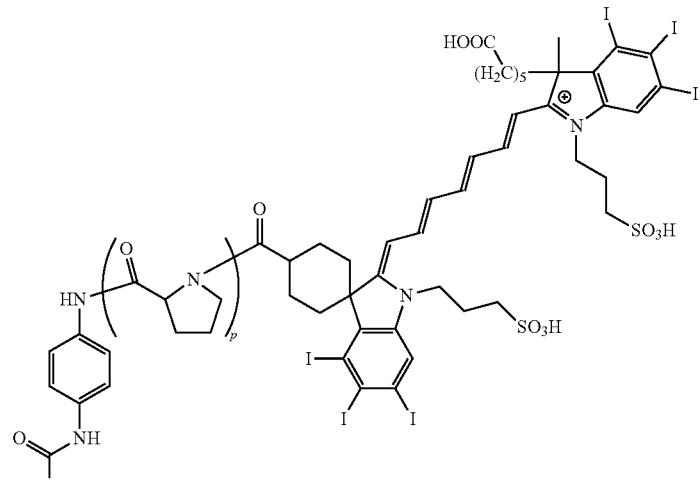

-continued
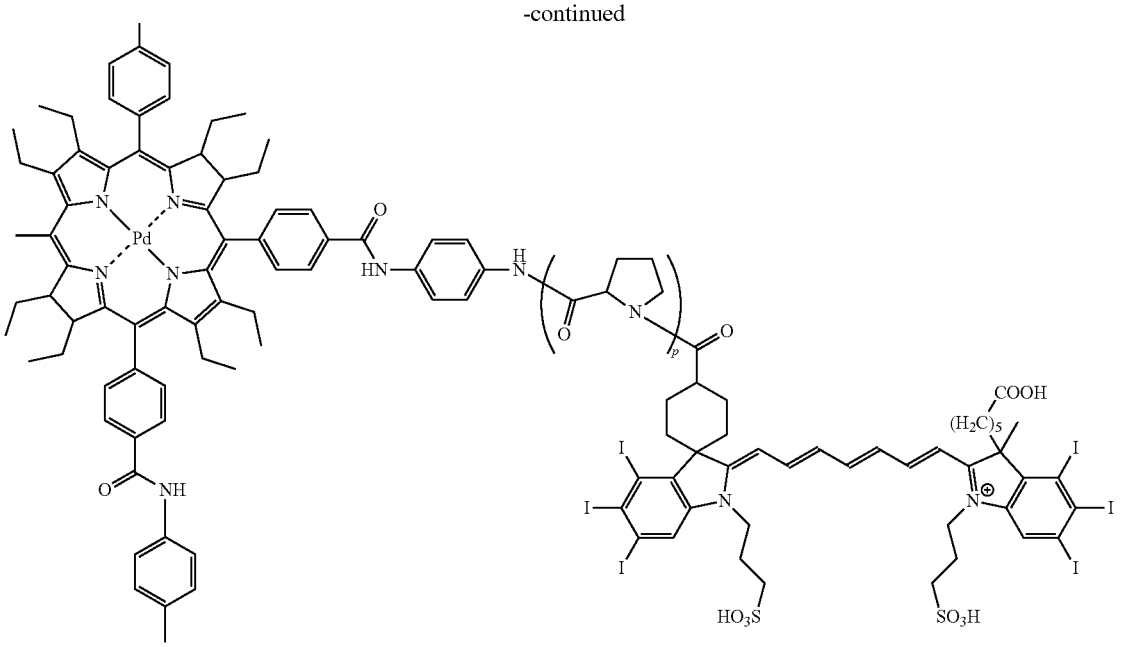
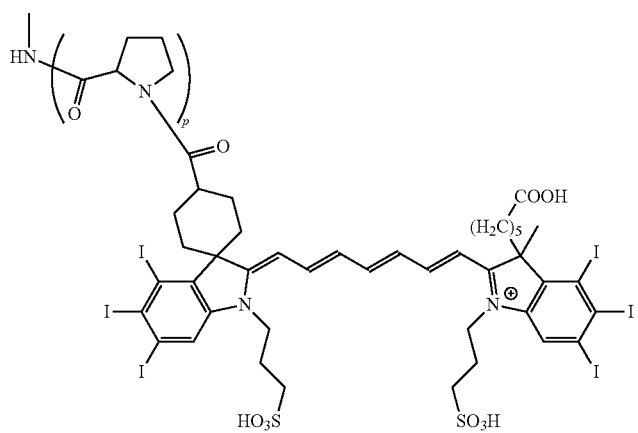
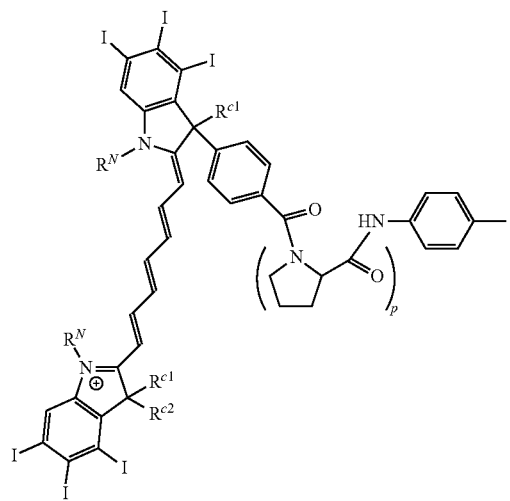

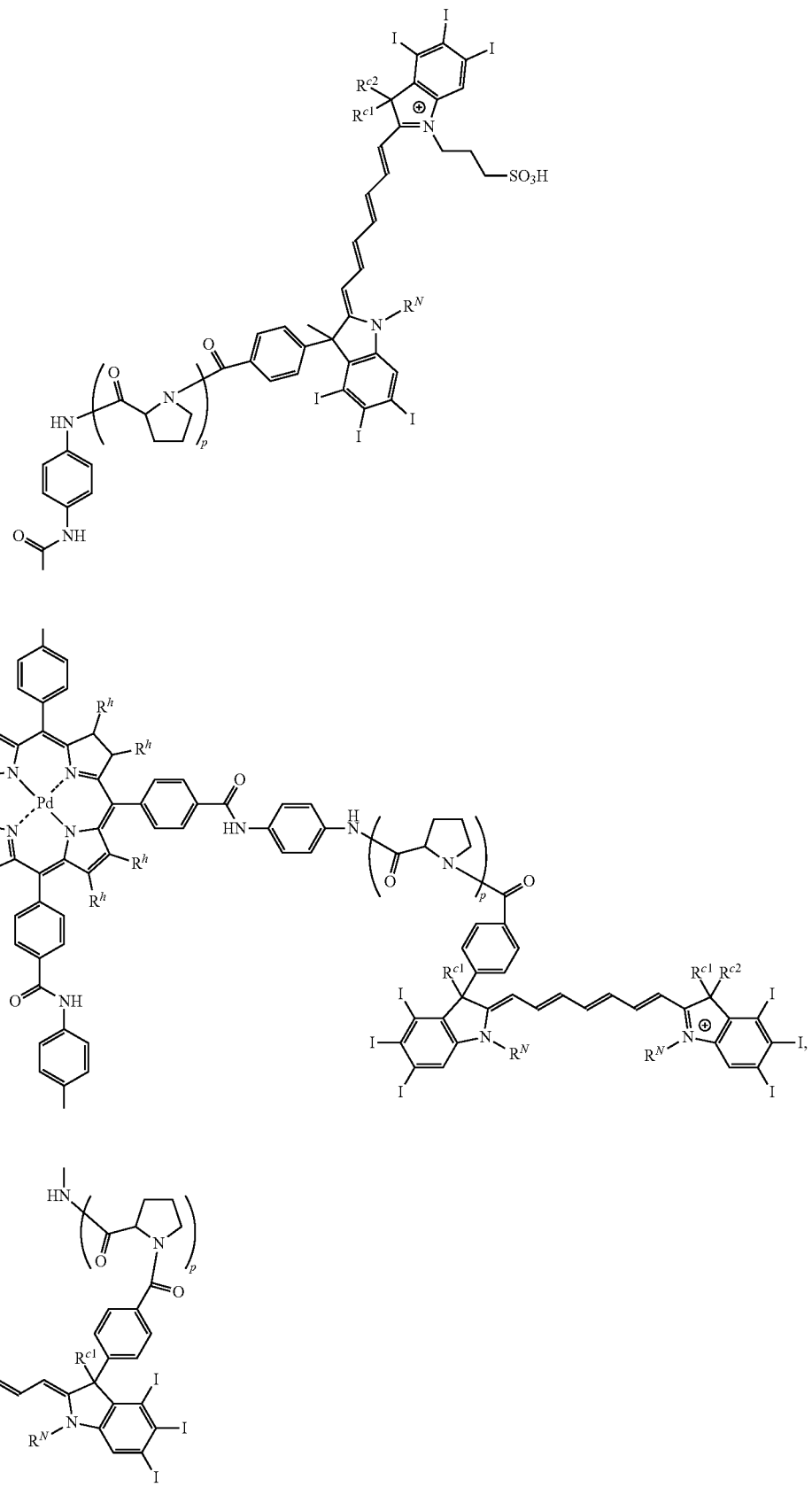

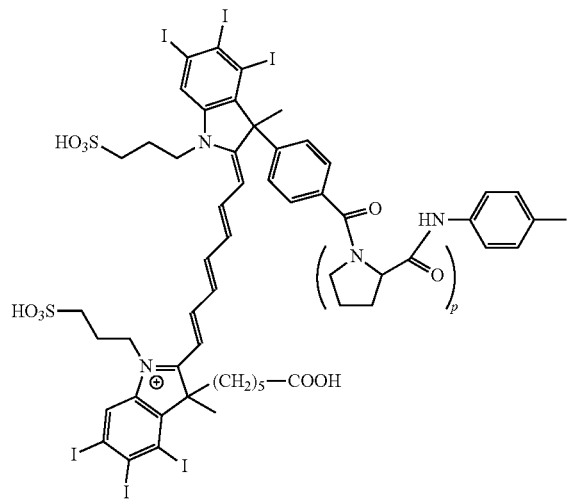
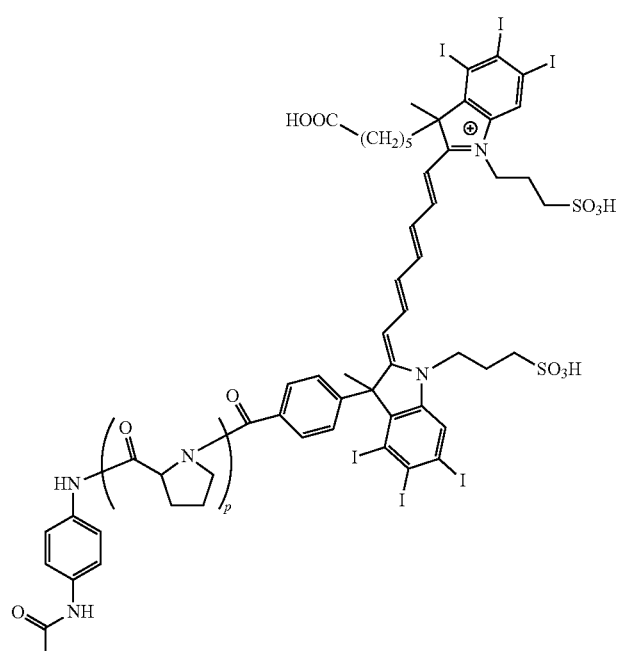
16

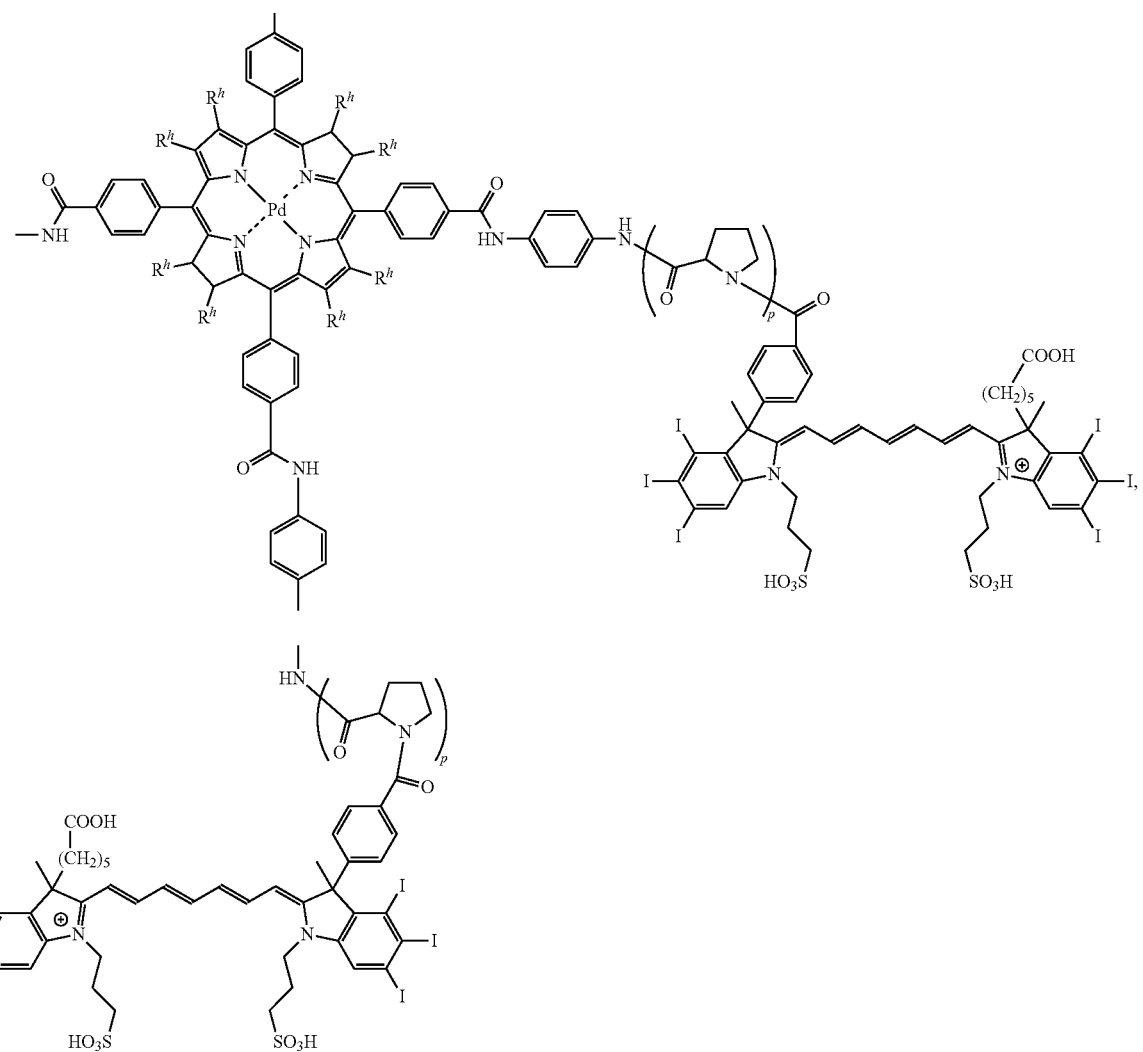
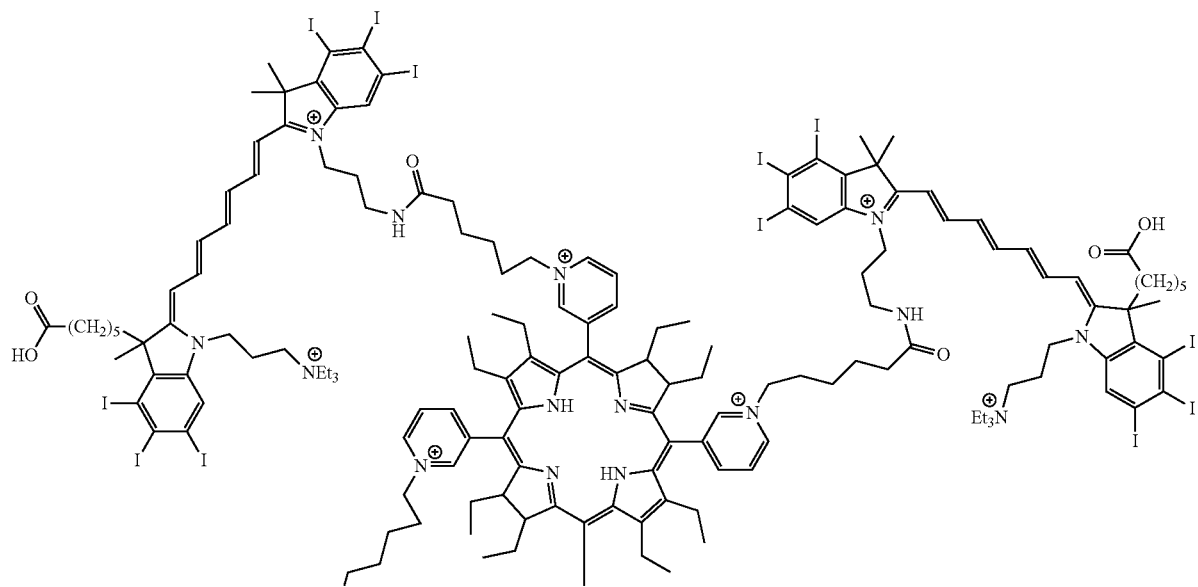

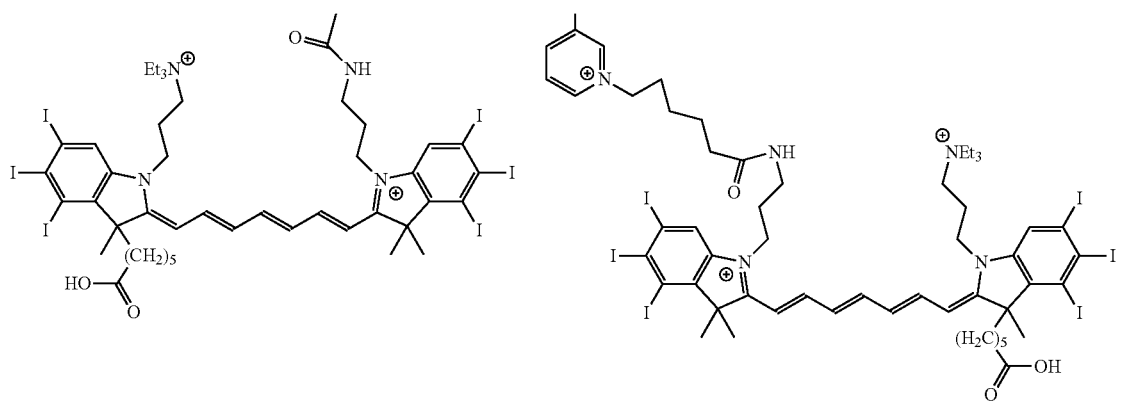
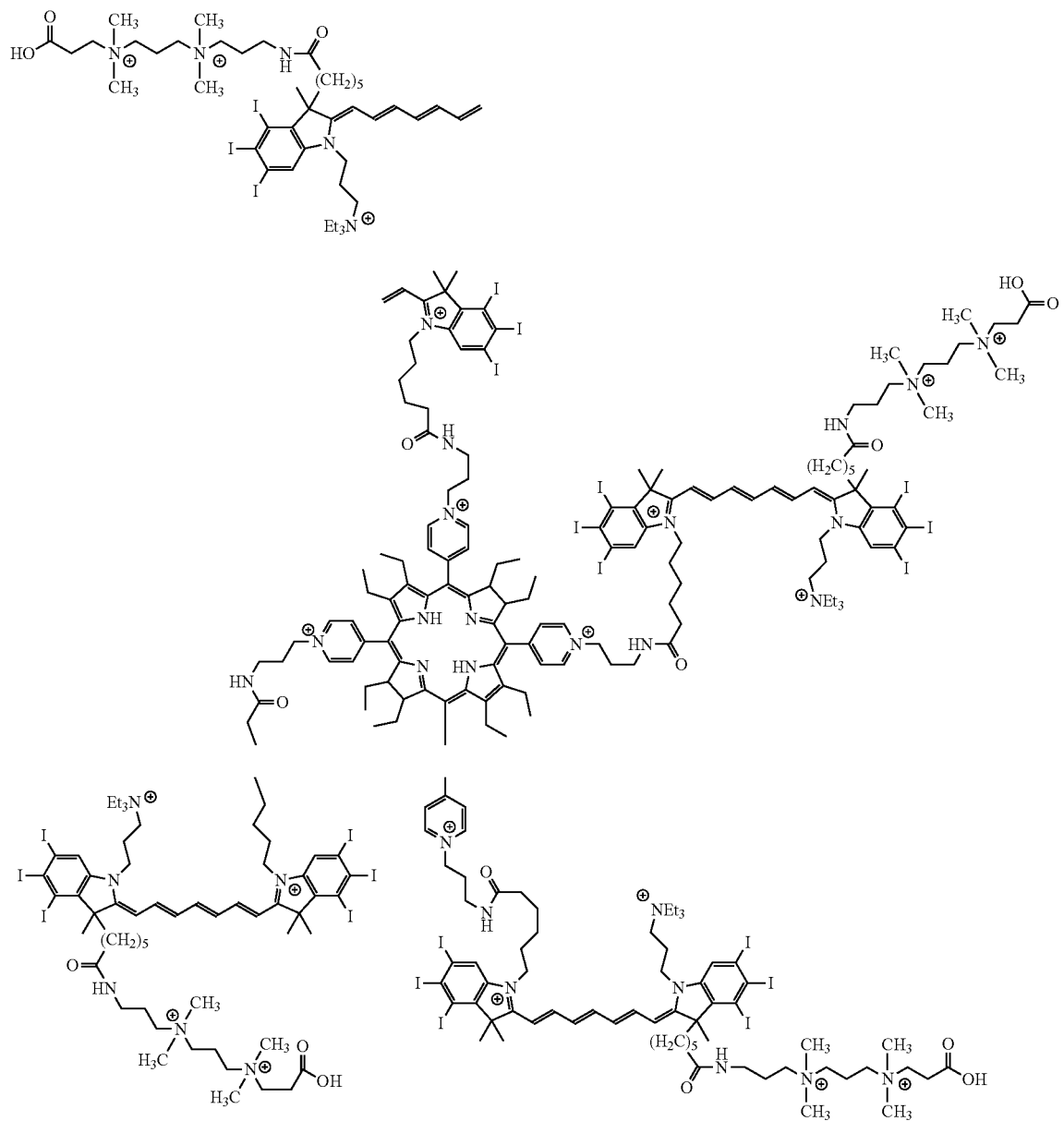

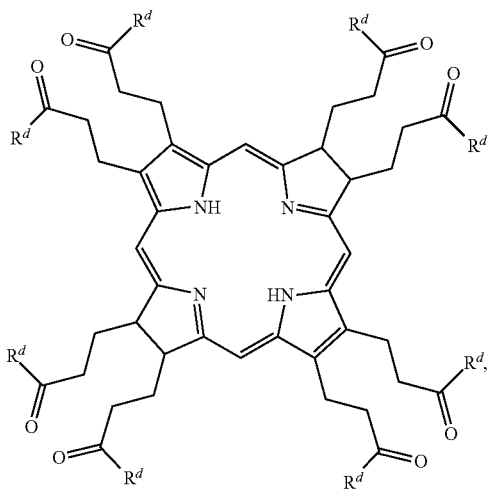
19
where: $R^d$ is:
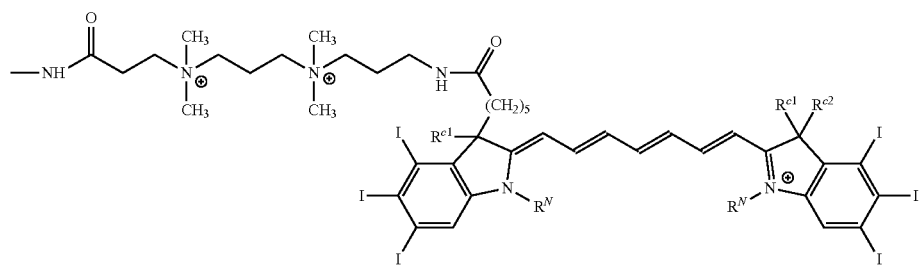
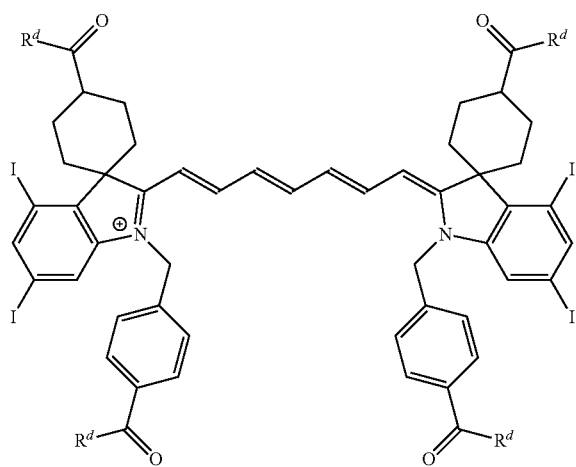
20

-continued where: $R^d$ is:

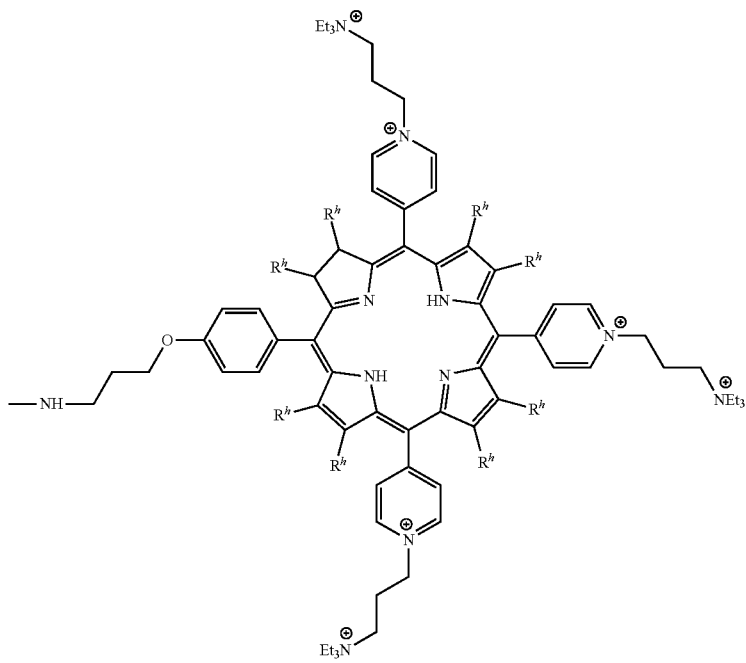

where:

each $R^{c1}$ and $R^{c2}$ is independently selected from alkyl, —$(CH_2)_n$—COOH, —$(CH_2)_n$—$SO_3H$,

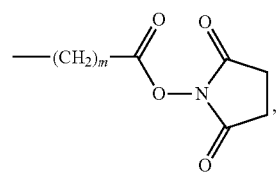

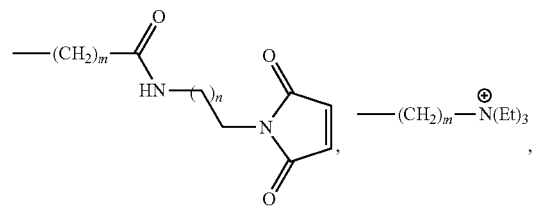

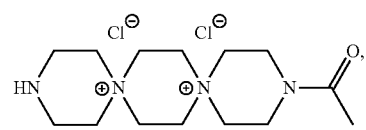

—$(CH_2)_n$—PO(OEt)$_2$, —$(CH_2)_n$—PO(OH)(OEt), or —$(CH_2)_n$—PO(OH)$_2$, or contains a dye;

each $R^N$ is independently selected from alkyl, —$(CH_2)_k$—COOH, —$(CH_2)_k$—$SO_3H$,

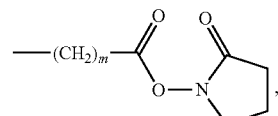

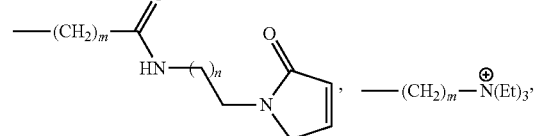

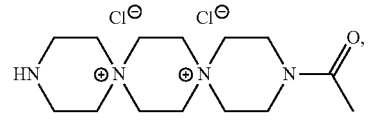

—$(CH_2)_k$—PO(OEt)$_2$, —$(CH_2)_k$—PO(OH)(OEt), or —$(CH_2)_k$—PO(OH)$_2$, or contains a dye;

each $R^h$ is independently selected from hydrogen, alkyl, aryl, or adjacent substituents $R^h$ form a cycle; and k=1-20; m=1-20; n=1-20; p=1-20.

Halogenated dendrimeric dyes of the present disclosure have substantially improved light sensitivity (extinction coefficients at the excitation wavelength), brightness (extinction coefficients multiplied by the fluorescence quantum yield), photostability, and sensitizing efficiency (minimal molar concentration threshold mediating a sensitizing effect).

Figure 2:
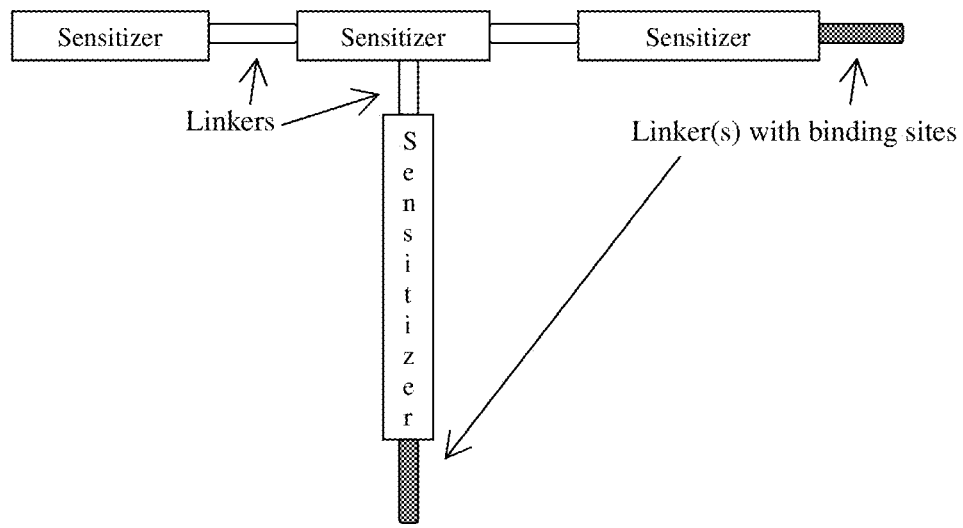
FIG. 2 is a schematic representation of sensitizer molecules bound to a carrier by linker-spacer groups with reactive group(s).
Figure 3:
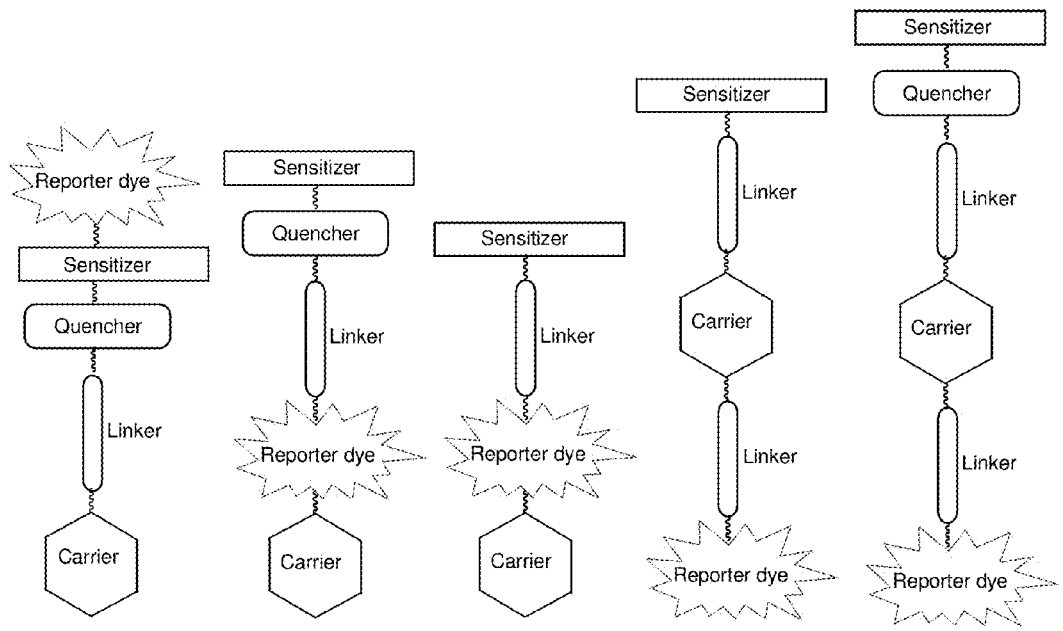
FIG. 3 is a schematic representation of conjugates of sensitizer molecules with quencher, reporter dye and carrier components.

Two or more polymethine dyes of the present disclosure can be bound together to form a larger molecular conjugate with greater overall fluorescence and/or greater ROS efficiency, as shown in FIGS. 1 and 2. Such conjugates can be formed as of multiples of the same polymethine dye, different polymethine dyes, or at least one polymethine dye with other photosensitizer, reporting, or photosonic dyes (see FIG. 3).

Figure 4:
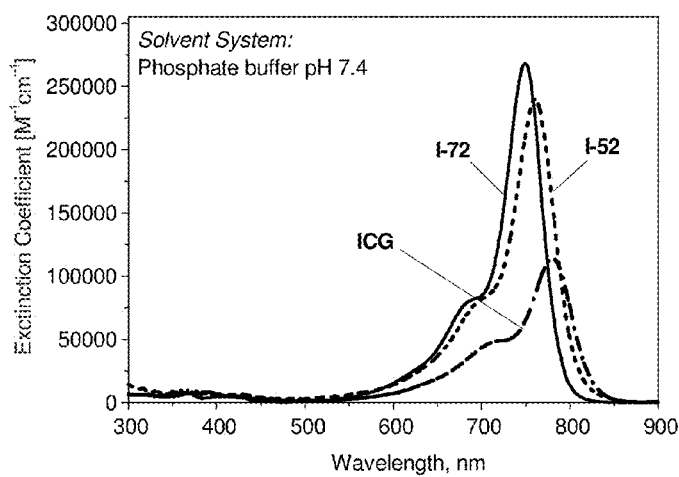
FIG. 4 is a graph of absorption spectra of iodinated cyanines I-52 and I-72 as compared to ICG in phosphate buffer (pH 7.4).
Figure 5:
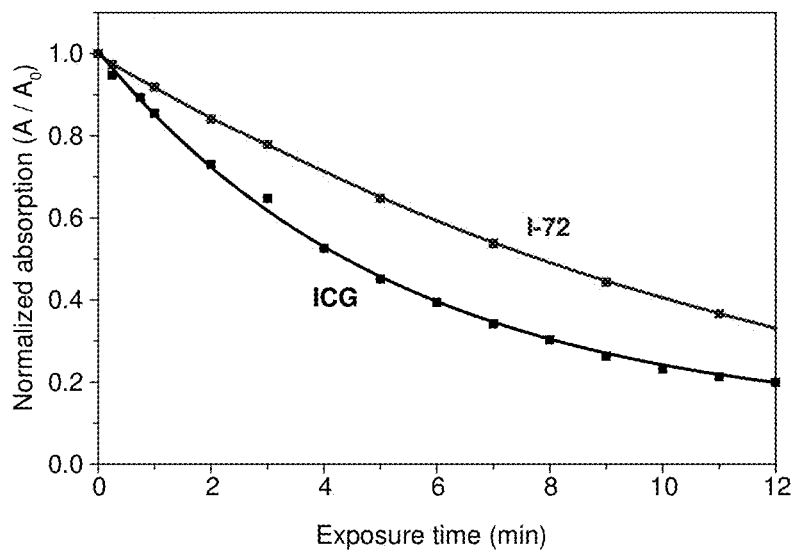
FIG. 5 is a graph of relative decrease of the long-wavelength absorption band (photostability) of iodinated cyanine I-72 as compared to ICG in water upon irradiation with a 200 mW 660-nm diode laser.
Figure 6:
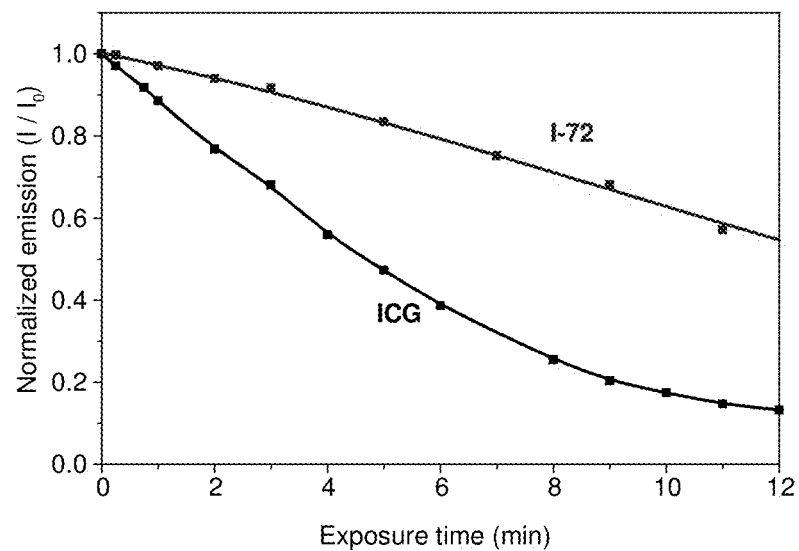
FIG. 6 is a graph of relative decrease of the emission intensity (photostability) of iodinated cyanine I-72 as compared to ICG in water upon irradiation with a 200 mW 660-nm diode laser.
Figure 7:
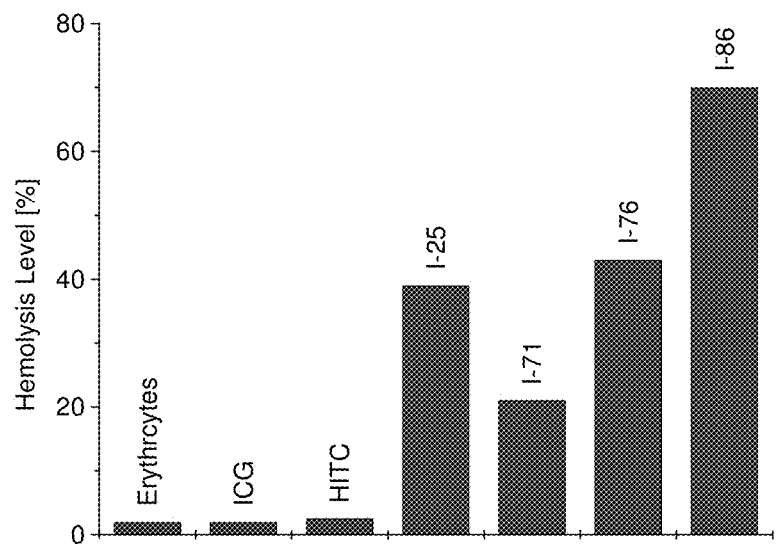
FIG. 7 is a graph of phototoxicity of sensitizers estimated via hemolysis level (0.1 µM, 250 W IR lamp, 60 min exposure time).
Figure 8:
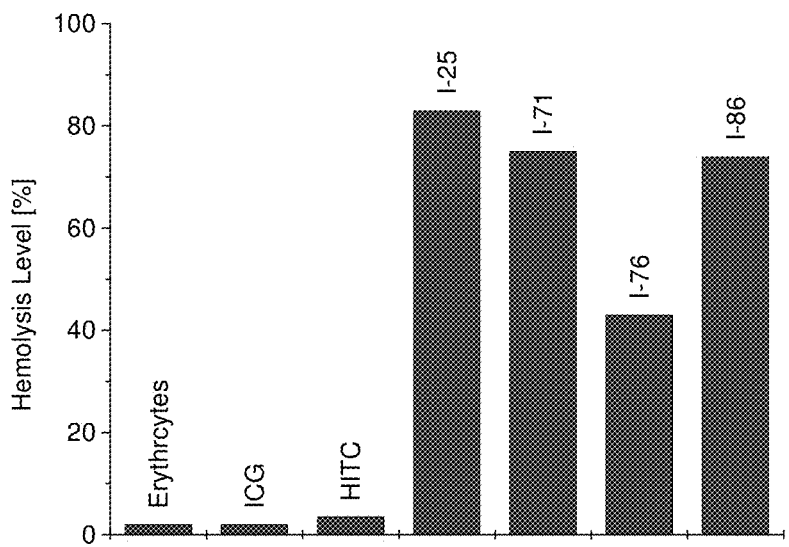
FIG. 8 is a graph of phototoxicity of sensitizers estimated via hemolysis level (0.5 µM, 250 W IR lamp, 30 min exposure time).

Spectral characteristics of selected polymethine dyes of the disclosure are set out in Table 1 in Example 38. Representative spectra are shown in FIG. 4, and photostability data are shown in FIGS. 5 and 6. These data demonstrate that the introduction of halogen atoms in accordance with the present disclosure increases both fluorescence quantum yield and photostability of the dyes.

The efficacy of halogenated compounds of the present disclosure has been demonstrated by both photodynamic and dark toxicity testing using erythrocytes as model cells.

The obtained data are shown in Table 2 (Example 42), FIGS. 7, 8, and FIGS. 10, 11 where the hemolysis percentage indicates the dark toxicity level and phototoxicity effectiveness. The hemolysis level was dependent on both sensitizing efficiency and cell uptake. The majority of compounds in Table 2 and FIGS. 7, 8, and FIGS. 10, 11 have generally similar hydrophobicity/hydrophilicity characteristics and therefore approximately equal uptake, as confirmed by fluorescence microscopy. The best sensitizers exhibit the lowest dark toxicity and highest phototoxicity at minimal concentrations. As can be seen from the data, the halogenated cyanines of the present disclosure exhibited sensitizing effectiveness that was substantially higher than non-halogenated cyanines such as ICG and HITC.

Direct chemical singlet oxygen generation (SOG) and ROS quantum yield were measured using 1,3-diphenylisobenzofuran (DPBF) as the single oxygen sensitive dye, according to the procedure of W. Spiller et al., J. Porphyrins Phthalocyanines, 2 (1998) 145-158; H. Mojzisova et al. Photochem. Photobiol. Sci., 8 (2009) 778-787. The obtained data (Table 2 in Example 42 hereof) evidenced that the introduction of iodine and bromine atoms increased the SOG and ROS quantum yield.

The dark cytotoxicity of almost all of the halogenated cyanines was found to be as low as that of non-halogenated cyanines of similar structure.

The present disclosure in other aspects contemplates the use of oxic agents and conditions, e.g., ozone, oxygen-carrying fluorocarbons, carbogen, high pressure oxygen, and increased oxygen, to improve photodynamic therapy in conjunction with the use of sensitizing and reporting halogenated compounds and compositions of the present disclosure. Therapeutic approaches in this respect may include blood oxygen enhancement using pressure and/or high oxygen concentration chambers, the use of oxygen on protein as a delivery vehicle for increasing localized oxygen, etc.

Halogenated compounds and compositions of the disclosure are useful as reporters and/or sensitizers and can be used to destroy cells and tissues following activation by light, including but not limited to applications such as photodynamic therapy, photodynamic antimicrobial chemotherapy (PACT), cancer treatment, targeted vascular disruption, lipid targeting on vascular walls, cosmetic applications, antimicrobial coating materials and sonodynamic therapy or diagnostic, analytical reporting and/or imaging. In general, the dyes and their compositions are administered in effective amount to a human or animal patient in whom it is desired to destroy certain cells or tissues or for diagnostic applications.

In one aspect, the disclosure relates to a method of generating reactive oxygen species (ROS) at a biological locus, comprising introducing a composition of the disclosure to such locus, and transmitting radiation to the composition at the locus that is effective to cause the composition to generate ROS at the locus. The composition includes a dye of the disclosure, and/or a conjugate thereof, that is effective under irradiation conditions to generate ROS at the locus, e.g., a corporeal site of a human or animal subject.

The method may further comprise introducing exogenous oxygen or ozone to the locus to increase available oxygen at the locus for generating ROS at the locus. The composition may be introduced to the locus on a carrier, e.g., at least one carrier species selected from the group consisting of bacteriophages and antibodies.

The method is desirably carried out so that the dye in the composition is substantially completely photobleached by the radiation transmitted to the locus. Correspondingly, the radiation transmitted to the locus is desirably limited to the amount required for the dye in the composition to be substantially completely photobleached by the radiation transmitted to the locus.

As discussed hereinabove, in vivo usage of photosensitizers for phototherapy targeting specific loci in the body entails many competing considerations deriving from the variable characteristics of the photosensitizer, including its photooxidation sensitivity, its concentration, its selectivity, its photostability/photolability properties, as well as associated variable properties of carriers that are used for delivery of the photosensitizer agent to the targeted corporeal locus, and the variables associated with the light source, such as intensity/flux characteristics, spectral characteristics of emitted radiation, permissible placement of the light source in relation to the body, etc., and the bodily variables themselves, e.g., size, shape and location of a tumoral mass or infected site and the characteristics of its proximate corporeal environment and constituent fluid, bone and tissue components.

In the context of this plethora of variables, it is necessary to effect the therapeutic intervention on the target locus of the body undergoing treatment, while functionally minimizing adverse effect on corporeal regions outside the target locus. In some instances, the imperfect targeting of photosensitizer carriers, e.g., antibodies, proteins, etc. that invariably occurs in the therapeutic intervention makes it necessary to deactivate the photosensitizer in a selective, or non-selective, manner in order to limit damage to non-targeted corporeal regions. In these circumstances, photosensitizer dyes and dye conjugates of the present disclosure are particularly advantageous, exhibiting photostability characteristics that enable rapid photobleaching and photooxidation of the photosensitizer to be achieved with moderated ROS generation, e.g., in high light dose regions near the light source when deep tissue activation is being conducted. The photosensitizer dyes and dye conjugates of the present disclosure thereby dramatically broaden the range and types of approaches that can be utilized for effective phototherapy.

In one embodiment, the disclosure contemplates a treatment methodology utilizing self-limiting ROS generator photosensitizers for photodynamic therapy where low intensity activating spectrum light is used over large areas of the body to slowly deactivate residual photosensitizer without inducing sufficient reactivity to do damage. As these concentrations should be low, a slowly increasing ramp of intensity can be used to remove sensitivity. The intensity and time matrix should be sufficient so as to leave the patient with unintended minimal photosensitizer activation risk from reasonable sun or other light source exposure (localized areas or full body, such as a tanning bed, but much higher intensity light at just the red to infra-red spectrum). This method can be accomplished by (1) using low intensity spectrum light for a long period of time sufficient for practical photosensitizer deactivation, (2) slowly ramping the activating light intensity upward over time to speed the deactivation process, (3) slowly changing the spectrum of the light from green or yellow light to red and near-infrared light, or (4) by changing both intensity and the spectrum over time.

In another technique, the disclosure relates to a treatment methodology utilizing self-limiting ROS generator photosensitizers for photodynamic therapy where activating spectrum light is used to activate photosensitizer over large areas of the body, wherever the targeted photosensitizer has concentrated, but avoiding an intensity that would induce significant damage to internal organs in which the photosensitizer-carrier conjugates may accumulate without being directly targeted (e.g., liver, kidney, spleen, lungs, etc., depending on the carrier characteristics). The procedures described in the preceding paragraph can be used to deactivate non-targeted shallow tissue prior to high intensity exposure to treat broadly distributed targeted carriers with photosensitizer for cancer, pathogens, or other biomaterials (e.g., arterial plaque, fat, circulating cancer or pathogens) deep in tissue, blood, or in the bone.

Light may also be used over long periods of time, e.g., in a range of from 4 to 5000 hours to activate the photosensitizer deep in tissue along with multiple oral, topically absorbed, or injected photosensitizer. Long term light applications can be accomplished with wearable light units or multiple long term light applications to activate the dye or dye conjugate in the administered composition.

The disclosure in another aspect relates to mediating deactivation of a photosensitizer by high frequency modulation of a light source. Such high frequency modulation enables high rate in vivo deactivation of photosensitizer to be achieved. In specific embodiments, frequency modulation of light in a range of from 100 kHz to 100 THz is carried out to photodegrade the photosensitizer.

In this frequency range of from 100 kHz to 100 THz, at the moderately high light intensities typically used in photodynamic therapy with photosensitizers, especially when activating the photosensitizer by light transmitted through a large volume of tissue, the photosensitizer exhibits a lower efficiency ROS generation and yet still exhibits high absorption and normal photodegradation.

As a result, the photosensitizer present than non-targeted tissue can be degraded without causing as much damage to such tissue, in relation to photosensitizer exposure to corresponding light lacking such frequency modulation. This "reduced damage" result is markedly less pronounced at frequency below 100 kHz.

The magnitude of the frequency modulated reduced damage effect and the optimal modulation frequency difference varies among photosensitizers and among different background environments, e.g., environments with different oxygen ($O_2$) concentration, but the effect is almost always significant.

Accordingly, the disclosure contemplates a method of treating a subject, e.g., a human or other animal subject, to whom photosensitizer has been administered resulting in presence of photosensitizer in a bodily region of the subject that is non-targeted for phototherapy, comprising transmitting to the non-targeted bodily region deactivatingly effective light that is frequency modulated in a range of from 100 kHz to 100 THz, to deactivate the photosensitizer present in such region. Such transmission of deactivatingly effective light is advantageously conducted contemporaneously with photodynamic therapy treatment of said subject, e.g., so that the PDT treatment of the subject in a targeted bodily region is carried out before, during, or after the deactivation of photosensitizer in the non-targeted bodily region of such subject, as part of a continuous or near-continuous therapeutic intervention.

The frequency modulated light can additionally be ramped in wavelength, from shorter wavelength to longer wavelength, or intensity of the light can be slowly increased while modulating light had high-frequency, in order to confine photosensitizer degradation (and accompanying inefficient generation of ROS or other reactive species) to shallow bodily regions near the light source utilized for phototherapy, prior to carrying out continuous light transmission or low frequency pulsing of the transmitted light to reach a deeper targeted cancer or pathogen.

The foregoing techniques for deactivating photosensitizers in non-targeted bodily regions are applicable to almost all photosensitizers and to all light source types that can be modulated at high frequencies, including light emitting diode (LED) and laser sources, and light sources that can be modulated with chopper devices. Such modulation frequency-controlled deactivation of photosensitizer with reduced cellular/tissue damage, in relation to damage occurring in the absence of such controlled deactivation, works particularly well with photosensitizer dyes and dye conjugates of the present disclosure.

The synthesis of the cyanines, squaraines, other polymethines of the present disclosure, and their precursors, can be carried out with the use of techniques such as those disclosed in Heterocyclic Polymethine Dyes: Synthesis, Properties and Applications, Ser.: Topics in Heterocyclic Chemistry, Vol. 14, L. Strekowski (Ed.) 2008, Springer-Verlag, Berlin, Heidelberg, and A. Mishra et al., Cyanines during the 1990s: a review, Chem. Rev., 2000, V.100, 1973-2011, and/or as otherwise described herein, including procedures that have been newly developed or improved to achieve better isolation yields. The synthesis of representative dyes, precursors, and conjugates is described in illustrative Examples hereafter. The dyes of the present disclosure can be fine-tuned to a desirable wavelength and made compatible with available light sources by appropriate modification of their chromophore system and substituents. These dyes can also be fine-tuned in respect of hydrophobic-hydrophilic properties, reactive groups, and other functionalities. Further improvements can be achieved by synthesizing dendrimeric dyes, as carried out in accordance with the present disclosure, utilizing generalized synthetic methods known in the art.

The features and advantages of the present disclosure, and compounds, compositions, and methods thereof, are more fully shown by the following non-limiting examples, wherein all parts and percentages are by weight, unless otherwise expressly stated.

EXAMPLES

1. Synthesis of Intermediates

Example 1

Synthesis of 3,5-diiodophenylhydrazine

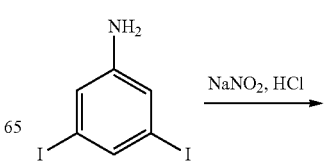

-continued

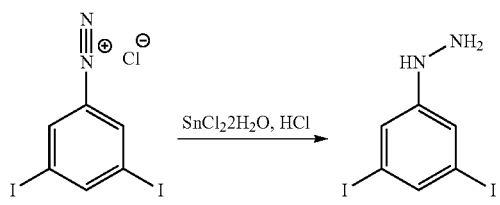

3,5-Diiodoaniline was obtained by the procedure of M. Bérubé (M. Bérubé, et al. Synthesis of Simplified Hybrid Inhibitors of Type 1 17β-Hydroxysteroid Dehydrogenase via the Cross-Metathesis and the Sonogashira Coupling Reactions, Organic Lett. 6 (2004) 3127-3130). 5 g (14.5 mmol) of 3,5-diiodoaniline were stirred with the solution of 5 mL of concentrated hydrochloric acid and 5 mL of water. The mixture was cooled to about −10° C. and 5.5 mL of 20% aqueous solution of $NaNO_2$ was added dropwise with continuous stirring. The suspension was allowed to stir for another 40 minutes. Next, the cooled solution of 10.8 g (47.9 mmol) of $SnCl_2 \cdot 2H_2O$ in 11 mL of concentrated HCl was added dropwise at −10° C. to the suspension of diazocompound. The reaction mixture was kept −10° C. for one hour and at 5° C. overnight. The obtained precipitate of a double salt with tin chloride was filtered off and washed with water. The residue was resuspended in water and added concentrated aqueous solution of NaOH to alkaline medium. The 3,5-diiodophenylhydrazine was extracted with ether, the organic layer was washed in turn with aqueous NaOH, $Na_2S_2O_3$ and water, and dried with $CaCl_2$. Ether was evaporated to give 4.2 g of 3,5-diiodophenylhydrazine. $^1$H-NMR (200 MHz, DMSO-$d_6$), δ, ppm: 7.10 (2H, d, 1.2 Hz, arom.), 6.92 (1H, d, 1.2 Hz, arom.), 5.51 (1H, s, NH), 4.12 (2H, broad s, $NH_2$).

Example 2

Synthesis of 4,6-diiodo-2,3,3-trimethyl-3H-indole

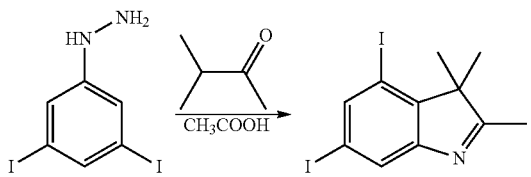

2 g of 3,5-diiodophenylhydrazine (5.5 mmol), and 1 mL (9.3 mmol) of 3-methyl-2-butanone were refluxed in 15 mL of acetic acid for 20 hours. The acetic acid was evaporated and the residue was dissolved in ether. Insoluble precipitate was filtered off, and the etheric solution was washed with aqueous solutions of $NaHCO_3$, followed by $Na_2S_2O_3$ and water. The organic layer was dried with $CaCl_2$ and ether was removed under reduced pressure by a rotary evaporator to give 1.4 g of 4,6-diiodo-2,3,3-trimethyl-3H-indole. $^1$H-NMR (200 MHz, DMSO-$d_6$), δ, ppm: 7.92 (1H, d, 1.1 Hz, arom.), 7.79 (1H, d, 1.1 Hz, arom.), 2.22 (3H, s, 2-$CH_3$), 1.32 (6H, s, $C(CH_3)_2$).

Example 3

Synthesis of 4,6-diiodo-1,2,3,3-tetramethyl-3H-indolium iodide

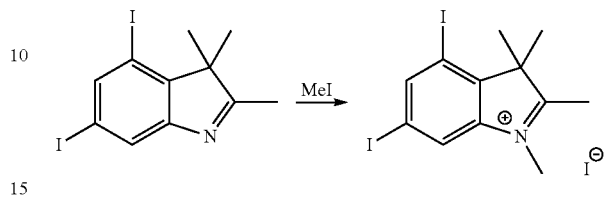

1.05 g (2.5 mmol) of 4,5,6-triiodo-2,3,3-trimethyl-3H-indole and 2 mL of iodomethane were heated at 45° C. for 6 hours in a sealed tube. The formed precipitate was filtered, washed with acetone. Yield: 900 mg. $^1$H-NMR (300 MHz, DMSO-$d_6$), δ, ppm: 8.37 (2H, d, 5.4 Hz, arom.), 3.92 (3H, s, $NCH_3$), 2.79 (3H, s, $CH_3$), 1.61 (6H, s, $C(CH_3)_2$).

Example 4

Synthesis of 3,4,5-triiodophenylhydrazine

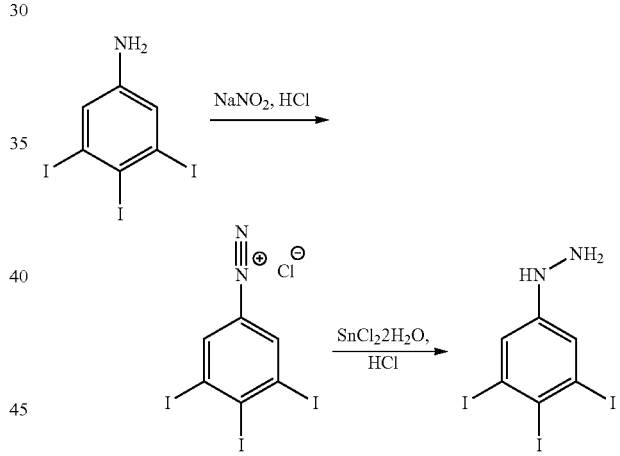

3,4,5-Triiodoaniline was obtained by the procedure of L. Kalb (L. Kalb et al., Über substituierte Indol-2-carbonsäure-8-propionsäuren and einige jodierte Bensolderivate, Chem. Ber. 59 (1926) 1860-1870). 4 g (8.5 mmol) of 3,4,5-triiodoaniline were stirred with the solution of 2.3 mL of concentrated hydrochloric acid and 2.3 mL of water. The mixture was cooled to about −10° C. and the equivalent quantity of 2.5M solution of $NaNO_2$ was added dropwise with intensive stirring. The reaction mixture was continued stirring for 30 min at −10° C. Next, the cooled solution of 5.75 g (25.5 mmol) of $SnCl_2 \cdot 2H_2O$ in 6 mL of concentrated HCl was added dropwise at −10° C. to the suspension of diazocompound. The reaction mixture was kept at −10° C. for one hour and at 5° C. overnight. The obtained precipitate was filtered off and washed with water to yield 4.7 g of 3,4,5-triiodophenylhydrazine, as a double salt with tin chloride, which was used for following step without additional treatment or purification. $^1$H-NMR (200 MHz, DMSO-$d_6$), δ, ppm: 10.14 (2H, broad s, $NH_2$), 8.46 (1H, s, NH), 7.5 (2H, s, arom.).

Example 5

Synthesis of 4,5,6-triiodo-2,3,3-trimethyl-3H-indole

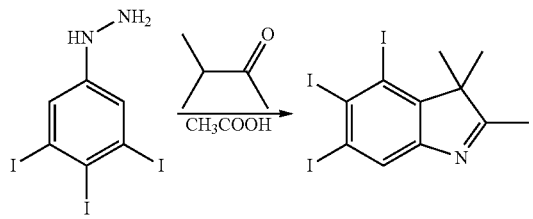

2 g of 3,4,5-triiodophenylhydrazine, and 0.86 g (10 mmol) of 3-methyl-2-butanone were refluxed in 15 mL of acetic acid for 16 hours. The acetic acid was evaporated, the residue was dissolved in chloroform, washed with aqueous solutions of $NaHCO_3$, followed by $Na_2S_2O_3$ and water. The organic layer was dried and chloroform was removed under reduced pressure by a rotary evaporator. The residue was column purified (Silica gel 60, 0-2% methanol-chloroform) to give 0.6 g of 4,5,6-triiodo-2,3,3-trimethyl-3H-indole. $^1$H-NMR (200 MHz, DMSO-$d_6$), δ, ppm: 8.04 (1H, s, arom.), 2.19 (3H, s, 2-$CH_3$), 1.30 (6H, s, $C(CH_3)_2$).

Example 6

Synthesis of 4,5,6-triiodo-1,2,3,3-tetramethyl-3H-indolium iodide

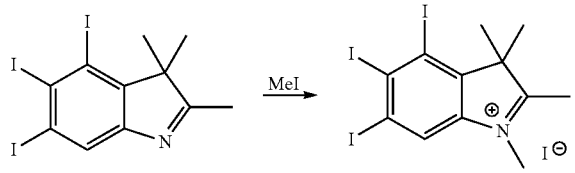 [SMILES: "MeI" ; CC1=Nc2cc(I)c(I)c(I)c2C1(C)C ; CC1=[N+](C)c2cc(I)c(I)c(I)c2C1(C)C ; [I-]]

0.6 g (1.1 mmol) of 4,5,6-triiodo-2,3,3-trimethyl-3H-indole and 0.78 g (5.5 mmol) of iodomethane were heated at 30-40° C. for 20 hours in a sealed tube. The formed precipitate was filtered, and washed with small amounts of benzene and acetone to yield 350 mg of 4,5,6-triiodo-1,2,3,3-tetramethyl-3H-indolium iodide. $^1$H-NMR (200 MHz, DMSO-$d_6$), δ, ppm: 8.53 (1H, s, arom.), 3.93 (3H, s, $NCH_3$), 2.77 (3H, s, $CH_3$), 1.60 (6H, s, $C(CH_3)_2$).

Example 7

Synthesis of 3-[3-(5-carboxypentyl)-4,5,6-triiodo-2,3-dimethyl-3H-1-indoliumyl]-1-propanesulfonate

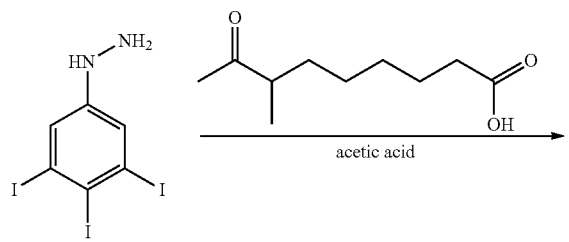

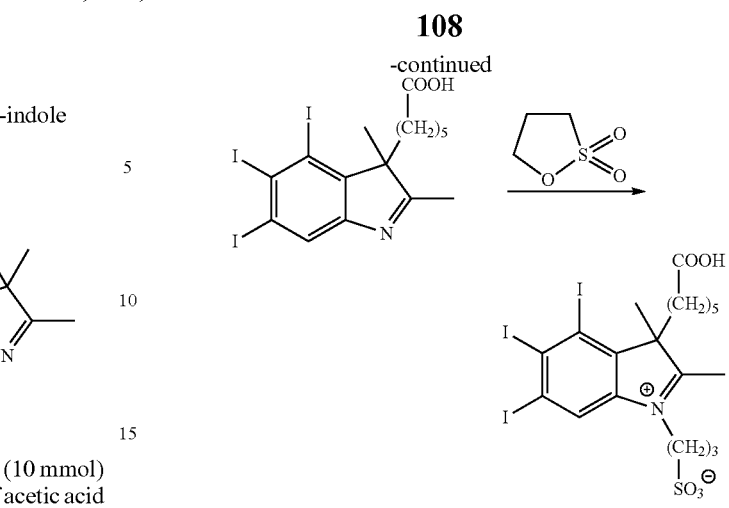

A mixture of 3,4,5-triiodophenylhydrazine 2 g (4 mmol) and 1 g (5 mmol) of 7-methyl-8-oxononanoic acid was refluxed in 15 mL of acetic acid for 16 hours. The acetic acid was evaporated, and the residue was dissolved in $CHCl_3$, and washed by aqueous $NaHCO_3$ and water. The organic layer was dried with $CaCl_2$ and solvent was removed under reduced pressure by a rotary evaporator. The residue was column purified (Silica gel 60, 0-4% methanol-chloroform) to give 0.6 g of 6-(4,5,6-triiodo-2,3-dimethyl-3H-3-indolyl)hexanoic acid. $^1$H-NMR (200 MHz, DMSO-$d_6$), δ, ppm: 8.02 (1H, s, arom.), 2.16 (3H, s, 2-$CH_3$), 2.07 (2H, t, $CH_2COOH$), 1.65-1.05 (6H, m, $CH_2$), 1.26 (3H, s, $CH_3$), 0.58-0.20 (2H, m, $CH_2$).

600 mg (0.94 mmol) of 6-(4,5,6-triiodo-2,3-dimethyl-3H-3-indolyl)hexanoic acid was heated with 600 mg (4.7 mmol) of 1,3-propane sultone at 100° C. for 40 minutes. The raw product was column purified (Silica gel 60, 0-40% methanol-chloroform) to give 300 mg of 3-[3-(5-carboxypentyl)-4,5,6-triiodo-2,3-dimethyl-3H-1-indoliumyl]-1-propanesulfonate: 7.39 (1H, s, arom.), 4.31 (2H, m, $NCH_2$), 3.27 (3H, s, $CH_3$), 2.34-2.02 (2H, m, $CH_2$), 2.19 (2H, t, $CH_2CO$), 1.98-1.65 (4H, m, $CH_2$), 1.31 (3H, s, $CH_3$), 1.43-1.00 (4H, m, $(CH_2)_3$), 0.62-0.35 (2H, m, $CH_2$).

Example 8

Synthesis of 2,3,3-trimethyl-1-(3-triethylammoniopropyl)-3H-indolium bromide chloride (1)

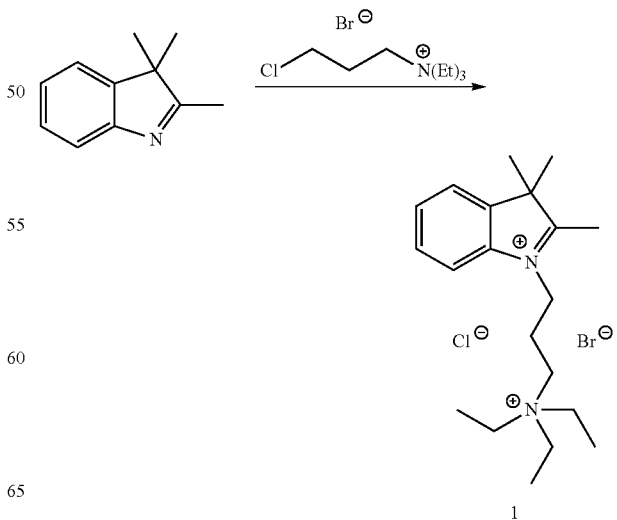

Freshly distilled 2,3,3-trimethylindolenine (0.53 g, 3.3 mmol) and N-(3-bromopropyl)triethylammonium chloride (1.01 g, 3.9 mmol) were mixed in the thick-wall tube and placed under an argon atmosphere. The mixture was then heated at 140° C. for 1.5 h, giving a deep red viscous product, which solidified to a glass on cooling. It was ground to a powder under acetone; product was collected by filtration, triturated 3 times with 10 mL portions of acetone and dried under vacuum to give 0.45 g (36%) of 2,3,3-trimethyl-1-(3-triethylammoniopropyl)-3H-indolium bromide chloride as a white powder. $\delta_H$ (200 MHz, DMSO-$d_6$) 8.10 (1H, d, 6.7 Hz, arom.), 7.87 (1H, d, 5.8 Hz, arom.), 7.75-7.58 (2H, m, arom.), 4.56 (2H, t, 7.3 Hz, $N^+CH_2$), 3.27 (6H, q, 6.0 Hz, $N^+(CH_2)_3$), 2.91 (3H, s, $CH_3$), 2.34-2.10 (2H, m, $N^+CH_2$), 1.56 (6H, s, $(CH_3)_2$) 1.36-1.05 (11H, m, $CH_2$, $(CH_3)_3$).

Example 9

Synthesis of 3-[3-(5-carboxypentyl)-5-iodo-2,3-dimethyl-3H-1-indoliumyl]-1-propanesulfonate (2)

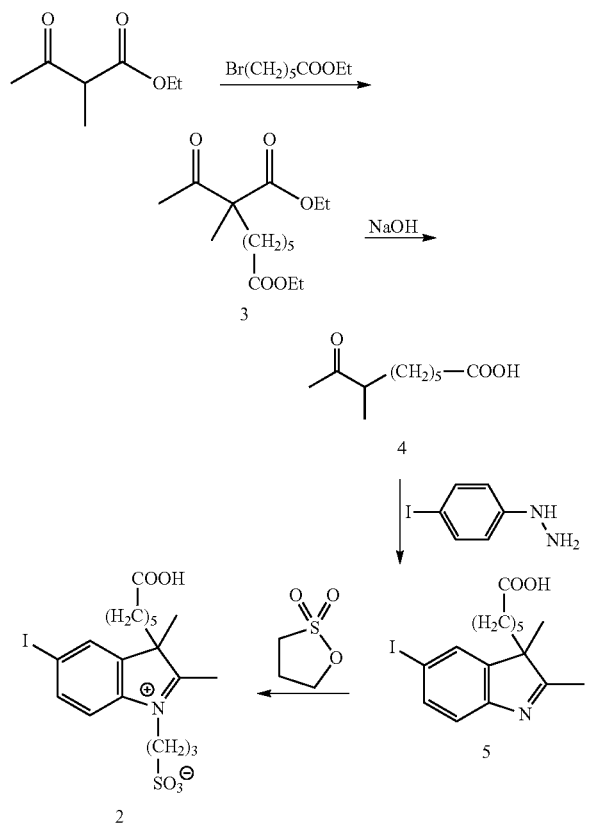

A mixture of 13.4 g (0.12 mol) of potassium tert-butoxide and 100 g of tert-butanol was stirred and heated until the tert-butoxide totally dissolved. The solution was cooled to about 50° C. and 17 g (0.12 mmol) of ethyl 2-methylacetoacetate was added dropwise. Ethyl-6-bromohexanoate (30 g, 0.13 mmol) was then added dropwise and the reaction mixture was stirred and refluxed for 5 hours. The mixture was filtered and the solvent was removed under reduced pressure. The residue was partitioned between 1M HCl and chloroform. The organic layer was dried over magnesium sulfate and purified on silica gel using 1:10 ethyl acetate/hexane as the eluent to yield 25 g (75%) of diethyl 2-acetyl-2-methyloctanedioate (3) as yellow liquid.

The compound 3 was dissolved in 160 mL of methanol. A solution of 5.4 g NaOH in 54 mL of water was added. The mixture was heated at 50° C. overnight. Then the solution was reduced to about 50 mL, acidified to pH 1 and extracted with ethyl acetate. The organic phase was collected, dried over $MgSO_4$ and evaporated to yield 7.35 g of 7-methyl-8-oxononanoic acid (4).

The 7-methyl-8-oxononanoic acid (4) 2 g (10.74 mmol) was refluxed in 15 mL of acetic acid with 2 g (8.55 mmol) of 4-iodophenylhydrazine for 20 hours. The acetic acid was evaporated and the product was purified on Silica gel 60 (0-15% methanol in chloroform) to yield 0.96 g (29%) of 6-(5-iodo-2,3-dimethyl-3H-3-indolyl)hexanoic acid (5) as an orange solid.

$^1$H-NMR (200 MHz, DMSO-$d_6$), δ, ppm: 11.95 (1H, COOH, broad s), 7.76 (1H, arom., d, 1.4 Hz), 7.62 (1H, arom., dd, 8.1 Hz, 1.5 Hz), 7.23 (1H, arom., d, 8.1 Hz), 2.15 (3H, 2-$CH_3$, s), 2.06 (2H, $CH_2$, t, 7.2 Hz), 1.99-1.60 (2H, $CH_2$, m), 1.42-1.24 (2H, $CH_2$, m), 1.22 (3H, 3-$CH_3$, s), 1.18-0.96 (2H, $CH_2$, m), 0.72-0.24 (2H, $CH_2$, m).

500 mg (1.30 mmol) of 6-(5-iodo-2,3-dimethyl-3H-3-indolyl)hexanoic acid was heated with 500 mg (4.09 mmol) of propane sultone at 100° C. for 30 minutes to generate the 450 mg of the final product 3-[3-(5-carboxypentyl)-5-iodo-2,3-dimethyl-3H-1-indoliumyl]-1-propanesulfonate (2).

Example 10

Synthesis of 3,4,5-tribromophenylhydrazine

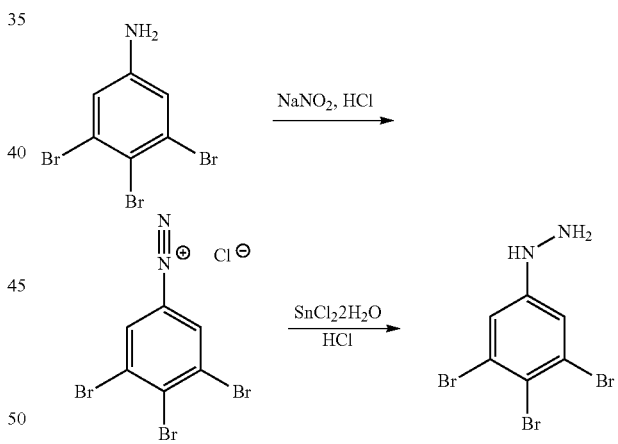

3,4,5-Tribromoaniline was obtained by the procedure of L. F. Tietze and T. Eicher (L. F. Tietze, T. Eicher. Reaktionen und Synthesen im organisch-chemischen Praktikum und Forschungslaboratorium. (1991) Georg Thieme Verlag, Stuttgart, New York). 7.8 g (24 mmol) of 3,4,5-tribromoaniline were stirred with a solution of 6.5 mL of concentrated hydrochloric acid and 6.5 mL of water. The mixture was cooled to about −10° C. and at this temperature the solution of 2.76 g of $NaNO_2$ in 11 mL of water was added for 20 min with intensive stirring. The reaction mixture was stirred for 30 min at −10° C. Then the cooled solution of 16.2 g of $SnCl_2·2H_2O$ in 17 mL of concentrated HCl was added dropwise at −10° C. to the suspension of diazocompound. The reaction mixture was kept at −10° C. for one hour and at 5° C. overnight. The obtained precipitate was filtered off and washed with water.

The residue was resuspended in 50 mL of water and concentrated aqueous solution of NaOH was added to get alkaline medium. The 3,4,5-tribromophenylhydrazine was extracted with ether. Organic layer was dried with MgSO$_4$ and ether was evaporated. Yield: 5.5 g (67%). $^1$H-NMR (200 MHz, DMSO-d$_6$), δ, ppm: 7.09 (2H, s, arom.), 7.34 (1H, s, NH), 4.19 (2H, d, NH$_2$).

Example 11

Synthesis of 4,5,6-tribromo-2,3,3-trimethyl-3H-indole

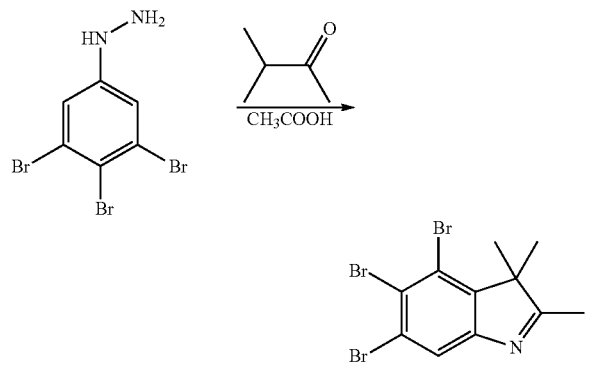

1.73 g of 3,4,5-tribromophenylhydrazine and 2 mL (18.5 mmol) of 3-methyl-2-butanone were refluxed for an hour. Next, 15 mL of concentrated HCl were added and refluxed for another 3.5 h. The reaction mixture was neutralized with concentrated aqueous solution of sodium carbonate, and the product was extracted with benzene. The organic layer was dried with MgSO$_4$ and benzene was removed under reduced pressure by a rotary evaporator to yield 1.12 g of 4,5,6-tribromo-2,3,3-trimethyl-3H-indole. $^1$H-NMR (200 MHz, DMSO-d$_6$), δ, ppm: 7.16 (1H, s, arom.), 2.22 (3H, s, CH$_3$), 1.35 (6H, s, C(CH$_3$)$_2$).

Example 12

Synthesis of 4,5,6-tribromo-1,2,3,3-tetramethyl-3H-indolium iodide

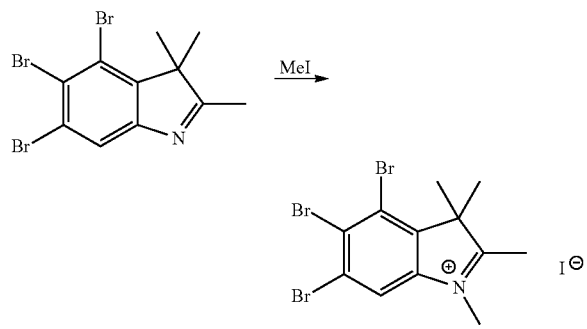

1.12 g (2.8 mmol) of 4,5,6-tribromo-2,3,3-trimethyl-3H-indole and 2 mL (32 mmol) of iodomethane were heated in a sealed tube at 30-35° C. for 24 hours. The formed precipitate was filtered, washed with small amounts of benzene and ether to yield 700 mg (47%) of 4,5,6-tribromo-1,2,3,3-tetramethyl-3H-indolium iodide. $^1$H-NMR (200 MHz, DMSO-d$_6$), δ, ppm: 8.50 (1H, s, arom.), 3.99 (3H, s, NCH$_3$), 2.77 (3H, s, CH$_3$), 1.60 (6H, s, C(CH$_3$)$_2$).

2. Synthesis of Polymethine Dyes

Example 13

Synthesis of 4,5,6-triiodo-1,3,3-trimethyl-2-[7-(4,5,6-triiodo-1,3,3-trimethyl-2,3-dihydro-1H-2-indolyliden)-1,3,5-heptatrienyl]-3H-indolium iodide (I-76)

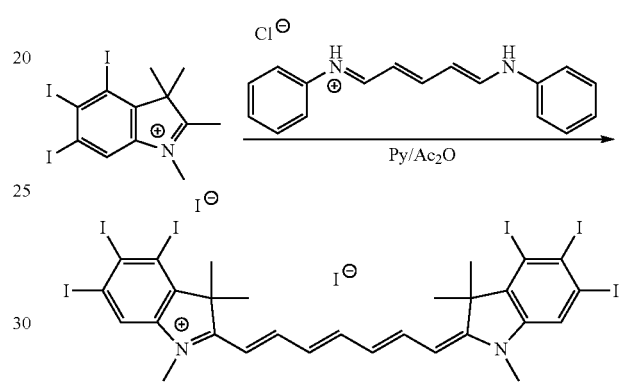

A mixture of 150 mg (0.22 mmol) of 4,5,6-triiodo-1,2,3,3-tetramethyl-3H-indolium iodide and 35 mg (0.12 mmol) of N-[5-(phenylamino)-2,4-pentadienylidene]aniline monohydrochloride (glutacondianil hydrochloride) was refluxed in 2 mL of pyridine-acetic anhydride (1:1, v/v) mixture for 15 min. The dye was precipitated with ether, filtered off and washed with ether. The product was purified by a column chromatography (Silica gel 60, 0-4% methanol-chloroform) to give 20 mg of the 4,5,6-triiodo-1,3,3-trimethyl-2-[7-(4,5,6-triiodo-1,3,3-trimethyl-2,3-dihydro-1H-2-indolyliden)-1,3,5-heptatrienyl]-3H-indolium iodide (I-76). $^1$H-NMR (200 MHz, CDCl$_3$), δ, ppm: 8.03-7.74 (3H, m, CH), 7.63 (2H, s, arom.), 6.75 (2H, m, CH), 6.37 (2H, m, CH), 3.65 (3H, s, NCH$_3$), 3.59 (3H, s, NCH$_3$), 1.65 (12H, s, (CH$_3$)$_2$). $\lambda_{max}$ (abs) 754 nm (methanol).

Example 14

Synthesis of 2-[7-(4,6-diiodo-1,3,3-trimethyl-2,3-dihydro-1H-2-indolyliden)-1,3,5-heptatrienyl]-4,6-diiodo-1,3,3-trimethyl-3H-indolium iodide (I-71)

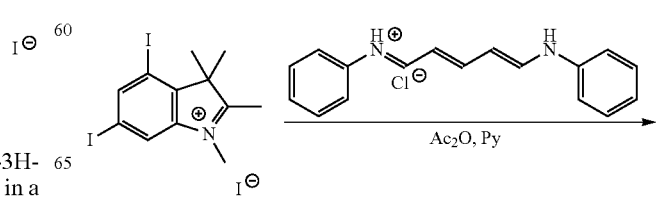

-continued

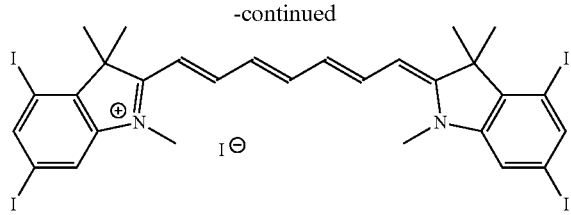

110 mg (0.20 mmol) of 4,6-diiodo-1,2,3,3-tetramethyl-3H-indolium iodide and 28.5 mg (0.10 mmol) of N-[5-(phenylamino)-2,4-pentadienylidene]aniline monohydrochloride were dissolved in 2 mL of acetic anhydride at 100-110° C., following which 2 mL of pyridine were added and the reaction mixture was stirred for 10 min at this temperature. The dye was precipitated with ether, filtered off and washed with ether. The raw product was column purified on Silica gel 60 using 5-10% methanol-chloroform as eluent. Yield: 20 mg. $^1$H-NMR (400 MHz, DMSO-$d_6$), δ, ppm: 7.95 (2H, s, arom.), 7.91 (2H, t, 13.1 Hz, CH), 7.81 (2H, s, arom.), 7.77 (1H, t, 13.0 Hz, CH), 6.59 (2H, t, 12.6 Hz, CH), 6.34 (2H, d, 14 Hz, CH), 3.53 (6H, s, NCH$_3$), 1.72 (12H, s, (CH$_3$)$_2$). $\lambda_{max}$ (abs) 745 nm (methanol), $\lambda_{max}$ (fluor) 773 nm (methanol), QY (fluor) 0.46.

Example 15

Synthesis of 4,5,6-tribromo-1,3,3-trimethyl-2-[7-(4,5,6-tribromo-1,3,3-trimethyl-2,3-dihydro-1H-2-indolyliden)-1,3,5-heptatrienyl]-3H-indolium iodide (I-88)

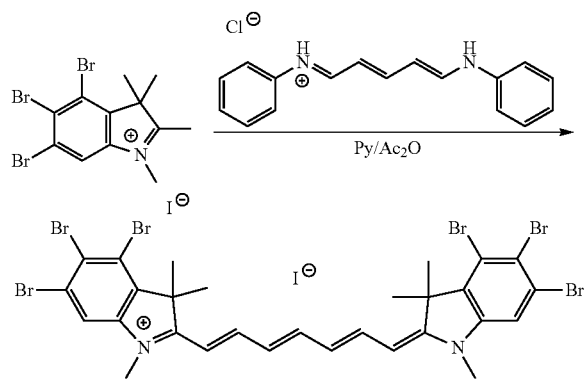

A mixture of 91 mg (0.17 mmol) of 4,5,6-tribromo-1,2,3,3-tetramethyl-3H-indolium iodide and 24 mg (0.085 mmol) of N[5-(phenylamino)-2,4-pentadienylidene]aniline monohydrochloride (glutacondianil hydrochloride) was refluxed in 4 mL of pyridine-acetic anhydride (1:1, v/v) mixture for 15 min. The dye was precipitated with ether, filtered off and washed with ether. The product was purified by a column chromatography (Silica gel 60, chloroform) to give 14 mg of the 4,5,6-tribromo-1,3,3-trimethyl-2-[7-(4,5,6-tribromo-1,3,3-trimethyl-2,3-dihydro-1H-2-indolyliden)-1,3,5-heptatrienyl]-3H-indolium iodide (1-88). $^1$H-NMR (200 MHz, DMSO-$d_6$), δ, ppm: 8.06-7.72 (3H, m, CH), 7.93 (2H, s, arom.), 6.23 (2H, t, 12.6 Hz, CH), 6.35 (2H, d, 13.6 Hz, CH), 3.55 (6H, s, NCH$_3$), 1.76 (12H, s, CH$_3$). $\lambda_{max}$ (abs) 748 nm (ε=240,000) (methanol), $\lambda_{max}$ (fluor) 778 nm (methanol), QY (fluor) 0.50 (methanol).

Example 16

Synthesis of 2-[6-anilino-1,3,5-hexatrienyl]-4,6-diiodo-1,3,3-trimethyl-3H-indolium iodide

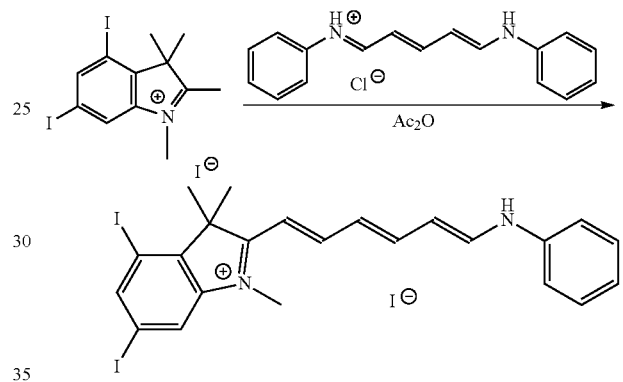

100 mg (0.18 mmol) of 4,6-diiodo-1,2,3,3-tetramethyl-3H-indolium iodide and 51 mg (0.18 mmol) of N-[5-(phenylamino)-2,4-pentadienylidene]aniline monohydrochloride were stirred in 2 mL of acetic anhydride at 110-120° C. for 15 min. After cooling the product was precipitated with ether, filtered off and washed with ether. Yield: 67 mg (53%). $\lambda_{max}$ (abs) 483 nm (methanol). This product was used for following step without additional purification.

Example 17

Synthesis of 1-(5-carboxypentyl)-2-[7-(4,6-diiodo-1,3,3-trimethyl-3H-2-indoliumyl)-2,4,6-heptatrienylidene]-3-methyl-3-(4-sulfobutyl)-5-indolinesulfonate (I-72)

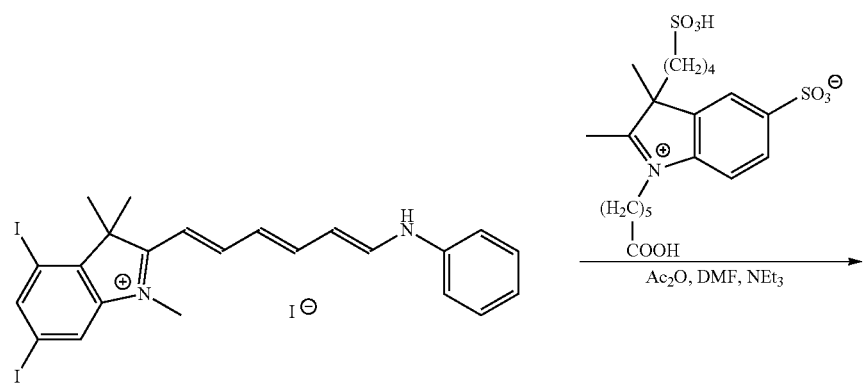

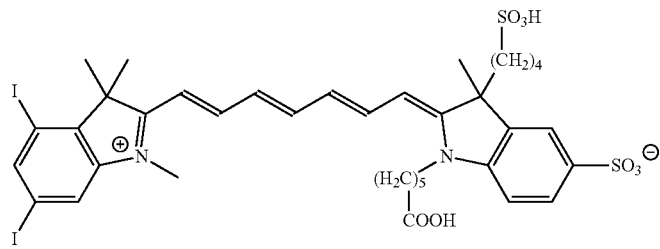

67 mg (0.095 mmol) of 2-[6-anilino-1,3,5-hexatrienyl]-4,6-diiodo-1,3,3-trimethyl-3H-indolium iodide and 45 mg (0.095 mmol) of 4-[1-(5-carboxypentyl)-2,3-dimethyl-5-sulfo-3H-3-indoliumyl]-1-butanesulfonate were dissolved in 2 mL of DMF-acetic anhydride mixture (1:1, v/v). Three drops of triethylamine were added, and the solution was stirred for 15 min at 115° C. After cooling the product was precipitated with ethyl acetate, filtered off, washed with ether and column purified on Lichroprep RP-18 using 0-35% acetonitrile-water as eluent. Yield: 26 mg.

$^1$H-NMR (200 MHz, DMSO-$d_6$), δ, ppm: 8.05 (1H, t, 12.8 Hz, CH), 7.81 (1H, s, arom.), 7.80-7.59 (5H, m, arom. and CH), 7.45 (1H, d, 8.4 Hz, arom.), 6.72-6.42 (3H, m, CH), 6.11 (1H, d, 13.0 Hz, CH), 4.19 (2H, m, NCH$_2$), 3.42 (3H, s, NCH$_3$), 2.20 (6H, t, 6.9 Hz, CH$_2$COOH and (CH$_2$)$_2$), 1.77-1.48 (2H, m, CH$_2$), 1.71 (6H, s, (CH$_3$)$_2$), 1.63 (3H, s, CH$_3$), 1.48-1.30 (6H, m, (CH$_2$)$_3$), 0.92-0.41 (2H, m, CH$_2$). $\lambda_{max}$ (abs) 750 nm (methanol), $\lambda_{max}$ (fluor) 780 nm (methanol), QY (fluor) 0.41 (methanol), $\lambda_{max}$ (abs) 750 nm (ε=270,000) (water), $\lambda_{max}$ (fluor) 777 nm (water), QY (fluor) 0.21 (water).

Example 18

Synthesis of 1-(5-carboxypentyl)-2-[7-(4,6-diiodo-1,3,3-trimethyl-3H-2-indoliumyl)-2,4,6-heptatrienylidene]-3,3-dimethyl-5-indolinesulfonate (I-73)

70 mg (010 mmol) of 2-[6-anilino-1,3,5-hexatrienyl]-4,6-diiodo-1,3,3-trimethyl-3H-indolium iodide and 35 mg (0.10 mmol) of 1-(5-carboxypentyl)-2,3,3-trimethyl-3H-5-indoliumsulfonate were dissolved in 2 mL of DMF-acetic anhydride mixture (1:1, v/v). Three drops of triethylamine were added, and the solution was stirred for 20 min at 110° C. After cooling the product was precipitated with ether, filtered off, washed with ether and column purified on Silica gel 60 using 15-55% methanol-chloroform as eluent. Yield: 28 mg (33%).

$^1$H-NMR (200 MHz, DMSO-$d_6$), δ, ppm: 8.03 (1H, t, 12.3 Hz, CH), 7.82 (1H, s, arom.), 7.80-7.59 (5H, m, arom. and CH), 7.47 (1H, d, 8.4 Hz, arom.), 6.72-6.41 (3H, m, CH), 6.11 (1H, d, 13.2 Hz, CH), 4.19 (2H, m, NCH$_2$), 3.42 (3H, s, NCH$_3$), 2.20 (2H, t, 6.4 Hz, CH$_2$COOH), 1.80-1.29 (6H, m, (CH$_2$)$_3$), 1.70 (6H, s, (CH$_3$)$_2$), 1.66 (6H, s, (CH$_3$)$_2$). $\lambda_{max}$ (abs) 748 nm (methanol), $\lambda_{max}$ (fluor) 779 nm (methanol), QY (fluor) 0.41 (methanol).

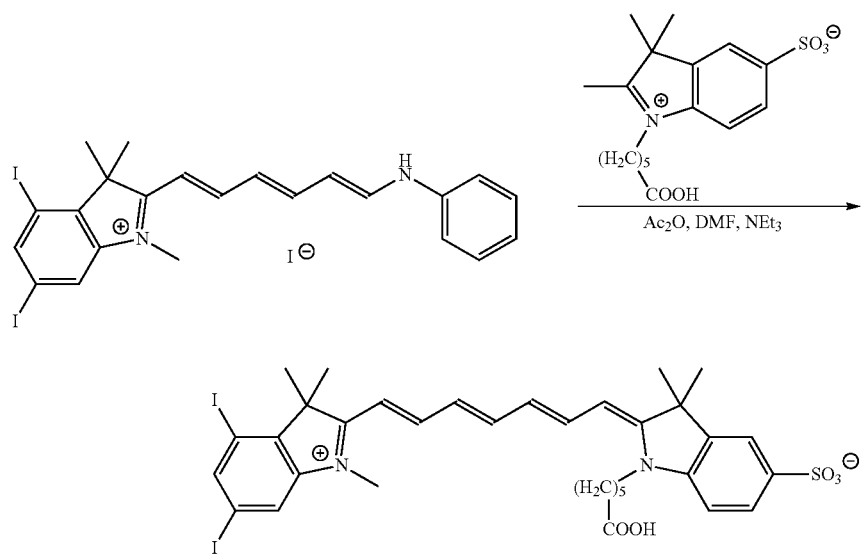

Example 19

Synthesis of 3-(5-carboxypentyl)-2-[7-(4,6-diiodo-1,3,3-trimethyl-2,3-dihydro-1H-2-indolyliden)-1,3,5-heptatrienyl]-1,1-dimethyl-6-sulfo-8-(1H-benzo[e]indolium)sulfonate (I-74)

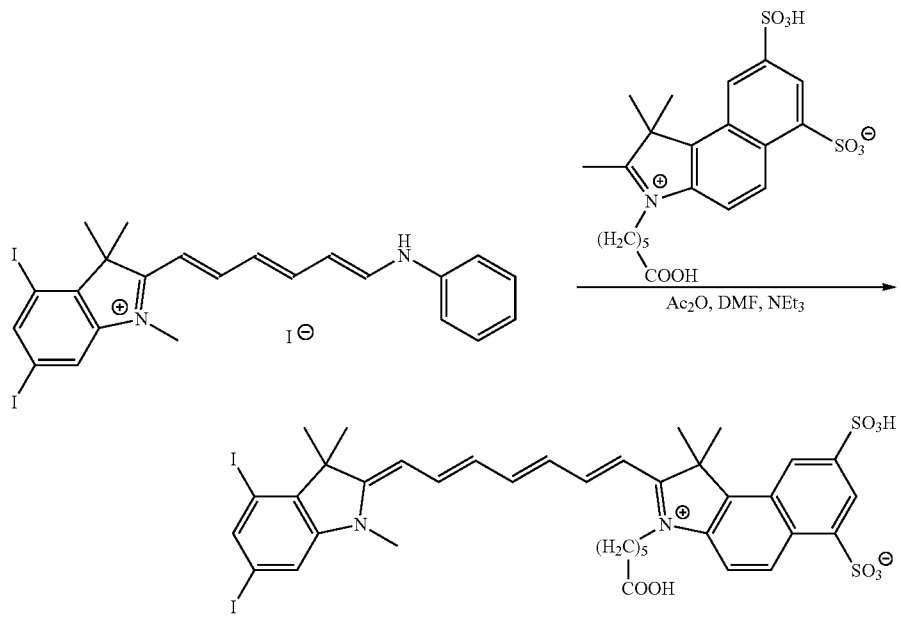

70 mg (0.10 mmol) of 2-[6-anilino-1,3,5-hexatrienyl]-4,6-diiodo-1,3,3-trimethyl-3H-indolium iodide and 52 mg (0.11 mmol) of 3-(5-carboxypentyl)-1,1,2-trimethyl-6-sulfo-8-(1H-benzo[e]indolium)sulfonate were dissolved in 2 mL of DMF-acetic anhydride mixture (1:1, v/v). Three drops of triethylamine were added, and the solution was stirred for 10 min at 110-115° C. After cooling to room temperature the product was precipitated with ethyl acetate, filtered off, washed with ethyl acetate and ether and column purified on Lichroprep RP-18 using 0-53% methanol-water as eluent. Yield: 10 mg (10%). $^1$H-NMR (200 MHz, DMSO-$d_6$), δ, ppm: 9.35 (1H, d, 6.2 Hz, CH), 9.08 (1H, d, 9.8 Hz, arom.), 8.47-7.55 (7H m, arom. and CH), 6.82-6.46 (3H, m, CH), 6.05 (1H, d, 12.8 Hz, CH), 4.37 (2H, m, NCH$_2$), 3.40 (3H, s, NCH$_3$), 2.21 (2H, t, 6.2 Hz, CH$_2$COOH), 1.91 (6H, s, (CH$_3$)$_2$), 1.71 (6H, s, (CH$_3$)$_2$), 1.66-1.29 (6H, m, (CH$_2$)$_3$). $\lambda_{max}$ (abs) 760 nm (methanol), $\lambda_{max}$ (fluor) 793 nm (methanol), QY (fluor) 0.22 (methanol).

Example 20

Synthesis of 3-(5-carboxypentyl)-2-7-[3-(5-carboxypentyl)-4,6-diiodo-1,3-dimethyl-2,3-dihydro-1H-2-indolyliden]-1,3,5-heptatrienyl-4,6-diiodo-1,3-dimethyl-3H-indolium iodide (I-79)

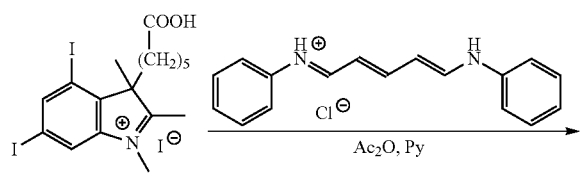

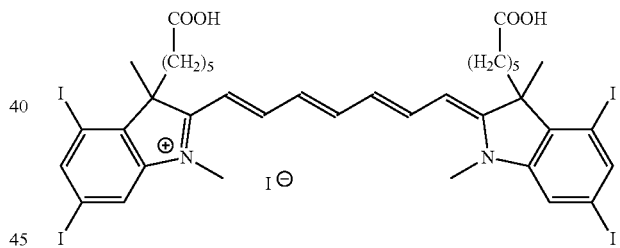

-continued 130.6 mg (0.20 mmol) of 3-(5-carboxypentyl)-4,6-diiodo-1,2,3-trimethyl-3H-indolium iodide and 28.5 mg (0.10 mmol) of N-[5-(phenylamino)-2,4-pentadienylidene]aniline monohydrochloride were stirred in 2 mL of pyridine-acetic anhydride (1:1, v/v) mixture at 115-120° C. for 12 min. After cooling to room temperature the dye was precipitated with 25 mL of ether, filtered off and washed with ether. The raw product was column purified on Silica gel 60 using 0-7% methanol-chloroform as eluent. Yield: 24.5 mg (10%). $^1$H-NMR (200 MHz, DMSO-$d_6$), δ, ppm: 7.95 (2H, s, arom.), 7.91-7.33 (3H, m, CH), 7.79 (2H, s, arom.), 6.59 (2H, t, 12.4 Hz, CH), 6.37 (2H, d, 13.5 Hz, CH), 3.56 (6H, s, NCH$_3$), 2.05 (4H, m, CH$_2$), 1.70 (6H, s, CH$_3$), 1.45-0.99 (12H, m, (CH$_2$)$_2$), 0.90-0.30 (4H, m, CH$_2$). $\lambda_{max}$ (abs) 763 nm (chloroform).

Example 21

Synthesis of NHS Ester of Dye I-72

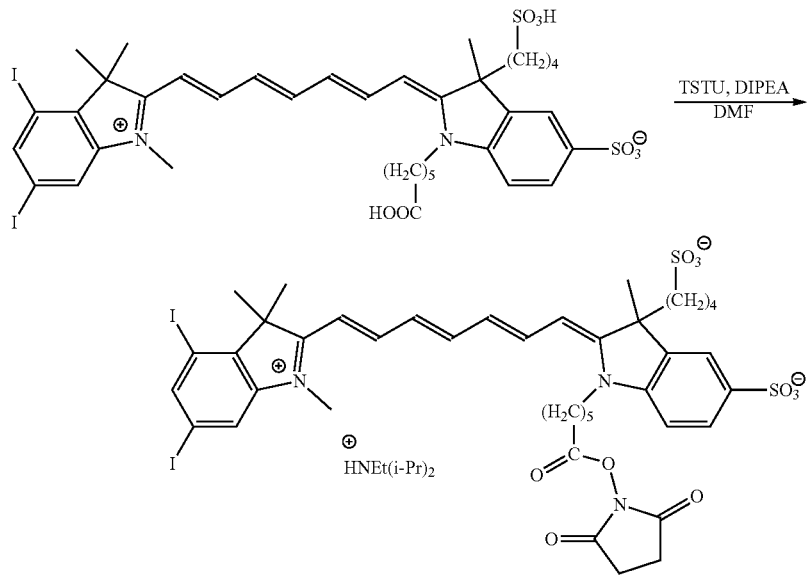

50 mg (52 μmol) of dye I-72 and 31 mg (104 μmol) of O—(N-succinimidyl)-N,N,N',N'-tetramethyluronium tetrafluoroborate (TSTU) were dissolved in 2 mL of DMF, 36 μL (207 μmol) of N,N-diisopropyl ethyl amine (DIPEA) were added and the solution was stirred at room temperature for 1 hour. The NHS ester was precipitated with ether, filtered off, and washed with ether (3×10 mL). Pure NHS ester was obtained by column chromatography (Lichroprep RP-18, 10-31% acetonitrile-water gradient). Yield: 22 mg (40%). $^1$H-NMR (200 MHz, DMSO-$d_6$), δ, ppm: 8.06 (1H, t, 12.5 Hz, CH), 7.82 (1H, s, arom.), 7.80-7.62 (5H, m, arom. and CH), 7.45 (1H, d, 8.4 Hz, arom.), 6.72-6.42 (3H, m, CH), 6.12 (1H, d, 13.0 Hz, CH), 4.19 (2H, m, NCH$_2$), 3.61 (2H, m, CH$_2$CH$_3$ (DIPEA)), 3.42 (3H, s, NCH$_3$), 3.14 (2H, m, CH i-Pr (DIPEA)), 2.81 (4H, s, CH$_2$ NHS), 2.69 (2H, t, CH$_2$CO), 2.20 (4H, m, CH$_2$), 1.84-1.58 (2H, m, CH$_2$), 1.70 (6H, s, CH$_3$), 1.64 (3H, s, CH$_3$), 1.58-1.34 (6H, m, (CH$_2$)$_3$), 1.34-1.16 (15H, CH$_3$ (DIPEA)), 0.90-0.35 (2H, m, CH$_2$).

Example 22

Synthesis of NHS ester of dye I-79 (3-[5-(2,5-dioxotetrahydro-1H-1-pyrrolyloxycarbonyl)pentyl]-2-7-{3-[5-(2,5-dioxotetrahydro-1H-1-pyrrolyloxycarbonyl)pen-tyl]-4,6-diiodo-1,3-dimethyl-2,3-dihydro-1H-2-indolyliden}-1,3,5-heptatrienyl)-4,6-diiodo-1,3-dimethyl-3H-indolium iodide)

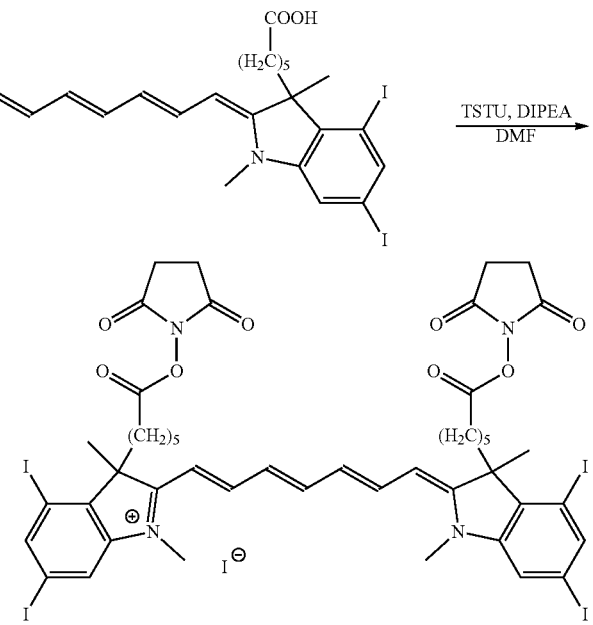

40 mg (32 μmol) of dye I-79 and 38.5 mg (128 μmol) of O—(N-succinimidyl)-N,N,N',N'-tetramethyluronium tetrafluoroborate (TSTU) were dissolved in 2 mL of DMF, 23 μL (132 μmol) of N,N-diisopropyl ethyl amine (DIPEA) were added and the solution was stirred at room temperature for 1 hour. The reaction was monitored by TLC (Sorbfil, methanol/chloroform azeotrope). The product was precipitated with ether, filtered off, washed with ether, and purified by column chromatography (Silica gel 60, 0-5% methanol-chloroform gradient). Yield: 18 mg (39.2%). $^1$H-NMR (200 MHz, DMSO-d$_6$), δ, ppm: 8.06-7.65 (3H, m, CH), 7.95 (2H, s, arom.), 7.80 (2H, s, arom.), 6.59 (2H, t, 12.6 Hz, CH), 6.38 (2H, d, 13.5 Hz, CH), 3.55 (6H, s, NCH$_3$), 2.78 (8H, s, CH$_2$ NHS), 2.23-2.10 (4H, m, CH$_2$CO), 1.71 (6H, s, CH$_3$), 1.59-1.00 (12H, m, (CH$_2$)$_2$), 0.94-0.30 (4H, m, CH$_2$).

Example 23

Synthesis of 4-2-[6-anilino-1,3,5-hexatrienyl]-3,3-dimethyl-5-sulfo-3H-1-indoliumyl-1-butanesulfonate

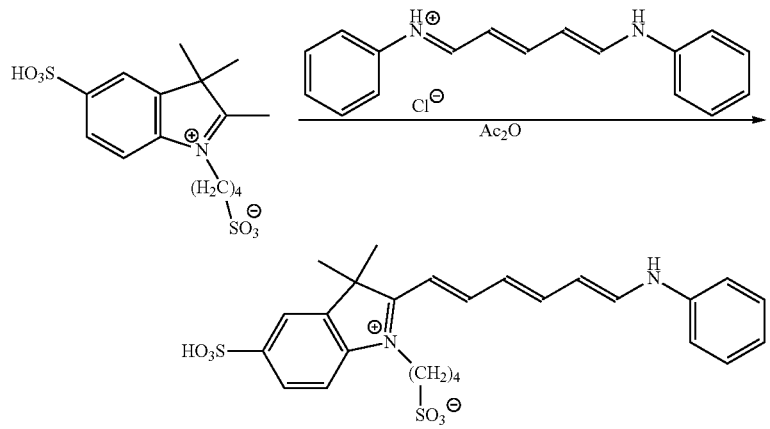

A mixture of 187 mg (0.5 mmol) of 4-(2,3,3-trimethyl-5-sulfo-3H-1-indoliumyl)-1-butanesulfonate, 152 mg (0.53 mmol) of N[5-(phenylamino)-2,4-pentadienylidene]aniline monohydrochloride, 2 mL of acetic anhydride, and 1 mL of acetic acid was stirred at 120-125° C. for 45 min. After cooling the product was precipitated with ethyl acetate, filtered off and washed with ethyl acetate and ether. Yield: 210 mg. This product was used for following step without additional purification.

Example 24

Synthesis of 4-(2-7-[3-(5-carboxypentyl)-4,6-diiodo-1-methyl-3H-2-indoliumyl]-2,4,6-heptatrienylidene-3,3-dimethyl-5-sulfo-2,3-dihydro-1H-1-indolyl)-1-butanesulfonate (I-83)

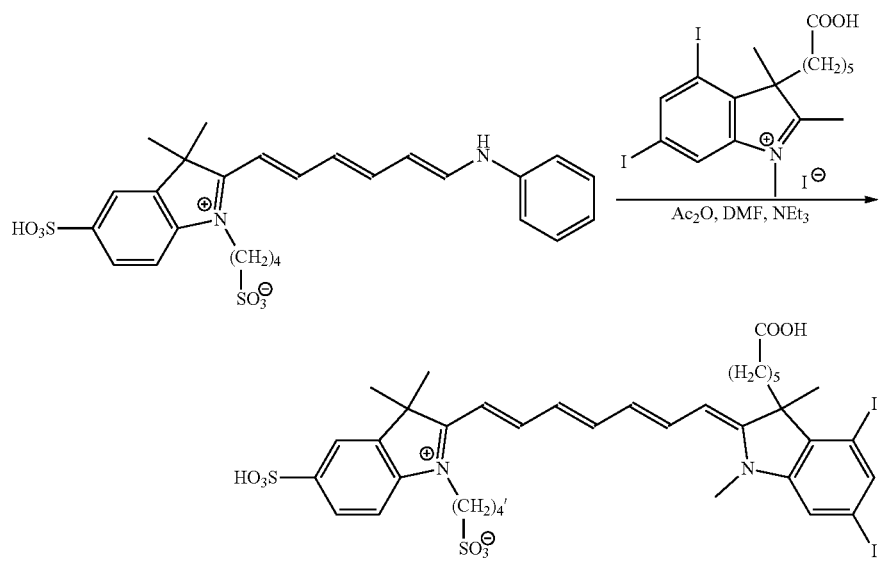

53 mg (0.10 mmol) of 4-2-[6-anilino-1,3,5-hexatrienyl]-3,3-dimethyl-5-sulfo-3H-1-indoliumyl-1-butanesulfonate were dissolved in a mixture of 1.5 mL of (1:1, v/v) acetic acid-acetic anhydride under gently warming. To the obtained solution 69 mg (0.11 mmol) of 345-carboxypentyl)-4,6-di-iodo-1,2,3-trimethyl-3H-indolium iodide, dissolved in 2 mL of DMF, were added followed by three drops of triethylamine. The mixture was allowed to stir for 10 min at 110° C. After cooling to room temperature the product was precipitated with 25 mL of ethyl acetate, filtered off, washed with ethyl acetate and ether. Purification by column chromatography on Lichroprep RP-18 using gradient 0-35% acetonitrile-water as eluent gave 9 mg (9%) of I-83. $^1$H-NMR (200 MHz, DMSO-$d_6$), δ, ppm: 8.04 (1H, t, 12.5 Hz, CH), 7.90-7.44 (7H, m, arom. and CH), 6.90-6.40 (3H, m, CH), 6.10 (1H, d, 13.0 Hz, CH), 4.21 (2H, m, NCH$_2$), 3.40 (3H, s, NCH$_3$), 2.72 (2H, t, CH$_2$SO$_3$H), 2.07 (2H, t, CH$_2$COOH), 1.90-1.47 (2H, m, CH$_2$), 1.75 (3H, s, CH$_3$), 1.67 (6H, s, CH$_3$), 1.43-1.00 (8H, m, CH$_2$), 0.90-0.32 (2H, m, CH$_2$).

Example 25

Synthesis of 4-[2-[6-anilino-1,3,5-hexatrienyl]-3-methyl-5-sulfo-3-(4-sulfobutyl)-3H-1-indoliumyl]-1-butanesulfonate 300 mg (0.55 mmol) of 2,3-dimethyl-5-sulfo-1,3-di(4-sulfobutyl)-3H-indolium and 190 mg (0.66 mmol) of N-[5-(phenylamino)-2,4-pentadienylidene]aniline monohydrochloride were heated in 6 mL acetic anhydride-acetic acid (1:1, v/v) mixture for 30 min at 110° C. After cooling the product was precipitated with ethyl acetate, filtered off and washed with ether to give 240 mg (56%) of 4-[2-[6-anilino-1,3,5-hexatrienyl]-3-methyl-5-sulfo-3-(4-sulfobutyl)-3H-1-indoliumyl]-1-butanesulfonate. $\lambda_{max}$ (abs) 505 nm (methanol). This product was used for following step without additional purification.

Example 26

Synthesis of 4-[2-7-[3-(5-carboxypentyl)-4,5,6-tri-iodo-3-methyl-1-(3-sulfopropyl)-2,3-dihydro-1H-2-indolyliden]-1,3,5-heptatrienyl-3-methyl-5-sulfo-3-(4-sulfobutyl)-3H-1-indoliumyl]-1-butanesulfonate (I-84)

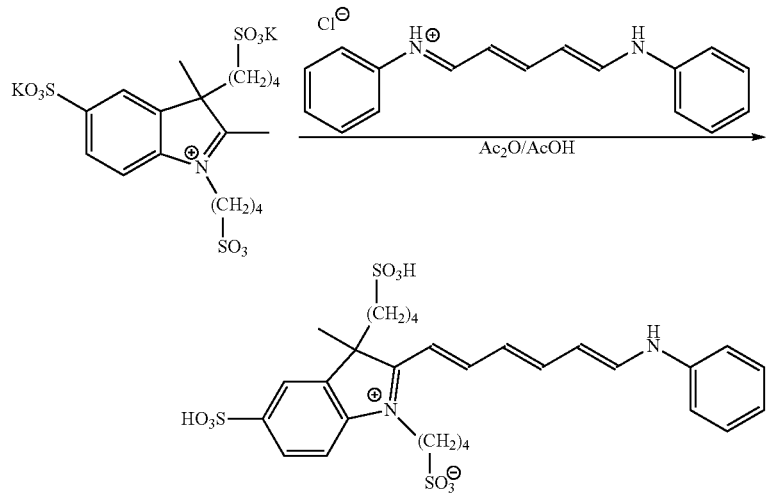

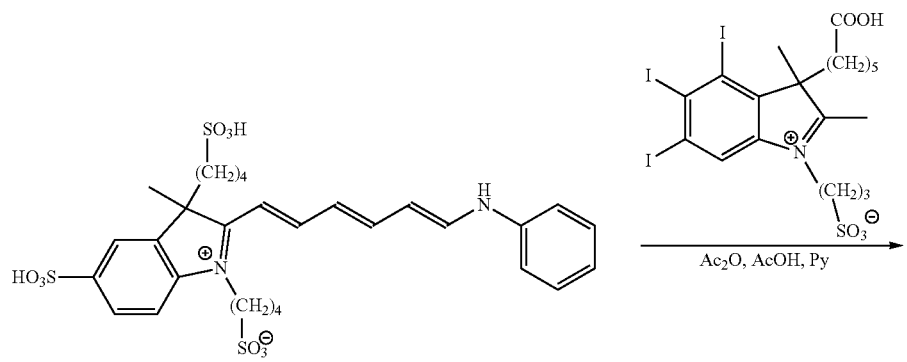

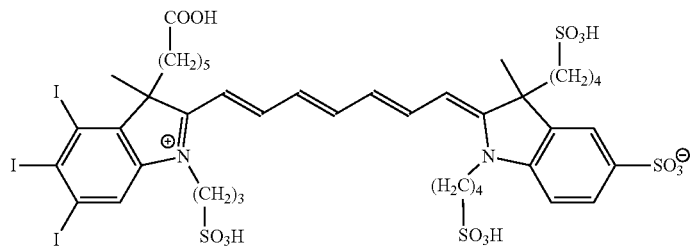

A mixture of 200 mg (0.26 mmol) of 4-[2-[6-anilino-1,3,5-hexatrienyl]-3-methyl-5-sulfo-3-(4-sulfobutyl)-3H-1-indoliumyl]-1-butanesulfonate, 197 mg (0.26 mmol) of 3-[3-(5-carboxypentyl)-4,5,6-triiodo-2,3-dimethyl-3H-1-indoliumyl]-1-propanesulfonate, 2 mL of acetic anhydride, 2 mL of acetic acid and 3 mL of pyridine were stirred for 20 min at 110° C. After cooling the product was precipitated with ethyl acetate, filtered off, washed with ether and column purified on Lichroprep RP-18 using 0-15% acetonitrile-water as eluent. Yield: 50 mg (10%). $\lambda_{max}$ (abs) 758 nm ($\epsilon$=270,000) (water), $\lambda_{max}$ (fluor) 787 nm (water), QY (fluor) 0.20 (water).

Example 27

Synthesis of 3-(3-(5-carboxypentyl)-2-7-[3-(5-carboxypentyl)-4,5,6-triiodo-3-methyl-1-(3-sulfopropyl)-2,3-dihydro-1H-2-indolyliden]-1,3,5-heptatrienyl-4,5,6-triiodo-3-methyl-3H-1-indoliumyl)-1-propanesulfonate (I-86)

150 mg (0.20 mmol) of 3-[3-(5-carboxypentyl)-4,5,6-triiodo-2,3-dimethyl-3H-1-indoliumyl]-1-propanesulfonate and 28.5 mg (0.1 mmol) of N-[5-(phenylamino)-2,4-pentadienylidene]aniline monohydrochloride (glutacondianil hydrochloride) were refluxed in a mixture of 1 mL of acetic anhydride, 1 mL of acetic acid and 2 mL of pyridine for 15 min at 110° C. The dye was precipitated with ether, filtered off and washed with ether. The product was purified by column chromatography (Silica gel 60, 0-10% methanol-chloroform) to give 22 mg (8%) of I-86. $^1$H-NMR (200 MHz, CDCl$_3$), $\delta$, ppm: 8.12 (2H, s, arom.), 7.94 (2H, t, CH), 7.71 (1H, t, CH), 6.58 (2H, t, CH), 6.37 (2H, d, CH), 4.20 (4H, m, NCH$_2$), 2.15 (4H, m, 4H, CH$_2$COOH), 1.95-1.80 (4H, m, (CH$_2$)$_2$), 1.48-0.98 (16H, s, (CH$_3$)$_2$), 0.55-0.30 (4H, m, CH$_2$). $\lambda_{max}$ (abs) 765 nm (methanol), $\lambda_{max}$ (fluor) 795 nm (methanol), QY (fluor) 0.44 (methanol), $\lambda_{max}$ (abs) 721 nm ($\epsilon$=210,000) (water), $\lambda_{max}$ (fluor) 786 nm (water), QY (fluor) 0.006 (water).

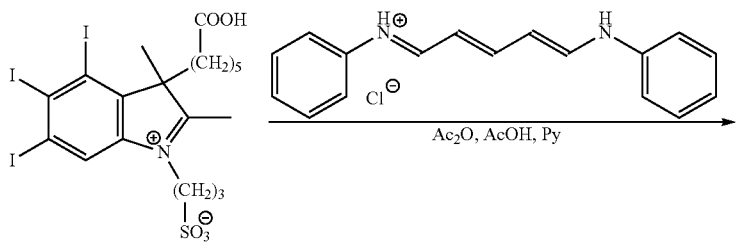

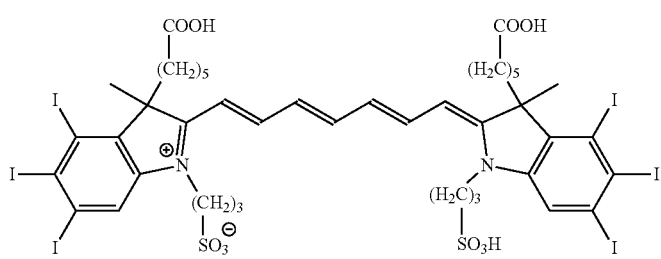

Example 28

Synthesis of NHS Ester of Dye I-84

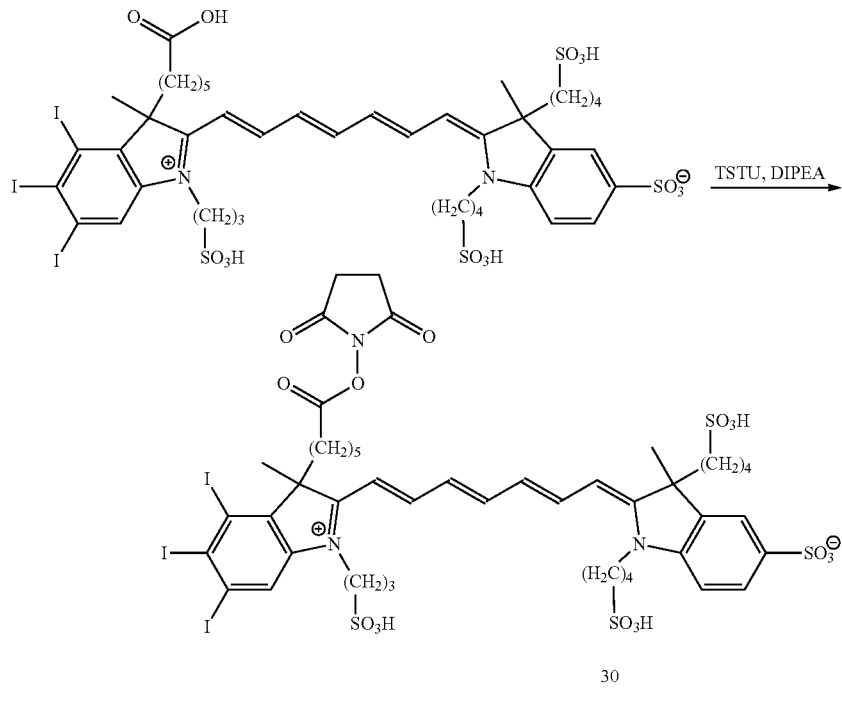

A mixture of 8 mg (6 μmol) of 4-[2-7-[3-(5-carboxypentyl)-4,5,6-triiodo-3-methyl-1-(3-sulfopropyl)-2,3-dihydro-1H-2-indolyliden]-1,3,5-heptatrienyl-3-methyl-5-sulfo-3-(4-sulfo-butyl)-3H-1-indoliumyl]-1-butanesulfonate (I-84) and 3.6 mg (12 μmol) of TSTU were dissolved in 0.5 mL of DMF, 10 μL of N,N-diisopropyl ethyl amine (DIPEA) were added and the solution was stirred at room temperature for an hour. The product was precipitated with ether, filtered off, washed with ether and column purified on Lichroprep RP-18 using 0-22% acetonitrile-water as eluent. Yield: 2 mg.

Example 29

Synthesis of NHS Ester of Dye I-86

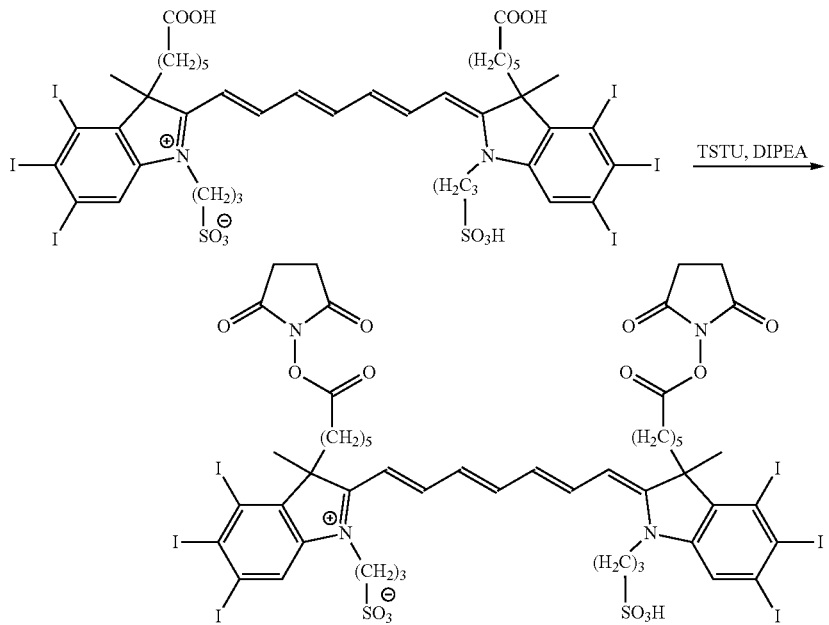

14 mg (8.8 µmol) of 3-(3-(5-carboxypentyl)-2-7-[3-(5-carboxypentyl)-4,5,6-triiodo-3-methyl-1-(3-sulfopropyl)-2,3-dihydro-1H-2-indolyliden]-1,3,5-heptatrienyl-4,5,6-triiodo-3-methyl-3H-1-indoliumyl)-1-propanesulfonate (1-86) and 10.6 mg (35.2 µmol) of TSTU were dissolved in 0.6 mL of DMF, 9 µL of N,N-diisopropyl ethyl amine (DIPEA) were added and the solution was stirred for 5 min at room temperature. The product was precipitated with ether, filtered off, washed with ether and column purified on Silica gel 60, 0-60% methanol-chloroform as eluent. Yield: 6 mg.

Example 30

Synthesis of 1-[5-(2-2-[2-(2-carboxyethoxy)ethoxy]ethoxyethylcarbamoyl)-pentyl]-2-[7-(4,6-diiodo-1,3,3-trimethyl-3H-2-indoliumyl)-2,4,6-heptatrienylidene]-3-methyl-3-(4-sulfobutyl)-5-indolinesulfonate (I-89)

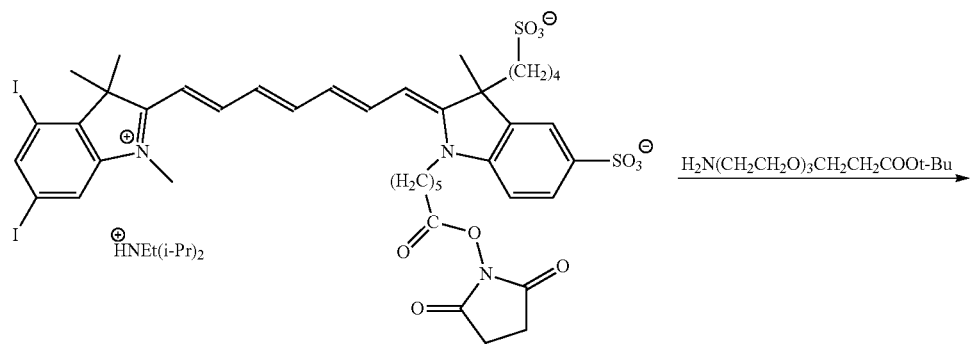

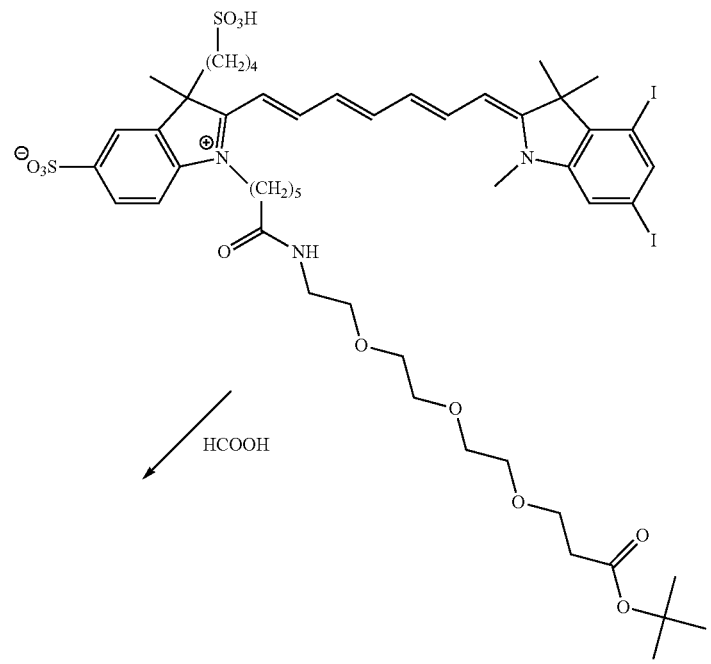

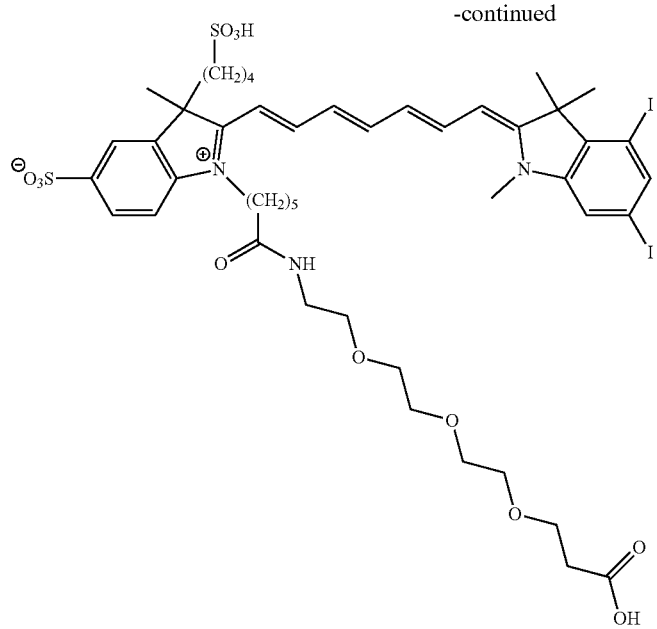

58 mg (55 μmol) of NHS ester of dye I-72 and 61 mg (220 μmol) of tert-butyl 3-2-[2-(2-aminoethoxy)ethoxy]ethoxypropanoate were dissolved in 2 mL of DMF, 35 μL of N,N-diisopropyl ethyl amine (DIPEA) were added and the solution was stirred for an hour at room temperature. The reaction was monitored by TLC (Silica gel 60 RP-18, acetonitrile/water (1:1, v/v)). The product was precipitated with ether, filtered off, washed with ether and dried in a vacuum desiccator. The residue was hydrolyzed in 400 μL of formic acid for 5 hours at room temperature. After completion of hydrolysis (TLC on Silica gel 60 RP-18, acetonitrile/water (1:1, v/v)) the dye was precipitated with ether, filtered off, washed with ether and column purified on Lichroprep RP-18, 15-35% acetonitrile-water as eluent. Yield: 28 mg (43%). $^1$H-NMR (200 MHz, DMSO-d$_6$), δ, ppm: 8.06 (1H, t, CH), 7.94-7.61 (6H, m, arom.), 7.45 (1H, d, 8.6 Hz, CH), 6.73-6.55 (3H, m, CH), 6.11 (1H, d, 13.1 Hz, CH), 4.31-4.07 (2H, m, NCH$_2$), 3.58 (2H, t, NHCH$_2$CH$_2$), 3.48 (8H, s, CH$_2$CH$_2$OCH$_2$CH$_2$), 3.42 (3H, s, NCH$_3$), 2.43 (2H, t, 6.2 Hz, CH$_2$COOH), 2.28-2.13 (m, 2H, CH$_2$), 2.05 (2H, t, 6.8 Hz, CH$_2$), 1.78-1.59 (2H, m, CH$_2$), 1.71 (6H, s, CH$_3$), 1.63 (3H, s, CH$_3$), 1.59-1.31 (8H, m, CH$_2$), 0.94-0.41 (2H, m, CH$_2$).

Example 31

Synthesis of NHS Ester of Dye I-89

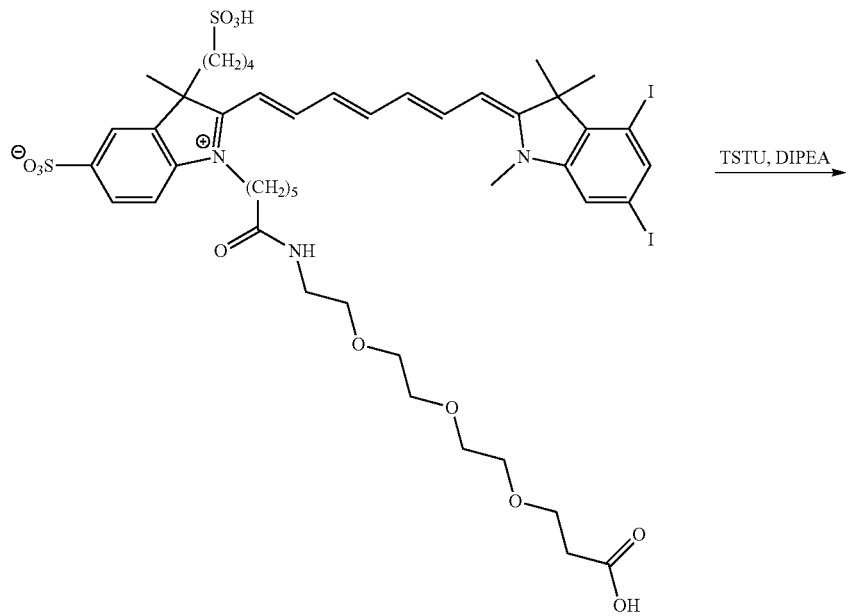

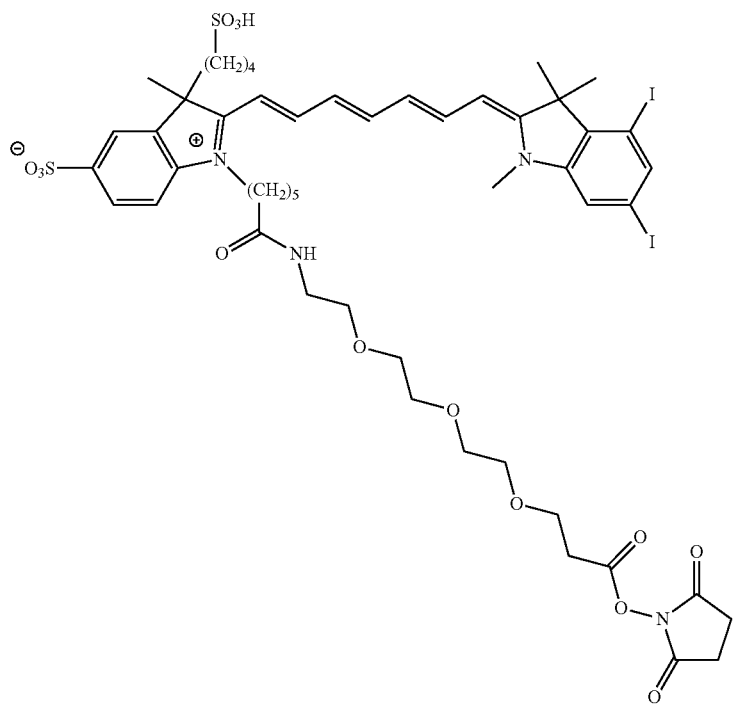

10 µL of DIPEA were added to a mixture of 17 mg (0.0146 mmol) of dye I-89 and 8.8 mg (0.029 mmol) of TSTU in 1 mL of dry DMF, stirred at room temperature for 40 min and then 10 µL of DIPEA were added and stirred for 30 min. The reaction was monitored using TLC (RP-18, AcCN-water, 1:1). The product was precipitated with diethyl ether (25 mL), filtered, washed with diethyl ether (2×10 mL), and dried using a vacuum dissicator. The resulted NHS ester was column purified (RP-18, 30-35% AcCN in water). Yield: 7.8 mg (35%).

Example 32

Synthesis of Dye I-90: Binding of Proline Decamer to Cyanine I-72 NHS Ester

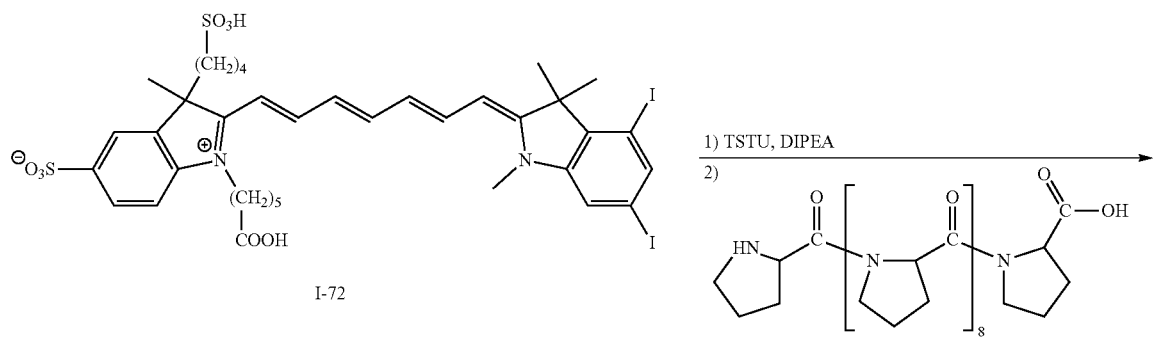

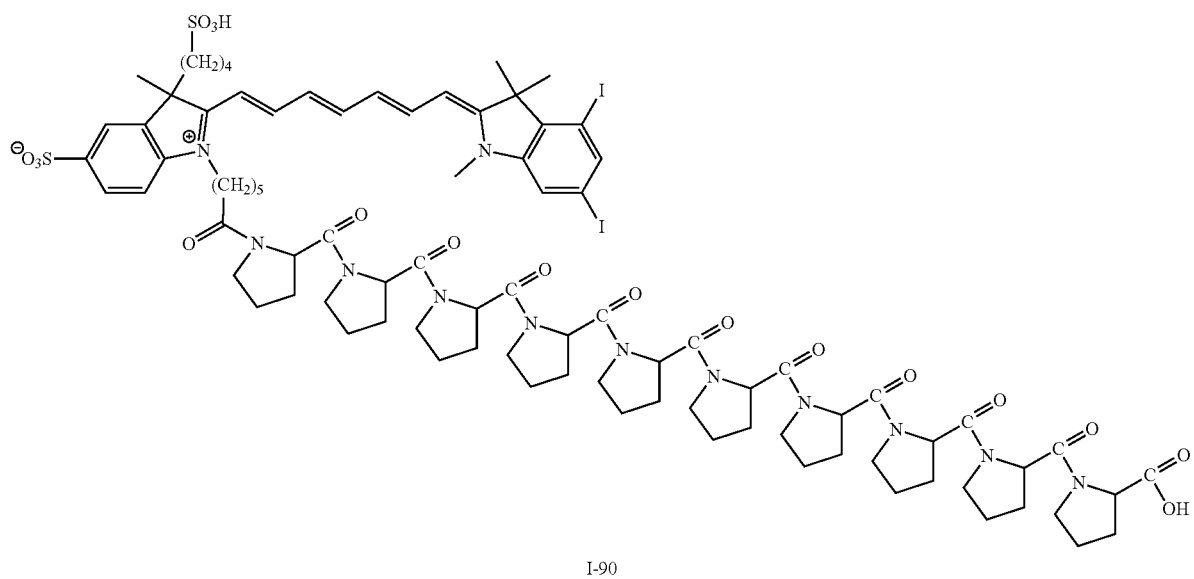

I-90

A solution of 30 mg (0.0246 mmol) of dye 1-72 NHS ester in 1 mL DMF was mixed with a solution of 36 mg (0.0251 mmol) of proline decamer in 0.5 mL DMF. Next, 8.5 mL (0.0492 mmol) of DIPEA were added to the above solution and stirred at room temperature for 20 h. The product was precipitated with diethyl ether, filtered, washed with diethyl ether, dried using a vacuum dissicator, and column purified (RP-18, 27-33% AcCN in water). Yield: 16.7 mg (41%).

Example 33

Synthesis of NHS Ester of Dye I-90

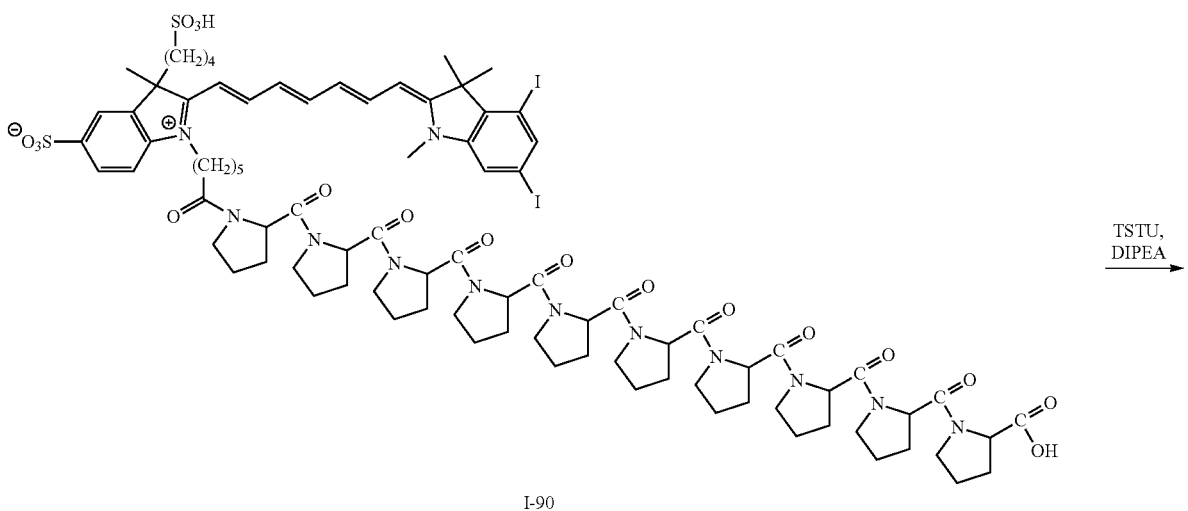

I-90

-continued

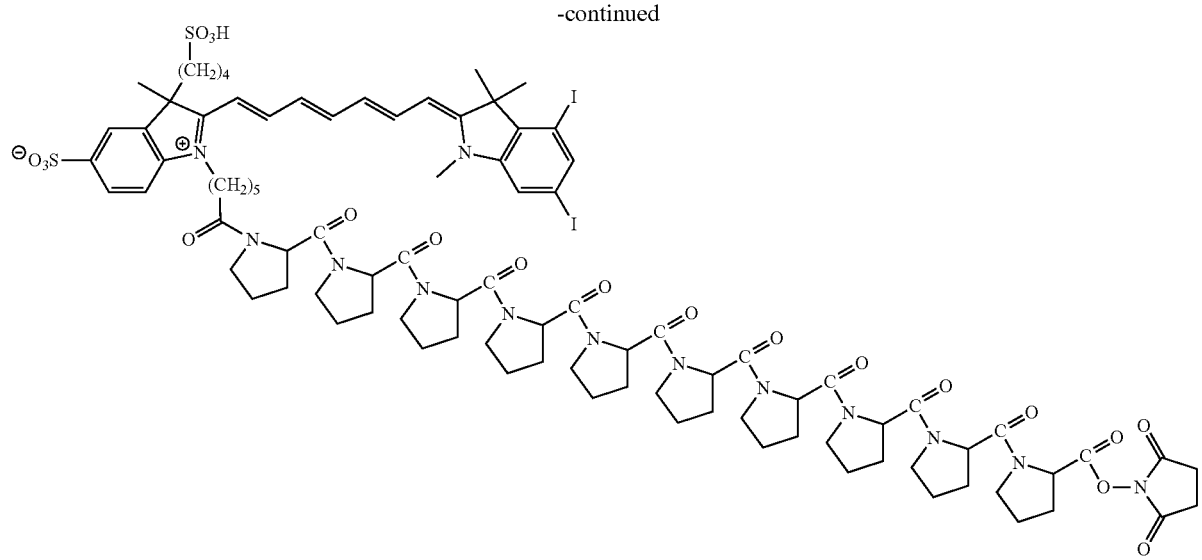

I-90 NHS ester 3.5 μL of DIPEA were added to a mixture of 10 mg (0.00517 mmol) of dye I-90 and 3 mg (0.01 mmol) of TSTU in 1 mL of dry DMF, stirred at room temperature for 40 min and then 3 μL of DIPEA were added and stirred for 30 min. The product was precipitated with diethyl ether (25 mL), filtered, washed with diethyl ether (2×10 mL), and dried using a vacuum dissicator for 12 h. The resultant NHS ester was column purified (RP-18, 33-35% AcCN in water). Yield: 4.6 mg (45%).

Example 34

Synthesis of Positively Charged Cyanine Dye I-91

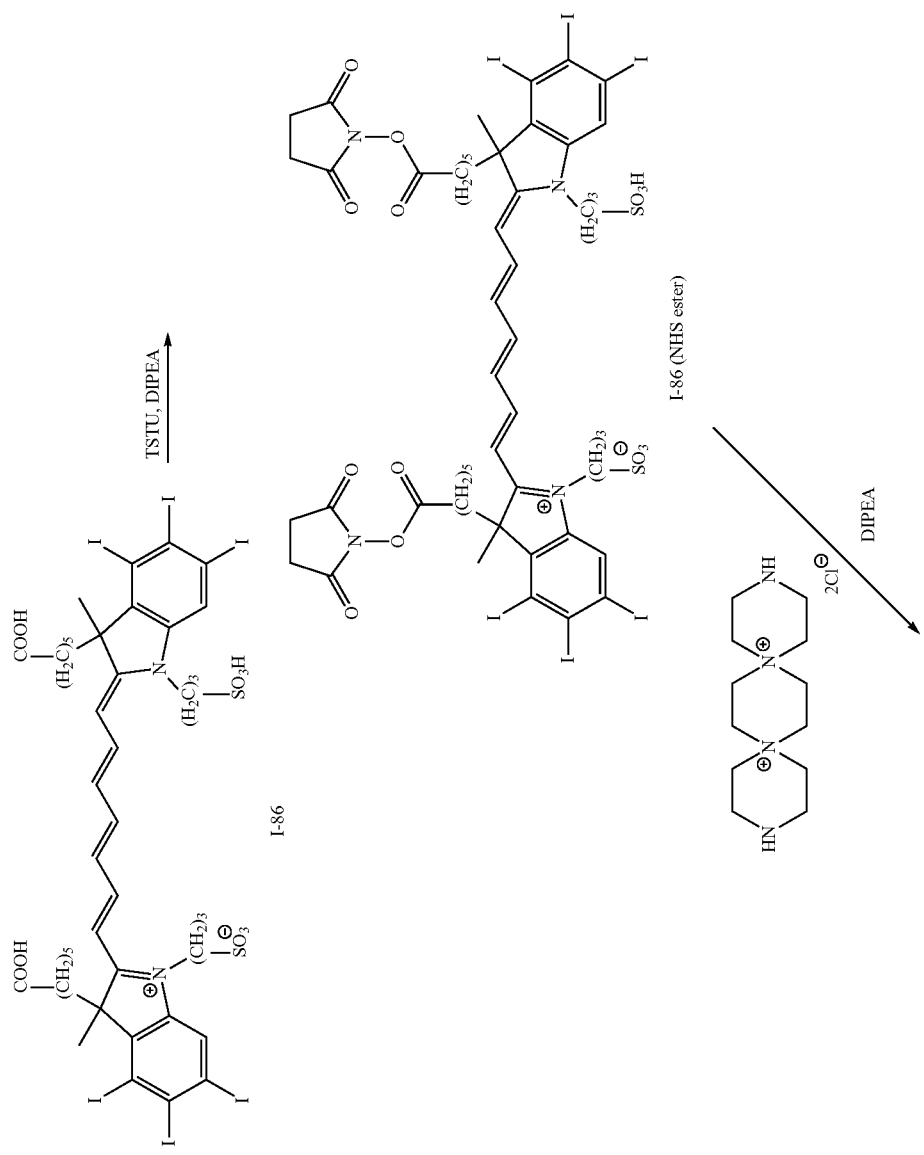

-continued
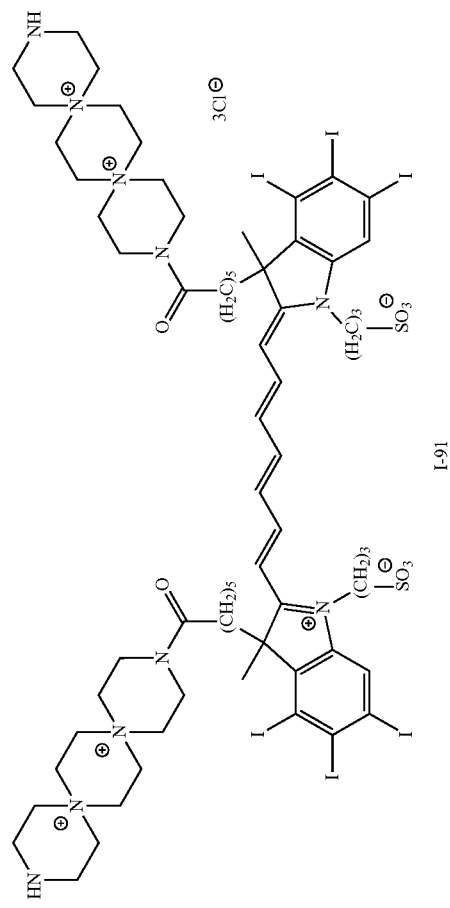
I-91

3. Synthesis of Conjugates

Example 35

General Protein Labeling Procedure

Amino-modified molecule or particle (protein, antibody, phage, etc.) labeling reactions were carried out using 50 mM bicarbonate buffer (pH 9.0). A stock solution of 0.5 mg of dye in 50 µL of anhydrous DMF was prepared. Amino-modified compound (1.5 mg in case of protein or antibody such as BSA or IgG) was dissolved in 0.5 mL of a 50 mM bicarbonate buffer pH 9.0. To obtain different dye-to-protein (D/P) ratio a series of these protein solutions were prepared. Then, various amounts of the dye stock solution (e.g. 3, 12, 25 uL) were added to the above protein solution(s) in order to obtain different dye-to-protein (D/P) ratios and the mixture was allowed to stir for 2 h at room temperature. Unconjugated dye was separated from the labeled proteins using gel permeation chromatography with Sephadex G25 for BSA conjugates or Sephadex G50 for IgG (0.5 cm×20 cm column) and a 67 mM phosphate buffer solution of pH 7.4 as the eluent. The first colored fraction containing the dye-protein conjugate is isolated, while the blue or bluish-green band with a much higher retention time (free label) was discarded. A series of labeling reactions as described above were set up to obtain different dye-to-protein ratios.

Example 36

Binding of Sensitizer Molecule to Carrier Via Rigid Polyproline Linker

This example demonstrates one of the possible ways to synthesize a conjugate of a sensitizer molecules bound to an amino-modified carrier with a polyproline linker.

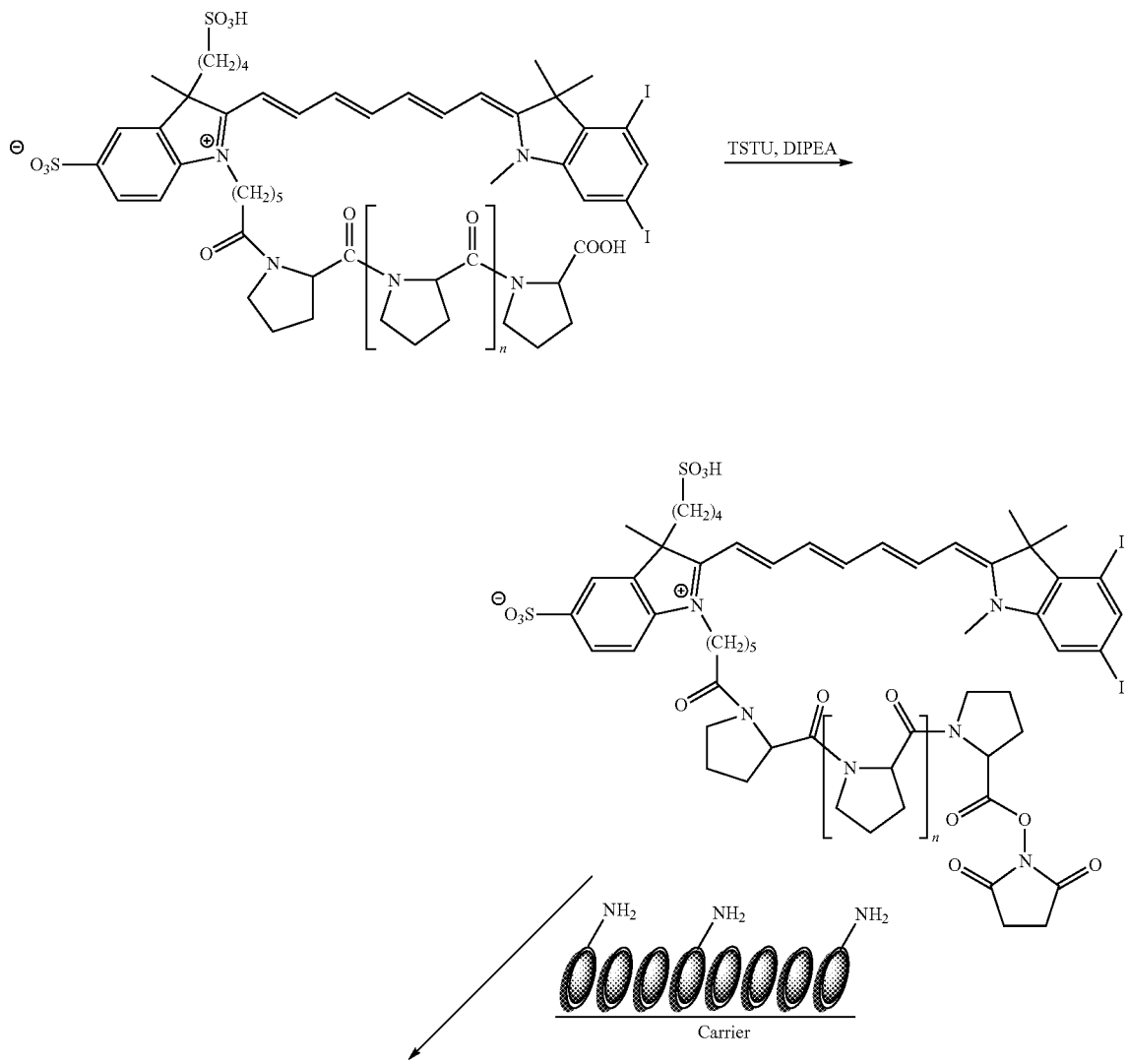

-continued
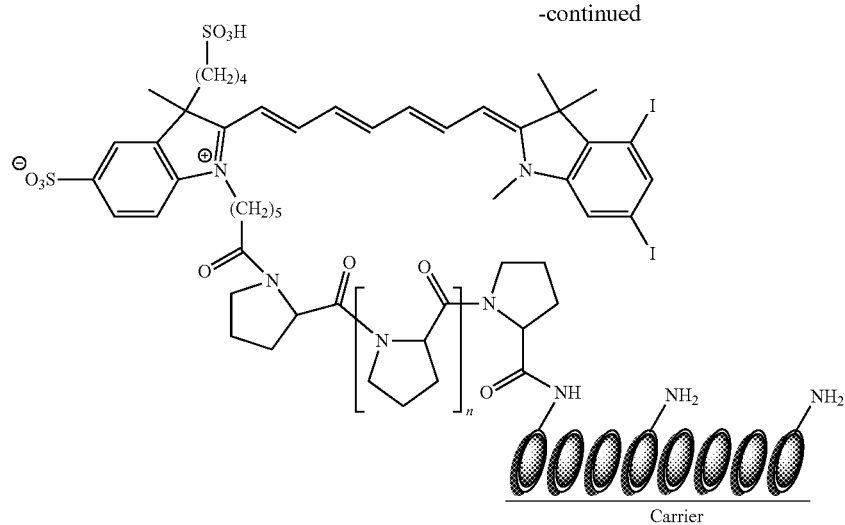
Example 37
Covalent Conjugate of Counterion with Heptamethine Cyanine
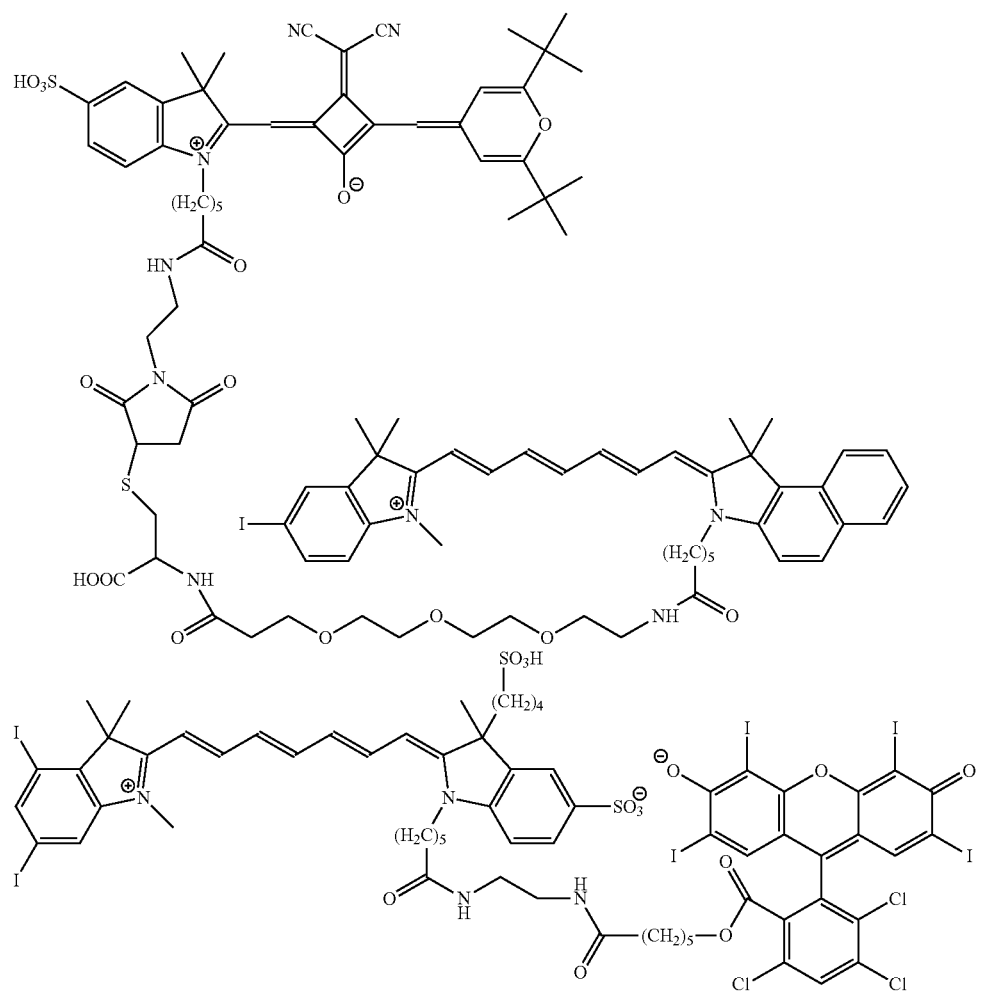

4. Spectral and Photophysical Characteristics

Example 38

Spectral Properties of the Invented Dyes

This example shows the spectral properties of the representative dyes (Table 1).

Absorption spectra were measured at RT on a Perkin-Elmer Lambda 35 UV/Vis spectrophotometer. For measurement of the extinction coefficients, each dye (7-10 mg) was dissolved in 50 mL of PB (pH 7.4). The stock solution was diluted (1:2000) and the absorbance was measured in a 5-cm standard quartz cell. All dye concentrations were in the range of 1.1 to $2.0 \times 10^{-7}$ M. The extinction coefficients were calculated according to Lambert-Beer's law.

Fluorescence spectra for the dyes were determined at RT on a Varian Cary Eclipse spectrofluorometer in a standard 1-cm quartz cell. The spectra were corrected. All concentrations of the fluorophores were chosen to be between 0.2 and 1.0 µM.

For the determination of the quantum yields (QY), the integrated relative intensities of the dyes or dye-protein conjugates, were measured against HITC as the reference. All absorbances at excitation wavelength ($\lambda_{exc}$) were in the range of 0.04-0.08 (when measured in a 1-cm cell). The fluorescence spectra of the solutions were measured and the absolute QYs were determined relative to HITC in methanol (QY 28%) by known methodology (Lakowicz J. R. Principles of Fluorescence Spectroscopy, 4th ed. Springer, N.Y., 2006).

The QY of each sample was independently measured 3-4 times and the average value was calculated.

Results are shown in Table 1 below.

TABLE 1

Spectral properties of representative dyes of this disclosure compared to prototypes (ICG and HITC)

| Sample | Media | Absorption max. [nm] | Extinction Coefficient [M$^{-1}$cm$^{-1}$] | Emission max. [nm] | Fluorescence quantum yield [%] |
|---|---|---|---|---|---|
| ICG | Water<br>Methanol | 780<br>784 | 114,000<br>200,000 | 810<br>818 | 16 |
| HITC | Methanol | 740 | | 768 | 28 |
| I-25 | Methanol<br>Water<br>Chloroform | 753<br>750<br>771 | | 784<br>779<br>801 | 30 |
| I-51 | Methanol<br>Chloroform | 758<br>783 | | 788<br>809 | |

TABLE 1-continued

Spectral properties of representative dyes of this disclosure compared to prototypes (ICG and HITC)

| Sample | Media | Absorption max. [nm] | Extinction Coefficient [M$^{-1}$cm$^{-1}$] | Emission max. [nm] | Fluorescence quantum yield [%] |
|---|---|---|---|---|---|
| I-52 | Methanol<br>Phosphate buffer (pH 7.4)<br>Conjugates with IgG (antibody) | 763<br>760<br>763-767 | 240,000 | 791<br>788<br>788 | |
| I-55 | Phosphate buffer (pH 7.4)<br>Chloroform<br>Methanol | 764<br>787<br>767 | 235,000 | 794<br>819<br>799 | |
| I-56 | Methanol | 784 | | 806 | 16 |

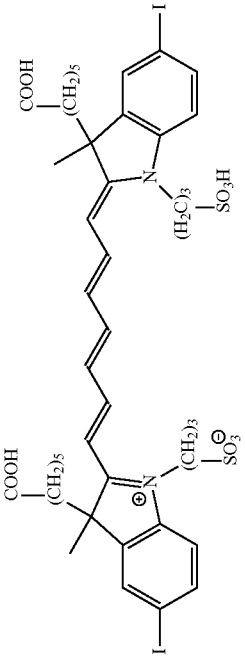

I-52

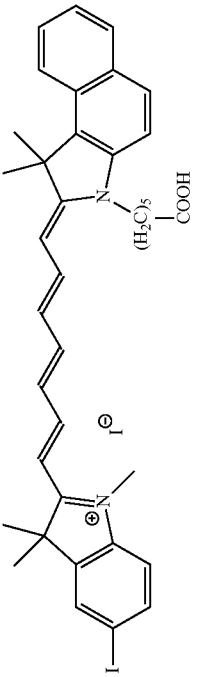

I-55

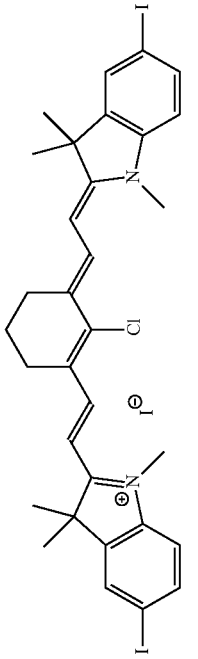

I-56

TABLE 1-continued

Spectral properties of representative dyes of this disclosure compared to prototypes (ICG and HITC)

| Sample | Media | Absorption max. [nm] | Extinction Coefficient [M⁻¹cm⁻¹] | Emission max. [nm] | Fluorescence quantum yield [%] |
|---|---|---|---|---|---|
| I-61 | Methanol | 792 | | 812 | 14 |
| I-68 | Methanol | 794 | | 826 | 6 |
| I-71 | Methanol | 745 | | 773 | 46 |

TABLE 1-continued
Spectral properties of representative dyes of this disclosure compared to prototypes (ICG and HITC)
| Sample | Media | Absorption max. [nm] | Extinction Coefficient [M⁻¹cm⁻¹] | Emission max. [nm] | Fluorescence quantum yield [%] |
|---|---|---|---|---|---|
| 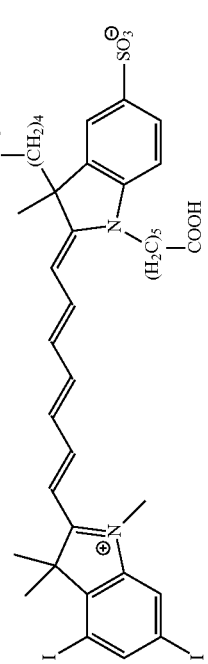 I-72 | Water<br>Methanol | 750<br>750 | 270,000 | 777<br>780 | 21<br>41 |
| 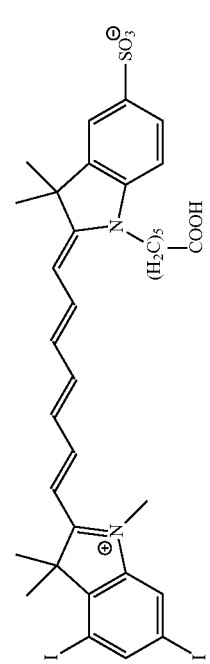 I-73 | Methanol | 748 | | 779 | 41 |
| 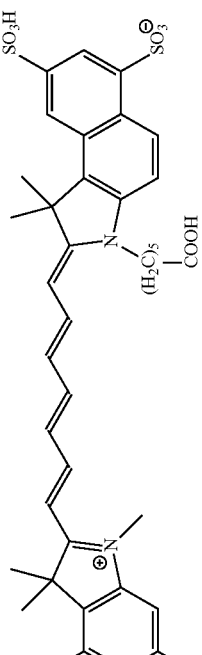 I-74 | Methanol | 760 | | 793 | 22 |

TABLE 1-continued
Spectral properties of representative dyes of this disclosure compared to prototypes (ICG and HITC)
| Sample | Media | Absorption max. [nm] | Extinction Coefficient [M⁻¹cm⁻¹] | Emission max. [nm] | Fluorescence quantum yield [%] |
|---|---|---|---|---|---|
| I-76 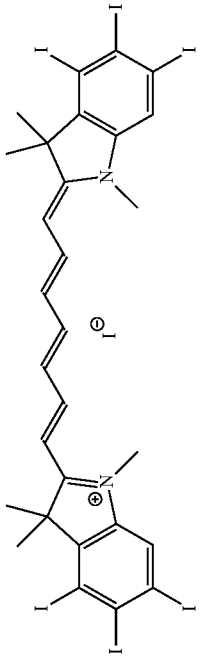 | Methanol | 755 | | 785 | 43 |
| I-79 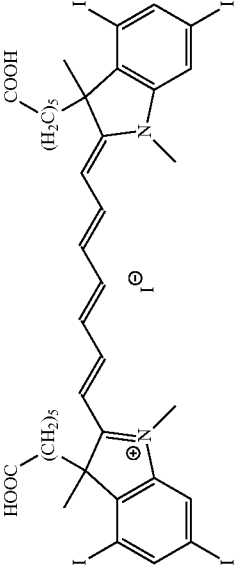 | Chloroform | 763 | | | |
| I-83 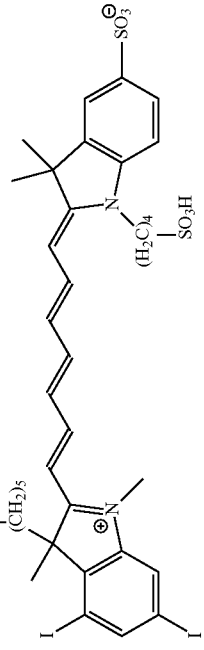 | Methanol<br>Water<br>Conjugates with IgG | 750<br>748<br>755 | | 779<br>776<br>776 | 43<br>22 |

TABLE 1-continued
Spectral properties of representative dyes of this disclosure compared to prototypes (ICG and HITC)
| Sample | Media | Absorption max. [nm] | Extinction Coefficient [M⁻¹cm⁻¹] | Emission max. [nm] | Fluorescence quantum yield [%] |
|---|---|---|---|---|---|
| 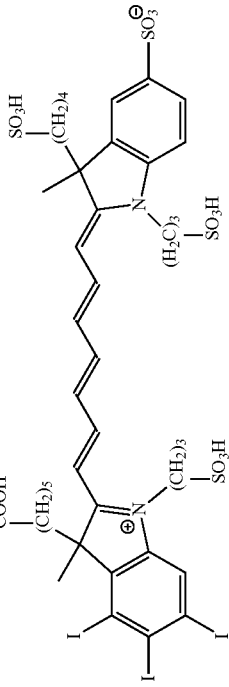 I-84 | Water (PB, pH 7.4) Conjugates with IgG | 758 762 | | 787 787 | 20 |
| 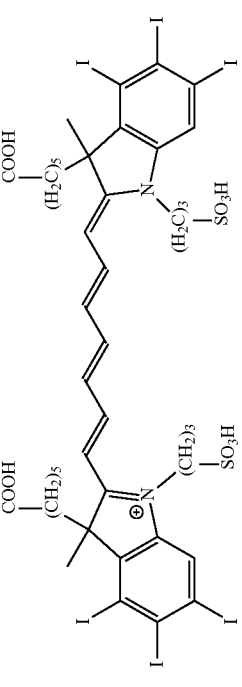 I-86 | Methanol Water BSA conjugate | 765 760 778 | 210,000 100,000 | 795 796 | 44 5-7 (subject to D/P) |
| 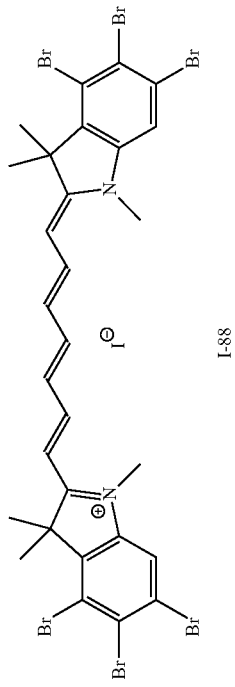 I-88 | Methanol | 748 | 240,000 | 778 | 50 |

TABLE 1-continued

Spectral properties of representative dyes of this disclosure compared to prototypes (ICG and HITC)

| Sample | Media | Absorption max. [nm] | Extinction Coefficient [M⁻¹cm⁻¹] | Emission max. [nm] | Fluorescence quantum yield [%] |
|---|---|---|---|---|---|
| I-89 | Water | 750 | 270,000 | 777 | 21.5 |

TABLE 1-continued
Spectral properties of representative dyes of this disclosure compared to prototypes (ICG and HITC)
| Sample | Media | Absorption max. [nm] | Extinction Coefficient [M⁻¹cm⁻¹] | Emission max. [nm] | Fluorescence quantum yield [%] |
|---|---|---|---|---|---|
| I-90 | Water<br>Methanol | 751<br>751 | 270,000 | 778<br>780 | 27<br>47 |
| I-91 | Methanol | 766 | | 795 | 26 |
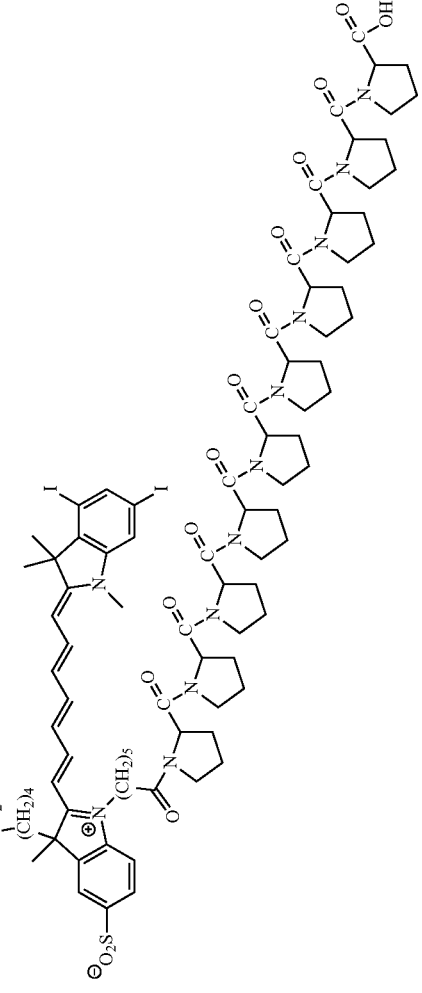

TABLE 1-continued
Spectral properties of representative dyes of this disclosure compared to prototypes (ICG and HITC)
| Sample | Media | Absorption max. [nm] | Extinction Coefficient [M⁻¹cm⁻¹] | Emission max. [nm] | Fluorescence quantum yield [%] |
|---|---|---|---|---|---|
| 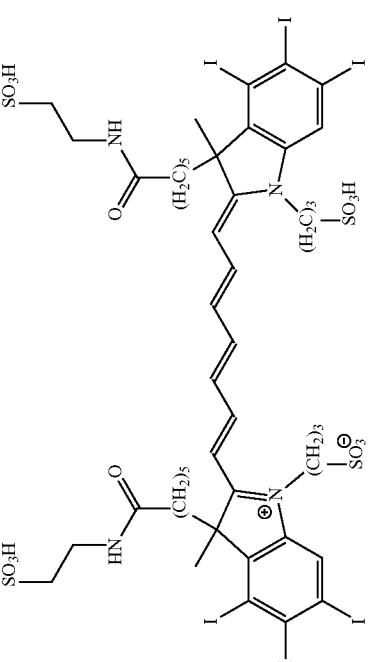 I-92 | Methanol | 764 | | 794 | 39 |
| 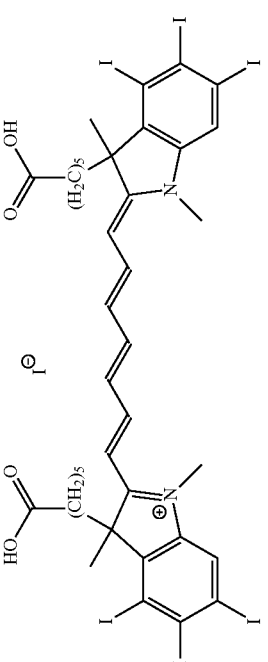 I-93 | Methanol<br>Water | 755<br>783 | | 783<br>n.f. | 47 |

TABLE 1-continued
Spectral properties of representative dyes of this disclosure compared to prototypes (ICG and HITC)
| Sample | Media | Absorption max. [nm] | Extinction Coefficient [M$^{-1}$cm$^{-1}$] | Emission max. [nm] | Fluorescence quantum yield [%] |
|---|---|---|---|---|---|
| I-94 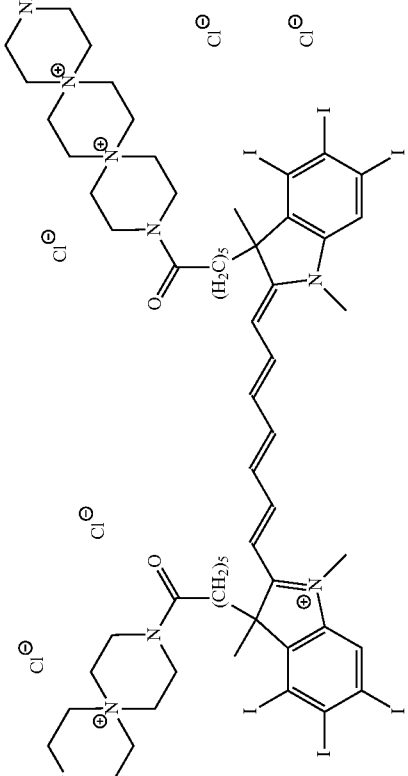 | Methanol Water | 759 695, 756 | | 788 782 | 38 1.8 |
| I-96 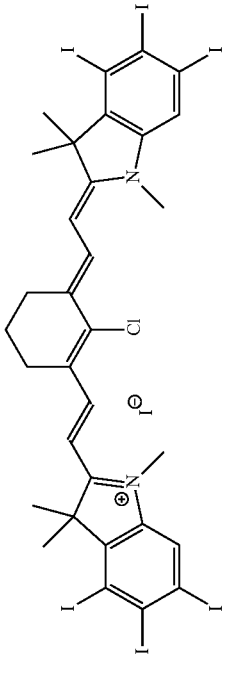 | Methanol | 787 | | 808 | 21 |

Example 39

Photostability of Halogenated Dyes

Photostability of the water soluble halogenated dyes was measured in water. Solutions with absorbance (optical density) in the range between 0.15 and 0.20 (measured in standard 1-cm quartz cells) at the excitation (laser) wavelength were prepared. The laser was placed on the top of a cuvette containing the dye solution with a magnetic stirrer, and the solution was irradiated with continuous stirring. The absorption and emission spectra of the solutions were measured before irradiation and during light exposure. Relative photostabilities were calculated as the ratio between (i) the measured absorbances at the long-wavelength maximum before and after exposure ($A/A_0$) and (ii) relative fluorescence intensities before and after exposure ($I/I_0$), and corresponding plots were generated. The plots showing $A/A_0$ and $I/I_0$ vs. the exposure time are shown in FIGS. 5 and 6, respectively.

5. Biological Testing

Example 40

Determination of the Dye-to-Protein Ratios

The molar dye-to-protein ratio (degree of labeling) for each purified dye conjugate was calculated as the molarity of dye divided by the molarity of protein. The dye concentration of the conjugate was determined according to Lambert-Beer's Law from the absorbance of the dye at the absorption maximum. The protein concentration was assessed by measurement of the absorption of the protein at 278 nm. The dye-to-protein ratios (D/P) were calculated using the following formula (with the assumption that the extinction coefficients for the free and conjugated dyes are approximately equal):

$$D/P = \frac{A_{conj(\lambda max)} \varepsilon_p}{(A_{conj(278)} - xA_{conj(\lambda max)}) \varepsilon_{dye}},$$

where $A_{conj(\lambda max)}$, $A_{conj(278)}$ are the absorbances (optical densities) at the long-wavelength absorption maxima and at 278 nm of the dye-protein conjugate respectively; $\varepsilon_{dye}$ is the extinction coefficient of the dye at $\lambda_{max}$, $\varepsilon_p$ is the extinction coefficient of the protein at 278 nm, for antibody (IgG): $\varepsilon_p = 201{,}700\ M^{-1}cm^{-1}$. The factor x ($x = A_{dye(278)}/A_{dye(max)}$) in the denominator accounts for dye absorption at 278 nm ($A_{dye(278)}$) which is a percent of the absorption of the dye at its maximum absorption ($A_{dye(\lambda max)}$).

Example 41

Preparation of Bovine Erythrocytes

Bovine erythrocytes were isolated from blood plasma stored with sodium citrate. 1 mL of bovine blood was treated at centrifuge (3,000 rpm) for 10 min to precipitate erythrocytes. The supernatant was decanted, 2 mL of physiological solution were added, treated and erythrocytes were precipitated with centrifuge. The washing procedure was repeated for 3 times and the precipitated erythrocytes were collected.

Example 42

Figure 9:
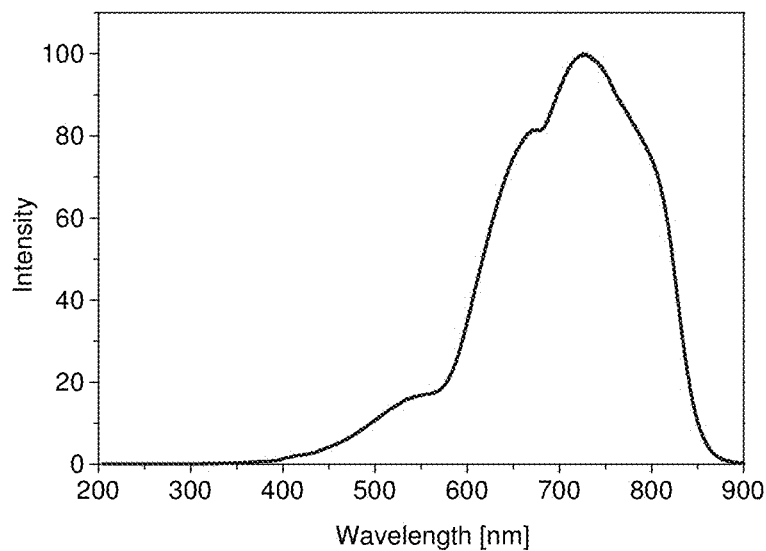
FIG. 9 is a graph of emission spectra of the 250 W IR lamp, which was used for irradiation.
Figure 10:
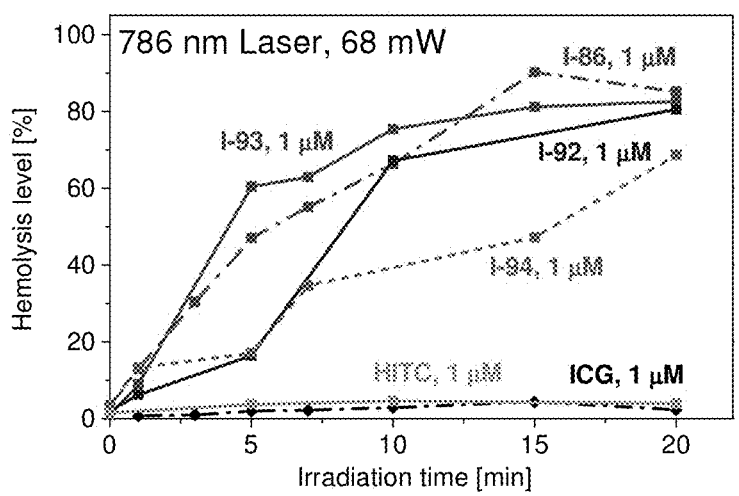
FIG. 10 is a graph of hemolysis level as a function of exposure time for 1 µM dye concentrations at irradiation with constant laser power (786 nm laser, 68 mW).
Figure 11:
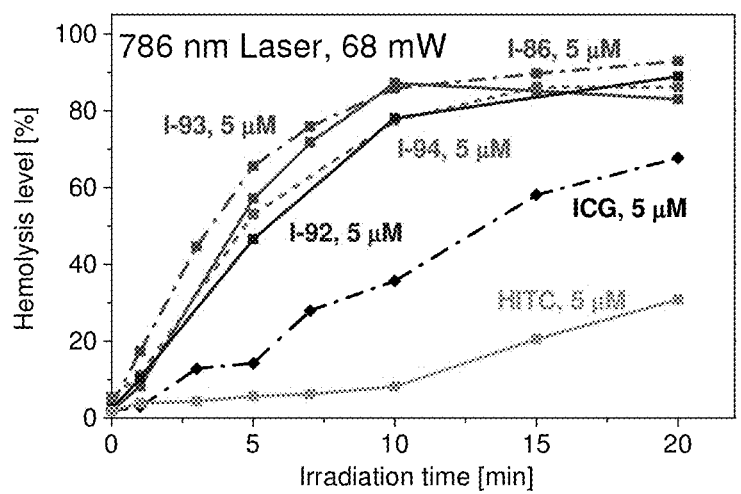
FIG. 11 is a graph of hemolysis level as a function of exposure time for 5 µM dye concentrations at irradiation with constant laser power (786 nm laser, 68 mW).

Testing of Phototoxicity Under Exposure with Glow Lamp and Dark Toxicity of Photosensitizing Compositions Using Bovine Erythrocytes For dye incubation approximately $725 \times 10^6$ erythrocytes were placed in a 1 mL physiological solution, containing a known dye concentration. Cells were dye-incubated for 45 minutes at 37° C. in the dark. Then the examined suspensions of cells (erythrocytes) were placed at a distance of 30-cm from a 250 W glow red-lamp equipped with a water-based heat filter and irradiated with occasional stirring. The emission spectrum of the lamp is shown in FIG. 9. After irradiation, cells were stored at 4° C. for 15 hours. Then the whole suspension was centrifuged and the absorbance of supernatant was measured at 542 nm. The hemolysis level (percentage of hemolyzed cells) was determined as the ratio of absorbances of the supernatant and a solution of 100% hemolysed cells. The 100% hemolysis was taken as the value obtained when the given number of erythrocytes were suspended in distilled water.

Representative data are shown in Table 2 below.

TABLE 2

Hemolysis level of bovine erythrocytes in dark and under light exposure with glow lamp

| Composition | Concentration [μM] | Excitation | Exposure Time [min] | Hemolysis [%] |
|---|---|---|---|---|
| 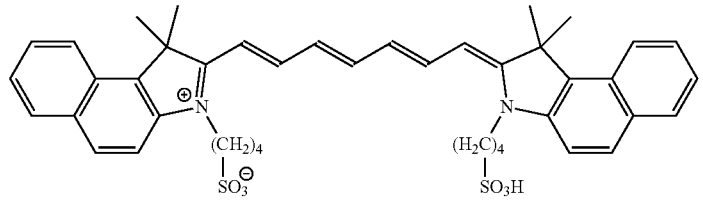 | 10 | Dark | — | 1.7 |
| | 5 | Dark | — | 1.6 |
| | | Glow Lamp | 120 | 65 |
| | | Glow Lamp | 60 | 16 |
| | 1 | Glow Lamp | 120 | 4 |

ICG

TABLE 2-continued

Hemolysis level of bovine erythrocytes in dark and under light exposure with glow lamp

| Composition | Concentration [μM] | Excitation | Exposure Time [min] | Hemolysis [%] |
|---|---|---|---|---|
| 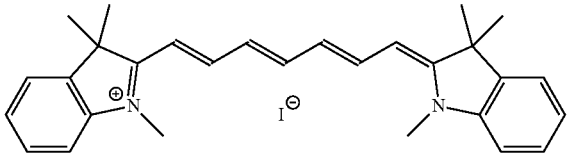<br>HITC | 10<br>5<br><br><br>1<br> | Dark<br>Dark<br>Glow Lamp<br>Glow Lamp<br>Glow Lamp<br>Glow Lamp | —<br>—<br>120<br>60<br>120<br>60 | 6.7<br>2.0<br>74<br>65<br>5.4<br>4.4 |
| 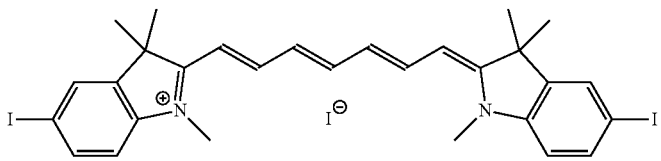<br>I-25 | 50<br>0.5<br>0.1 | Dark<br>Glow Lamp<br>Glow Lamp | <br>30<br>60 | 51<br>83<br>39 |
| 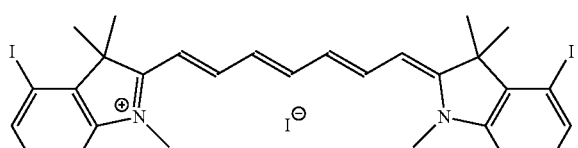<br>I-71 | 50<br>5<br>0.5<br>0.1 | Dark<br>Dark<br>Glow Lamp<br>Glow Lamp | <br><br>30<br>60 | 30<br>2<br>75<br>21 |
| 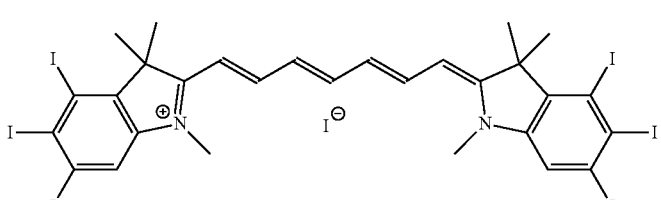<br>I-76 | 50<br>5<br>0.5<br>0.1 | Dark<br>Dark<br>Glow Lamp<br>Glow Lamp | <br><br>30<br>60 | 12<br>2<br>46<br>43 |
| 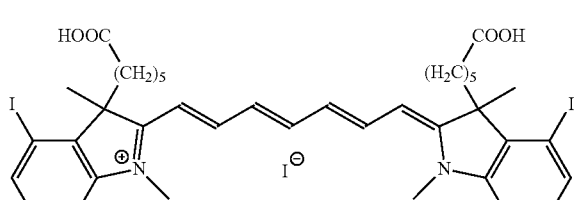<br>I-79 | 50<br>1<br>0.5 | Dark<br>Glow Lamp<br>Glow Lamp | <br>30<br>60 | 4<br>80<br>75 |
| 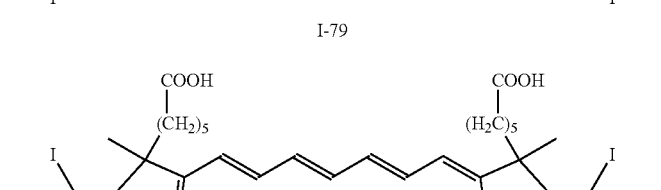<br>I-86 | 10<br>0.5<br>0.1 | Dark<br>Glow Lamp<br>Glow Lamp | <br>30<br>60 | 3<br>74<br>70 |

Example 43

Testing of Phototoxicity Under Irradiation with Laser and Dark Toxicity of Photosensitizing Compositions Using Bovine Erythrocytes For dye incubation, approximately $725 \times 10^6$ erythrocytes were placed in a 1 mL physiological solution, containing a known dye concentration. Cells were incubated for 45 minutes at 37° C. in the dark. Then the examined suspensions of cells (erythrocytes) were irradiated with diode laser (786 nm, 68 mW) with occasional stirring. After irradiation, cells were stored at 4° C. for 15 hours. Then erythrocytes were precipitated using centrifugation and the absorbance of supernatant was measured at 542 nm. The hemolysis level was determined as the ratio of absorbances of the investigated supernatant and a solution of 100% hemolysed cells. The 100% hemolysis was taken as the value obtained when the given number of erythrocytes were suspended in distilled water. Representative data are shown in FIG. 9.

6. The Singlet Oxygen Generation Efficiency

Example 44

Determination of the Singlet Oxygen Quantum Yield ($\Phi_\Delta$)

The modified relative photochemical method of Spiller W. et al. (J. Porphyrins Phthalocyanines, 1998, V.2, 145-158) utilizing 1,3-diphenylisobenzofuran (DPBF) as a chemical scavenger was used to determine the photosensitiser's singlet oxygen quantum yields ($\Phi_\Delta$) in ethanol solutions. ICG ($\Phi_\Delta = 12\%$) was used as a reference compound (J. A. Cardillo, et al. Br. J. Ophthalmol., 2008, V.92, 276-280).

Ethanolic solutions containing DPBF (10 µM) and sensitizers with absorbance (optical density) in a range between 0.09 and 0.10 at 650 nm (measured in a standard 1-cm quartz cell) were prepared. Samples were saturated with oxygen by bubbling. Next, 3 mL of the solution were placed in a 1-cm cell equipped with a stirring bar and a 10 mW, 650 nm diode laser was hermetically attached to the top of cuvette so as to avoid solvent evaporation and to provide a light beam direction from top to bottom of the cuvette. The solution in the cuvette was irradiated with the diode laser under continuous stirring for a certain time. DPBF consumption was determined by monitoring DPBF bleaching over irradiation time using absorption spectroscopy at 411 nm (extinction coefficient 22,000 $M^{-1}cm^{-1}$). At least six absorption spectra were obtained for each solution at different irradiation times until the DPBF absorbance reduced at least to the 10% of the initial absorbance.

The decrease of DPBF absorbance at 411 nm versus irradiation time was plotted for each photosensitizer and the DPBF degradation rate constant (K) characterizing the reaction rate of singlet oxygen with DPBF in presence of a sensitizer was calculated.

The $\Phi_\Delta$ values were calculated according to the following formula:

$$\Phi_\Delta = \Phi_{\Delta Ce6} \times K/K_{Ce6} \times A_{Ce6}/A,$$

where $\Phi_\Delta$ and $\Phi_{\Delta Ce6}$ are the singlet oxygen quantum yield of a SOG and the reference (ICG);

K and $K_{Ce6}$ are the DPBF degradation rate constant of a SOG and ICG, respectively, and A and $A_{Ce6}$ are the absorbances (optical densities) of SOG of the dye sample and of ICG at the excitation wavelength (650 nm).

Representative $\Phi_\Delta$ data are shown in Table 3 below.

TABLE 3

Singlet oxygen generation quantum yield ($\Phi_\Delta$) measured in ethanol

| Composition | Singlet oxygen generation quantum yield $\Phi_\Delta$ [%] |
|---|---|
| 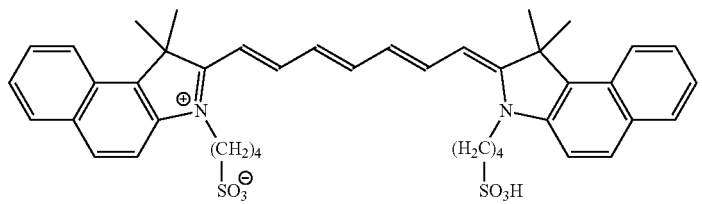 ICG | 12 |
| 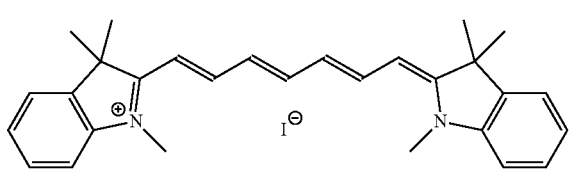 HITC | 5 |

TABLE 3-continued

Singlet oxygen generation quantum yield ($\Phi_\Delta$) measured in ethanol

| Composition | Singlet oxygen generation quantum yield $\Phi_\Delta$ [%] |
|---|---|
| I-25 | 20 |
| I-71 | 19 |
| I-72 | 12 |
| I-76 | 50 |
| I-86 | 13 |

TABLE 3-continued

Singlet oxygen generation quantum yield ($\Phi_\Delta$) measured in ethanol

| Composition | Singlet oxygen generation quantum yield $\Phi_\Delta$ [%] |
|---|---|
| I-89 | 13 |
| I-88 | 11 |
| I-90 | 11 |

What is claimed is:
1. A heterocyclic compound of the formula

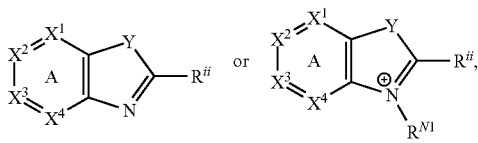

wherein:
ring A is an aromatic or heterocyclic ring wherein each of $X^1$, $X^2$, $X^3$, and $X^4$ is C—$R^X$, with the proviso that ring A has at least two halo substituents thereon, and at least two halo substituents in ring A are iodine or at least two halo substituents in ring A are bromine;

$R^X$ is H, F, Cl, Br, I, L-$S_c$, L-$R^R$, L-$R^\pm$; aliphatic, alicyclic, or aromatic group; amino or substituted amino; sulfo, trifluoromethyl, hydroxy, alkoxy, carboxy, phosphate, phosphonate, or sulfate; or adjacent $R^X$ substituents, taken in combination, form a fused aromatic or heterocyclic ring that is itself optionally further substituted by H, F, Cl, Br, I, L-$S_c$, L-$R^R$, L-$R^\pm$; aliphatic, alicyclic, or aromatic group; amino or substituted amino; sulfo, trifluoromethyl, hydroxy, alkoxy, carboxy, phosphate, phosphonate, or sulfate;

$R^{N1}$ is selected from the group consisting of H, L-$S_c$, L-$R^R$, L-$R^\pm$, aliphatic groups, alicyclic groups, alkylaryl groups, and aromatic groups, wherein each aliphatic residue may incorporate up to ten heteroatoms selected from the group consisting of N, O, and S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

Y is C($R^{C1}$)($R^{C2}$);

each $R^{C1}$ and $R^{C2}$ is independently $R^C$, or adjacent substituents ($R^{C1}$, $R^{C2}$) form a cyclic or heterocyclic system that further may be substituted or fused;

$R^C$ is H, L-$S_c$, L-$R^R$, L-$R^\pm$, aliphatic, alicyclic, aromatic, heteroatom-substituted aliphatic, polyether, alkyl-aryl, aryl-alkyl, F, Cl, Br, I, $NH_2$, —COOH, —CN, azido, —OH, —$NO_2$, —$SO_3H$, —$SO_2NHR^m$, —$SO_2NHN(R^m)_2$, —$SO_2R^C$, —$C_6H_4$—$SO_3H$, —$C_6H_4$—$PO_3H$, —$CH_2$—$C_6H_4$—$SO_3H$, —$CH_2$—$C_6H_4$—$PO_3H$, pyridylium, pyrylium, —PO(OH)$_2$, —O—PO(OH)$_2$, —PO(OH)(O$R^m$), —O—P(OH)(O$R^m$), —PO(O$R^m$)$_2$, —($CH_2CH_2O)_n$PO(O$R^m$)$_2$, —(O$CH_2CH_2$)$_n$PO(O$R^m$)$_2$, wherein n=1-30, —$CONH_2$, —CON($R^m$)$_2$, —CONHN($R^m$)$_2$, —COO—NHS or —COO—$R^m$, wherein $R^m$ is selected from the group consisting of H, L-$S_c$, L-$R^R$, L-$R^\pm$, aliphatic substituents, and aromatic substituents, and each aliphatic residue may incorporate up to ten heteroatoms selected from the group consisting of N, O, and S, and can be substituted by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

L is a single covalent bond or is a covalent linkage that is linear or branched, cyclic or heterocyclic, saturated or unsaturated, having 1-20 non-hydrogen atoms selected from the group consisting of C, N, P, O and S, arranged so that the linkage contains any combination of ether, thioether, amine, ester, amide bonds; single, double, triple or aromatic carbon-carbon bonds; or carbon-sulfur bonds, carbon-nitrogen bonds, phosphorus-sulfur, nitrogen-nitrogen, nitrogen-oxygen or nitrogen-platinum bonds, or aromatic or heteroaromatic bonds;

$R^R$ is a reactive group;

$S_c$, is a moiety that is conjugated to ring A through linker, L, and is selected from the group consisting of alkanes, alkenes, alkynes, polyethers, polyamines, cycloparaffins, cycloolefins, cyclynes, heteroalicyclic groups, aromatic groups, heteroaromatic groups, organic dyes, polymethines, dendrimers, nanoparticles, biological molecules, and biological compounds, and wherein the alkanes, alkenes, alkynes, polyethers, polyamines, cycloparaffins, cycloolefins, cyclynes, heteroalicyclic groups, aromatic groups, heteroaromatic groups, organic dyes, polymethines, and dendrimers are optionally substituted with one or more substituents selected from the group consisting of F, Cl, Br, I, carboxylic acid, sulfonic acid, CN, nitro, hydroxy, phosphate, phosphonate, sulfate, cyano, azido, amine, alkyl, alkoxy, trialkylammonium and aryl, $R^\pm$ is an ionic or hydrophilic group;

$R^{ii}$ is $CH_2R^1$, $SR^S$, or $SO_3H$;

$R^1$ is selected from H, F, Cl, Br, I, L-$S_c$, L-$R^R$, L-$R^\pm$, aliphatic group, alicyclic group, heteroatom-substituted aliphatic group, aromatic group, polyether, cyano, carboxy, carboxamide, carboxylic ester, formyl, amine group, nitro, sulfonic acid, phosphonic acid, phosphonic ester, sulfone, and sulfamide, or ($R^1$ and $R^{C1}$) or ($R^1$ and $R^{C2}$) may form a cyclic or heterocyclic system, which further may be substituted or fused; and $R^S$ is H or alkyl.

2. A heterocyclic compound represented by the formula

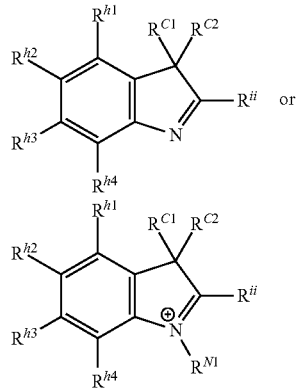

wherein:
$R^{h1}$, $R^{h2}$, $R^{h3}$ and $R^{h4}$ are each independently $R^X$ with the proviso that at least two of $R^{h1}$, $R^{h2}$, $R^{h3}$ and $R^{h4}$ are halo and at least one of $R^{h1}$, $R^{h2}$, $R^{h3}$, and $R^{h4}$ is iodine or bromine;

$R^X$ is H, F, Cl, Br, I, L-$S_c$, L-$R^R$, L-$R^\pm$; aliphatic, alicyclic, or aromatic group; amino or substituted amino; sulfo, trifluoromethyl, hydroxy, alkoxy, carboxy, phosphate, phosphonate, or sulfate; or adjacent $R^x$ substituents, taken in combination, form a fused aromatic or heterocyclic ring that is itself optionally further substituted by H, F, Cl, Br, I, L-$S_c$, L-$R^R$, L-$R^\pm$; aliphatic, alicyclic, or aromatic group; amino or substituted amino; sulfo, trifluoromethyl, hydroxy, alkoxy, carboxy, phosphate, phosphonate, or sulfate;

$R^{N1}$ is selected from the group consisting of H, L-$S_c$, L-$R^R$, L-$R^\pm$, aliphatic groups, alicyclic groups, alkylaryl groups, and aromatic groups, wherein each aliphatic residue may incorporate up to ten heteroatoms selected from the group consisting of N, O, and S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

each $R^{C1}$ and $R^{C2}$ is independently $R^C$, or adjacent substituents ($R^{C1}$, $R^{C2}$) form a cyclic or heterocyclic system that further may be substituted or fused;

$R^C$ is H, L-$S_c$, L-$R^R$, L-$R^\pm$, aliphatic, alicyclic, aromatic, heteroatom-substituted aliphatic, polyether, alkyl-aryl, aryl-alkyl, F, Cl, Br, I, $NH_2$, —COOH, —CN, azido, —OH, —$NO_2$, —$SO_3H$, —$SO_2NHR'''$, —$SO_2NHN(R''')_2$, —$SO_2R^C$, —$C_6H_4$—$SO_3H$, —$C_6H_4$—$PO_3H$, —$CH_2$—$C_6H_4$—$SO_3H$, —$CH_2$—$C_6H_4$—$PO_3H$, pyridylium, pyrylium, —$PO(OH)_2$, —O—$PO(OH)_2$, —$PO(OH)(OR''')$, —O—$P(OH)(OR''')$, —$PO(OR''')_2$, —$(CH_2CH_2O)_nPO(OR''')_2$, —$(OCH_2CH_2)_nPO(OR''')_2$, wherein n=1-30, —$CONH_2$, —$CON(R''')_2$, —CONHN$(R''')_2$, —COO—NHS or —COO—$R'''$, wherein $R'''$ is selected from the group consisting of H, L-$S_c$, L-$R^R$, L-$R^\pm$, aliphatic substituents, and aromatic substituents, and each aliphatic residue may incorporate up to ten heteroatoms selected from the group consisting of N, O, and S, and can be substituted by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

$R^R$, is a reactive group;

L is a single covalent bond or is a covalent linkage that is linear or branched, cyclic or heterocyclic, saturated or unsaturated, having 1-20 non-hydrogen atoms selected from the group consisting of C, N, P, O and S, arranged so that the linkage contains any combination of ether, thioether, amine, ester, amide bonds; single, double, triple or aromatic carbon-carbon bonds; or carbon-sulfur bonds, carbon-nitrogen bonds, phosphorus-sulfur, nitrogen-nitrogen, nitrogen-oxygen or nitrogen-platinum bonds, or aromatic or heteroaromatic bonds;

$S_c$, is a moiety that is conjugated to the benzene ring through linker, L, and is selected from the group consisting of alkanes, alkenes, alkynes, polyethers, polyamines, cycloparaffins, cycloolefins, cyclynes, heteroalicyclic groups, aromatic groups, heteroaromatic groups, organic dyes, polymethines, dendrimers, nanoparticles, biological molecules, and biological compounds, and wherein the alkanes, alkenes, alkynes, polyethers, polyamines, cycloparaffins, cycloolefins, cyclynes, heteroalicyclic groups, aromatic groups, heteroaromatic groups, organic dyes, polymethines, and dendrimers are optionally substituted with one or more substituents selected from the group consisting of F, Cl, Br, I, carboxylic acid, sulfonic acid, CN, nitro, hydroxy, phosphate, phosphonate, sulfate, cyano, azido, amine, alkyl, alkoxy, trialkylammonium and aryl, and $R^\pm$ is an ionic or hydrophilic group.

3. The heterocyclic compound of claim 2, wherein at least one of $R^{h1}$, $R^{h2}$, $R^{h3}$, and $R^{h4}$ is iodine.

4. The heterocyclic compound of claim 2, wherein at least one of $R^{h1}$, $R^{h2}$, $R^{h3}$, and $R^{h4}$ is bromine.

5. The heterocyclic compound of claim 2, of the formula:

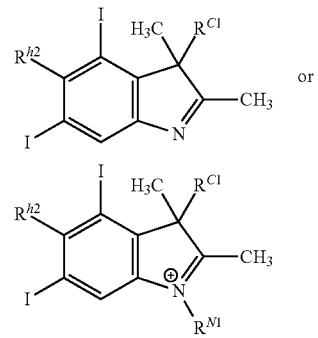

wherein:

$R^{h2}$ is H, I, Br, sulfo, —$(CH_2)_mSO_3H$, —$(CH_2)_mCOOH$, —$O(CH_2)_mCOOH$, or —$S(CH_2)_mCOOH$, wherein m=0-20;

$R^{C1}$ is alkyl, aryl, —$(CH_2)_n$—COOH, —$(CH_2)$—$NH_2$, —$(CH_2)_n$—$SO_3H$, —$(CH_2)_n$—$PO(OEt)_2$, —$(CH_2)_n$—PO(OH)(OEt), or —$(CH_2)_n$—$PO(OH)_2$, wherein n=1-20; and $R^{N1}$ is alkyl, —$(CH_2)_k$—COOH, —$(CH_2)_k$—$SO_3H$, —$(CH_2)_k$—$PO(OEt)_2$, —$(CH_2)_k$—PO(OH)(OEt), —$(CH_2)_k$—$PO(OH)_2$, or —$(CH_2)_k$—$N^+(Alk)_3$, wherein k=1-20.

6. The heterocyclic compound of claim 1, of the formula:

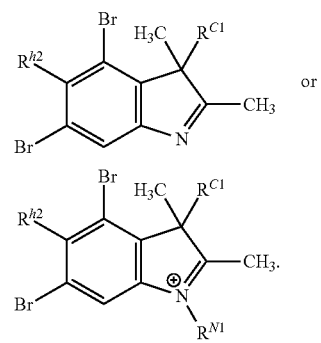

7. The heterocyclic compound of claim 2, selected from the group consisting of compounds of the formulae:

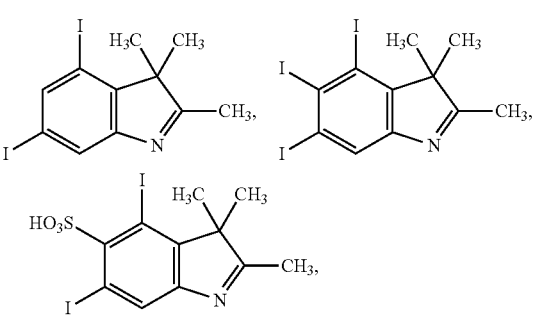

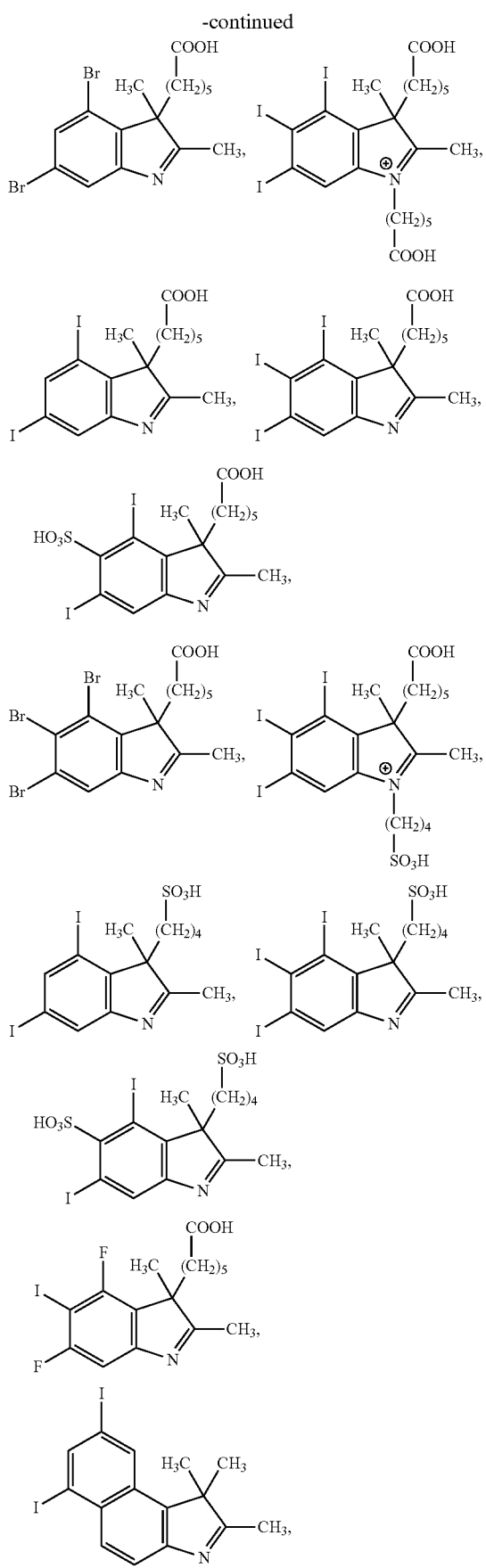
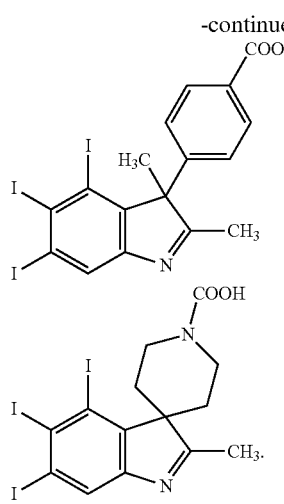

8. A method of generating reactive oxygen species (ROS) at a biological locus, comprising introducing a composition comprising a compound of claim 2 to said locus, and transmitting radiation to said composition at said locus that is effective to cause the composition to generate ROS at said locus.

9. The method of claim 8, further comprising introducing exogenous oxygen or ozone to said locus to increase available oxygen at said locus for generating ROS at said locus.

10. The method of claim 8, wherein said composition is introduced to said locus on a carrier.

11. The method of claim 10, wherein the carrier comprises at least one carrier species selected from the group consisting of bacteriophages and antibodies.

12. The method of claim 8, wherein the compound in said composition is substantially completely photobleached by said radiation transmitted to said locus.

13. The method of claim 12, wherein the radiation transmitted to said locus is limited to the amount required for the compound in said composition to be substantially completely photobleached by said radiation transmitted to said locus.

14. The method of claim 8, wherein the biological locus comprises a corporeal locus of a human or animal subject.

15. The method of claim 8, wherein the composition comprises a self-limiting ROS generator photosensitizer dye or dye conjugate, the biological locus comprises a human body, and the radiation transmitted to said locus comprises low intensity activating spectrum light that is exposed over large areas of the body to deactivate residual photosensitizer dye or dye conjugate without inducing sufficient reactivity to damage the body.

16. The method of claim 15, wherein the transmitted radiation is progressively increased in intensity to remove sensitivity of the dye of the dye conjugate.

17. The method of claim 15, wherein the transmitted radiation is changed in intensity and/or spectrum during the transmission thereof to the locus.

18. The method of claim 8, wherein the composition comprises a self-limiting ROS generator photosensitizer dye or dye conjugate, the biological locus comprises a human body, and the radiation transmitted to said locus comprises light that is effective to activate the photosensitizer dye or dye conjugate to treat the body for cancer, pathogen, or other biomaterial in tissue, blood or bone of the body.

19. The method of claim 8, wherein the radiation is transmitted to said locus over a period of time in a range of from 4 to 5000 hours.

20. A method of treating a subject to whom a compound of claim 2, which is a photosensitizer, has been administered resulting in presence of photosensitizer in a bodily region of the subject that is non-targeted for phototherapy, comprising transmitting to the non-targeted bodily region deactivatingly effective light that is frequency modulated in a range of from 100 kHz to 100 THz, to deactivate photosensitizer present in such region, wherein treating does not include prophylaxis.

21. The method of claim 20, wherein said transmitting of deactivatingly effective light is conducted contemporaneously with photodynamic therapy treatment of said subject.

22. A heterocyclic compound of the formula

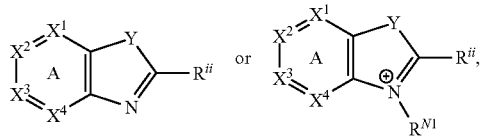

wherein:
ring A is an aromatic or heterocyclic ring wherein each of $X^1$, $X^2$, $X^3$, and $X^4$ is C—$R^X$, with the proviso that ring A has at least two halo substituents thereon, and at least one of said halo substituents on ring A is iodine or bromine;

$R^X$ is H, F, Cl, Br, I, L-$S_c$, L-$R^R$, L-$R^\pm$; aliphatic, alicyclic, or aromatic group; amino or substituted amino; sulfo, trifluoromethyl, hydroxy, alkoxy, carboxy, phosphate, phosphonate, or sulfate; or adjacent $R^x$ substituents, taken in combination, form a fused aromatic or heterocyclic ring that is itself optionally further substituted by H, F, Cl, Br, I, L-$S_c$, L-$R^R$, L-$R^\pm$; aliphatic, alicyclic, or aromatic group; amino or substituted amino; sulfo, trifluoromethyl, hydroxy, alkoxy, carboxy, phosphate, phosphonate, or sulfate;

$R^{N1}$ is selected from H, L-$S_c$, L-$R^R$, L-$R^\pm$, aliphatic groups, alicyclic groups, alkylaryl groups, and aromatic groups, wherein each aliphatic residue may incorporate up to ten heteroatoms selected from N, O, and S, and can be substituted one or more times by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

Y is C($R^{C1}$)($R^{C2}$);

each $R^{C1}$ and $R^{C2}$ is independently $R^C$, or adjacent substituents ($R^{C1}$, $R^{C2}$) form a cyclic or heterocyclic system that further may be substituted or fused;

$R^C$ is H, L-$S_c$, L-$R^R$, L-$R^\pm$, aliphatic, alicyclic, aromatic, heteroatom-substituted aliphatic, polyether, alkyl-aryl, aryl-alkyl, F, Cl, Br, I, NH$_2$, —COOH, —CN, azido, —OH, —NO$_2$, —SO$_3$H, —SO$_2$NHR$^m$, —SO$_2$NHN(R$^m$)$_2$, —SO$_2$R$^C$, —C$_6$H$_4$—SO$_3$H, —C$_6$H$_4$—PO$_3$H, —CH$_2$—C$_6$H$_4$—SO$_3$H, —CH$_2$—C$_6$H$_4$—PO$_3$H, pyridylium, pyrylium, —PO(OH)$_2$, —O—PO(OH)$_2$, —PO(OH)(OR$^m$), —O—P(OH)(OR$^m$), —PO(OR$^m$)$_2$, —(CH$_2$CH$_2$O)$_n$PO(OR$^m$)$_2$, —(OCH$_2$CH$_2$)$_n$PO(OR$^m$)$_2$, wherein n=1-30, —CONH$_2$, —CON(R$^m$)$_2$, —CONHN(R$^m$)$_2$, —COO—NHS or —COO—R$^m$, wherein R$^m$ is selected from a the group consisting of H, L-$S_c$, L-$R^R$, L-$R^\pm$, aliphatic substituents, and aromatic substituents, and each aliphatic residue may incorporate up to ten heteroatoms selected from the group consisting of N, O, and S, and can be substituted by F, Cl, Br, I, hydroxy, alkoxy, carboxy, sulfo, phosphate, amino, sulfate, phosphonate, cyano, nitro, azido, alkyl-amino, dialkyl-amino or trialkylammonium;

L is a single covalent bond or is a covalent linkage that is linear or branched, cyclic or heterocyclic, saturated or unsaturated, having 1-20 non-hydrogen atoms selected from the group consisting of C, N, P, O and S, arranged so that the linkage contains any combination of ether, thioether, amine, ester, amide bonds; single, double, triple or aromatic carbon-carbon bonds; or carbon-sulfur bonds, carbon-nitrogen bonds, phosphorus-sulfur, nitrogen-nitrogen, nitrogen-oxygen or nitrogen-platinum bonds, or aromatic or heteroaromatic bonds;

$R^R$ is a reactive group;

$S_c$ is a moiety that is conjugated to ring A through linker, L, and is selected from the group consisting of alkanes, alkenes, alkynes, polyethers, polyamines, cycloparaffins, cycloolefins, cyclynes, heteroalicyclic groups, aromatic groups, heteroaromatic groups, organic dyes, polymethines, dendrimers, nanoparticles, biological molecules, and biological compounds, and wherein the alkanes, alkenes, alkynes, polyethers, polyamines, cycloparaffins, cycloolefins, cyclynes, heteroalicyclic groups, aromatic groups, heteroaromatic groups, organic dyes, polymethines, and dendrimers are optionally substituted with one or more substituents selected from the group consisting of F, Cl, Br, I, carboxylic acid, sulfonic acid, CN, nitro, hydroxy, phosphate, phosphonate, sulfate, cyano, azido, amine, alkyl, alkoxy, trialkylammonium and aryl, $R^\pm$ is an ionic or hydrophilic group;

$R^{ii}$ is CH$_2$R$^1$ or SO$_3$H; and $R^1$ is selected from H, F, Cl, Br, I, L-$S_c$, L-$R^R$, L-$R^\pm$, aliphatic group, alicyclic group, heteroatom-substituted aliphatic group, aromatic group, polyether, cyano, carboxy, carboxamide, carboxylic ester, formyl, amine group, nitro, sulfonic acid, phosphonic acid, phosphonic ester, sulfone, and sulfamide, or ($R^1$ and $R^{C1}$) or ($R^1$ and $R^{C2}$) may form a cyclic or heterocyclic system, which further may be substituted or fused.

23. The heterocyclic compound of claim 1, wherein the polymethine is selected from the group consisting of cyanines, stryryls, merocyanines, squaraines, and croconates.

24. The heterocyclic compound of claim 22, wherein the polymethine is selected from the group consisting of cyanines, stryryls, merocyanines, squaraines, and croconates.

25. The heterocyclic compound of claim 2, wherein the polymethine is selected from the group consisting of cyanines, stryryls, merocyanines, squaraines, and croconates.

* * * * *

UNITED STATES PATENT AND TRADEMARK OFFICE
CERTIFICATE OF CORRECTION

PATENT NO. : 8,748,446 B2  
APPLICATION NO. : 13/411539  
DATED : June 10, 2014  
INVENTOR(S) : Gary W. Jones et al.

Page 1 of 18

It is certified that error appears in the above-identified patent and that said Letters Patent is hereby corrected as shown below:

In the Specification

Column 1, line 31: "in vitro or in vivo" should be -- *in vitro* or *in vivo* --.

Column 6, line 9: "in vitro" should be -- *in vitro* --.

Columns 19-20, the chemical formula (formula 5) should read,

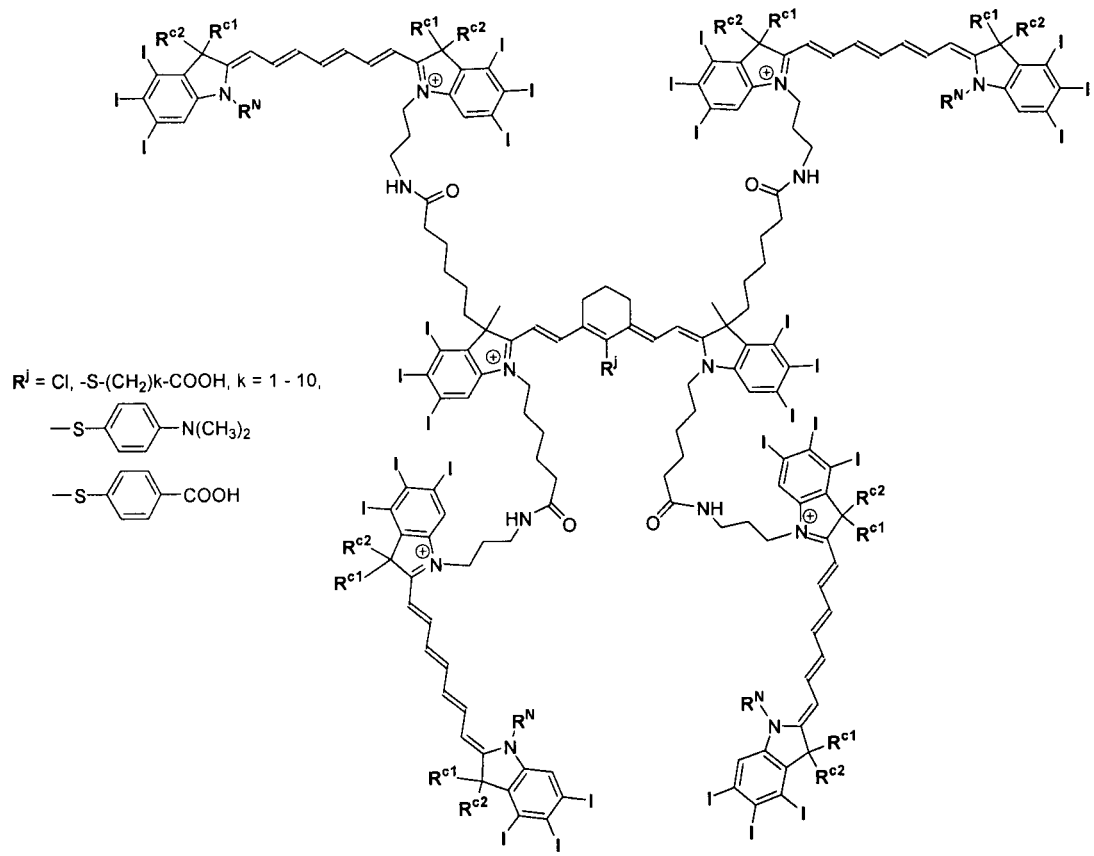

--                                                                                                                         --.

Signed and Sealed this  
Twenty-fourth Day of February, 2015

Michelle K. Lee  
*Deputy Director of the United States Patent and Trademark Office*

CERTIFICATE OF CORRECTION (continued)
U.S. Pat. No. 8,748,446 B2

Columns 21-22, the chemical formula (formula 6) should read,

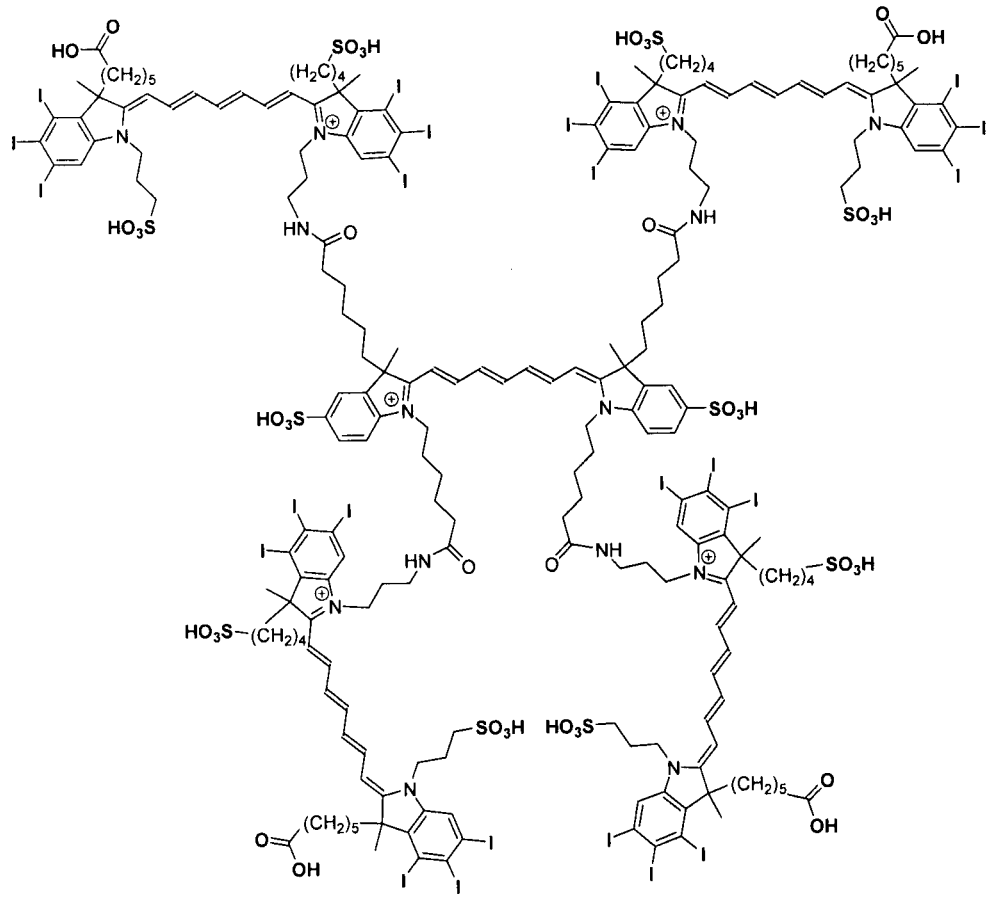

-- --.

Columns 23-24, the formula (formula 7) should read,
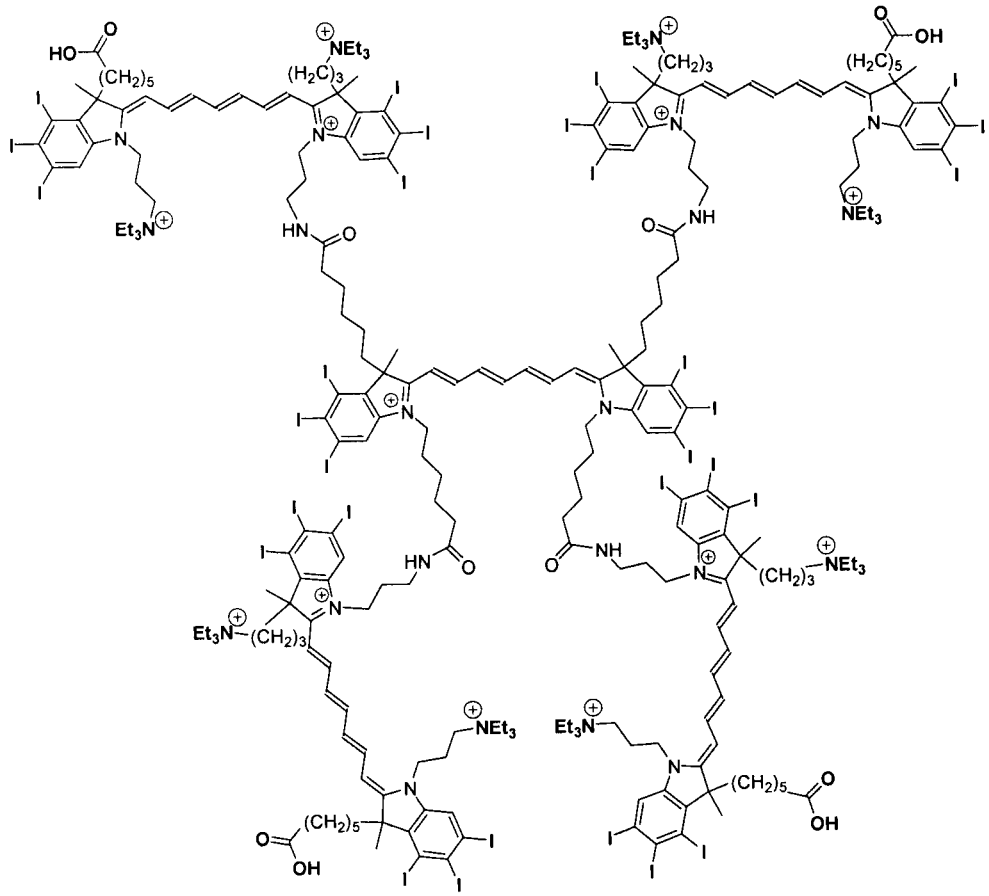
-- --.

CERTIFICATE OF CORRECTION (continued)
U.S. Pat. No. 8,748,446 B2

Columns 25-26, the formula (formula 8) should read,

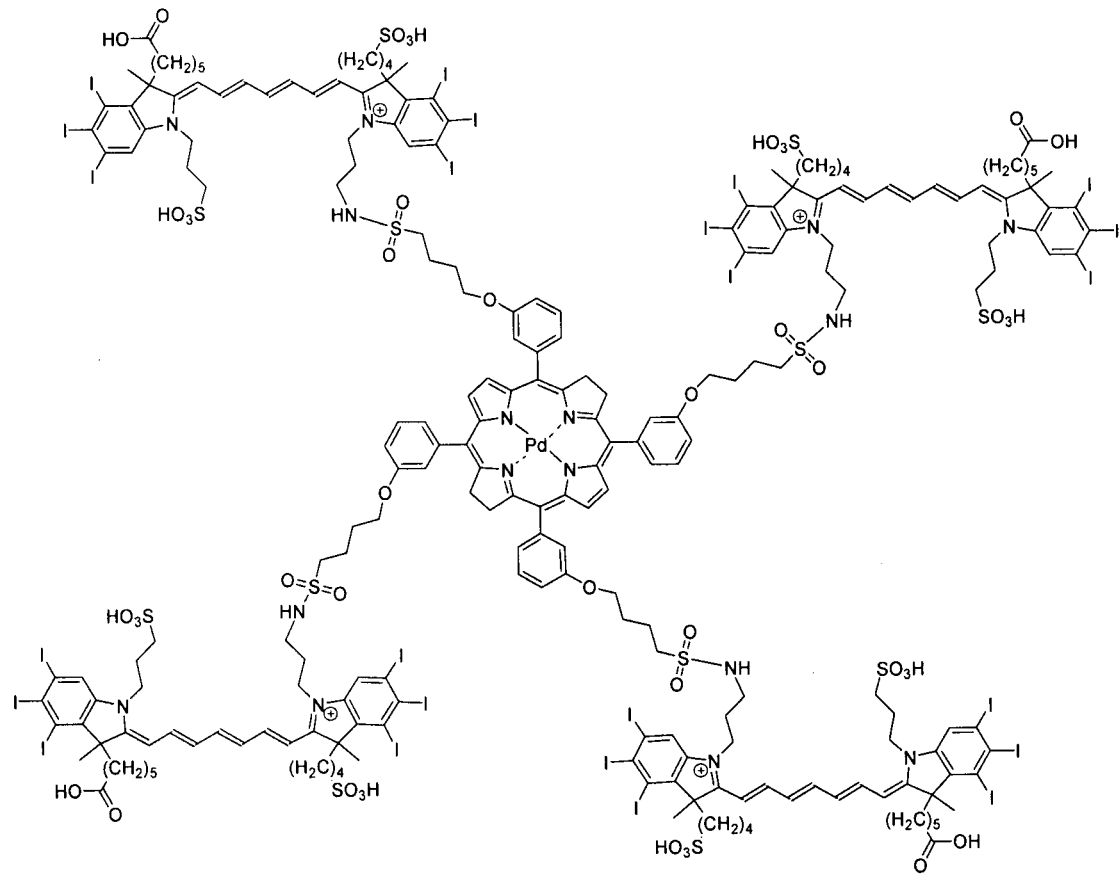

-- --.

Columns 27-28, the formula (formula 10) should read,
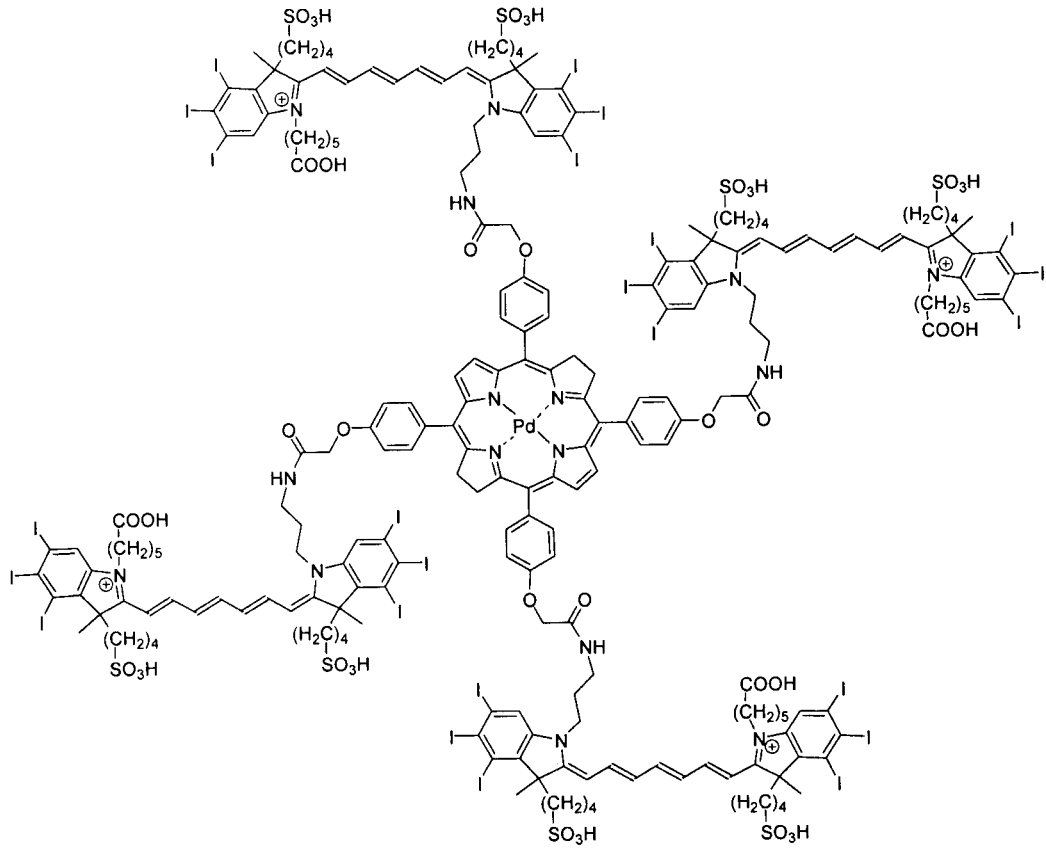
Columns 29-30, the chemical formula (formula 11) should read,
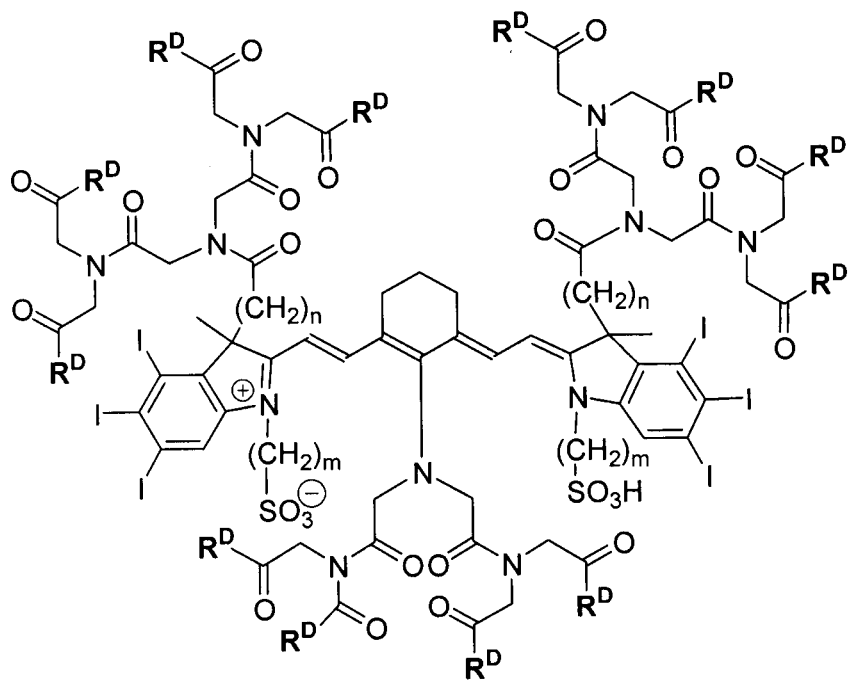
wherein $R^D$ contains a dye; --.

CERTIFICATE OF CORRECTION (continued)

Columns 31-32, the chemical formula (formula 13) should read,

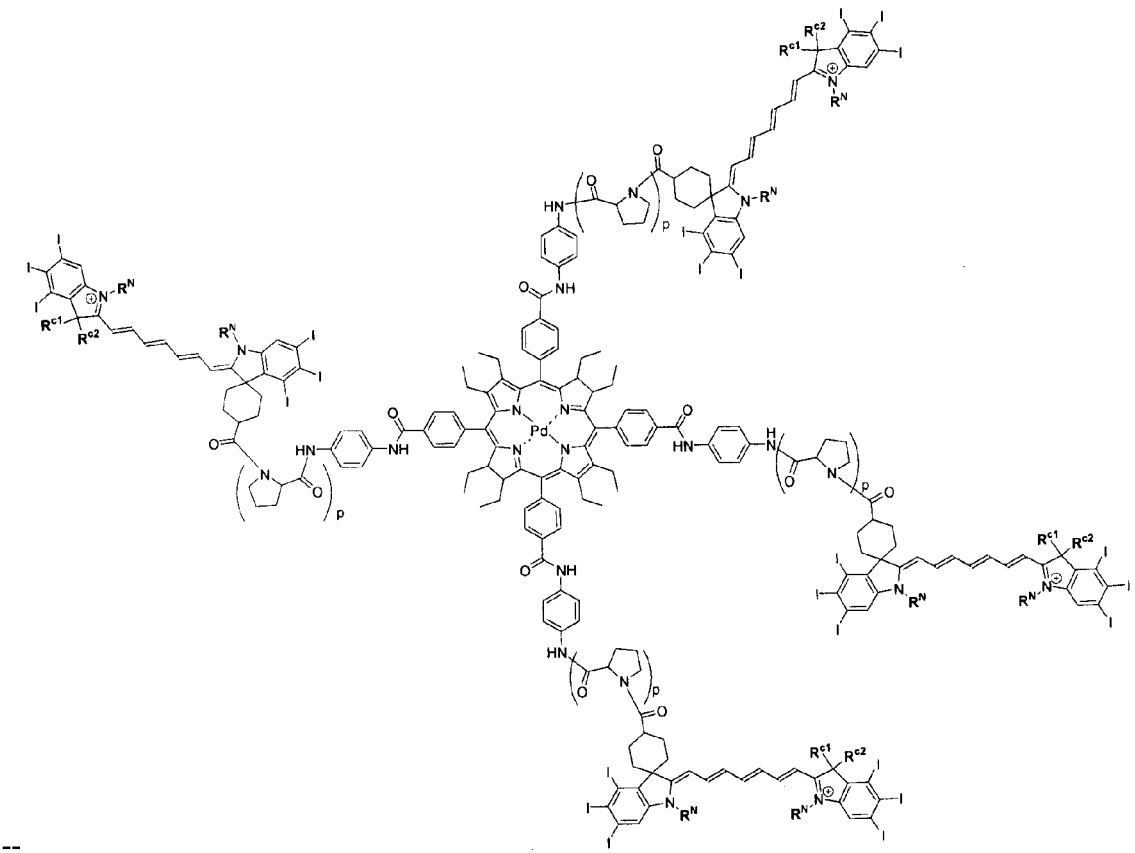

-- --.

Columns 31-32 and 33-34, the chemical formula (formula 14) should read,
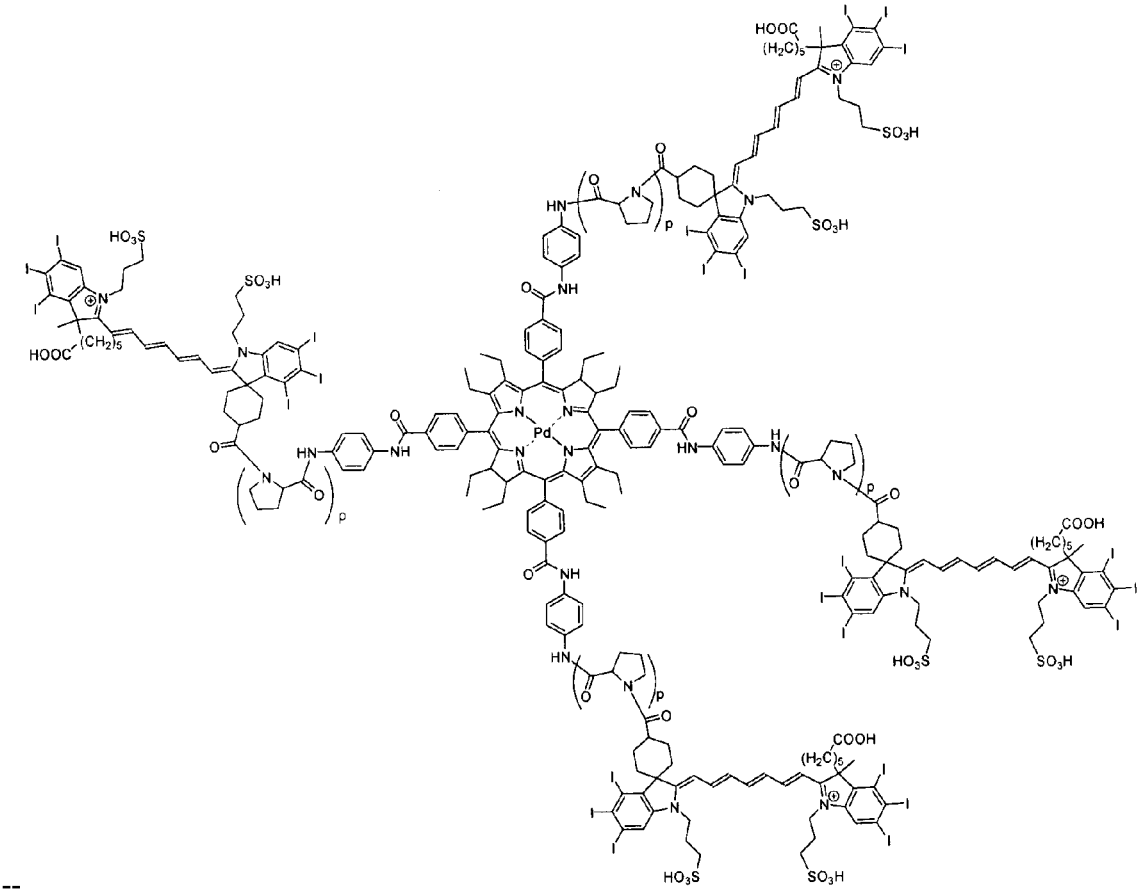
-- --.

Columns 33-34, the chemical formula (formula 15) should read,
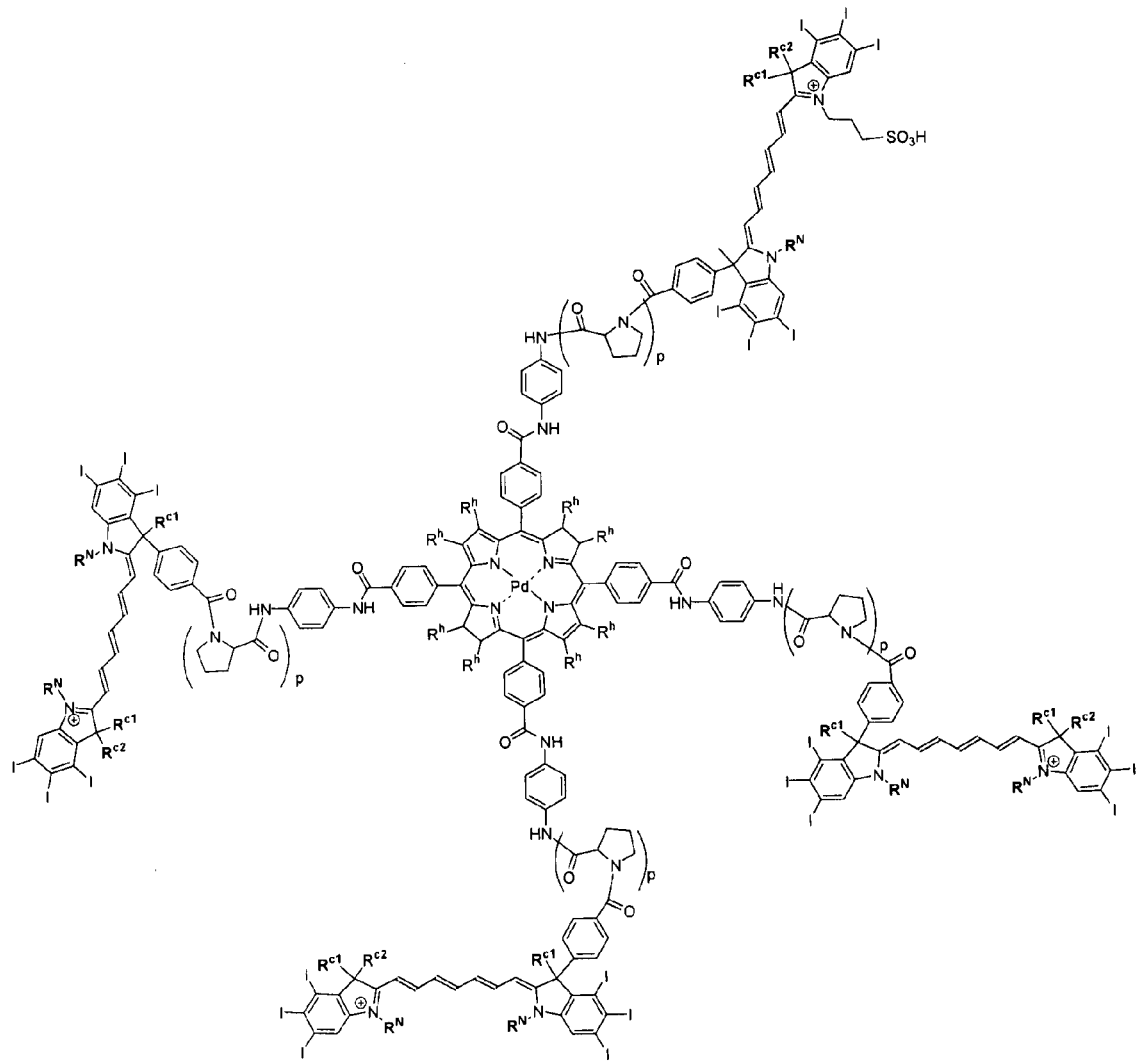
-- --.

Columns 35-36, the chemical formula (formula 16) should read,
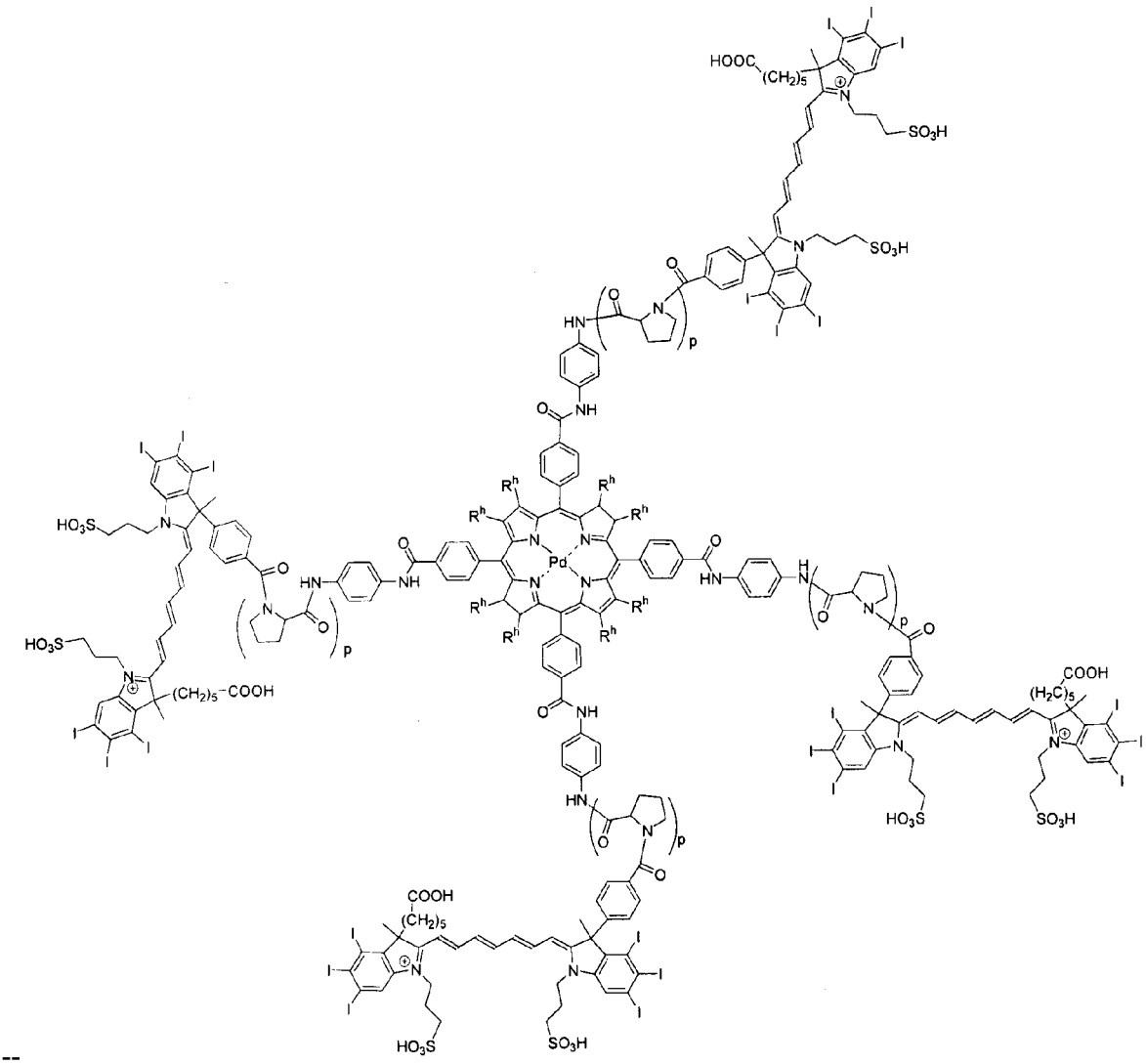
--                                                                                                                        --.

CERTIFICATE OF CORRECTION (continued)
U.S. Pat. No. 8,748,446 B2

Columns 37-38, the chemical formula (formula 17) should read,

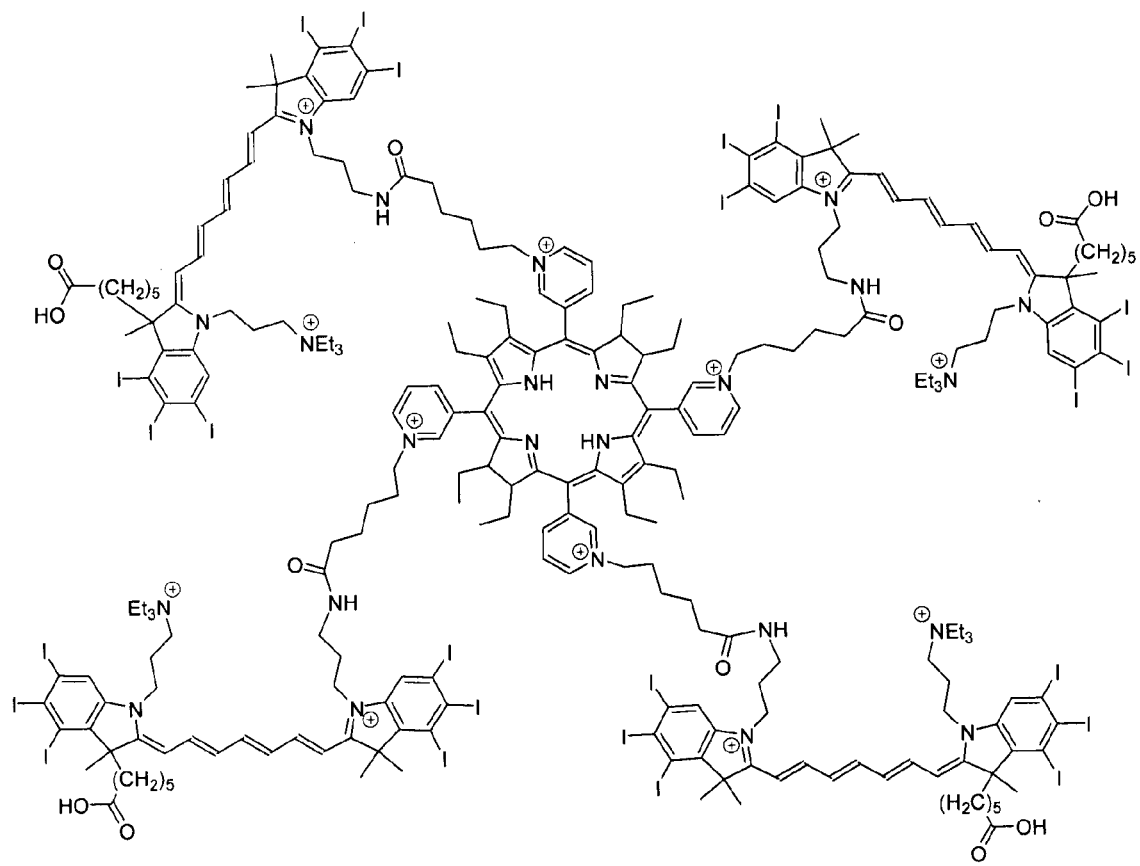

--

Columns 37-38 and 39-40, the chemical formula (formula 18) should read,

CERTIFICATE OF CORRECTION (continued)
U.S. Pat. No. 8,748,446 B2

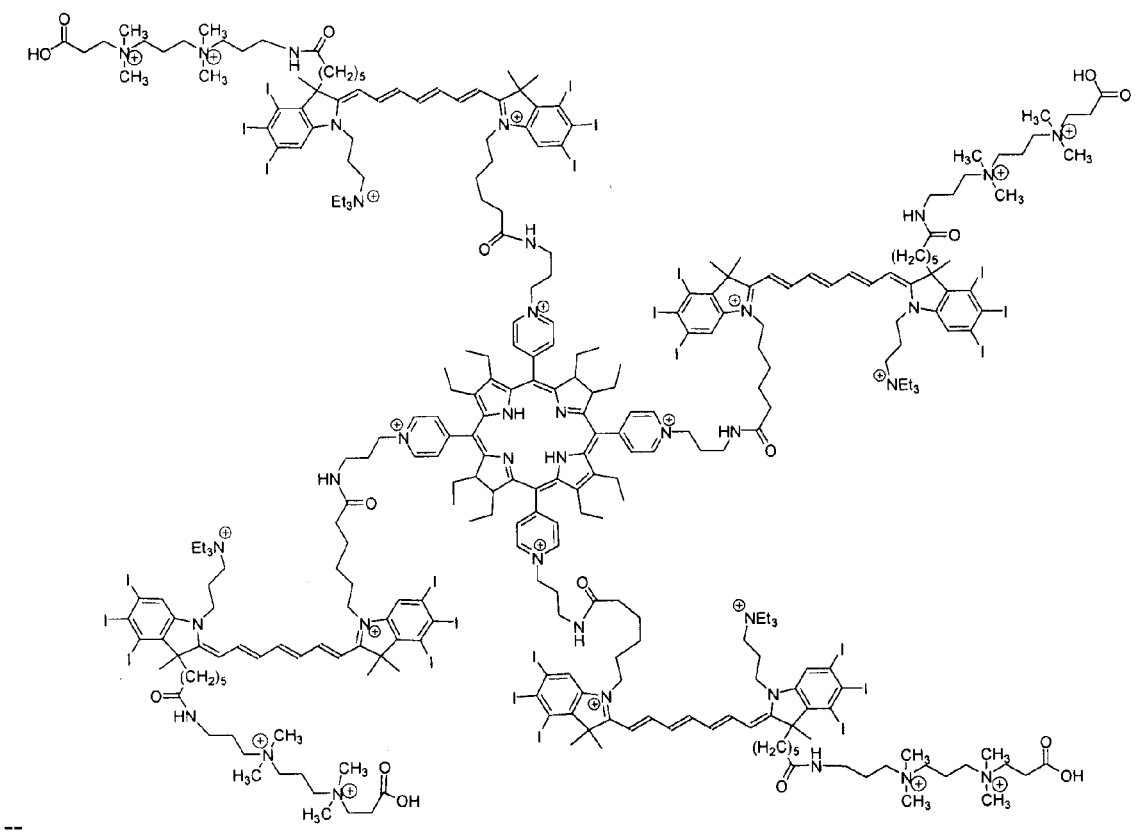

-- --.

Columns 39-40, the formula (formula 19) should read,

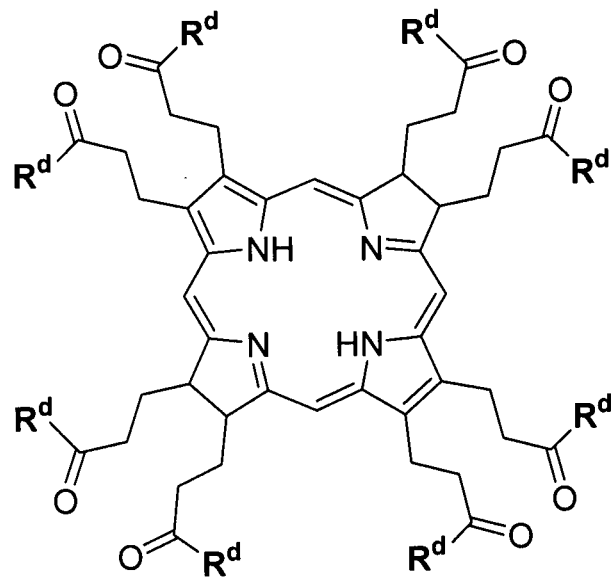
where: $R^d$ is:
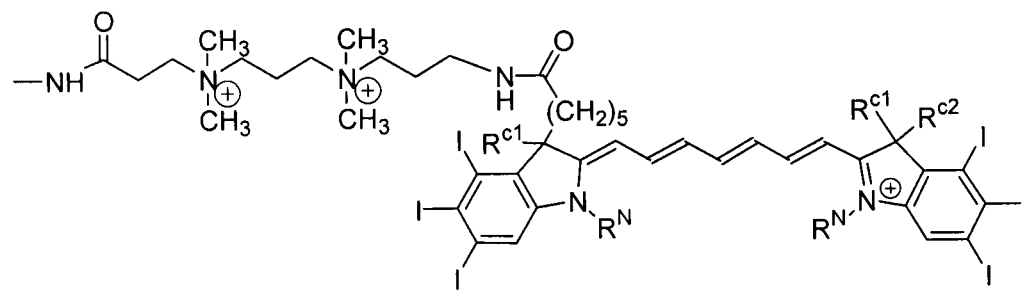
Column 44, line 17: "m" should be -- $m$ --.
Column 44, line 29: "q" should be -- $q$ --.
Column 44, line 31: "s" should be -- $s$ --.
Column 44, line 34: "t" should be -- $t$ --.
Column 56, lines 2-9, the chemical formula should read,
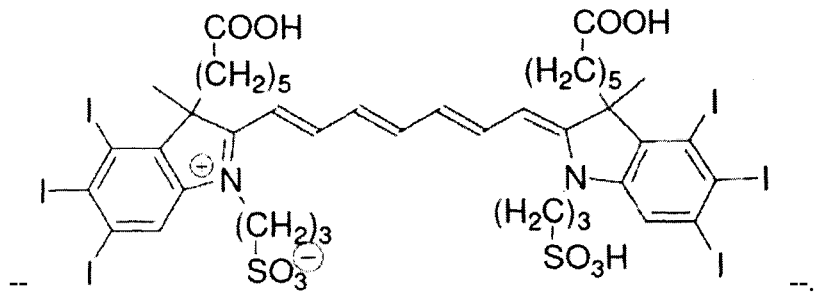
Column 60, lines 9-18, the chemical formula should read,

CERTIFICATE OF CORRECTION (continued)
U.S. Pat. No. 8,748,446 B2

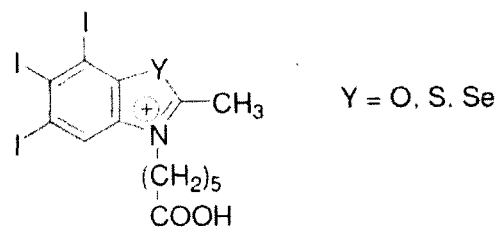

Column 61-62, the chemical formula (figure 13) should read,

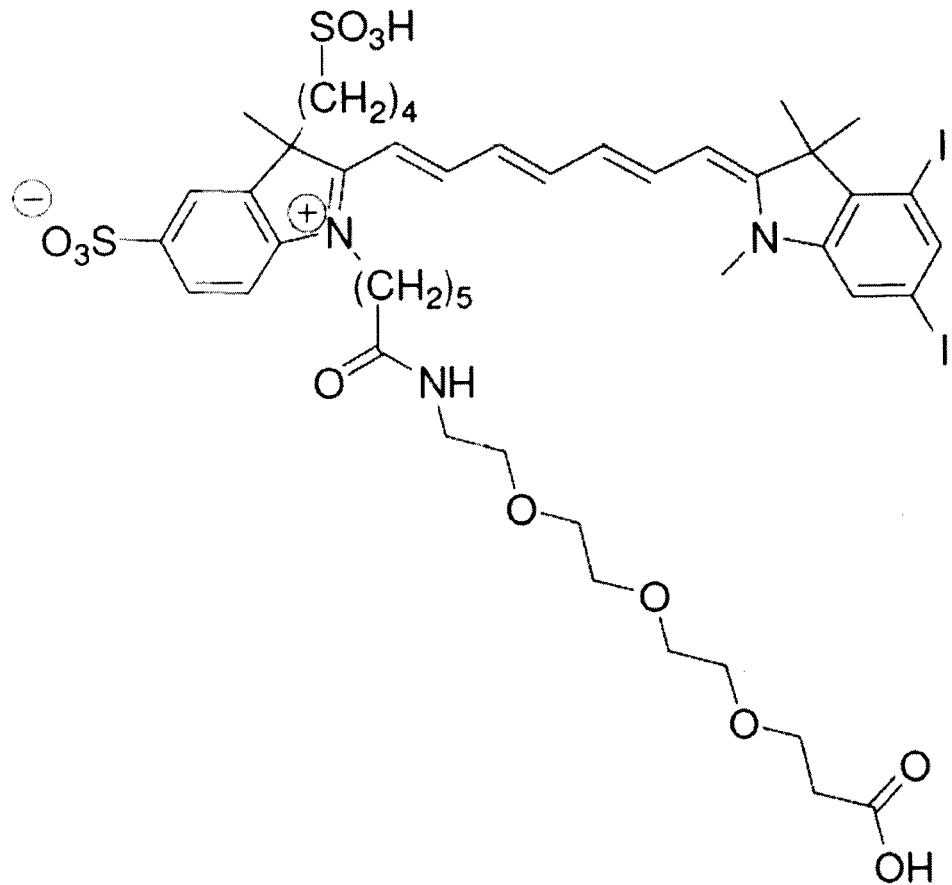

Columns 65-66, the chemical formula (formula 1) should read,

CERTIFICATE OF CORRECTION (continued)
U.S. Pat. No. 8,748,446 B2

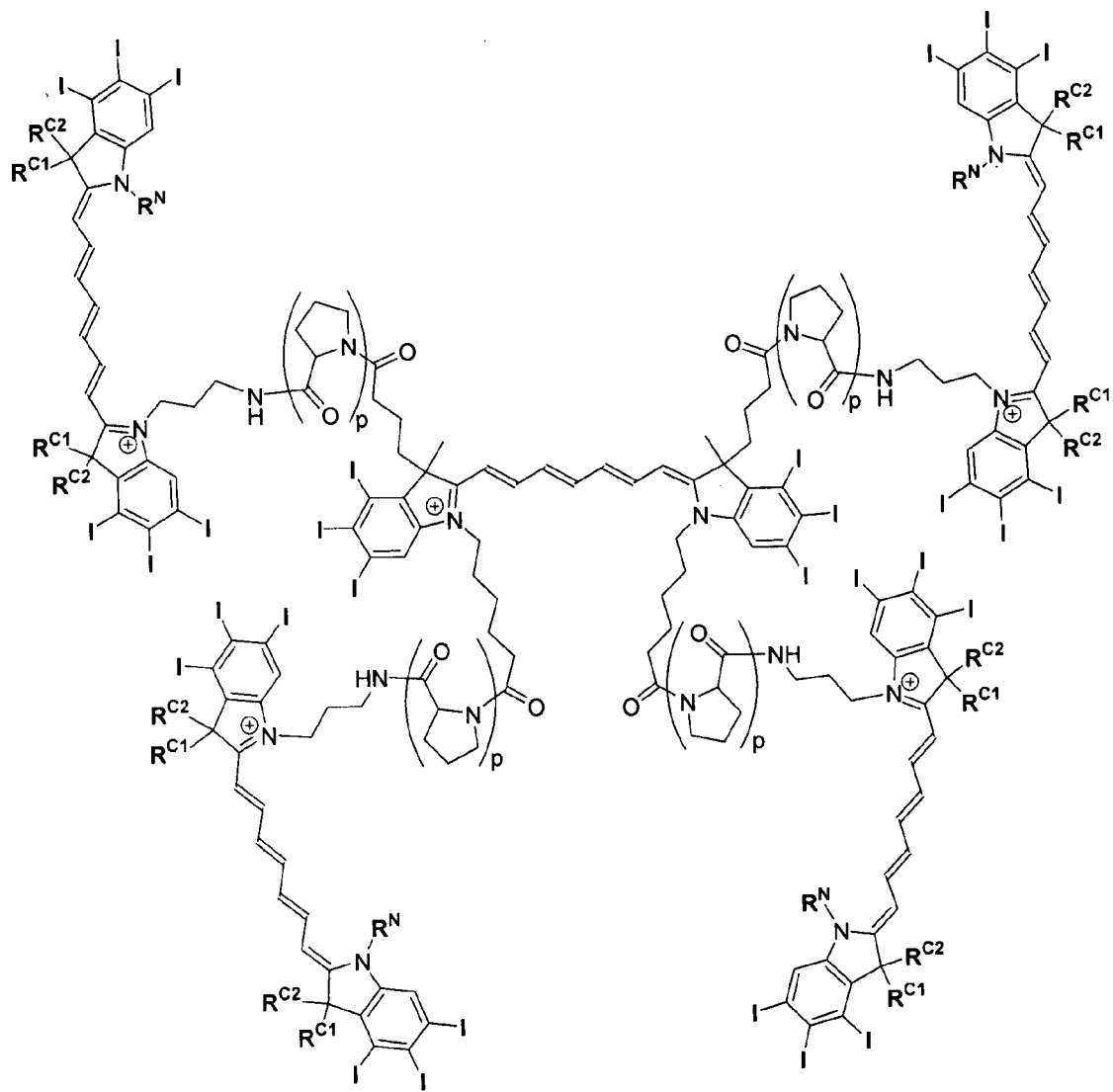

-- --.

Columns 67-68, the chemical formula (figure 2) should read,

CERTIFICATE OF CORRECTION (continued)
U.S. Pat. No. 8,748,446 B2

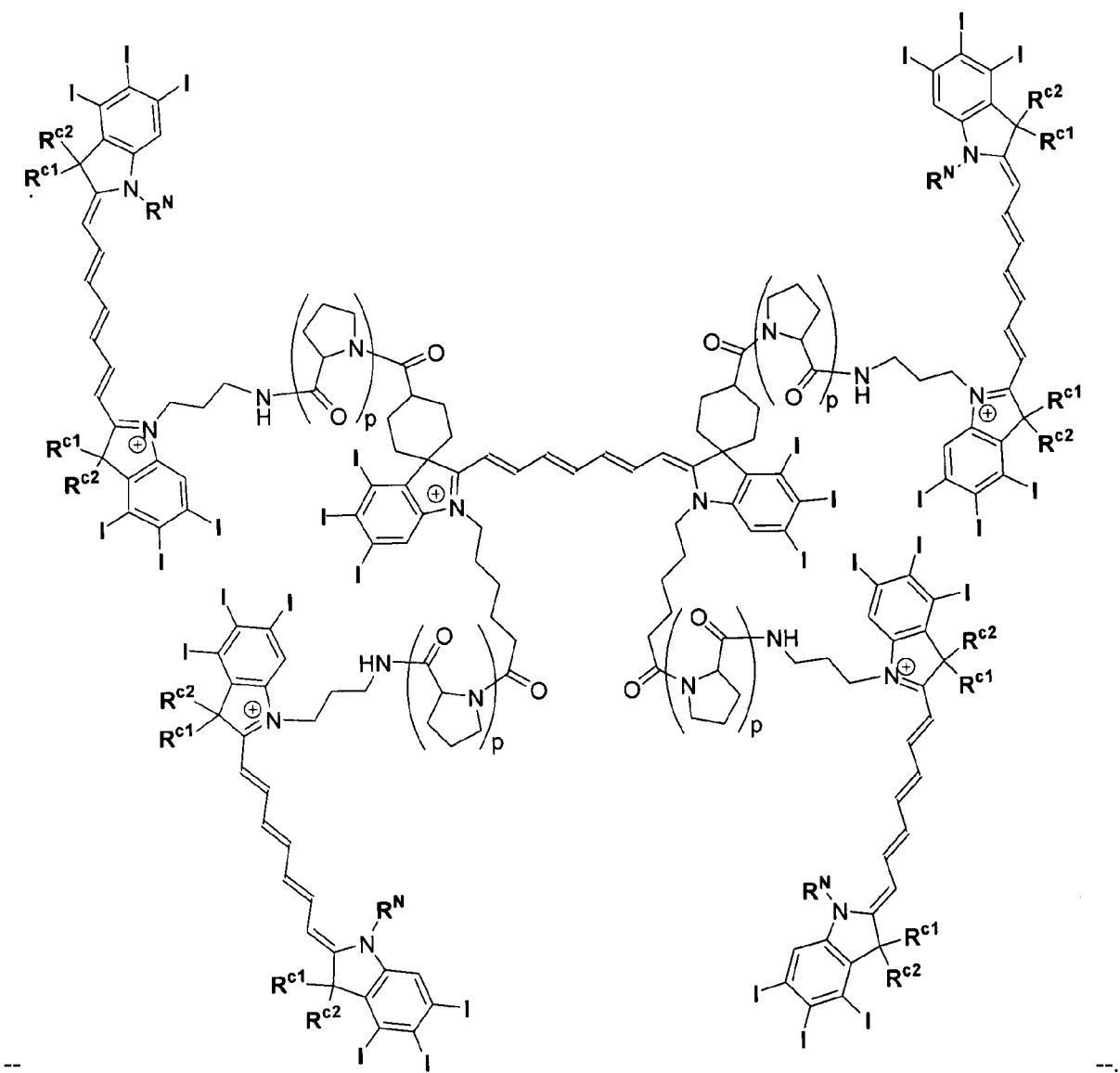

-- 	 --.

Columns 69-70, the formula (formula 3) should read,

CERTIFICATE OF CORRECTION (continued)
U.S. Pat. No. 8,748,446 B2

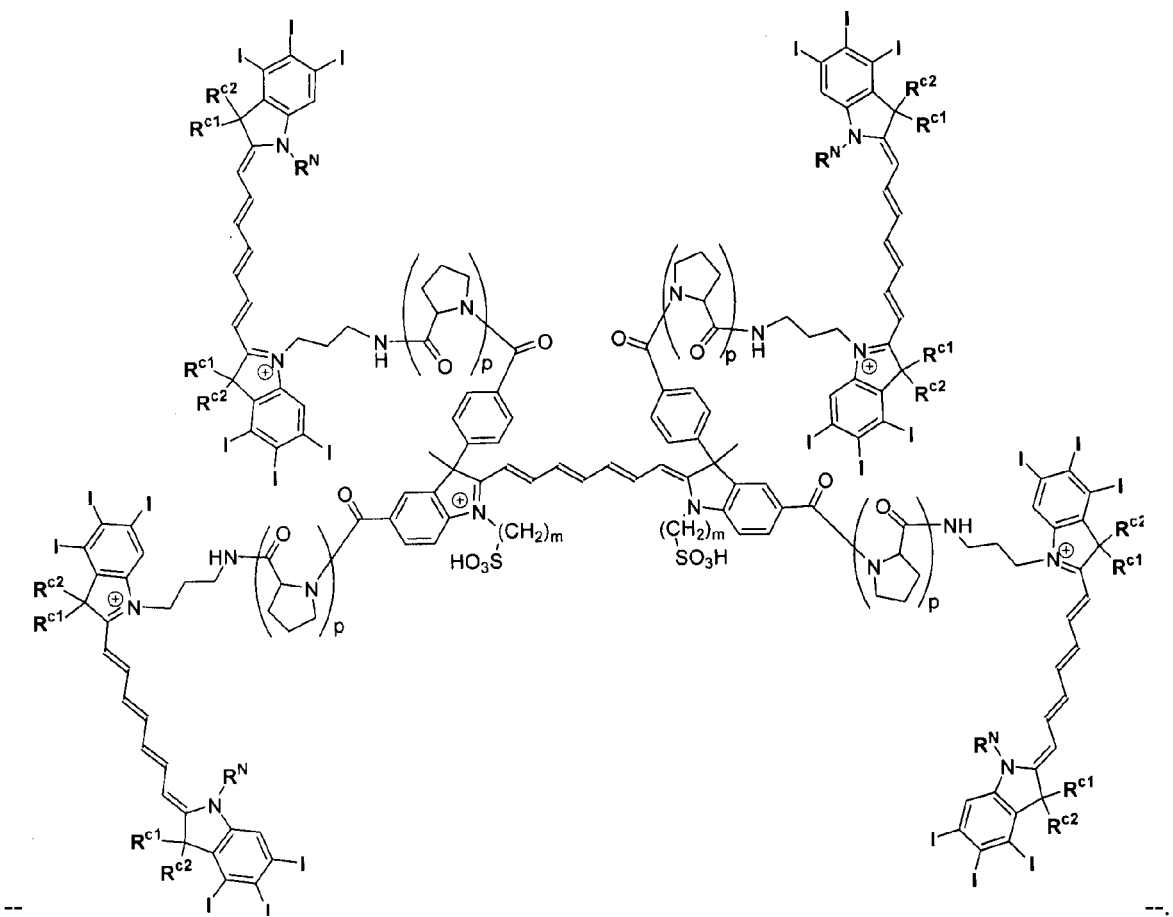

--

Column 109, line 57: "tert-butoxide" should be -- *tert*-butoxide --.

Column 109, line 58: "tert-butanol" should be -- *tert*-butanol --.

Column 109, line 59: "tert-butoxide" should be -- *tert*-butoxide --.

Column 114, line 1: "N[5" should be -- N-[5 --.

Column 114, line 9: "(1-88)" should be -- I-88 --.

Column 120, line 37: "pen-tyl" should be -- pentyl --.

Column 120, Example 22, the chemical reaction equation should read,

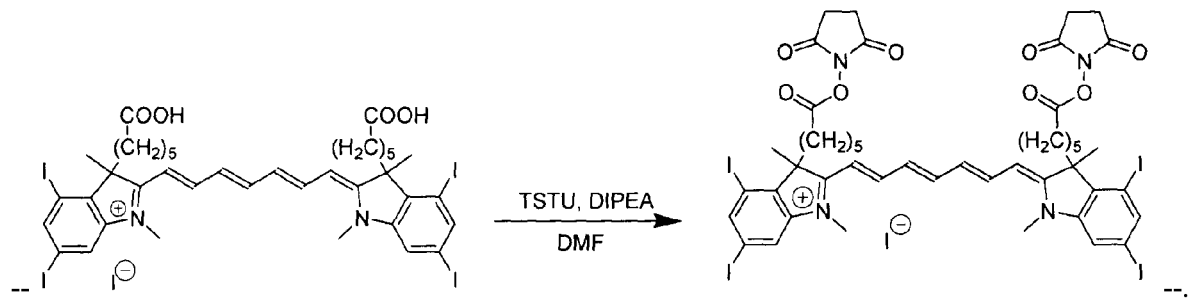

Column 122, line 31: "N[5" should be -- N-[5 --.

Column 123, line 5: "345-carboxypentyl" should be -- 3-5-carboxypentyl --.

CERTIFICATE OF CORRECTION (continued)
U.S. Pat. No. 8,748,446 B2

Column 123, line 13: "(1-83)" should be -- I-83 --.

Column 128, Example 29, the chemical reaction should read,

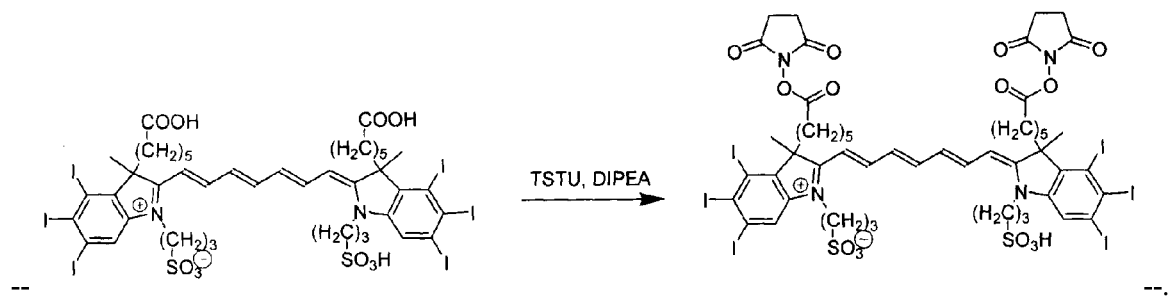

--.

Column 129, line 4: "(1-86)" should be -- I-86 --.

Column 135, line 35: "(1-72)" should be -- I-72 --.

Column 147, line 9: "UV/V is" should be -- UV/Vis --.

Column 159, Table 1, the chemical formula for I-84 should read,

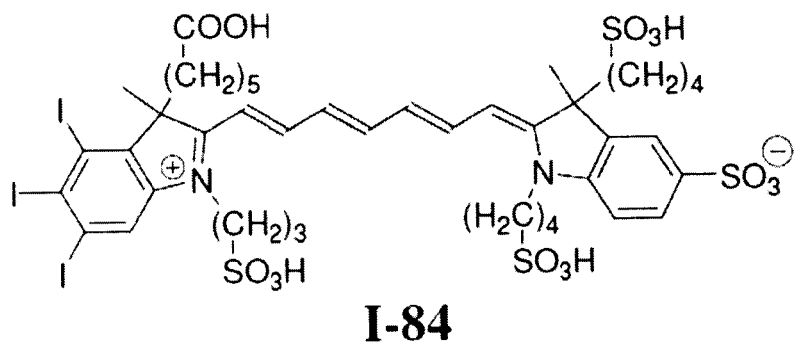

--.

Columns 159-160, Table 1, the chemical formula for I-86 should read,

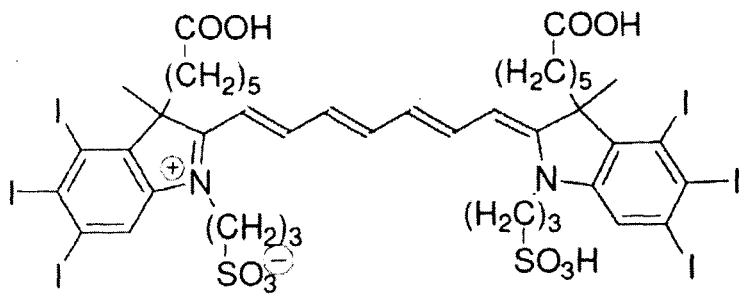

--.

Column 163, Table 1, the chemical formula for I-90 should read,

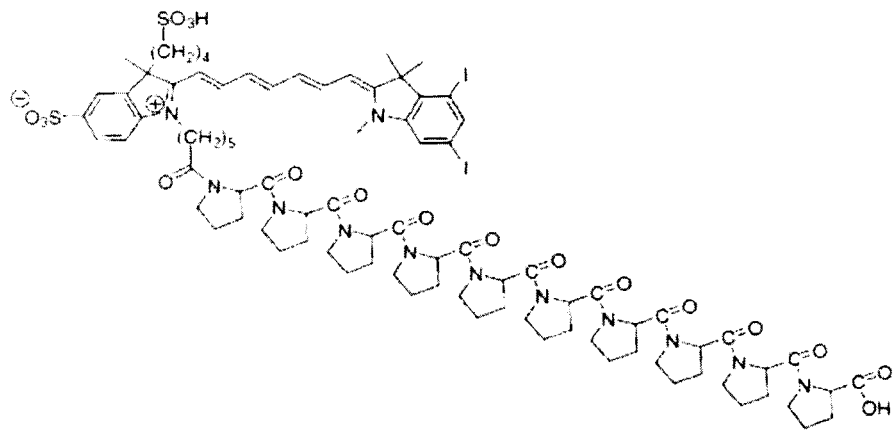
I-90
-- --.
Column 177, Table 3, the chemical formula for I-90 should read,
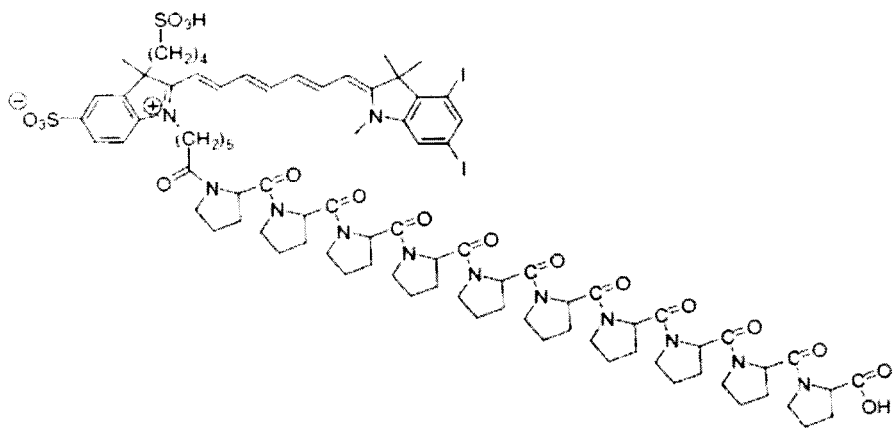
I-90
-- --.
In the Claims
Column 186, line 3: "from a the group" should be -- from the group --.